US012797488B2

(12) United States Patent
Sankaran et al.

(10) Patent No.: US 12,797,488 B2
(45) Date of Patent: Nov. 17, 2026

(54) COMPOSITIONS AND METHODS FOR THE TREATMENT OF DBA USING GATA1 GENE THERAPY

(71) Applicant: THE CHILDREN'S MEDICAL CENTER CORPORATION, Boston, MA (US)

(72) Inventors: Vijay G. Sankaran, Roslindale, MA (US); Richard A. Voit, Watertown, MA (US); Leif S. Ludwig, Cambridge, MA (US)

(73) Assignee: THE CHILDREN'S MEDICAL CENTER CORPORATION, Boston, MA (US)

(*) Notice: Subject to any disclaimer, the term of this patent is extended or adjusted under 35 U.S.C. 154(b) by 1015 days.

(21) Appl. No.: 17/612,465

(22) PCT Filed: Jun. 8, 2020

(86) PCT No.: PCT/US2020/036600
§ 371 (c)(1),
(2) Date: Nov. 18, 2021

(87) PCT Pub. No.: WO2020/251887
PCT Pub. Date: Dec. 17, 2020

(65) Prior Publication Data

US 2022/0265863 A1 Aug. 25, 2022

Related U.S. Application Data

(60) Provisional application No. 62/859,369, filed on Jun. 10, 2019.

(51) Int. Cl.

| | |
|---|---|
| *C12N 15/86* | (2006.01) |
| *A61K 38/17* | (2006.01) |
| *A61K 48/00* | (2006.01) |
| *A61P 7/06* | (2006.01) |

(52) U.S. Cl.
CPC ...... *A61K 48/0066* (2013.01); *A61K 38/1709* (2013.01); *A61P 7/06* (2018.01)

(58) Field of Classification Search
CPC ............ A61K 48/0066; A61K 38/1709; A61K 48/005; A61K 48/0058; A61K 31/7105; A61P 7/06; C12N 2310/141; C12N 2740/16043; C12N 2830/008;
(Continued)

(56) References Cited

U.S. PATENT DOCUMENTS

2007/0161031 A1* 7/2007 Trinklein .......... C12N 15/1086 435/325
2010/0233135 A1 9/2010 Arnaout
(Continued)

OTHER PUBLICATIONS

Ludwig et al., Altered translation of GATA1 in Diamond-Blackfan anemia, Nature Medicine 20(7): 748-753, 2014.*
(Continued)

*Primary Examiner* — Tracy Vivlemore
*Assistant Examiner* — Thomas R. Amick
(74) *Attorney, Agent, or Firm* — Nixon Peabody LLP; David S. Resnick; Nicole D. Kling

(57) ABSTRACT

Described herein are methods and compositions related to GATA-1 gene therapy for the treatment of Diamond-Blackfan anemia.

15 Claims, 42 Drawing Sheets

Specification includes a Sequence Listing.

(58) Field of Classification Search
CPC .......... C12N 2830/48; C12N 2840/203; C12N 15/86; C07K 14/4702
See application file for complete search history.

(56) References Cited

U.S. PATENT DOCUMENTS

| | | | | |
|---|---|---|---|---|
| 2015/0111955 A1* | 4/2015 | High | C12N 15/86 435/456 |
| 2018/0223360 A1 | 8/2018 | Hatchwell et al. | |
| 2019/0002886 A1 | 1/2019 | Zon et al. | |
| 2023/0103708 A1* | 4/2023 | Vetter | A61K 48/0075 424/93.21 |

OTHER PUBLICATIONS https://www.calculator.net/exponent-calculator; last visited Mar. 10, 2025.*
Moriguchi et al, The Human GATA1 Gene Retains a 5' Insulator That Maintains Chromosomal Architecture and GATA1 Expression Levels in Splenic Erythroblasts, Molecular and Cellular Biology 25(10):1825-1837, 2015.*
GenBank AC231533 (human BAC clone RP11-67K1, X chromosome, GATA1, 2009).*
GenBank AC233300 (human BAC clone RP11-956P9 X chromosome, GATA1, 2009).*
Kingdoms of Life, waynesword.palomar.edu/trfeb98.htm, last visited Apr. 8, 2021.*
Mammal, en.wikipedia.org/wiki/Mammal, last visited Aug. 31, 2022.*
Mingozzi and High, Immune responses to AAV vectors: overcoming barriers to successful gene therapy, Blood 122(1): 23-36, 2013.*
Kattenhorn et al, Adeno-Associated Virus Gene Therapy for Liver Disease, Human Gene Therapy 27(12): 947-961, Nov. 28, 2016.*
Perrin, Make Mouse Studies Work, Nature (507): 423-425, 2014.*
Greenberg, Gene Therapy for heart failure, Trends in Cardiovascular Medicine 27: 216-222, 2017.*
Maguire et al, Viral vectors for gene delivery to the inner ear, Hearing Research 394: e107927, 13 pages, doi.org/10.1016/j.heares.2020.107927, 2020.*
Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023.*
Ohneda et al, A minigene containing four discrete cis elements recapitulates GATA-1 gene expression in vivo, Genes to Cells 7: 1243-1254, 2002.*
NovoPro, pSVbeta vector map, www.novoprolabs.com, 2025.*
GenBank NM_002049, human GATA-1, Feb. 5, 2018.*
Iwasaki et al, GATA-1 Converts Lymphoid and Myelomonocytic Progenitors into the Megakaryocyte/Erythrocyte Lineages, Immunity 19: 451-462, 2003.*
Hamlett et al, Characterization of megakaryocyte GATA1-interacting proteins: the corepressor ETO2 and GATA1 interact to regulate terminal megakaryocyte maturation, Blood 112(7): 2738-2749, 2008.*
Moreau-Gaudry et al, High-level erythroid-specific gene expression in primary human and murine hematopoietic cells with self-inactivating lentiviral vectors, Blood 98(9): 2664-2672, 2001.*
Hartikka et al, Sodium phosphate enhances plasmid DNA expression in vivo, Gene Therapy 7: 1171-1182, 2000.*
Tiscornia et al, Production and purification of lentiviral vectors, Nature Protocols 1(1): 241-245, 2006.*
Li et al. "Binary transgenic mouse model for studying the trans control of globin gene switching: Evidence that GATA-1 is an in vivo repressor of human ε gene expression." Proceedings of the National Academy of Sciences 94.6 2444-2448 (1997).
Romano et al. "Transcriptional, epigenetic and retroviral signatures identify regulatory regions involved in hematopoietic lineage commitment." Scientific Reports 6.1 (2016).
Romano et al.: "Supplementary Information Transcriptional, epigenetic and retroviral signatures identify regulatory regions involved in hematopoietic lineage commitment", (2016).
Shimizu et al. "Gene expression regulation and domain function of hematopoietic GATA factors." Seminars in cell & developmental biology. vol. 16. No. 1. Academic Press (2005).
Toscano, M. G., et al. "Physiological and tissue-specific vectors for treatment of inherited diseases." Gene therapy 18.2 117-127 (2011).
Whyatt et al. "The level of the tissue-specific factor GATA-1 affects the cell-cycle machinery." Genes and function 1.1 11-24 (1997).
Bertrand et al. "Definitive hematopoiesis initiates through a committed erythromyeloid progenitor in the zebrafish embryo." Development. vol. 134, No. 23, Dec. 2007, pp. 4147-4156. DOI: 10.1242/dev.012385.
Voit et al. "Regulated GATA1 expression as a universal gene therapy for Diamond-Blackfan anemia." Cell Stem Cell. vol. 32, No. 1, Jan. 2025, pp. 38-52. DOI: 10.1016/j.stem.2024.10.012.
Ludwig et al. "Transcriptional states and chromatin accessibility underlying human erythropoiesis." Cell Reports 27 (11):3228-3240.e.7, Jun. 2019, (35 pp.).
Romano et al. "Transcriptional, epigenetic and retroviral signatures identify regulatory regions involved in hematopoietic lineage commitment." Scientific Reports 6(1):24724, Apr. 2016, (15 pp.).
Romano et al.: "Supplementary Information Transcriptional, epigenetic and retroviral signatures identify regulatory regions involved in hematopoietic lineage commitment" Scientific Reports 6(1):24724, Apr. 2016 (49 pp.).
Shimizu et al. "Gene expression regulation and domain function of hematopoietic GATA factors." Seminars in Cell & Developmental Biology. 16(1):129-136, Dec. 2004, (8 pp.).
Debnath et al. "Lentiviral Vectors with Cellular Promoters Correct Anemia and Lethal Bone Marrow Failure in a Mouse Model for Diamond-Blackfan Anemia" American Society of Gene & Cell Therapy 25(8): 1805-1814 (2017).
Gentner et al. "Identification of Hematopoietic Stem Cell-Specific miRNAs Enables Gene Therapy of Globoid Cell Leukodystrophy" 2(58): 58ra84 (2010).
Ingolia et al. "Genome-Wide Analysis in Vivo of Translation with Nucleotide Resolution Using Ribosome Profiling." Science 324(5924): 218-223 (2009).
Ingolia et al. "Ribosome Footprint Profiling of Translation throughout the Genome" Cell 165(1): 22-33 (2016).
Iwasaki et al. "GATA-1 Converts Lymphoid and Myelomonocytic Progenitors into the Megakaryocyte/Erythrocyte Lineages" Immunity 19(3): 451-462 (2003).
Ludwig et al., "Altered Translation of GATA1 in Diamond-Blackfan Anemia." Nat Med., 20(7): 748-753 (2014).
Surinya et al., "Identification and Characterization of a Conserved Erythroid-Specific Enhancer Located in Intron 8 of the Human 5-Aminolevulinate Synthase 2 Gene." Biol. Chem. 273(27): 16798-16809 (1998).
Takai et al. "The Gata1 5' region harbors distinct cis-regulatory modules that direct gene activation in erythroid cells and gene inactiviation in HSCs" Blood 122(20): 3450-3460 (2013).
Ohneda et al. "A minigene containing four discrete cis elements recapitulates GATA-1 gene expression in vivo" Genes to Cells 7(12):1243-1254 (2002).
Tanabe et al. "The TR2 and TR4 orphan nuclear receptors repress Gata1 transcription, Genes & Development" 21 (21):2832-2844 (2007).
Baron et al. "The embryonic origins of erythropoiesis in mammals." Blood, The Journal of the American Society of Hematology 119.21 (2012): 4828-4837.
Bertrand et al. "Definitive hematopoiesis initiates through a committed erythromyeloid progenitor in the zebrafish embryo." (2007): 4147-4156.
Voit et al. "Regulated GATA1 expression as a universal gene therapy for Diamond-Blackfan anemia." Cell Stem Cell 32.1 (2025): 38-52.
Buenrostro et al. "Transposition of native chromatin for fast and sensitive epigenomic profiling of open chromatin, DNA-binding proteins and nucleosome position." Nature methods 10.12: 1213-1218 (Dec. 2013).

(56) References Cited

OTHER PUBLICATIONS

Romano et al. "Transcriptional, epigenetic and retroviral signatures identify regulatory regions involved in hematopoietic lineage commitment." Scientific Reports 6.1 (Apr. 2016).
Romano et al. "Transcriptional, epigenetic and retroviral signatures identify regulatory regions involved in hematopoietic lineage commitment." Scientific Reports 6.1, Supplementary Information (Apr. 2016).
Shimizu et al. "Gene expression regulation and domain function of hematopoietic GATA factors." Seminars in cell & developmental biology. vol. 16. No. 1. Academic Press (Dec. 2004).

* cited by examiner

M

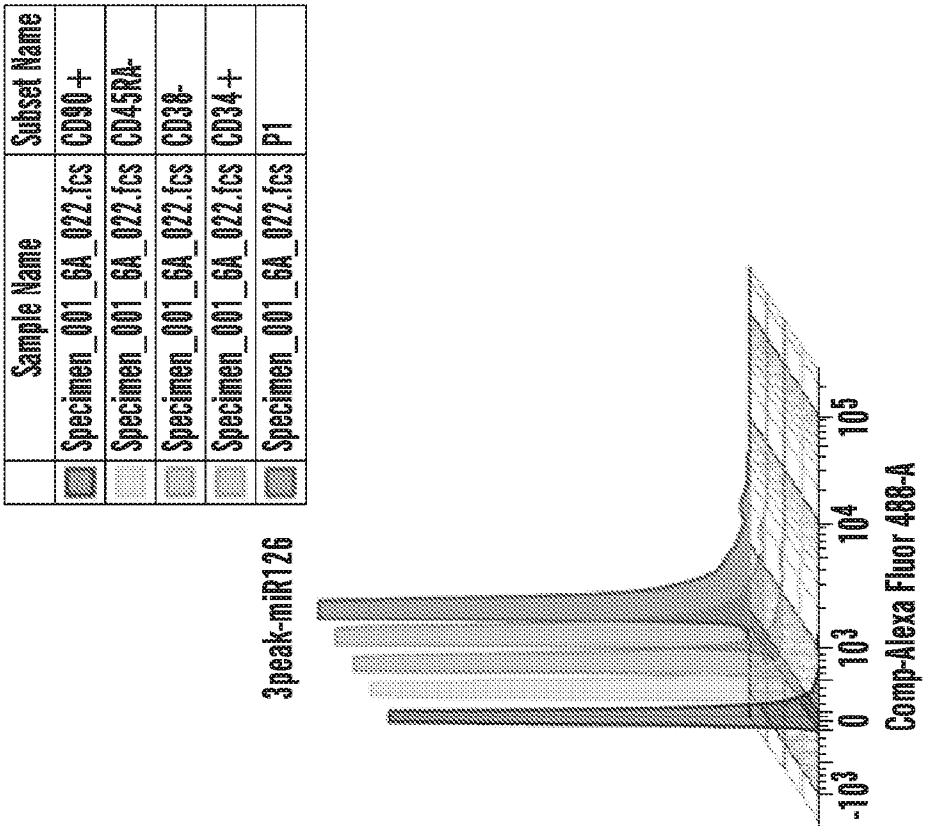
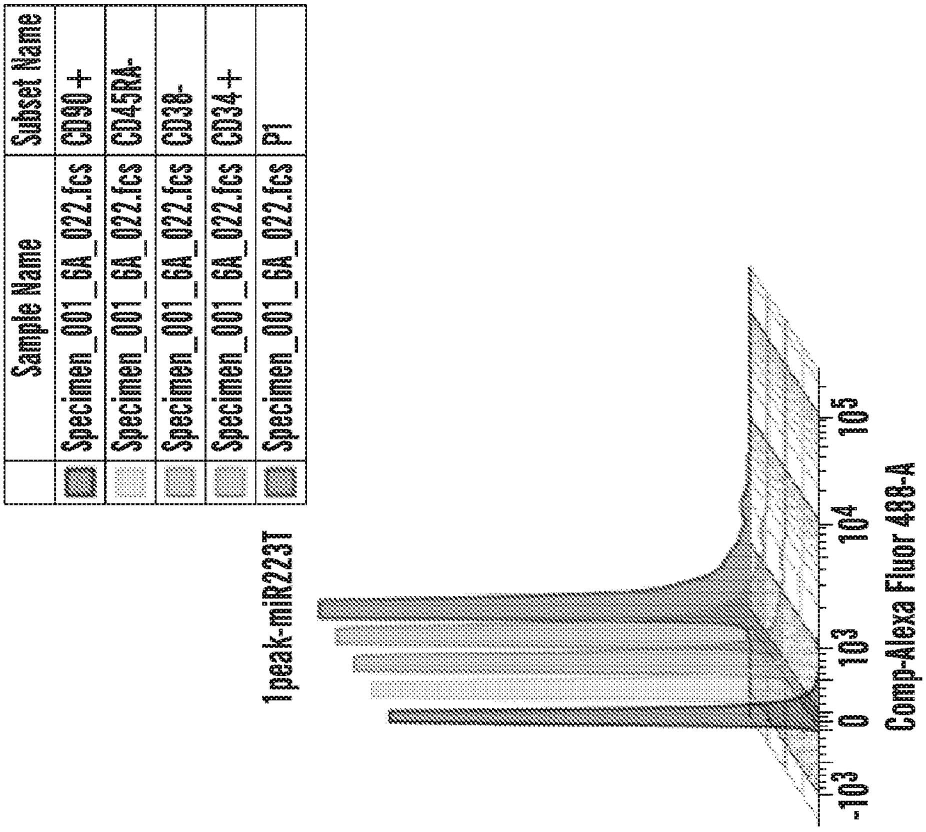
*FIG. 17 (cont.)*

GFP expression in CD34+CD38-CD45RA-CD90+ subset

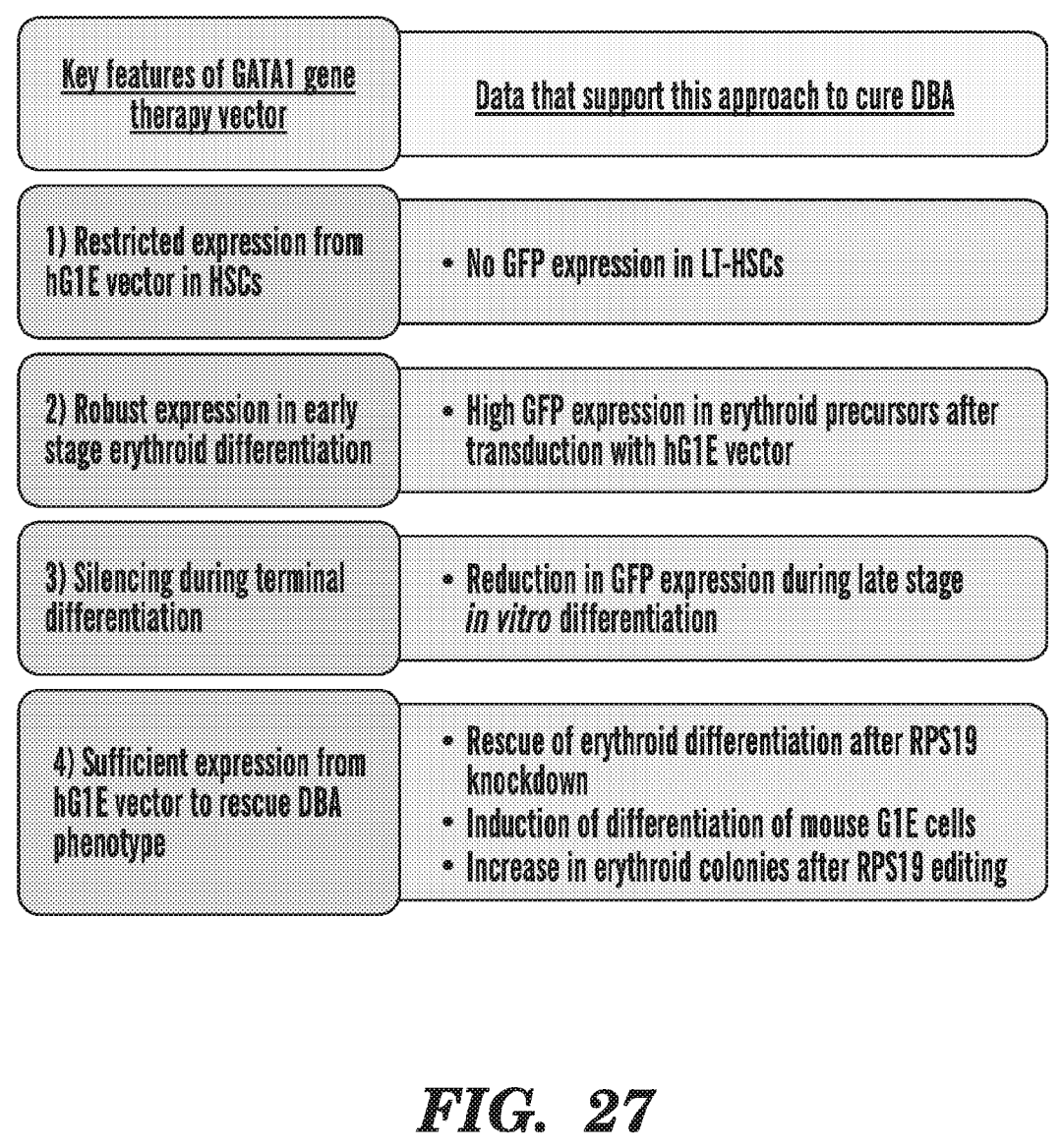

| Key features of GATA1 gene therapy vector | Data that support this approach to cure DBA |
|---|---|
| 1) Restricted expression from hG1E vector in HSCs | • No GFP expression in LT-HSCs |
| 2) Robust expression in early stage erythroid differentiation | • High GFP expression in erythroid precursors after transduction with hG1E vector |
| 3) Silencing during terminal differentiation | • Reduction in GFP expression during late stage *in vitro* differentiation |
| 4) Sufficient expression from hG1E vector to rescue DBA phenotype | • Rescue of erythroid differentiation after RPS19 knockdown<br>• Induction of differentiation of mouse G1E cells<br>• Increase in erythroid colonies after RPS19 editing |

*FIG. 27*

SEQUENCE LISTING

<160> NUMBER OF SEQ ID NOS: 69

<210> SEQ ID NO 1
<211> LENGTH: 1242
<212> TYPE: DNA
<213> ORGANISM: Homo sapiens

<400> SEQUENCE: 1

```
atggagttcc ctggcctggg gtccctgggg acctcagagc cctcccccca gtttgtggat     60
cctgctctgg tgtcctccac accagaatca ggggttttct tcccctctgg gcctgagggc    120
ttggatgcag cagcttcctc cactgccccg agcacagcca ccgctgcagc tgcggcactg    180
gcctactaca gggacgctga ggcctacaga cactccccag tctttcaggt gtacccattg    240
ctcaactgta tggaggggat cccagggggc tcaccatatg ccggctgggc ctacggcaag    300
acggggctct accctgcctc aactgtgtgt cccacccgcg aggactctcc tccccaggcc    360
gtggaagatc tggatggaaa aggcagcacc agcttcctgg agactttgaa gacagagcgg    420
ctgagcccag acctcctgac cctgggacct gcactgcctt catcactccc tgtccccaat    480
agtgcttatg gggccctga cttttccagt accttctttt ctcccaccgg gagccccctc    540
aattcagcag cctattcctc tcccaagctt cgtggaactc tcccccctgcc tccctgtgag    600
gccagggagt gtgtgaactg cggagcaaca gccactccac tgtggcggag ggacaggaca    660
ggccactacc tatgcaacgc ctgcggcctc tatcacaaga tgaatgggca gaacaggccc    720
ctcatccggc ccaagaagcg cctgattgtc agtaaacggg caggtactca gtgcaccaac    780
tgccagacga ccaccacgac actgtggcgg agaaatgcca gtggggatcc cgtgtgcaat    840
gcctgcggcc tctactacaa gctacaccag gtgaaccggc cactgaccat gcggaaggat    900
ggtattcaga ctcgaaaccg caaggcatct ggaaaaggga aaaagaaacg gggctccagt    960
ctgggaggca caggagcagc cgaaggacca gctggtggct ttatggtggt ggctgggggc   1020
agcggtagcg ggaattgtgg ggaggtggct tcaggcctga cactgggccc cccaggtact   1080
gcccatctct accaaggcct gggccctgtg gtgctgtcag ggcctgttag ccacctcatg   1140
cctttccctg gacccctact gggctcaccc acgggctcct tccccacagg ccccatgccc   1200
cccaccacca gcactactgt ggtggctccg ctcagctcat ga                       1242
```

<210> SEQ ID NO 2
<211> LENGTH: 1501
<212> TYPE: DNA
<213> ORGANISM: Homo sapiens

<400> SEQUENCE: 2

```
gacacccct gggatcacac tgagcttgcc acatccccaa ggcggccgaa ccctccgcaa     60
ccaccagccc aggttaatcc ccagaggctc catggagttc cctggcctgg ggtccctggg    120
gacctcagag cccctccccc agtttgtgga tcctgctctg gtgtcctcca caccagaatc    180
aggggttttc ttcccctctg ggcctgaggg cttggatgca gcagcttcct ccactgcccc    240
gagcacagcc accgctgcag ctgcggcact ggcctactac agggacgctg aggcctacag    300
acactcccca gtctttcagg tgtacccatt gctcaactgt atggagggga tcccaggggg    360
ctcaccatat gccggctggg cctacggcaa gacggggctc taccctgcct caactgtgtg    420
```

```
tcccacccgc gaggactctc ctccccaggc cgtggaagat ctggatggaa aaggcagcac    480

cagcttcctg gagactttga agacagagcg gctgagccca gacctcctga ccctgggacc    540

tgcactgcct tcatcactcc ctgtccccaa tagtgcttat gggggccctg acttttccag    600

taccttcttt tctcccaccg ggagccccct caattcagca gcctattcct ctcccaagct    660

tcgtggaact ctcccccctgc ctccctgtga ggccagggag tgtgtgaact gcggagcaac    720

agccactcca ctgtggcgga gggacaggac aggccactac ctatgcaacg cctgcggcct    780

ctatcacaag atgaatgggc agaacaggcc cctcatccgg cccaagaagc gcctgattgt    840

cagtaaacgg gcaggtactc agtgcaccaa ctgccagacg accaccacga cactgtggcg    900

gagaaatgcc agtggggatc ccgtgtgcaa tgcctgcggc ctctactaca agctacacca    960

ggtgaaccgg ccactgacca tgcggaagga tggtattcag actcgaaacc gcaaggcatc   1020

tggaaaaggg aaaaagaaac ggggctccag tctgggaggc acaggagcag ccgaaggacc   1080

agctggtggc tttatggtgg tggctggggg cagcggtagc gggaattgtg gggaggtggc   1140

ttcaggcctg acactgggcc ccccaggtac tgcccatctc taccaaggcc tgggccctgt   1200

ggtgctgtca gggcctgtta gccacctcat gcctttccct ggaccccctac tgggctcacc   1260

cacgggctcc ttccccacag gccccatgcc ccccaccacc agcactactg tggtggctcc   1320

gctcagctca tgagggcaca gagcatggcc tccagaggag gggtggtgtc cttctcctct   1380

tgtagccaga attctggaca acccaagtct ctgggcccca ggcacccccct ggcttgaacc   1440

ttcaaagctt ttgtaaaata aaaccaccaa agtcctgaaa aaaaaaaaaa aaaaaaaaaa   1500

a                                                                  1501
```

<210> SEQ ID NO 3
<211> LENGTH: 1501
<212> TYPE: DNA
<213> ORGANISM: Homo sapiens

<400> SEQUENCE: 3

```
gacacccccct gggatcacac tgagcttgcc acatccccaa ggcggccgaa ccctccgcaa     60

ccaccagccc aggttaatcc ccagaggctc catggagttc cctggcctgg ggtccctggg    120

gacctcagag cccctccccc agtttgtgga tcctgctctg gtgtcctcca caccagaatc    180

aggggttttc ttcccctctg ggcctgaggg cttggatgca gcagcttcct ccactgcccc    240

gagcacagcc accgctgcag ctgcggcact ggcctactac agggacgctg aggcctacag    300

acactcccca gtctttcagg tgtacccatt gctcaactgt atggagggga tcccaggggg    360

ctcaccatat gccggctggg cctacggcaa gacggggctc taccctgcct caactgtgtg    420

tcccacccgc gaggactctc ctccccaggc cgtggaagat ctggatggaa aaggcagcac    480

cagcttcctg gagactttga agacagagcg gctgagccca gacctcctga ccctgggacc    540

tgcactgcct tcatcactcc ctgtccccaa tagtgcttat gggggccctg acttttccag    600

taccttcttt tctcccaccg ggagccccct caattcagca gcctattcct ctcccaagct    660

tcgtggaact ctcccccctgc ctccctgtga ggccagggag tgtgtgaact gcggagcaac    720

agccactcca ctgtggcgga gggacaggac aggccactac ctatgcaacg cctgcggcct    780

ctatcacaag atgaatgggc agaacaggcc cctcatccgg cccaagaagc gcctgattgt    840

cagtaaacgg gcaggtactc agtgcaccaa ctgccagacg accaccacga cactgtggcg    900

gagaaatgcc agtggggatc ccgtgtgcaa tgcctgcggc ctctactaca agctacacca    960

ggtgaaccgg ccactgacca tgcggaagga tggtattcag actcgaaacc gcaaggcatc   1020
```

```
tggaaaaggg aaaaagaaac ggggctccag tctgggaggc acaggagcag ccgaaggacc   1080

agctggtggc tttatggtgg tggctggggg cagcggtagc gggaattgtg gggaggtggc   1140

ttcaggcctg acactgggcc ccccaggtac tgcccatctc taccaaggcc tgggccctgt   1200

ggtgctgtca gggcctgtta gccacctcat gcctttccct ggacccctac tgggctcacc   1260

cacgggctcc ttccccacag gccccatgcc ccccaccacc agcactactg tggtggctcc   1320

gctcagctca tgagggcaca gagcatggcc tccagaggag ggtggtgtc cttctcctct   1380

tgtagccaga attctggaca acccaagtct ctgggcccca ggcacccccct ggcttgaacc   1440

ttcaaagctt ttgtaaaata aaaccaccaa agtcctgaaa aaaaaaaaaa aaaaaaaaaa   1500

a                                                                   1501
```

<210> SEQ ID NO 4
<211> LENGTH: 1273
<212> TYPE: DNA
<213> ORGANISM: Homo sapiens

<400> SEQUENCE: 4

```
ggaagggagc ctcaaaggcc aaggccagcc aggacacccc ctgggatcac actgagcttg     60

ccacatcccc aaggcggccg aaccctccgc aaccaccagc ccagtctttc aggtgtaccc    120

attgctcaac tgtatggagg ggatcccagg gggctcacca tatgccggct gggcctacgg    180

caagacgggg ctctaccctg cctcaactgt gtgtcccacc cgcgaggact ctcctcccca    240

ggccgtggaa gatctggatg gaaaaggcag caccagcttc ctggagactt tgaagacaga    300

gcggctgagc ccagacctcc tgaccctggg acctgcactg ccttcatcac tccctgtccc    360

caatagtgct tatgggggcc ctgacttttc cagtaccttc ttttctccca ccgggagccc    420

cctcaattca gcagcctatt cctctcccaa gcttcgtgga actctccccc tgcctccctg    480

tgaggccagg gagtgtgtga actgcggagc aacagccact ccactgtggc ggagggacag    540

gacaggccac tacctatgca acgcctgcgg cctctatcac aagatgaatg ggcagaacag    600

gcccctcatc cggcccaaga agcgcctgat tgtcagtaaa cgggcaggta ctcagtgcac    660

caactgccag acgaccacca cgacactgtg gcggagaaat gccagtgggg atcccgtgtg    720

caatgcctgc ggcctctact acaagctaca ccaggtgaac cggccactga ccatgcggaa    780

ggatggtatt cagactcgaa accgcaaggc atctggaaaa gggaaaaaga aacggggctc    840

cagtctggga ggcacaggag cagccgaagg accagctggt ggctttatgg tggtggctgg    900

gggcagcggt agcgggaatt gtggggaggt ggcttcaggc ctgacactgg gcccccccagg    960

tactgcccat ctctaccaag gcctgggccc tgtggtgctg tcagggcctg ttagccacct   1020

catgcctttc cctggacccc tactgggctc acccacgggc tccttcccca caggccccat   1080

gccccccacc accagcacta ctgtggtggc tccgctcagc tcatgagggc acagagcatg   1140

gcctccagag gaggggtggt gtccttctcc tcttgtagcc agaattctgg acaacccaag   1200

tctctgggcc ccaggcaccc cctggcttga accttcaaag cttttgtaaa ataaaaccac   1260

caaagtcctg aaa                                                      1273
```

<210> SEQ ID NO 5
<211> LENGTH: 1501
<212> TYPE: DNA
<213> ORGANISM: Homo sapiens

<400> SEQUENCE: 5

```
gacaccccct gggatcacac tgagcttgcc acatccccaa ggcggccgaa ccctccgcaa      60
ccaccagccc aggttaatcc ccagaggctc catggagttc cctggcctgg ggtccctggg     120
gacctcagag cccctccccc agtttgtgga tcctgctctg gtgtcctcca caccagaatc     180
aggggttttc ttcccctctg ggcctgaggg cttggatgca gcagcttcct ccactgcccc     240
gagcacagcc accgctgcag ctgcggcact ggcctactac agggacgctg aggcctacag     300
acactcccca gtctttcagg tgtacccatt gctcaactgt atggagggga tcccaggggg     360
ctcaccatat gccggctggg cctacggcaa gacggggctc taccctgcct caactgtgtg     420
tcccacccgc gaggactctc ctccccaggc cgtggaagat ctggatggaa aaggcagcac     480
cagcttcctg gagactttga agacagagcg gctgagccca gacctcctga ccctgggacc     540
tgcactgcct tcatcactcc ctgtccccaa tagtgcttat gggggccctg acttttccag     600
taccttcttt tctcccaccg ggagccccct caattcagca gcctattcct ctcccaagct     660
tcgtggaact ctccccctgc ctccctgtga ggccagggag tgtgtgaact gcggagcaac     720
agccactcca ctgtggcgga gggacaggac aggccactac ctatgcaacg cctgcggcct     780
ctatcacaag atgaatgggc agaacaggcc cctcatccgg cccaagaagc gcctgattgt     840
cagtaaacgg gcaggtactc agtgcaccaa ctgccagacg accaccacga cactgtggcg     900
gagaaatgcc agtggggatc ccgtgtgcaa tgcctgcggc ctctactaca agctacacca     960
ggtgaaccgg ccactgacca tgcggaagga tggtattcag actcgaaacc gcaaggcatc    1020
tggaaaaggg aaaaagaaac ggggctccag tctgggaggc acaggagcag ccgaaggacc    1080
agctggtggc tttatggtgg tggctggggg cagcggtagc gggaattgtg gggaggtggc    1140
ttcaggcctg acactgggcc ccccaggtac tgcccatctc taccaaggcc tgggccctgt    1200
ggtgctgtca gggcctgtta gccacctcat gcctttccct ggacccctac tgggctcacc    1260
cacgggctcc ttccccacag gccccatgcc ccccaccacc agcactactg tggtggctcc    1320
gctcagctca tgagggcaca gagcatggcc tccagaggag gggtggtgtc cttctcctct    1380
tgtagccaga attctggaca acccaagtct ctgggcccca ggcaccccct ggcttgaacc    1440
ttcaaagctt ttgtaaaata aaaccaccaa agtcctgaaa aaaaaaaaaa aaaaaaaaaa    1500
a                                                                    1501
```

<210> SEQ ID NO 6
<211> LENGTH: 413
<212> TYPE: PRT
<213> ORGANISM: Homo sapiens

<400> SEQUENCE: 6

```
Met Glu Phe Pro Gly Leu Gly Ser Leu Gly Thr Ser Glu Pro Leu Pro
1               5                   10                  15

Gln Phe Val Asp Pro Ala Leu Val Ser Ser Thr Pro Glu Ser Gly Val
            20                  25                  30

Phe Phe Pro Ser Gly Pro Glu Gly Leu Asp Ala Ala Ala Ser Ser Thr
        35                  40                  45

Ala Pro Ser Thr Ala Thr Ala Ala Ala Ala Ala Leu Ala Tyr Tyr Arg
    50                  55                  60

Asp Ala Glu Ala Tyr Arg His Ser Pro Val Phe Gln Val Tyr Pro Leu
65                  70                  75                  80

Leu Asn Cys Met Glu Gly Ile Pro Gly Gly Ser Pro Tyr Ala Gly Trp
                85                  90                  95

Ala Tyr Gly Lys Thr Gly Leu Tyr Pro Ala Ser Thr Val Cys Pro Thr
```

```
            100                 105                 110

Arg Glu Asp Ser Pro Pro Gln Ala Val Glu Asp Leu Asp Gly Lys Gly
        115                 120                 125

Ser Thr Ser Phe Leu Glu Thr Leu Lys Thr Glu Arg Leu Ser Pro Asp
    130                 135                 140

Leu Leu Thr Leu Gly Pro Ala Leu Pro Ser Ser Leu Pro Val Pro Asn
145                 150                 155                 160

Ser Ala Tyr Gly Gly Pro Asp Phe Ser Ser Thr Phe Phe Ser Pro Thr
                165                 170                 175

Gly Ser Pro Leu Asn Ser Ala Ala Tyr Ser Ser Pro Lys Leu Arg Gly
            180                 185                 190

Thr Leu Pro Leu Pro Pro Cys Glu Ala Arg Glu Cys Val Asn Cys Gly
        195                 200                 205

Ala Thr Ala Thr Pro Leu Trp Arg Arg Asp Arg Thr Gly His Tyr Leu
    210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
            260                 265                 270

Ala Ser Gly Asp Pro Val Cys Asn Ala Cys Gly Leu Tyr Tyr Lys Leu
        275                 280                 285

His Gln Val Asn Arg Pro Leu Thr Met Arg Lys Asp Gly Ile Gln Thr
    290                 295                 300

Arg Asn Arg Lys Ala Ser Gly Lys Gly Lys Lys Lys Arg Gly Ser Ser
305                 310                 315                 320

Leu Gly Gly Thr Gly Ala Ala Glu Gly Pro Ala Gly Gly Phe Met Val
                325                 330                 335

Val Ala Gly Gly Ser Gly Ser Gly Asn Cys Gly Glu Val Ala Ser Gly
            340                 345                 350

Leu Thr Leu Gly Pro Pro Gly Thr Ala His Leu Tyr Gln Gly Leu Gly
        355                 360                 365

Pro Val Val Leu Ser Gly Pro Val Ser His Leu Met Pro Phe Pro Gly
    370                 375                 380

Pro Leu Leu Gly Ser Pro Thr Gly Ser Phe Pro Thr Gly Pro Met Pro
385                 390                 395                 400

Pro Thr Thr Ser Thr Thr Val Val Ala Pro Leu Ser Ser
                405                 410


<210> SEQ ID NO 7
<211> LENGTH: 418
<212> TYPE: PRT
<213> ORGANISM: Homo sapiens

<400> SEQUENCE: 7

Met Glu Phe Pro Gly Leu Gly Ser Leu Gly Thr Ser Glu Pro Leu Pro
1               5                   10                  15

Gln Phe Val Asp Pro Ala Leu Val Ser Ser Thr Pro Glu Ser Gly Val
            20                  25                  30

Phe Phe Pro Ser Gly Pro Glu Gly Leu Asp Ala Ala Ala Ser Ser Thr
        35                  40                  45

Ala Pro Ser Thr Ala Thr Ala Ala Ala Ala Ala Leu Ala Tyr Tyr Arg
    50                  55                  60
```

```
Asp Ala Glu Ala Tyr Arg His Ser Pro Val Phe Gln Val Tyr Pro Leu
65                  70                  75                  80

Leu Asn Cys Met Glu Gly Ile Pro Gly Gly Ser Pro Tyr Ala Gly Trp
                85                  90                  95

Ala Tyr Gly Lys Thr Gly Leu Tyr Pro Ala Ser Thr Val Cys Pro Thr
            100                 105                 110

Arg Glu Asp Ser Pro Pro Gln Ala Val Glu Asp Leu Asp Gly Lys Gly
        115                 120                 125

Ser Thr Ser Phe Leu Glu Thr Leu Lys Thr Glu Arg Leu Ser Pro Asp
    130                 135                 140

Leu Leu Thr Leu Gly Pro Ala Leu Pro Ser Ser Leu Pro Val Pro Asn
145                 150                 155                 160

Ser Ala Tyr Gly Gly Pro Asp Phe Ser Ser Thr Phe Phe Ser Pro Thr
                165                 170                 175

Gly Ser Pro Leu Asn Ser Ala Ala Tyr Ser Ser Pro Lys Leu Arg Gly
            180                 185                 190

Thr Leu Pro Leu Pro Pro Cys Glu Ala Arg Glu Cys Val Asn Cys Gly
        195                 200                 205

Ala Thr Ala Thr Pro Leu Trp Arg Arg Asp Arg Thr Gly His Tyr Leu
    210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
            260                 265                 270

Ala Ser Gly Asp Pro Val Cys Asn Ala Cys Gly Leu Tyr Tyr Lys Leu
        275                 280                 285

His Gln Pro Pro Phe Trp Gln Val Asn Arg Pro Leu Thr Met Arg Lys
    290                 295                 300

Asp Gly Ile Gln Thr Arg Asn Arg Lys Ala Ser Gly Lys Gly Lys Lys
305                 310                 315                 320

Lys Arg Gly Ser Ser Leu Gly Gly Thr Gly Ala Ala Glu Gly Pro Ala
                325                 330                 335

Gly Gly Phe Met Val Val Ala Gly Gly Ser Gly Ser Gly Asn Cys Gly
            340                 345                 350

Glu Val Ala Ser Gly Leu Thr Leu Gly Pro Pro Gly Thr Ala His Leu
        355                 360                 365

Tyr Gln Gly Leu Gly Pro Val Val Leu Ser Gly Pro Val Ser His Leu
    370                 375                 380

Met Pro Phe Pro Gly Pro Leu Leu Gly Ser Pro Thr Gly Ser Phe Pro
385                 390                 395                 400

Thr Gly Pro Met Pro Pro Thr Thr Ser Thr Thr Val Val Ala Pro Leu
                405                 410                 415

Ser Ser
```

<210> SEQ ID NO 8
<211> LENGTH: 8244
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

-continued

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg gccgctgatc ttcagacctg gaggaggaga   1560
tatgagggac aattggagaa gtgaattata taaatataaa gtagtaaaaa ttgaaccatt   1620
aggagtagca cccaccaagg caaagagaag agtggtgcag agagaaaaaa gagcagtggg   1680
aataggagct ttgttccttg ggttcttggg agcagcagga agcactatgg gcgcagcgtc   1740
aatgacgctg acggtacagg ccagacaatt attgtctggt atagtgcagc agcagaacaa   1800
tttgctgagg gctattgagg cgcaacagca tctgttgcaa ctcacagtct ggggcatcaa   1860
gcagctccag gcaagaatcc tggctgtgga aagataccta aaggatcaac agctcctggg   1920
gatttggggt tgctctggaa aactcatttg caccactgct gtgccttgga atgctagttg   1980
gagtaataaa tctctggaac agatttggaa tcacacgacc tggatggagt gggacagaga   2040
aattaacaat tacacaagct taatacactc cttaattgaa gaatcgcaaa accagcaaga   2100
aaagaatgaa caagaattat tggaattaga taaatgggca agtttgtgga attggtttaa   2160
cataacaaat tggctgtggt atataaaatt attcataatg atagtaggag gcttggtagg   2220
tttaagaata gtttttgctg tactttctat agtgaataga gttaggcagg gatattcacc   2280
attatcgttt cagacccacc tcccaacccc gaggggaccc gacaggcccg aaggaataga   2340
agaagaaggt ggagagagag acagagacag atccattcga ttagtgaacg gatcggcact   2400
```

gcgtgcgcca attctgcaga caaatggcag tattcatcca caattttaaa agaaaagggg 2460
ggattggggg gtacagtgca ggggaaagaa tagtagacat aatagcaaca gacatacaaa 2520
ctaaagaatt acaaaaacaa attacaaaaa ttcaaaattt tcgggtttat tacagggaca 2580
gcagagatcc agtttggtta gtaccgggcc cgctctagcg tgaggctccg gtgcccgtca 2640
gtgggcagag cgcacatcgc ccacagtccc cgagaagttg gggggagggg tcggcaattg 2700
aaccggtgcc tagagaaggt ggcgcggggt aaactgggaa agtgatgtcg tgtactggct 2760
ccgccttttt cccgagggtg ggggagaacc gtatataagt gcagtagtcg ccgtgaacgt 2820
tctttttcgc aacgggtttg ccgccagaac acaggtaagt gccgtgtgtg gttcccgcgg 2880
gcctggcctc tttacgggtt atggcccttg cgtgccttga attacttcca cctggctgca 2940
gtacgtgatt cttgatcccg agcttcgggt tggaagtggg tgggagagtt cgaggccttg 3000
cgcttaagga gccccttcgc ctcgtgcttg agttgaggcc tggcctgggc gctggggccg 3060
ccgcgtgcga atctggtggc accttcgcgc ctgtctcgct gctttcgata agtctctagc 3120
catttaaaat ttttgatgac ctgctgcgac gctttttttc tggcaagata gtcttgtaaa 3180
tgcgggccaa gatctgcaca ctggtatttc ggtttttggg gccgcgggcg gcgacggggc 3240
ccgtgcgtcc cagcgcacat gttcggcgag gcggggcctg cgagcgcggc caccgagaat 3300
cggacggggg tagtctcaag ctggccggcc tgctctggtg cctggcctcg cgccgccgtg 3360
tatcgccccg ccctgggcgg caaggctggc ccggtcggca ccagttgcgt gagcggaaag 3420
atggccgctt cccggccctg ctgcagggag ctcaaaatgg aggacgcggc gctcgggaga 3480
gcgggcgggt gagtcaccca cacaaaggaa aagggccttt ccgtcctcag ccgtcgcttc 3540
atgtgactcc acggagtacc gggcgccgtc caggcacctc gattagttct cgagcttttg 3600
gagtacgtcg tctttaggtt ggggggaggg gttttatgcg atggagtttc cccacactga 3660
gtgggtggag actgaagtta ggccagcttg gcacttgatg taattctcct tggaatttgc 3720
cctttttgag tttggatctt ggttcattct caagcctcag acagtggttc aaagtttttt 3780
tcttccattt caggtgtcgt gagcggccgc tgagttaact attctagacc cgggctagga 3840
tccgcccctc tccctccccc ccccctaacg ttactggccg aagccgcttg gaataaggcc 3900
ggtgtgcgtt tgtctatatg ttattttcca ccatattgcc gtcttttggc aatgtgaggg 3960
cccggaaacc tggccctgtc ttcttgacga gcattcctag gggtctttcc cctctcgcca 4020
aaggaatgca aggtctgttg aatgtcgtga aggaagcagt tcctctggaa gcttcttgaa 4080
gacaaacaac gtctgtagcg accctttgca ggcagcggaa ccccccacct ggcgacaggt 4140
gcctctgcgg ccaaaagcca cgtgtataag atacacctgc aaaggcggca caaccccagt 4200
gccacgttgt gagttggata gttgtggaaa gagtcaaatg gctctcctca agcgtattca 4260
acaaggggct gaaggatgcc cagaaggtac cccattgtat gggatctgat ctggggcctc 4320
ggtacacatg ctttacatgt gtttagtcga ggttaaaaaa acgtctaggc cccccgaacc 4380
acggggacgt ggttttcctt tgaaaaacac gatgataata tggccacaac catggtgagc 4440
aagggcgagg agctgttcac cggggtggtg cccatcctgg tcgagctgga cggcgacgta 4500
aacggccaca agttcagcgt gtccggcgag ggcgagggcg atgccaccta cggcaagctg 4560
accctgaagt tcatctgcac caccggcaag ctgcccgtgc cctggcccac cctcgtgacc 4620
accctgacct acggcgtgca gtgcttcagc cgctaccccg accacatgaa gcagcacgac 4680
ttcttcaagt ccgccatgcc cgaaggctac gtccaggagc gcaccatctt cttcaaggac 4740
gacggcaact acaagacccg cgccgaggtg aagttcgagg gcgacaccct ggtgaaccgc 4800
atcgagctga agggcatcga cttcaaggag gacggcaaca tcctggggca caagctggag 4860
tacaactaca acagccacaa cgtctatatc atggccgaca agcagaagaa cggcatcaag 4920
gtgaacttca agatccgcca caacatcgag gacggcagcg tgcagctcgc cgaccactac 4980
cagcagaaca cccccatcgg cgacggcccc gtgctgctgc ccgacaacca ctacctgagc 5040
acccagtccg ccctgagcaa agaccccaac gagaagcgcg atcacatggt cctgctggag 5100
ttcgtgaccg ccgccgggat cactctcggc atggacgagc tgtacaagta aagcggccgc 5160
atcgataatc aacctctgga ttacaaaatt tgtgaaagat tgactggtat tcttaactat 5220
gttgctcctt ttacgctatg tggatacgct gctttaatgc ctttgtatca tgctattgct 5280
tcccgtatgg ctttcatttt ctcctccttg tataaatcct ggttgctgtc tctttatgag 5340
gagttgtggc ccgttgtcag gcaacgtggc gtggtgtgca ctgtgtttgc tgacgcaacc 5400
cccactggtt ggggcattgc caccacctgt cagctccttt ccgggacttt cgctttcccc 5460
ctccctattg ccacggcgga actcatcgcc gcctgccttg cccgctgctg gacaggggct 5520
cggctgttgg gcactgacaa ttccgtggtg ttgtcgggga agctgacgtc ctttccatgg 5580
ctgctcgcct gtgttgccac ctggattctg cgcgggacgt ccttctgcta cgtcccttcg 5640
gccctcaatc cagcggacct tccttcccgc ggcctgctgc cggctctgcg gcctcttccg 5700
cgtcttcgcc ttcgccctca gacgagtcgg atctcccttt gggccgcctc cccgcgaatt 5760
cgcattatta ctcacggtac gagcattatt actcacggta cgagcattat tactcacggt 5820
acgagcatta ttactcacgg tacgagcgat cgccctcagg tacctttaag accaatgact 5880
tacaaggcag ctgtagatct tagccacttt ttaaaagaaa aggggggact ggaagggcta 5940
attcactccc aacgaagaca agatatcctt gatctgtgga tctaccacac acaaggctac 6000
ttccctgatt ggcagaacta cacaccaggg ccagggatca gatatccact gacctttgga 6060
tggtgctaca agctagtacc agttgagcaa gagaaggtag aagaagccaa tgaaggagag 6120
aacacccgct tgttacaccc tgtgagcctg catgggatgg atgacccgga gagagaagta 6180
ttagagtgga ggtttgacag ccgcctagca tttcatcaca tggcccgaga gctgcatccg 6240
gactgtactg ggtctctctg gttagaccag atctgagcct gggagctctc tggctaacta 6300
gggaacccac tgcttaagcc tcaataaagc ttgccttgag tgcttcaagt agtgtgtgcc 6360
cgtctgttgt gtgactctgg taactagaga tccctcagac ccttttagtc agtgtggaaa 6420
atctctagca gcatgtgagc aaaaggccag caaaaggcca ggaaccgtaa aaaggccgcg 6480
ttgctggcgt ttttccatag gctccgcccc cctgacgagc atcacaaaaa tcgacgctca 6540
agtcagaggt ggcgaaaccc gacaggacta taaagatacc aggcgtttcc ccctggaagc 6600
tccctcgtgc gctctcctgt tccgaccctg ccgcttaccg gatacctgtc cgcctttctc 6660
ccttcgggaa gcgtggcgct ttctcatagc tcacgctgta ggtatctcag ttcggtgtag 6720
gtcgttcgct ccaagctggg ctgtgtgcac gaaccccccg ttcagcccga ccgctgcgcc 6780
ttatccggta actatcgtct tgagtccaac ccggtaagac acgacttatc gccactggca 6840
gcagccactg gtaacaggat tagcagagcg aggtatgtag gcggtgctac agagttcttg 6900
aagtggtggc ctaactacgg ctacactaga agaacagtat ttggtatctg cgctctgctg 6960
aagccagtta ccttcggaaa aagagttggt agctcttgat ccggcaaaca aaccaccgct 7020
ggtagcggtg gtttttttgt ttgcaagcag cagattacgc gcagaaaaaa aggatctcaa 7080
gaagatcctt tgatcttttc tacggggtct gacgctcagt ggaacgaaaa ctcacgttaa 7140
gggattttgg tcatgagatt atcaaaaagg atcttcacct agatcctttt aaattaaaaa 7200
tgaagtttta aatcaatcta aagtatatat gagtaaactt ggtctgacag ttaccaatgc 7260
ttaatcagtg aggcacctat ctcagcgatc tgtctatttc gttcatccat agttgcctga 7320
ctccccgtcg tgtagataac tacgatacgg gagggcttac catctggccc cagtgctgca 7380
atgataccgc gagacccacg ctcaccggct ccagatttat cagcaataaa ccagccagcc 7440
ggaagggccg agcgcagaag tggtcctgca actttatccg cctccatcca gtctattaat 7500
tgttgccggg aagctagagt aagtagttcg ccagttaata gtttgcgcaa cgttgttgcc 7560
attgctacag gcatcgtggt gtcacgctcg tcgtttggta tggcttcatt cagctccggt 7620
tcccaacgat caaggcgagt tacatgatcc cccatgttgt gcaaaaaagc ggttagctcc 7680
ttcggtcctc cgatcgttgt cagaagtaag ttggccgcag tgttatcact catggttatg 7740
gcagcactgc ataattctct tactgtcatg ccatccgtaa gatgcttttc tgtgactggt 7800
gagtactcaa ccaagtcatt ctgagaatag tgtatgcggc gaccgagttg ctcttgcccg 7860
gcgtcaatac gggataatac cgcgccacat agcagaactt taaaagtgct catcattgga 7920
aaacgttctt cggggcgaaa actctcaagg atcttaccgc tgttgagatc cagttcgatg 7980
taacccactc gtgcacccaa ctgatcttca gcatctttta ctttcaccag cgtttctggg 8040
tgagcaaaaa caggaaggca aaatgccgca aaaaagggaa taagggcgac acggaaatgt 8100
tgaatactca tactcttcct ttttcaatat tattgaagca tttatcaggg ttattgtctc 8160
atgagcggat acatatttga atgtatttag aaaaataaac aaataggggt tccgcgcaca 8220
tttccccgaa aagtgccacc tgac 8244

<210> SEQ ID NO 9
<211> LENGTH: 6780
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900

```
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg gccgctgatc ttcagacctg gaggaggaga   1560
tatgagggac aattggagaa gtgaattata taaatataaa gtagtaaaaa ttgaaccatt   1620
aggagtagca cccaccaagg caaagagaag agtggtgcag agagaaaaaa gagcagtggg   1680
aataggagct ttgttccttg ggttcttggg agcagcagga agcactatgg gcgcagcgtc   1740
aatgacgctg acggtacagg ccagacaatt attgtctggt atagtgcagc agcagaacaa   1800
tttgctgagg gctattgagg cgcaacagca tctgttgcaa ctcacagtct ggggcatcaa   1860
gcagctccag gcaagaatcc tggctgtgga aagataccta aaggatcaac agctcctggg   1920
gatttggggt tgctctggaa aactcatttg caccactgct gtgccttgga atgctagttg   1980
gagtaataaa tctctggaac agatttggaa tcacacgacc tggatggagt gggacagaga   2040
aattaacaat tacacaagct taatacactc cttaattgaa gaatcgcaaa accagcaaga   2100
aaagaatgaa caagaattat tggaattaga taaatgggca agtttgtgga attggtttaa   2160
cataacaaat tggctgtggt atataaaatt attcataatg atagtaggag gcttggtagg   2220
tttaagaata gtttttgctg tactttctat agtgaataga gttaggcagg gatattcacc   2280
attatcgttt cagacccacc tcccaacccc gaggggaccc gacaggcccg aaggaataga   2340
agaagaaggt ggagagagag acagagacag atccattcga ttagtgaacg gatcggcact   2400
gcgtgcgcca attctgcaga caaatggcag tattcatcca caattttaaa agaaaagggg   2460
ggattggggg gtacagtgca ggggaaagaa tagtagacat aatagcaaca gacatacaaa   2520
ctaaagaatt acaaaaacaa attacaaaaa ttcaaaattt tcgggtttat tacagggaca   2580
gcagagatcc agtttggtta gtaccgggcc cgctctagcg tgaggctccg gtgcccgtca   2640
gtgggcagag cgcacatcgc ccacagtccc cgagaagttg gggggagggg tcggcaattg   2700
aaccggtgct agcatggcgg gcaagaagtt gaggccactg tccctgggtg ttcctacccc   2760
cacaccctca ccccaagaca gcctgttact gcggcgccaa cagccacggt cgcctacatc   2820
tgataagact tatctgctgc cccagggcag gccggagctg gcgtaagccc cagtggggcg   2880
ctaagtgagt gtgcccctgc ctcccgccag cactggcctg gcctgcaggc ttagcctggg   2940
tcatcaaggt atcccacagg ctctagttca aatccagcag aacctctctg agcctcactc   3000
ttctcacctg caaaatgggt acagccacat cccttctctc cctgcagcca ggaagacgca   3060
catacacagg agtctagccc acaccggccc cgcacaaatt aagggcttta ctctctgaaa   3120
agcccagtga agtcatgaaa ccatatctgc tattttcatt tatcttggtt tcagcctatt   3180
ttgcttgtct ggacactaca gtccacggga gcctaggtcg agcgaggtcc aagaatcccc   3240
```

-continued

```
agggtgggca gggagggtgg aagagggcct ccagtgccca agaggtgccc cacaagcatg   3300
ggacccgccc cctcccctgg actgccccac ccactggggc accagccact ccctggggag   3360
gagggaggag ggagaaggga gggagggagg gagggaggaa gggagcctca aaggccaagg   3420
ccagccagga cacccccctgg gatcacactg agcttgccac atccccaagg cggccgaacc   3480
ctccgcaacc accagcccag agatctagag ttaatcccca gaggctccat ggtgagcaag   3540
ggcgaggagc tgttcaccgg ggtggtgccc atcctggtcg agctggacgg cgacgtaaac   3600
ggccacaagt tcagcgtgtc cggcgagggc gagggcgatg ccacctacgg caagctgacc   3660
ctgaagttca tctgcaccac cggcaagctg cccgtgccct ggcccaccct cgtgaccacc   3720
ctgacctacg gcgtgcagtg cttcagccgc taccccgacc acatgaagca gcacgacttc   3780
ttcaagtccg ccatgcccga aggctacgtc caggagcgca ccatcttctt caaggacgac   3840
ggcaactaca agacccgcgc cgaggtgaag ttcgagggcg acaccctggt gaaccgcatc   3900
gagctgaagg gcatcgactt caaggaggac ggcaacatcc tggggcacaa gctggagtac   3960
aactacaaca gccacaacgt ctatatcatg gccgacaagc agaagaacgg catcaaggtg   4020
aacttcaaga tccgccacaa catcgaggac ggcagcgtgc agctcgccga ccactaccag   4080
cagaacaccc ccatcggcga cggccccgtg ctgctgcccg acaaccacta cctgagcacc   4140
cagtccgccc tgagcaaaga ccccaacgag aagcgcgatc acatggtcct gctggagttc   4200
gtgaccgccg ccgggatcac tctcggcatg gacgagctgt acaagtaaag cggccgcatc   4260
gataccgtcg acctcgatcg agacctagaa aaacatggag caatcacaag tagcaataca   4320
gcagctacca atgctgattg tgcctggcta gaagcacaag aggaggagga ggtgggtttt   4380
ccagtcacac ctcaggtacc tttaagacca atgacttaca aggcagctgt agatcttagc   4440
cactttttaa aagaaaaggg gggactggaa gggctaattc actcccaacg aagacaagat   4500
atccttgatc tgtggatcta ccacacacaa ggctacttcc ctgattggca gaactacaca   4560
ccagggccag ggatcagata tccactgacc tttggatggt gctacaagct agtaccagtt   4620
gagcaagaga aggtagaaga agccaatgaa ggagagaaca cccgcttgtt acaccctgtg   4680
agcctgcatg ggatggatga cccggagaga gaagtattag agtggaggtt tgacagccgc   4740
ctagcatttc atcacatggc ccgagagctg catccggact gtactgggtc tctctggtta   4800
gaccagatct gagcctggga gctctctggc taactaggga acccactgct taagcctcaa   4860
taaagcttgc cttgagtgct tcaagtagtg tgtgcccgtc tgttgtgtga ctctggtaac   4920
tagagatccc tcagaccctt ttagtcagtg tggaaaatct ctagcagcat gtgagcaaaa   4980
ggccagcaaa aggccaggaa ccgtaaaaag gccgcgttgc tggcgttttt ccataggctc   5040
cgcccccctg acgagcatca caaaaatcga cgctcaagtc agaggtggcg aaacccgaca   5100
ggactataaa gataccaggc gtttccccct ggaagctccc tcgtgcgctc tcctgttccg   5160
accctgccgc ttaccggata cctgtccgcc tttctccctt cgggaagcgt ggcgctttct   5220
catagctcac gctgtaggta tctcagttcg gtgtaggtcg ttcgctccaa gctgggctgt   5280
gtgcacgaac cccccgttca gcccgaccgc tgcgccttat ccggtaacta tcgtcttgag   5340
tccaacccgg taagacacga cttatcgcca ctggcagcag ccactggtaa caggattagc   5400
agagcgaggt atgtaggcgg tgctacagag ttcttgaagt ggtggcctaa ctacggctac   5460
actagaagaa cagtatttgg tatctgcgct ctgctgaagc cagttacctt cggaaaaaga   5520
gttggtagct cttgatccgg caaacaaacc accgctggta gcggtggttt ttttgtttgc   5580
aagcagcaga ttacgcgcag aaaaaaagga tctcaagaag atcctttgat cttttctacg   5640
```

```
gggtctgacg ctcagtggaa cgaaaactca cgttaaggga ttttggtcat gagattatca   5700
aaaaggatct tcacctagat ccttttaaat taaaaatgaa gttttaaatc aatctaaagt   5760
atatatgagt aaacttggtc tgacagttac caatgcttaa tcagtgaggc acctatctca   5820
gcgatctgtc tatttcgttc atccatagtt gcctgactcc ccgtcgtgta gataactacg   5880
atacgggagg gcttaccatc tggccccagt gctgcaatga taccgcgaga cccacgctca   5940
ccggctccag atttatcagc aataaaccag ccagccggaa gggccgagcg cagaagtggt   6000
cctgcaactt tatccgcctc catccagtct attaattgtt gccgggaagc tagagtaagt   6060
agttcgccag ttaatagttt gcgcaacgtt gttgccattg ctacaggcat cgtggtgtca   6120
cgctcgtcgt ttggtatggc ttcattcagc tccggttccc aacgatcaag gcgagttaca   6180
tgatccccca tgttgtgcaa aaaagcggtt agctccttcg gtcctccgat cgttgtcaga   6240
agtaagttgg ccgcagtgtt atcactcatg gttatggcag cactgcataa ttctcttact   6300
gtcatgccat ccgtaagatg cttttctgtg actggtgagt actcaaccaa gtcattctga   6360
gaatagtgta tgcggcgacc gagttgctct tgcccggcgt caatacggga taataccgcg   6420
ccacatagca gaactttaaa agtgctcatc attggaaaac gttcttcggg gcgaaaactc   6480
tcaaggatct taccgctgtt gagatccagt tcgatgtaac ccactcgtgc acccaactga   6540
tcttcagcat cttttacttt caccagcgtt tctgggtgag caaaaacagg aaggcaaaat   6600
gccgcaaaaa agggaataag ggcgacacgg aaatgttgaa tactcatact cttccttttt   6660
caatattatt gaagcattta tcagggttat tgtctcatga gcggatacat atttgaatgt   6720
atttagaaaa ataaacaaat aggggttccg cgcacatttc cccgaaaagt gccacctgac   6780
```

<210> SEQ ID NO 10
<211> LENGTH: 401
<212> TYPE: DNA
<213> ORGANISM: Homo sapiens

<400> SEQUENCE: 10

```
actttcatga aattactgac ataattttgg gtccaaaatt tcaaaatttt aaatattttt     60
atttggaatt ttaaaataat ttatatgctc tttttactgg ctaataatgc tattcattat    120
aatctgatat tcaaactgtc taaaaaagtt aacaatcatt gatttatttg ttgtatatac    180
agtttatttc tatgacagtt ttaatgtcac ctaatattat ttttaatgtt tcaatttctc    240
atttaaatac attttgtgtt gtttatttta atctcattca atctgtatgt gcaaatggct    300
tagaaaaaaa ggccatatat gacaagccca cagctaacat catatagtca acagtgaaaa    360
actaaaagct tctcctttaa gatcaggaac aaggcaagga t                        401
```

<210> SEQ ID NO 11
<211> LENGTH: 501
<212> TYPE: DNA
<213> ORGANISM: Homo sapiens

<400> SEQUENCE: 11

```
ttttattatt tatttatttt tttgagacag attctcactc tgtcgcctag gctggaatgc     60
aatggcgtga tcccggctca ctgcaacctc tgcctcccag gttcaagcga ttctcctgcc    120
tcagcctccc gagtagctgg gattacaggc atgcgccacc acgcctggct aatttttttgt   180
atttttagta gagacagggt ttctccatgt tggtcaggct ggtctcgaac taccgacctt    240
aggtaatcct cccacctcgg cctccgaaag tgctgggatt acaggcgtga gccactgcgc    300
```

```
ccggcctaca tttattttta aataaatgga tttaaatgtt aagacctgaa cctataaaaa    360

tgggacacct gcatagggca ttaaccatga gtagagcttg caggactgga agttgctatg    420

ggtgagtcag tgtgtgagtg gtgagtgaat gggaaggcct aggacattcc tgtacactac    480

catggacttt ataaattctg t                                              501


<210> SEQ ID NO 12
<211> LENGTH: 851
<212> TYPE: DNA
<213> ORGANISM: Homo sapiens

<400> SEQUENCE: 12

tcatagaaac aaaacactag gatggtggtt gccaggggct gagaggatgg ggaaatgggg     60

agttgctgtt caatggatat tgcgcccggc cagccacacc aattcttaca ccaagaagtg    120

atggagcaca agtgctgatg ggccttaaca ccatcataaa catcttttgt ttgtcccggg    180

gaagaaattc ccaactcctt ccaaaggtct gccaaagtct accagtatcc caagctgatt    240

tccttatccc ctcagcagat gctggaaagc tggaagtctc cttccttctc actctcctgc    300

ttgacatctg cacagccatt cttcttcctc cccttgctcc ccttcctccc cttctccttc    360

tcctacttat tgagacagag tctcgctctg tcgccgaggc tggagtgcag tggtgtcatc    420

tcggctcact gcaacctctg cctcctgggt tcaagcaatt ctcttgcctc cacctcctga    480

gtaggtggga ttacaggtgt gtgccaccac agcaggctaa tttttgtatt tttagtagag    540

acggggtttc accatattgg ccaggatggt ctcgaactcc tgacctcagg tgatctgcct    600

gtcttggcct cccaaagtgc cgggattaca ggcatgagcc accggcgccc ggcccttttt    660

attattatat attattttg agactgggtc tcactctgta atccaggctg gagggcagtg    720

gcgtgatcac agctcactgc agccctgacc tcttgggcac aagcagtcct cccgcgtcag    780

ccacccaaag tgctgggtct acaggcatga gctactgtgc ccagtctacg atttttttaa    840

aatttataat t                                                         851


<210> SEQ ID NO 13
<211> LENGTH: 1010
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

accggtggcg cgccgatcca aggaagagag gacattagca tgggtctcaa atggaagcct     60

gacagagaag acgcttcaac ccggacaccc cacccccgcc tgcaatgggc tcccccaagc    120

ctagcctggc ccccgctgat tcccttatct atgccttccc agctgcctcc ctgctggctg    180

aactgtggcc acagacttct gggccttgca ccccctccac tgccccccag ccccaagaca    240

gcctgttact gcggcaccaa cagccacagt cgagtccatc tgataagact tatctgctgc    300

cccagagcag gccagagctg gcgtaagccc caggcacgag ccgaagcact aaagaagtgt    360

atgtaccctt acccactagt agtaaaacat gaaacttaga tcttgactaa ttgctcatat    420

gacttgactg gacactggac tccacagaag ccaaaggcaa aggggatcca acaacctgca    480

ggatagacag gaagggcgga gggactagag cctaaaaggt cctccacaag gaggcggcac    540

accccctccc ctgcactgcc ccacccactg gggcaccagc cactccctgg ggaggaaaga    600

ggagggagaa ggtgagtggg agggagggag ggcgggcggg ctggcaggag ggagagaagg    660
```

```
gagactcaga ggccgagctc caaggataaa ttacttgttg aataaggatc taatgtgtag    720

aacccatact gacatggtag caggcacatc agcacagttt tagggaaatg ggagatggag    780

aagactcact ggaggctcac aggcctgtcc tggtacacac ggtggaaaaa tatgagaccc    840

tctttaaaaa ggaagtggat ggtaaggacc aacacccatg tttgtccact gacctccaga    900

tagatagata gatagataga tagatagata gatagataga tagatagata gatagacaga    960

ctgactgact gactgactga ctgactgact gactgactga ttgactgcag              1010
```

<210> SEQ ID NO 14
<211> LENGTH: 170
<212> TYPE: DNA
<213> ORGANISM: Homo sapiens

<400> SEQUENCE: 14

```
cacagaacca caagttgggt agcctggcag tgtcagaagt ctgaacccag catagtggtc     60

agcaggcagg acgaatcaca ctgaatgcaa accacagggt ttcgcagcgt ggtaaaagaa    120

atcattgagt cccccgcctt cagaagaggg tgcattttca ggaggaagcg              170
```

<210> SEQ ID NO 15
<211> LENGTH: 511
<212> TYPE: DNA
<213> ORGANISM: Homo sapiens

<400> SEQUENCE: 15

```
acaagggcct ctgggtgtcc tggcagagag gggagatggc acaggcacca ggtgctaggg     60

tgccagggcc tcccgagaag gaacaggtgc aaagcaggca attagcccag aaggtatccg    120

tggggcaggc agcctagatc tgatggggga agccaccagg attacatcat ctgctgtaac    180

aactgctctg aaaagaagat atttttcaac ctgaacttgc agtagctagt ggagaggcag    240

gaaaaaggaa atgaaaccag agacagaggg aagctgagcg aaaatagacc ttcccgagag    300

aggaggaagc ccggagagag acgcacggtc cctccccgc ccctaggccg ccgccccctc    360

tctgccctcg gcggcgagca gcgcgccgcg acccgggccg aaggtgcgag gggctccggg    420

cggccgggcg ggcgcacacc atccccgcgg gcggcgcgga gccggcgaca gcgcgcgaga    480

gggaccgggc ggtggcggcg gcgggaccgg g                                  511
```

<210> SEQ ID NO 16
<211> LENGTH: 453
<212> TYPE: DNA
<213> ORGANISM: Homo sapiens

<400> SEQUENCE: 16

```
cgtcagtttc tgcactgaaa ctctcaagat caatgagcaa agagctttct cagttctgcc     60

tttcagtttc tctcttccag gaaggaaaac attcgagaga gcgagggaga gccgcgggag    120

ggcggggggc gggggcgccg gctgcgggtg ggaggagaga ccgggaggcc ggccgggctg    180

cgtcccgggt ccccgcgccg cgccgcgacc tgcagacccc gccgccgcgc tcgggcccgt    240

ctcccacgcc cccgccgccc cgcgcgccca actccgccgg ccgccccgcc ccgccccgcg    300

cgctccagac ccccggggcg gctgccggga gagatgctgg aagaaacttc ttaaatgacc    360

gcgtctggct ggccgtggag cctttctggg ttggggagag gaaaggaaag tggaaaaaac    420

ctgagaactt cctgatctct ctcgctgtga gac                                453
```

<210> SEQ ID NO 17
<211> LENGTH: 5283

<212> TYPE: DNA
<213> ORGANISM: Homo sapiens

<400> SEQUENCE: 17

```
cttttcgca acgggtttgc cgccagaaca caggtaagtg ccgtgtgtgg ttcccgcggg     60
cctggcctct ttacgggtta tggcccttgc gtgccttgaa ttacttccac gcccctggct    120
gcagtacgtg attcttgatc ccgagcttcg ggttggaagt gggtgggaga gttcgaggcc    180
ttgcgcttaa ggagcccctt cgcctcgtgc ttgagttgag gcctggcttg ggcgctgggg    240
ccgccgcgtg cgaatctggt ggcaccttcg cgcctgtctc gctgctttcg ataagtctct    300
agccatttaa aatttttgat gacctgctgc gacgcttttt ttctggcaag atagtcttgt    360
aaatgcgggc caagatctgc acactggtat ttcggttttt ggggccgcgg gcggcgacgg    420
ggcccgtgcg tcccagcgca catgttcggc gaggcggggc ctgcgagcgc ggccaccgag    480
aatcggacgg gggtagtctc aagctggccg gcctgctctg gtgcctggcc tcgcgccgcc    540
gtgtatcgcc ccgccctggg cggcaaggct ggcccggtcg gcaccagttg cgtgagcgga    600
aagatggccg cttcccggcc ctgctgcagg gagctcaaaa tggaggacgc ggcgctcggg    660
agagcgggcg ggtgagtcac ccacacaaag gaaaagggcc tttccgtcct cagccgtcgc    720
ttcatgtgac tccacggagt accgggcgcc gtccaggcac ctcgattagt tctcgagctt    780
ttggagtacg tcgtctttag gttgggggga ggggttttat gcgatggagt ttccccacac    840
tgagtgggtg gagactgaag ttaggccagc ttggcacttg atgtaattct ccttggaatt    900
tgcccttttt gagtttggat cttggttcat tctcaagcct cagacagtgg ttcaaagttt    960
ttttcttcca tttcaggtgt cgtgaaaact accccctaaaa gccaaaatgg gaaaggaaaa   1020
gactcatatc aacattgtcg tcattggaca cgtagattcg ggcaagtcca ccactactgg   1080
ccatctgatc tataaatgcg gtggcatcga caaaagaacc attgaaaaat ttgagaagga   1140
ggctgctgag gtatgtttaa taccagaaag ggaaagatca actaaaatga gttttaccag   1200
cagaatcatt aggtgatttc cccagaacta gtgagtggtt tagatctgaa tgctaatagt   1260
taagacctta cttatgaaat aattttgctt ttggtgactt ctgtaatcgt attgctagtg   1320
agtagatttg gatgttaata gttaagatcc gacttataaa agtttgattt ttggttgctt   1380
ctgtaaccca aagtgactaa aatcactttg gacttggagt tgtaaagtgg aaactgccaa   1440
ttaagggctg gggacaagga aattgaagct ggagtttgtg ttttagtaac caagtaacga   1500
ctcttaatcc ttacagatgg gaaagggctc cttcaagtat gcctgggtct tggataaact   1560
gaaagctgag cgtgaacgtg gtatcaccat tgatatctcc ttgtggaaat ttgagaccag   1620
caagtactat gtgactatca ttgatgcccc aggacacaga gactttatca aaaacatgat   1680
tacagggaca tctcaggttg gtgggattaa taattctagg tttctttatc ccaaaaggct   1740
tgctttgtac actggttttg tcatttggag agttgacagg gatatgtctt tgctttcttt   1800
aaaggctgac tgtgctgtcc tgattgttgc tgctggtgtt ggtgaatttg aagctggtat   1860
ctccaagaat gggcagaccc gagagcatgc ccttctggct tacacactgg gtgtgaaaca   1920
actaattgtc ggtgttaaca aaatggattc cactgagcca ccctacagcc agaagagata   1980
tgaggaaatt gttaaggaag tcagcactta cattaagaaa attggctaca accccgacac   2040
agtagcattt gtgccaattt ctggttggaa tggtgacaac atgctggagc caagtgctaa   2100
cgtaagtggc tttcaagacc attgttaaaa agctctggga atggcgattt catgcttaca   2160
caaattggca tgcttgtgtt tcagatgcct tggttcaagg gatggaaagt cacccgtaag   2220
```

-continued gatggcaatg ccagtggaac cacgctgctt gaggctctgg actgcatcct accaccaact 2280
cgtccaactg acaagccctt gcgcctgcct ctccaggatg tctacaaaat tggtggtaag 2340
ttggctgtaa acaaagttga atttgagttg atagagtact gtctgccttc ataggtattt 2400
agtatgctgt aaatattttt aggtattggt actgttcctg ttggccgagt ggagactggt 2460
gttctcaaac ccggtatggt ggtcaccttt gctccagtca acgttacaac ggaagtaaaa 2520
tctgtcgaaa tgcaccatga agctttgagt gaagctcttc ctggggacaa tgtgggcttc 2580
aatgtcaaga atgtgtctgt caaggatgtt cgtcgtggca acgttgctgg tgacagcaaa 2640
aatgacccac caatggaagc agctggcttc actgctcagg taacaattta aagtaacatt 2700
aacttattgc agaggctaaa gtcatttgag actttggatt tgcactgaat gcaaatcttt 2760
tttccaaggt gattatcctg aaccatccag gccaaataag cgccggctat gcccctgtat 2820
tggattgcca cacggctcac attgcatgca agtttgctga gctgaaggaa aagattgatc 2880
gccgttctgg taaaaagctg gaagatggcc ctaaattctt gaagtctggt gatgctgcca 2940
ttgttgatat ggttcctggc aagcccatgt gtgttgagag cttctcagac tatccacctt 3000
tgggtaagga tgactactta aatgtaaaaa agttgtgtta aagatgaaaa atacaactga 3060
acagtacttt gggtaataat taactttttt tttaataggt cgctttgctg ttcgtgatat 3120
gagacagaca gttgcggtgg gtgtcatcaa agcagtggac aagaaggctg ctggagctgg 3180
caaggtcacc aagtctgccc agaaagctca gaaggctaaa tgaatattat ccctaatacc 3240
tgccacccca ctcttaatca gtggtggaag aacggtctca gaactgtttg tttcaattgg 3300
ccatttaagt ttagtagtaa aagactggtt aatgataaca atgcatcgta aaaccttcag 3360
aaggaaagga gaatgttttg tggaccactt tggttttctt ttttgcgtgt ggcagtttta 3420
agttattagt ttttaaaatc agtacttttt aatggaaaca acttgaccaa aaatttgtca 3480
cagaattttg agacccatta aaaaagttaa atgagaaacc tgtgtgttcc tttggtcaac 3540
accgagacat ttaggtgaaa gacatctaat tctggtttta cgaatctgga aacttcttga 3600
aaatgtaatt cttgagttaa cacttctggg tggagaatag ggttgtttc ccccacata 3660
attggaaggg gaaggaatat catttaaagc tatgggaggg ttgctttgat tacaacactg 3720
gagagaaatg cagcatgttg ctgattgcct gtcactaaaa caggccaaaa actgagtcct 3780
tgtgttgcat agaaagcttc atgttgctaa accaatgtta agtgaatctt tggaaacaaa 3840
atgtttccaa attactggga tgtgcatgtt gaaacgtggg ttaaaatgac tgggcagtga 3900
aagttgacta tttgccatga cataagaaat aagtgtagtg gctagtgtac accctatgag 3960
tggaagggtc cattttgaag tcagtggagt aagctttatg ccagtttgat ggtttcacaa 4020
gttctattga gtgctattca gaataggaac aaggttctaa tagaaaaaga tggcaatttg 4080
aagtagctat aaaattagac taatctacat tgcttttctc ctgcagagtc taatacctt 4140
tatgctttga taattagcag tttgtctact tggtcactag gaatgaaact acatggtaat 4200
aggcttaaca ggtgtaatag cccacttact cctgaatctt taagcatttg tgcatttgaa 4260
aaatgctttt cgcgatcttc ctgctgggat tacaggcatg agccactgtg cctgacctcc 4320
catatgtaaa agtgtctaaa ggtttttttt tggttataaa aggaaaattt ttgcttaagt 4380
ttgaaggata ggtaaaatta aaggacatgc tttctgtttg tgtgatggtt tttaaaaatt 4440
tttttaaga tggagttctt gttgcccagg ctagaatgca atggcaaaat ctcactgcaa 4500
tctcctcctc ctgggttcaa gcaattctcc tacttcagcc tcccaagtag ctgggattac 4560
aggcatgtgc taatttggtg tttttaatag agatgaggtt tttccatgtt ggtcaggctg 4620
gtctcaaact cctgacctta ggtgatcgcc tcggcctcct aaagtgctgg aattacaggc 4680
atgagccacc atgcctggcc aggacatgtg ttcttaagga catgctaagc aggagttaaa 4740
gcagcccaag agataaggcc tcttaaagtg actggcaatg tgtattgctc aagattcaaa 4800
ggtacttgaa ttggccatag acaagtctgt aatgaagtgt tatcgttttc cctcatctga 4860
gtctgaatta gataaaatgc cttcccatca gccagtgctc tgaggtatca agtctaaatt 4920
gaactagaga tttttgtcct tagtttcttt gctatctaat gtttacacaa gtaaatagtc 4980
taagatttgc tggatgacag aaaaaacagg taaggccttt aatagatggc caatagatgc 5040
cctgataatg aaagttgaca cctgtaagat ttaccagtag agaattcttg acatgcaagg 5100
aagcaagatt taactgaaaa attgttccca ctggaagcag gaatgagtca gtttacttgc 5160
atatactgag attgagatta acttcctgtg aaacccagtg tcttagacaa ctgtggcttg 5220
agcaccacct gctggtattc attacaaact tgctcactac aataaatgaa ttttaagctt 5280
taa 5283

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 18
uacccuguag auccgaauuu gug 23

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 19
aacccguaga uccgaucuug ug 22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
acaggugagg uucuugggag cc 22

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 21
cauuauuacu uuugguacgc g 21

<210> SEQ ID NO 22

<211> LENGTH: 65
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
cuguuaaugc uaaucgugau agggguuuuu gccuccaacu gacuccuaca uauuagcauu 60
aacag 65

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
aacauucaac gcugucggug agu 23

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 24
aacuggccua caaaguccca gu 22

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 25
caacaacauu aaaccacccg a 21

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 26
ugucaguuug ucaaauaccc ca 22

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 27
ugugacagau ugauaacuga aa 22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 28
ugagguagga gguuguauag uu 22

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 29
gcucuuuuca cauugugcua cu 22

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 30
cauaaaguag aaagcacuac u 21

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
cacaaattcg gatctacagg gta 23

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
gcattattac tcacggtacg a 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 33
ccaacaacag gaaactacct a 21

<210> SEQ ID NO 34

<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 34
tgtcagtttg tcaaataccc c 21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 35
aactatacaa cctactacct ca 22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 36
cagtgcaatg ttaaaagggc at 22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 37
tccataaagt aggaaacact aca 23

<210> SEQ ID NO 38
<211> LENGTH: 1179
<212> TYPE: DNA
<213> ORGANISM: Unknown
<220> FEATURE:
<223> OTHER INFORMATION: Description of Unknown:
Heterologous enhancer element sequence

<400> SEQUENCE: 38
atgaaaccat atctgctatt ttcatttatc ttggtttcag cctattttgc ttgtctggac 60
actacagtcc acgggagcct aggtcgagcg aggtccaaga atccccaggg tgggcaggga 120
gggtggaaga gggcctccag tgcccaagag gtgccccaca agcatgggac ccgccccctc 180
ccctggactg ccccacccac tggggcacca gccactccct ggggaggagg gaggagggag 240
aagggaggga gggagggagg gaggaaggga gcctcaaagg ccaaggccag ccaggacacc 300
ccctgggatc acactgagct tgccacatcc ccaaggcggc cgaaccctcc gcaaccacca 360
gcccagagat ctagagttaa tccccagagg ctccatggtg agcaagggcg aggagctgtt 420
caccggggtg gtgcccatcc tggtcgagct ggacggcgac gtaaacggcc acaagttcag 480
cgtgtccggc gagggcgagg gcgatgccac ctacggcaag ctgaccctga agttcatctg 540

```
caccaccggc aagctgcccg tgccctggcc caccctcgtg accaccctga cctacggcgt    600

gcagtgcttc agccgctacc ccgaccacat gaagcagcac gacttcttca agtccgccat    660

gcccgaaggc tacgtccagg agcgcaccat cttcttcaag gacgacggca actacaagac    720

ccgcgccgag gtgaagttcg agggcgacac cctggtgaac cgcatcgagc tgaagggcat    780

cgacttcaag gaggacggca acatcctggg gcacaagctg gagtacaact acaacagcca    840

caacgtctat atcatggccg acaagcagaa gaacggcatc aaggtgaact tcaagatccg    900

ccacaacatc gaggacggca gcgtgcagct cgccgaccac taccagcaga acacccccat    960

cggcgacggc cccgtgctgc tgcccgacaa ccactacctg agcacccagt ccgccctgag   1020

caaagacccc aacgagaagc gcgatcacat ggtcctgctg gagttcgtga ccgccgccgg   1080

gatcactctc ggcatggacg agctgtacaa gtaaagcggc cgcatcgata ccgtcgacct   1140

cgatcgagac ctagaaaaac atggagcaat cacaagtag                         1179
```

<210> SEQ ID NO 39
<211> LENGTH: 796
<212> TYPE: DNA
<213> ORGANISM: Unknown
<220> FEATURE:
<223> OTHER INFORMATION: Description of Unknown:
Heterologous enhancer element sequence

<400> SEQUENCE: 39

```
atggcgggca agaagttgag gccactgtcc ctgggtgttc ctacccccac accctcaccc     60

caagacagcc tgttactgcg gcgccaacag ccacggtcgc ctacatctga taagacttat    120

ctgctgcccc agggcaggcc ggagctggcg taagccccag tggggcgcta agtgagtgtg    180

cccctgcctc ccgccagcac tggcctggcc tgcaggctta gcctgggtca tcaaggtatc    240

ccacaggctc tagttcaaat ccagcagaac ctctctgagc ctcactcttc tcacctgcaa    300

aatgggtaca gccacatccc ttctctccct gcagccagga agacgcacat acacaggagt    360

ctagcccaca ccggccccgc acaaattaag ggctttactc tctgaaaagc ccagtgaagt    420

catgaaacca tatctgctat tttcatttat cttggtttca gcctattttg cttgtctgga    480

cactacagtc cacgggagcc taggtcgagc gaggtccaag aatccccagg gtgggcaggg    540

agggtggaag agggcctcca gtgcccaaga ggtgccccac aagcatggga cccgcccccct    600

cccctggact gccccaccca ctggggcacc agccactccc tggggaggag ggaggaggga    660

gaagggaggg agggagggag ggaggaaggg agcctcaaag gccaaggcca gccaggacac    720

cccctgggat cacactgagc ttgccacatc cccaaggcgg ccgaaccctc cgcaaccacc    780

agcccagaga tctaga                                                    796
```

<210> SEQ ID NO 40
<211> LENGTH: 21303
<212> TYPE: DNA
<213> ORGANISM: Homo sapiens

<400> SEQUENCE: 40

```
gggaggagaa gcctgggtgc cccccactga taagcaggct ccacccagag gccagtcctg     60

tgtgtctggg gacaaggcga aagagcagca gaagtgcccc ttctccagga tcaaggaact    120

ggggcggggg gtgtttcctg gaccccagtc ctccgaatca gctcctagag tggaaccagg    180

aaggattctg gagccacaga agatagacag atggtaagtc ccctttttgga gtcagaggct    240

tagcggggag gggtgagggt ggctgtgtgc aaaagtcctg cccccactgg aggggaggga    300
```

atgtaaggct tacagagtag aaaggtgggg agagagggag gtaatgggag agggatcgag 360
aaatggcaca ttcaggggac aggttcgttc tgaagcccat ctgggaacac tgctccgaga 420
taaaaatatg tgtgtggggg cagggcaggc agcgagggta tcaaaatggc ctgataaaac 480
tctcttcaat gcaccatttc ctgaaccagc ttctctctcc tccttctccc tccactcact 540
tcaggaaggt ggggaccaaa gtgaggaaga gccgagggaa cgcagccagg caggtggaat 600
gggaactctc tggagccaag aggtaagtgg cctcctctcc tgggtctgga atacactgat 660
gttgtcactc tcggctctaa aatcccacaa acactcatct actaactgtc tgcttcatcc 720
tcacccaaaa cagttgacat tccttgtttt ctcatctccc aggagttaaa gtagggctgg 780
gtttaggaag aattgggata attatttctg tataaaggga ctgtagcacc aacagattca 840
ttctctctcc tcttcttccc atccctgtct ctcaaccccc atcttgtatc tttcacctct 900
tggttcctcc cacagagcac tccagaagag aggctgcccg tggaagggag caggccatgg 960
gcagtggcca ggcgggtgct gacagctatc ctgattttgg gcctgctcct ttgtttttct 1020
gtgcttttgt tctacaactt ccagaactgt ggccctcgta agcaagatcc cagaccccct 1080
aacctagtca gccctccccc agccctgggg cccaggccca gtccctgctc ctggggcttc 1140
tgcccaccct gacccttggg gtccccatgg ttcttcttcc tccctgcatc ctaaccattt 1200
ctttttcatc agctccccac ttagttactc acctgatgtt ctttgcctag ccccttgggg 1260
gagcccttgt ctttttgcct cttctttccc agctctgagc ttttccccac aggcccctgt 1320
gagacatctg tgtgtttgga tctccgggat cattacctgg cctctgggaa cacaagtgtg 1380
gccccctgca ccgacttctt cagctttgcc tgtggaaggg ccaaagagac caataattct 1440
tttcaggagc ttgccacaaa gaacaaaaac cgacttcgga gaatactggg tgaggaaagc 1500
agggtggaag atgctctgtg caagtgggtg actctgtgcc taaaatgacc atgactgctc 1560
caaaccctgt gtagttgtgg aacaactgat ttgcaccatc ccaggtggga ttatacgggt 1620
ggatgattgg agatgatggg ggagtaaaag aggcaggatg gcgggagctg cctgggtttg 1680
ctcatctctc actgtttcct gttgccttgc cttgggtacc cttcttccgt ttctcttggt 1740
ccctttctgc atttttttct ttatctaatt tccatcttct ttgcttctcc atgtatccat 1800
aattactcca ttctctccaa cttgtccctt ttagcaagct ccatctttgt tgcttcctcc 1860
aaatgttcag tttctatcct atgcatggtg ttttcctcca caagcatctc ttcagcatct 1920
cctgcatttc aattcttttg tccatcactc tcattctcta acctccaaaa cctcagtctc 1980
ccaatgactc cttgtcaaca ttaccctctc cctctcacca tgccggagct cccctctctc 2040
acaatgatct cttgcttctt gcttctccat tgaaaccttg aaccatggca agcaagttga 2100
cctggaacaa gtgggatgtt agagatggat gattggagat gatggatgat ggtggaatga 2160
aaggggtagg atggtggggt gagaagtgag agagggcttc atcactgtgc ataagagaaa 2220
aagtgggtaa gtacaaagga tatgctggaa gaagaggaga gctgagttaa ttggcagtgg 2280
aagtaaagtt cctgcagatg gaggctggag aggaaaactg ccaggactga gaggaaaacc 2340
agaaggatga gctgaaactg agtaggaggt tggaagtgcg tcccaggaag ttggtggatg 2400
gtggtgagga tttgggaata agaacatata agatagacat gcatttccag tgcaagggaa 2460
cctaaagaat gtgttgacac tatcaattag aatctgggaa aagtaaatgc acccctctgc 2520
cctctttttt tgatggggaa agagtgggag ggggcctctc tttgggtaaa tggatacttt 2580
cagggaaggc acagagataa aaagaaaaaa tatgctcagg ataaattata ttgcctacaa 2640
tgggatgaat agatatcagg gggactgagg gtgaaaagag tgttagatat tagagggtgg 2700

```
atgattcaga gagacttgca tttgattatt gtagtgtgtt tgtttcctgg gatcaatgga   2760
tgaggagtct ggactagaag agtcttcccc tgtttcttct ctttgctaaa cctttcctta   2820
tgagttttct tctctccaaa tccttaaagt tctctagttc cctgaatttg tctaatttct   2880
tcaatcattt cttttgtctt tcatttctct cttttctcct ttgcccatat cccacttatt   2940
gctacctttc tcctttcttc cctgtctttt ccttcttggt ttcttcccca catttctttt   3000
attttccata ttgtcttctt ctcctcattc tctttccctg ctttcatcat ttcatcaagt   3060
tgatccattc caaattgggc agtcctctca tctttcttat tttcctcatc tctattcctc   3120
cccctccttc catattctgt gggagtcttt ctttcctgta agctccctgt ctcccaccct   3180
ccctctttgc ctctatacca gttgccactc ctttaattct cctgccgaca aaaagagtca   3240
aactctgtaa aatatttgaa aagatttatt ttgagccaaa tatgagtgac catggcccat   3300
gatacagtcc tcaggagatc ctgagaacat gtgcccaagg tggctggggc acagcttggt   3360
tttatacatt ttagagagtc atgagacatc aatcaaatac atttaagaaa tacattggtt   3420
tggtccagaa aggtggaaca actcaaaggg gtgggggtgg cttccagggt acaggtgaat   3480
ttaaacattt ccggattgac agttgcttga gtttgtctaa agatctggga tagatagaaa   3540
gggaatgttc agggtaagat aaagattgcg gagaccgaag ttcttttgaa gtcttatagt   3600
ggctgccctt agagacaata ggtgacaaat gtttcctatt cagatcttag ttaatcaaaa   3660
gatctagcta tgttaatgag atatgttaat agctaataga gatgctttac agatgcaaat   3720
tttcctccac aaagaacagc tttgcagggc catttcaaaa tgtggcaaag aaacatgttt   3780
tggggtaaaa tatttttgtt ttcttctttg tctcgtaatg ttatgccaga atcaggttag   3840
aaagtaaatc atgttacatg ggttaaataa aacccatctg atgagaactt atgatatagg   3900
gcatgactcc ccagacccct ttgataggaa tttggggcaa gataaaaaaa atcagagttt   3960
agtcctcact cccatgcttc ctttctagag gtccagaatt cctggcaccc aggctctggg   4020
gaggagaaag ccttccagtt ctacaactcc tgcatggata cacttgccat tgaagctgca   4080
gggactggtc ccctcagaca agttattgag gaggtgagaa aagttgggat attaactttt   4140
ctggatacat aacatatggg accaatgcat gcttagggct gccatttttt tttctagagg   4200
gtgggtcttc ttcctagggc cccccaattt ctaggaggga gatggagatg gaaatggtta   4260
tgccctatga aagtatcagg accttgggag aaggcagata aaaaaggata gatgtggctt   4320
cctagaggaa tcgaagggcg cagggcagag gtcaggcagt agcagctgtg taagagccga   4380
tccagacaat gggggatggg ctccacggat ccttatgctc agccccctct ctctccttta   4440
aagcttggag gctggcgcat ctctggtaaa tggacttcct taaactttaa ccgaacgctg   4500
agacttctga tgagtcagta tggccatttc cctttcttca gagcctacct aggacctcat   4560
cctgcctctc cacacacacc agtcatccag gtgagggatg cactggcgaa gacacagttg   4620
gacctggcct gcctccaact ctagccaatc atcccttaga ggaaggttgc aggttgggaa   4680
gagaggacac ctgtgtgata taggaaacaa ccctacctta agggaaaatt attgatgtga   4740
aagtcaggga cattagctgg gggtgggaaa tggagcagca gagccagtgc tgggaagaca   4800
gaagtaggcc tggtctttct tactgttaat ctggattagt ctcagagccc cttaaccagt   4860
cctcctatct ctaggattgc cctcatttta tttactcttt atttttacta gagggaactt   4920
ttctaaacca agggctaact aactatgcta ctgtctgtat ttaaatgctt gtcagtgacc   4980
cagtggcttg ccaggtcatc agaatctagt ccctaatctt tagtaaagct ttgcaagcac   5040
```

cttgtgatct gacccctaca cacttctcca gccttatctc ccgtacattc cttctctccc 5100
ttacccccaa gccatgctga ctcactgctg cttccaggaa tattcctcag ttctttgcct 5160
atgctgctcc ctgtgcctgc aaccatcccc cacactgaac ctggaaaact tacatgtttt 5220
tcaaatgttg gctttattat ctcttccagg aagtcttcac cgacacccta gttatgagtt 5280
aggtgaagcc ctgctctccc tactttcgtt tcctcatgct ctcagcattt atcactctgt 5340
gttgaagatt gtgagcctct ttagaacagg accatgcttt attcaccttt gtttctcagg 5400
acctatcaca gggccaggca gctagaagtt ttgccaggta tttgtagtga gtgagtaact 5460
aaataaaaac actggagcta tcactcttgt ggttaaacaa tgtaatgcta tctgcatatt 5520
tgggccctac tgtcaaaaga gccacaaaat taccaaagga taagtacaaa agaagaattg 5580
attatcatta tgaggtgttc taaaatttag ttttaaacag tctgctcagg agtttaactg 5640
atgtggcctt taggggccgg ttaagatctg gttaaggaga ggctcagaga ggagagaatg 5700
agagaaggtg agctaagcca gccttgaaac atggttaatt cacacaagtg gaggtgaagc 5760
tatggggcgt tggaaatgct gagccagggg gaggacctgg aatggtgtga ttccttcgtg 5820
gagtcagtga ggaggctgat ctatttaatt gaggatttgg gaggcaaggt ggggtgcagt 5880
gggaggtaaa agtgagactg aagacataag gttgagcctg attatttcta agaagccagg 5940
cgaaggtgaa acatttgaca taatagaaaa aaaaaaaaga gctactgagg ccatccaact 6000
cttatgacaa ttgtgcatag agcaagtatt ttgatggttg tgcgtagagt cagcagtttt 6060
gaaggtcagt ctgggggtgt tgaggaaact aaatgagcat ttttgaggcc ctgagataga 6120
ggtagaaatg gaaaggaaga gccaggcaca aggatttagg caacttcacc ctagtgatga 6180
tagttcatgc tgtttctaga ggatttggtg actgattgga tataaagaaa gaaagtgggg 6240
gattacacag tgatcccatt gttttgattt agtgtgagtg ggaggagggt gattatcatc 6300
agtgtgagcc tggatagtct cttgggttaa aagcaggtag gaagaatgga ctacagaaag 6360
agaagtccaa agactgaggg cagaagggag ccagggaaga gagagtacta ttggagagat 6420
gggagctaga ccagtatggt gggccacaaa ggaaagaaaa ggagcttcag gaaggagggg 6480
tcagctcaga gaagaaggaa tgagaagaca cccttggata cctagagata ctttccaaac 6540
agttatggca gtggacacag actgcacaga gcttaggagg aagataagaa agtggaaaca 6600
atgggcatag atgctttttt gttctttgaa ctgtggacat acaatgtagc aaaagggtca 6660
agtgaaagtt tttttcgaga cagaaggaaa agtatatggc tcaagataag agtgggatat 6720
tgaaattgga gaagaaaagg gaaagagtag aagcaaagat cttcagaata gaaacaaggg 6780
ttcatcaggg ccagactaag gtgaaatata catggtgctt acctggggtg ctaatttaag 6840
aaggtcccca aaactcagta tcatgataaa tagtatttta ttaaatattc ctaaaaaatc 6900
aaaatcaatg caacaataca tgatggaaca aaatatcaaa cttttcttca ttatgaattt 6960
ttttgaaaaa agattatgct ttttttccca aaaaatggga caaaattctg tgtgaatctt 7020
tttgaaaata ctaatttttt tattcaaaat gaatcaaaaa tacattgagg actttttcttg 7080
aacacatcat gattcttttc aaaattgact aaaagtatgt ttttttgggg aaaaaaagtc 7140
catgataagc aaagttttga gattttattt atcatacatt tttggtagta attttgattt 7200
tttaaaatgt taattattta tcttgattac tgagtttttt taaaaaagag tttatttgag 7260
caaagactga tttatgaatt gggcagcatc ctgaagcagt agaggttcag agagctccac 7320
ccaacaatgc aggcaggcag tatttacaga aagaggaagt gacacccaga aacagcttga 7380
ttggttacag cttagcaatt gtctttaatg ggcatggtct gatcacttga cagcctgtgg 7440
ttgcctgaag atcagctggt atggctggct gagatggagc tacctgttgc aagaatatac 7500
tcctaagtta ggttgcagtt tgattactga gtttttggta cctcttagat tttgtacctg 7560
ggacaggttc ctcacctcac tcaccctggc cctgttcctg agacaaggaa tagctccttt 7620
taagatgctg attatcatgc ttctgccttg ctgggcacac ccacactggt tgtaatactc 7680
accatctctt cccattttca catctggact cttcttctca tgcccctcaa cccttaatcc 7740
ctccctttct ttgtactctt gcttctcttc tgtccaatct ttgtgtccat ctcccaaggc 7800
catctcccat ggtatattcc ccacctcccc acacctgccc tctccatccg ccatgctccc 7860
tgcttctctc cagtctctct tgtgcccaga tagaccagcc agagtttgat gttcccctca 7920
agcaagatca agaacagaag atctatgccc aggtaagatg gcacatggac aaaggccctg 7980
ccctctgagg ccaggagaaa agcagggacc tctggcacct gtgactgaca tttccttcct 8040
ccagatcttt cgggaatacc tgacttacct gaatcagctg ggaaccttgc tgggaggaga 8100
cccaagcaag gtgcaagaac actcttcctt gtcaatctcc atcacttcac ggctgttcca 8160
gtttctgagg cccctggagc agcggcgggc acagggcaag ctcttccaga tggtcactat 8220
cgaccagctc aaggtgcctg gaactggggg ccagaagact gtgggcatgg ggatcttcct 8280
ctcaaacatt acctcctttc cttcttcctc ctagtgccct taataccttt tcattctgtc 8340
tctgactcca tcccctcccc cagttagcct gttctcttct ttttctcaca cccaagggga 8400
agccctttcc ccttccttct cttttccttt tccccctcag ctttgtgtcc ctcctctaag 8460
gaaatggccc ccgccatcga ctggttgtcc tgcttgcaag cgacattcac accgatgtcc 8520
ctgagccctt ctcagtccct cgtggtccat gacgtggaat atttgaaaaa catgtcacaa 8580
ctggtggagg agatgctgct aaagcagagg ttcgccgcag gtgggattgg ggagatcatg 8640
gaaatggagg agagcctgag caccgtagat cttgggggca aaggaaacct tggggaaggc 8700
aggctggtaa gggcctccca ggaggataag aggaacctgc cacctgtgcg ggcagagaag 8760
cgtggggtgg gtggcacaga gaggatggag ggatcaagaa ggatgtgtct tgggagcacg 8820
agtaagggag gatacacacg acatgaggaa cgcagggtca gccaagacac ggggtttcct 8880
gagagtagaa caccagccag tcaagagcct ctgagctgta gaagatgctg gaagacccag 8940
acacagaaga cagttaagtg tatgtatgtc tttttagcag ctgaggactg tgggcaggag 9000
gaggaggcac atgagatgag gagatgaaga tggtgaaggc tggggatgct taggggaaga 9060
aaggaagagg aggggccatt cctcaggtgt ggtgtgaaga tgctggagct cttatgggaa 9120
acaatgtcta agagcatttc tgctggtgtc aggaaatcaa gggggtgttg gggttgggga 9180
catgaaagag tggctctttg ttgggctctc tgcctcccct gatacctggg tggctaccac 9240
ctgaaagcag tggctttctt ccaggggctt ggacctaagg gccttcttca tggtggcagc 9300
agcatctgga aatccttttt gagggaggta gctgcccatt cacatggcag tgagcaggct 9360
tacataaggg tgcaatgcag ccctggcagg agcattgctg gtggaggaga gagcagtcac 9420
agagaccagc ttacttatgc ttatgagata catctgagga taaccagaga tatcttgact 9480
gtggaagcag aatctgtttc atgacatgag tccagactcc atctagccca gaactttctt 9540
tccctgtgac tttgaaggct gcctcttcat ctagtttctt ttactaagga gctagatccc 9600
accccaacct acatcatgaa aagctctttt tgacttgggt gcatgttaaa acacttatta 9660
atacagagga gaaggagctg ccttcacgag tatcaaggtg acttacacaa ggagaggctc 9720
ttcttgaagc atccccagat tcctggggta tatgtgtggg tctcttttgt ctccataggg 9780

```
actttctgca gagccacatg atcttagggc tggtggtgac cctttctcca gccctggaca   9840
gtcaattcca ggaggcacgc agaaagctca gccagaaact gcgggaactg acagagcaac   9900
cacccatggt gaggagagga gcgggtgtat ttgcccagat actcgaaagg agtatctact   9960
cttttgaggg gtaaatgtcg gcatctctct ctcagggagg gggccgtgat ggtagatgcc  10020
cctccatgtc ttggctttcc atagaagcag gcaagttgga cagacaaagt ttaacttgaa  10080
aaccaagatg ccacgtgcca gaccttcagg cacacatctc ccagcctgac tacctctctg  10140
gcttcttgct gggtgtttga gctcaaatat aaaactctga tattatcaaa actgcccttt  10200
ctttgtcatg atgcttacac tatttgctca ggataacttg gacttagagc ttacaattta  10260
ttgggatgac agagagatat gttacgcagt ggccttcctt atgtctagtt gattccatgt  10320
tcaaacgtgc ttcacaaaga gtttatctct gacatccagt gggatccact gggccacatg  10380
tagactttgt ggcacagatg tggatatatc tgaggagggg cctgggtaga aaatgcactt  10440
cactaaccag agtctactta ttacataaga tgcagagatg ctcctttgct gagaatcttg  10500
aaatcccaag ttggatatat ccaaatgcaa gcagaagagt ctagtacatt ggatacatcc  10560
caacctcagt gaaggcctca gtttagtctt aaaaatcact ggattttttt tcttagtaat  10620
ttgtggtcca tttccctgcc ttggagaaac tctctgcttt ggcaacctaa aattgctgtg  10680
gaattcagag aagataaatg tattcacagg gactggaatg tagttattgc ttatcaagag  10740
ctaatggtgt gctagacact ctgaaatcct ttagatctaa atctagattt agatttaatc  10800
tttacaattc catgaggtac catggatgcc atttggttcc tattttaaag aggaggagac  10860
agaggcacga aagataagga agttgctcag gtatgacagt aagttagtgg ggtgaggatt  10920
tgaaccctgg cagtctggct ccagggtctg tgttgtttac tcattgtgct aaaaaagcag  10980
tcttcctgag gaacatcact tgggttggag agtggccaag aagcttctgc ccagcttttc  11040
tcttgattca gatgaagcag accagagccc caagttatct taattggggt tgctacaaaa  11100
tcctggcaac aaacagctac ctataaatgc cagcaccatg gcctcatggc acttcttgga  11160
ggctgtaaga gtgctaatgt tgaggcttag gcttaaagaa tgcagaaggc ttagatgtcc  11220
tgaagccatt atcttttcca ctagggcaca taattgtcct tgggcttaaa agctgaacta  11280
atctctgcca acaaatagtt gtgtgacctt ggggacgcca cttcaccttt ctggaacaat  11340
agtataaaag atggcactta ataataatga taatagctgc tatacatgga gtagtcactg  11400
tctgtcagca cttgggacag gttattcatt taaatcttcc agaaacactt ggaggttttt  11460
aatccccatt ttgcagaagc aaaaataggc tcagaaaggt caagaaactt tctcaagacc  11520
acacagctca caagtaagtg aacagactcc aaaacagatg ttttggctca taaagtcatg  11580
tttttaacca cacactatac aggattgaga aacaagtagg tgctacaaac aaaggttaga  11640
aaactttttt ataaagggca acatagtaaa tatcgacttc gtgatccata aatggttggt  11700
gttacaaact actcaactct gtccctgtag tgcaaaaaca actgtacact aagtaaatgc  11760
tgtgttccca ggggatcctg gttgagacag cagatattct tggagttccc aagagggaga  11820
gatcagggag catttgaagg atcagtggca tctctgtgca ggaggcagaa ctgacaaaat  11880
gtctagagag aggaaggagt tttctggtga agaaaggggt atcatctcat ggggacaggg  11940
caggaggcag gctggctaaa acttggtgca gggtgaggga tcctcctggt ggctctggtt  12000
gagaggagaa gactaggctt gctgtgtcca ctgatgcccc tggagcatgc tccaggtgtt  12060
tgagaatcag caagggagcc agggcacctg gatcagagtg actaggacaa tagtggggag  12120
ggaatcagag caggaaggag agaaccatac aaggtctggt aggttgctga aggacttttg  12180
```

```
cttctctctg tatgaaataa agacatgcag agggatttat ctcatttatg ttttaaaaga  12240
acatatttta aggttagtaa tgggatgtcc tgatgatgag tgatgtgaga aggagaatgg  12300
aatcaaagac atcacctaga gtttggcctt gatatgatca aaatgtttgg ttttattcag  12360
tggccattaa ttaccgactt ctgatcatat tcttttgaat gaattataat ttatagtgcc  12420
cttatacaga aagatttcta aatctcatta ttggcccatc tttggatgat tagttttgaa  12480
tagagttata gtcaatgaaa atggctgtta agtcaggttt tcttttatga aacttgggaa  12540
ggtgggtttt gagaagtaaa agcagaactt cacatttgtg atgattaaat gtgaatgatt  12600
tatattcagc ccaacatctc aatttattca ggtcttccag ctttggatca tttgcaattt  12660
tattcagtgt atcttcgtcc agactactgt taagatcctg aagggagaag ggcatcgggt  12720
caggttattg aagacctaga tatggattta tgcattcatt tatgtaacaa acatttattg  12780
agaacctagt gtacttcagg tacttctcca ggcacttgga atgcagcaat gaacaaaaaa  12840
gacaaataaa taatcctgcc ttcagccaca tatcctggtg aaagaagaaa gacaataaac  12900
aaactaataa aataataaaa tatgttagga ggtgttatga agaaaagcaa aacaggaaat  12960
gaggaaagga aatgctaagt gagtggtagt taggattctt agtaggaatg tcactggagg  13020
tcaagttaac ttgaaatcat tcaccattga tgtttacttt tgattcagcc agatgagact  13080
ccactcaaat tgcactatca ttcaacatca gtttctctat ctaattcacg aggactcaat  13140
ctgtgttttt caagcctggc taaatcaaga taatgccaac agagtggggt agtgccttag  13200
agtacttgaa aggtattatt tcacctgatc cccaaacctg tgaggaaggt agactagata  13260
ttgttttcat ttcgacaact ggtgtcactg aaccacaggg gtttaagtta ataactcaaa  13320
cttagtaagt gctaatactc tattcagtgg taggatggta gtggtgcttg aggatgtatt  13380
tcgtctatag atgtgttttg ttagcctgta gaatcttttg caaactttga attaatcacc  13440
aacattcaaa aactaggata tggcatgcca gcattcaggt ttctagtgtg tgtgtgtgtg  13500
tgtgtgtgtg tgtgtgtctg tgaagcttgg gaaacactgg gctacccttc tcctgtggca  13560
acaactgact gtcgctacat gatgcagctc agggctgggt gcgctctctg aagccccacc  13620
acagcctgta gctctgatgt tgcactgctg ttctctgtta tgcctctgca tggcccctat  13680
tggagtttgc ggcttccggt ctttcatatg cctcagttac ataagccttt tagccagaag  13740
aatttttatc attttggcat tatttttctt cagtgatcct atcatagccc ttagtagtta  13800
cacattattt tccaagtgtt aaaaaactgt ttaatgattc gttccacaat tttgtttaga  13860
aattaacatt aaggattcct ggttggctcg taatccctaa aatttccttt catcctatag  13920
aagattggtc aaatttttgc ttccctccgg actcttagaa tctgtcctga tttctatcat  13980
ttctcaaata ctatctgtgg ttctgaggtt gtatatggaa cttttttttt ctggtgccct  14040
aaaattagtc cactgagttt cattatcttg ggtttgaagt atttcttcta ttgtttatat  14100
tttggagact ttttttctc gaattctatt tctctccctc tctttctctc tctgactctc  14160
cctttgcagt caatgtggta tacactacca ttccacatct tgagagagag ctgtagtagt  14220
ggtctgaggt ggcgattgta ttatccagta gtcaggtccc acggcaaagc atgttggaga  14280
aatgatcagg ctccagcaaa gggcatcagg aaacaaatca agaatgagaa ggggtgagaa  14340
gaataggcag atctacactt ccaagctcaa gtggtctccc tgctgatgct ggttgctgct  14400
ccacatgtag caactgtctg gtaagaggta ttcctggagc caagcttgtc cagcagaatg  14460
tggctggcag attctcaact tggcctataa ttgctttcag acccggactt ctttttagtt  14520
```

```
cctgttgttt cagagctcca actcatgcag catgagaaga atctgagcct cttctcttta  14580
tcagagacaa ggttggccag gtgcggtggc tcttgcctgc aatcccagca ctttgggagg  14640
ccaaggcaga tggaccactt gagcccagga gtttgagacc agcctggcca acatggcaaa  14700
acttcatctc tggtggtagc cacctgtaat cccagctact tgggagactg aagcagaaga  14760
ctcacttgaa cccgggaggt gaaagttgca gtgagccgag attgcaccac tgcactccag  14820
cctgggtcac agagtgagac tctgttacaa aataaaaata aaaataagac tcaaggttag  14880
cagacctcaa ggttcaatag aacacagatg tggacagcca ggcctgcagc aacctccaaa  14940
atgataacct ctttaactgg tgggttcggg agtttttct tcggtgacta ccagactggc  15000
ctctttggtc tgtttcctgt agtgggatgc acataaaccc cctccattcc caggaccagc  15060
ctagctcctg cggggagagt attagtggca gccttcctac cttccccgtg ggcaggtctt  15120
tgggaagtaa aaaaatcaca ggaataaagt tttgaggctt catcctgcct aacccaaatt  15180
agcatattag ctggtattta tcagttccag ctcagctttc cctcaggcca gctacctcct  15240
cctgtccctg ggttccttga gtgtgtgtct ccatttaccg tgtcatctct gggtttatgc  15300
cttggtcaag tttttaaagc catgcaagcc caccgccaag accttctcag catctgtctc  15360
ttctgtttct cattcttgag gtcctcagct ggcactgccc tcttggatgt ttgtccatgg  15420
cctcctgcct ctgcagtgaa agccctccac cttcctgttc tattctctcc tctctgactt  15480
ggctggaagt cttccagctc tatgaattta tacactgagt cttgtcttgt gtcctctttt  15540
cctagcaaac aatatggcat ctaaaaccca gttctactct gataattttt tctttacaag  15600
atgctacagt atgatacacc atgcccacct ggagagagga taaaggtgat ggtggtagga  15660
cagaatttcc atccgcaatc tccgttttga gcaaagaagc atggaggatg gaagtcattg  15720
ctgggacccc ggagtagagt ggtggtgggg gaacaggggg aacatcagac tgccgaggta  15780
tgagtttggg ttctcatctt cttcccagga ggcttttgaa accccaggat gatgcctcct  15840
agaggccttg ctgtcaaatt caataggcaa taacatgaag gatttactca gccaggctca  15900
tgagaccagc tctgaggaag ctgtgctttt cttgtactga tcggtgatgt gcatcaccct  15960
aagggatagt aaacagatga aacccagaaa gtccagtcaa aagagcaccc tctgggaatg  16020
aagatctagt gaagactggg gagacagatg aggaaagagt cctgaacagg agccactcat  16080
tccagctttg tctccatagc ctgcccgccc acgatggatg aagtgcgtgg aggagacagg  16140
cacgttcttc gagcccacgc tggcggcttt gtttgttcgt gaggcctttg gcccgagcac  16200
ccgaagtgct gtatgtgaga gctcttccca gcccacatcc ctccacccct tcctacccaa  16260
agcagccttc cctcttctat taactttgac tttctcagtg gtgtgtgtga ttggggaatt  16320
gggcagtcag agaagggcca ctgagagagg gaacccaaag gcctgctcca tccctggtgt  16380
ggaaacagtt cagcttcagg ccacaaattc tccatgacat gctctcactt ggacaagtca  16440
cccaactttc ctggtcttgt gtttcttcaa ccatcaaatg agaaaatcga gccaggctcg  16500
gtggctcaca cctgtaatcc cagcactttg ggaggctgag gtgggcggat cacctgaggt  16560
caggagttca agaccagcct gaccaacatg gagaaacccc atctctacta aaaatacaaa  16620
attagctggg cgtggtggtg catgcctgta atcccagcta ctcgggaggc cgaggcaggc  16680
gaatcgcttg aacctgggcg gcagaggttg cagtgagccg agatcacgcc attgtactct  16740
agcctgggtg acaagagtga aactccatct ccaaaaaaaa aaaaggaaaa ttgaacacta  16800
tcatctctaa gtctcctccc tgttgtagct aagatttttt taacaacaca tgacgtgaca  16860
tcagaacaga tgacataatc ttgaagaggg caaataaatc aaataaatca ccactgaata  16920
```

```
ctttctgagt acctaccaca tgcctgggac tccttcaaga actttgcatg aactacgtca  16980
tttagttcct attatgatcc tgattttata caagagggaa ctgaagcaaa gagaggttaa  17040
gtgacttgcc caaagtcaca cagttaccaa aaagcagaga cagggtttga actcaggcat  17100
tctgatgcca gagcccaggc tctcgatatt gcctttcatt ttcctccagg aaaggattta  17160
catgagatgg caggtggctg gggaagcagt gagtacacac tcacgttgtg aaggcaggga  17220
gacttgtggg ggacttgctg ggaagctgaa gagctcagga ggatgaggag agggagtgga  17280
cggtttaaaa aagacagtgt gagaacaaga gccctgagcc agaggagaaa atgacagccc  17340
tctcctccct ctgatttctg agaggtgttc ctgcccccag gagtgaggac actgtctttc  17400
tcctgtgtca ggctatttcc ccatggaaag gaactatatc tccctgatgg ccctcacgga  17460
tggccaggcc ccaccttccc tttgtgggct tggcactgcc ttcctttctc cacagatcct  17520
ttagttgctt tagttgagct gctcctctag cagcagctcc agcccaggca gctccttggg  17580
gccaagccct tttccaaggg tcagaagctg tgggcagggc caggctgagg cctctcctga  17640
tcctgtcccc ctgtccctgg acctcactcc cacaggccat gaaattattc actgcgatcc  17700
gggatgccct catcactcgc ctcagaaacc ttccctggat gaatgaggag acccagaaca  17760
tggcccagga caaggtcagg ccaggcgtcc tggctggtgt gggagcctgt gcagggaatg  17820
gagtattgga acaagcgaga tggggattgg aagcaaatgc caaaggcccc cccaggcaca  17880
tgctaagtag ggaagccact gggctgtata ctcacactgg caacaatgtg agaggctggg  17940
acagggcaac gagtgggaga aatttcctct ggtagactcg gagagtattc ctagcctctt  18000
ctgtgtctct ctccaggttg ctcaactgca ggtggagatg ggggcttcag aatgggccct  18060
gaagccagag ctggcccgac aagaatacaa cgatgtgggt ccctgtgttt tccagctcct  18120
tttcagtcct tgacttctcg tcacttctct gaccctccta agtctttgtt ggacaatcag  18180
ttttccctgg gtgacttagc tctgtcctta ctctggtgct ggctggggtt gatggggaaa  18240
tatccacact gtacgtcttg ctggcagaag aacagaatct tttcaggtcc caacgcatgt  18300
gccaacacac atgcatgcat cctgtgactt gtctgggcgt gttcatctgt gtgctgatat  18360
gtgtaaagcc tgggtgtgct gtgtagtgat gccattgggc tgctctctcc taatccctgg  18420
atgcctgcct gtcagggctt gcctgtttgg ggtcaaatgg tcccattggt gtttgtcagc  18480
gtgcatctat agaagtctct gtgtgcccaa gtcacctcct gcctcttccc cagatacagc  18540
ttggatcgag cttcctgcag tctgtcctga gctgtgtccg gtccctccga gctagaattg  18600
tccagagctt cttgcagcct cacccccaac acaggtatga cagcagggga gacacaggca  18660
ctccatccca gagagaccca tccatgattc acaggaaagg aagccagggc tcagggcagg  18720
cagcatgaac agtaatggta gttgggaggg actgtgtagg tctcagggtg gcagggcaat  18780
acgtggtggg ggctggagtt cacatgtcct cttcccacag gtggaaggtg tccccttggg  18840
acgtcaatgc ttactattcg gtatctgacc atgtggtagt ctttccagct ggactcctcc  18900
aacccccatt cttccaccct ggctatccca ggtatgggtc actctgtaag ggtaggtagg  18960
gagtttccca agaggggccg acaggtgtta tgatggatgg gacttacggt tggagaattg  19020
gggtcacaaa tgctgagaga ttctggggt caaataagcc cttgtctccc tagagccgtg  19080
aactttggcg ctgctggcag catcatggcc cacgagctgt tgcacatctt ctaccagctc  19140
tgtgggtaac aggggccact gggaggtggg ataataggga acctaaggga agaccacaag  19200
ggaggcctgg aggggaaagg gaggttattt gagggtttga ggtggggcag tcctgggaac  19260
```

```
tttgccatgc tcctgggagc tgattcagtc tgtggtacca cccacatcct cacctaggca  19320
gcaccaaccc tatgttctct tgctgtatgt tctcttgtcc cattttcaac agtactgcct  19380
gggggctgcc tcgcctgtga caaccatgcc ctccaggaag ctcacctgtg cctgaagcgc  19440
cattatgctg cctttccatt acctagcaga acctccttca atgactccct cacattctta  19500
gagaatgctg cagacgttgg ggggctagcc atcgcgctgc aggtatgcaa gtgtcaaggg  19560
ccacagttta tgtgtactgg cagactagaa aacatgtcct caagttttcc ttccaccatt  19620
cctgacacaa gtacagttgc atggctttct gcccttcgca tccccactga atagacggca  19680
acttggggat ccccctccta ccccagagat cctccatttt aggacatcta taggtcttct  19740
gggaagtact ctttcttctg gctcagatca actagtcagt gcagaaccag tgagcaaggg  19800
ccatgggttt tgggtactgt gtggagggac tttcaaatgg ccacaggtct agagcctgat  19860
ggcccttctc tacccacccc tacccaggca tacagcaaga ggctgttacg gcaccatggg  19920
gagactgtcc tgcccagcct ggacctcagc cccagcaga tcttctttcg aagctatgcc  19980
caggtaggca gcggccacct cccgccacag cttgctttat gtcagttgaa cgccttatta  20040
ctgaagctca tggaagtccc ctcttcagac actccgtcaa ataccccaaa ccctcttctg  20100
cagatgtcct cactgttatc ttttctcttc cctccctacc ccttggaatc acccctcaga  20160
tgactacagg ttcttctacc taattcagca cccccacaac tcaaaaggta gaaaaaactc  20220
tattcccaag ttcctccagg agaggaggag accaactttt ttttcctctc atacccccaa  20280
aatacagatg ccttaaaaat gagcctgtgg ttgggcacag tggctcacac ctgtaatcct  20340
ggcactctag gaggccgagg tgggcggatc acttgagatc aggagtttaa gaccagcctg  20400
gccaatatgg tgaaaccccg tctctactaa aaatacaaaa cttagctggg cttggtggcg  20460
ggcgcctgta atcccagcta cttgagaggc tgaggcacga gaatcgcttg aacctgggag  20520
gcggaggttg cagtgagcca agatcatgcc actgcactcc aggctgggtg gtagagcaag  20580
actcagtctc acaaaaaaaa aaaaaaagcc tgcgacaggc tgactgtgtg ccacattcct  20640
cttcagacac ctgaccttag gtgtggcgcc cacttgacat cacctcctta agcaccctgt  20700
actccctcaa cagactcagg tgccaggtct tcaacacgct tagattagac ttcaccccag  20760
agctcctgcg ctagaccctg cctctctgtc attgataaat ggtatcatta cacagcccag  20820
gccctcctcc tggactccta ttgccagatt aaatgaacta tacatttcaa atgctccatg  20880
tggcccttgg ggcacttgat cccctggttc ccctctttgt ctgctgtccc tgatcacccc  20940
ttgtcaccgg gtcagctttg tcctgtggac cctccccctt caatgacctc tcttcctgct  21000
caggtgatgt gtaggaagcc cagcccccag gactctcacg acactcacag ccctccacac  21060
ctccgagtcc acgggcccct cagcagcacc ccagcctttg ccaggtattt ccgctgtgca  21120
cgtggtgctc tcttgaaccc ctccagccgc tgccagctct ggtaacttgg ttaccaaaga  21180
tgccacagca cagaaatatc gaccaacacc tccctggtca catccatgga atcagagcaa  21240
gatttccttt ctgcttctgt tccaaaaata aaagctggca cttggcttcc gcttgtctct  21300
taa                                                                21303
```

<210> SEQ ID NO 41
<211> LENGTH: 21923
<212> TYPE: DNA
<213> ORGANISM: Homo sapiens

<400> SEQUENCE: 41

```
acctgtcatt cgttcgtcct cagtgcaggg caacaggtaa gagctgcttt cagcctggca     60
```

```
ccctatctct ggtctgccag ctggtctctc agggctgtac acactgactc tctggtctga    120
gtagatctga ctttttcctt tgtttgtttc ttagaatctg tctctttttc attttctttt    180
tatctcccat gtctctttct gtctttcctc attttcagct tttttctctc tttttccctt    240
cgttactttc ttttgttagt tttcaagatc attcatttca tttcatcatt ctctgacact    300
cttgctttct cttatttttc cctctgaatt ctaactatct ttttctctaa atttctttct    360
ctcccccttt ttgtctcttt cctcggcttt gtatctctcc gtctctgtgt ttctgtctct    420
ctcttcctct ctatcaagaa cgatggctta atatttcttc ctgcaattcc ccattcctct    480
ctccctttga ctccctctac ctgctgggct gacagcagag ctcagtgggt cagagcccat    540
ggggagccta ggggtggggg aagagctagg gagggaaact aagaggatgt gggggtgatg    600
ggaatgatga attgggtaag gagagatttg gggaattgag agatgaataa ttagcagaaa    660
taagtgaaga aagtggaaga ggaatgtagt gtcactatac agaaagtaaa cagatttcta    720
ttctcatcct aattcactgt gagaccctag gcaagtcatt cactctctga aaaaaaggct    780
tggcctgtaa tttccaccac cctttctagt tttgattttg tgatcttcta aattttcctg    840
tttctaagaa tttctgattc tctgattaca gttatctaaa gttctgtatg attctttcat    900
ggtgggaaag gggtactagg aagagaagta aggcctgatg tttccaactc ctgaagagaa    960
attaccactt cccttccaga cctaattgac ttttgcaaag caggccacaa aaggggtggg   1020
ggggtggggg acaaggaatg ctgcaatgag tgtttttctgg ctgtctgctg gggtagagtt   1080
gcagttggcc cttttcacct ctgggagtac agattgggtg ctgacacaag agaggatttt   1140
aaagtcgtag ggaaaaactt tcagtaatga tctgttactt ggtctcaaat ttcaccatca   1200
tctctttggt taaaagtatt gttttaagaa gatgcctggc aagcattatc acacattagg   1260
tacataagtt attgaatggt agagtaaatg aatattcaac agtacctgaa attccactgt   1320
agttacagat ctgttccttt ggtaaggcat tggtgacaaa tggcatatga cctggaaaga   1380
ggcctatgtt agtgcagcag aggagataaa tgtctagagt caggccctca gtcaagaaaa   1440
aaaggtagta atatttgaat cacagatcca taatggttaa gttaggaatc tctggaaaca   1500
gattgcctag gttcaaatcc tgcttctcct atgtactagc tttctgatct agacaggtta   1560
cttaatcttt ttgggattca gtttccctat catcacaggg ttgacatgag aacacggcct   1620
ggcacagagg gctctgtaag tgtttgacta tcagaactag gcggaatcta tgaaattatc   1680
tagtccaatg tcagtggaga aacggaagcc cagagagggg aattacagag cccaagttca   1740
cacaataaat tgtaacagga ttgggacaag aatcaattct ctagcttccc aaacccagcc   1800
tggtatattc atgtgacttc ccttggctgt acgttcattt tttctacatg ggaaatggag   1860
aaaataaaaa taataaagtc tatcaattaa atataatatt taacactttt ttactgttta   1920
ctctgggata ggtactctgc taaatgcttt atatggatta tcttactgaa tcttcacaac   1980
attcctgtga tgcagattgt ccttgttatt accaacattt tccagatata agatgtacag   2040
cagggaagtg acttttctaa ggtcccaaag ctagtgagtg gtggagccag gattcaaacc   2100
caagtagttt ggctctagag cctatactct ttataccta aattgactaa aatgcttcct   2160
tgattcaatt ttactcactc tagtctcttg gtaggtaatg agatggaata gaaacagagc   2220
ccatggtaac tagactacaa ggtcatgggt ataatgatgg ccaggcagag tgaggcagag   2280
caaatttcag gaaaggagta acagaacaag agaaatgaga acaggagctt gaaagaactt   2340
gagaattcaa caaattccaa gaagtggtct atattttccc aggaccctga gcatatcatg   2400
```

```
gccaaaagcc ccctagtaat gatgtgtgtt aatttctcct gtttttatat acaggaggta   2460
ggtcttctcc accatcccaa ggcaggactg gactttgcct ccaatattgg gggctttcct   2520
tcccactaca taccccaatg ttgttggcat tattgttgcc agtattgatg ttaggggagt   2580
ttacaggagc ctggagcctt gtcatctgcc ttgcctgcac ttctgggcca tccatttctt   2640
accaccaata gccagggcca gctctagcca gatgctcaga cgtgattcca ggaaggggct   2700
cctcttctct cccacgccct ggtctcagct tggggagtgg tcagacccca atggcgataa   2760
actctggcaa ctttatctgt ggtctgcagg ctcagcccca agtgctttag ctttcacaag   2820
caggcagggg aagggaaaca catatctcca gatatgaggt aggcactgga tccaattcct   2880
tacctacctt gtgaagtggc cataattacc tcacgtttga cagctgatga aggccaagat   2940
ccagagaggg gaagtgattt gaacaagaac atccaacaat gaaattggag agctggaatt   3000
ttaataagaa aagctaacat ttattgaaga tttactatgt gccaaaaact atactaaagg   3060
cttaacttgg attgtttcat ttagtccctc caacaaccct tctgtctttt ccaatttcag   3120
ggcccacatg ccttggcccc acataccaac ccaggctgct gtgacagccc atgagagggg   3180
gagaggttgc tctgggatgg aacaagaaaa agaggttgtt ttgtgaggta cggggagggt   3240
gcttgttcta tgagatcagg aagggaggga gatgaaggag gttgccatat gagggcaggg   3300
ccatgagctg acctgtccct caaaacataa ggctgagggt gctagtagat tctactcagt   3360
aactttcttc acagtgtcag tgctttagtc ttctcacatt ctcccatgtc tctcccattg   3420
tactgtccct tatcttgtct cactttttga ctctgtcttt ccaatttgcc ctttttcttt   3480
acatctgtct ctccttcttg ctctctctag ctgtctttct cttggtgtct ctcagctctc   3540
acccctctta accctcatcc ccctgcttta gtcacctctc tgtctctatc ctttgatctt   3600
gtcattttct ctactctctt ctctctgtcc ctcagtctct ctctcatctc cctcaattag   3660
ggccatgatt ctcttcccta aacttactta gccttttgca atttctggca gcattttttt   3720
atgtttgtgt ctgactgact ctctacccct gctggatcct ctccactcct gttctcactt   3780
ctatgaatct ttgtataatc ctctagactc attgatccct cctcatgtcc ctttcgtgcc   3840
ccttggtcta tctgtctctg cctttatccc tgtgtgcact atcaccaccc cctttttctt   3900
ttttcatttt ctctttctct cgactcaatc tctgttttca tctctaccct gctccctttc   3960
cctctacctt tgatctcttt ttccccctca atttctgttc ttttaactct accaccacca   4020
ccacatcttt gttctctctc tactttcctc cttttatctt tcctaaattt tcttttcttc   4080
tggcttttct cctagtccct tctccttcct caatttcaga ctctgttcat tcatcaattt   4140
accccaaaat tcaacaaata tttattgagt gcctgtgtgt catttgcttt ctctttttct   4200
gatctctttg ccccctttct cttctctgtc ttggcctctg cctgtttcac taatccatag   4260
actatgtctt tgtccctgtt ttccagcccc actgggactt gctttcacct cttcctatat   4320
ctgtgcttat ccaagagaca ggagcaaatt caaagacagc ataatatcag gctggtggta   4380
cacattctgt aggacctagg gcctaccctt ccttccggat cccttgattt ccttaaactg   4440
atacatgtga cctcaagctc cttctcccct ctggctgatc ctgcttagga aacaccctgg   4500
gccaagcctc aggagctcta ctcaatgaca tatgtttgca ttagcaggct gaatcttcac   4560
ttggctaaga ccaacattct tagaaagatt cttggcctta agtattgatc aaagggttag   4620
tgggttggca gttctcatcc tgccacacaa aaacacattt cagtgatcct catcatcaca   4680
gaggtagtca gtgccagaat gtgagtcaga atccaggctt tctgacctcc agttagaact   4740
gtttccttca cccctttgcc cagtagtcag tttcctattt cttcctccct catgttttat   4800
```

```
tggtacatgt taacattggg aaagaagttc tttccctgga agggcaataa gagcatctcg   4860
gaggcagcaa gttttgggtg ggaagctgaa gacgaggatc aaaggcttgg ctttttgcca   4920
ggccctcatg atggaacctc atctcttcca tgtcttctgc aggactttag gttcaagatg   4980
gtgactgcag ccatgctgct acagtgctgc ccagtgcttg cccggggccc cacaagcctc   5040
ctaggcaagg tggttaagac tcaccagttc ctgtttggta ttggacgctg tcccatcctg   5100
gctacccaag gaccaaactg ttctcaaatc caccttaagg caacaaaggc tggaggaggt   5160
aagaagaggc tgctagcaaa aggggagaat gttagggtcc tggggtaaaa gttccaagtt   5220
atactggcca tctttgccta ataattagga cggttcatgt gaaaagtgtc aagatagcat   5280
gaactggccc caaaatatac ccagaatctg tcttctgcca ggttctctag aaagagtctc   5340
attctcggcc aggcacagtg gctcacgcct gtaatcccag cactttggga ggccgaggcg   5400
agtggatcac gaggtcagga gttcaagacc accctggcca agatggtgaa atcccatatc   5460
tactaaaaat aaaaaaatta gccaggagtg gtggtgggcg cctgtaatcc cagctgcttg   5520
ggaggctgag gcagagaatt gcttgaaccc aggaggcgga ggttgcagtg agccaagatc   5580
atgccactgc actccagcct gggcaacaga gcgagaatct gtcaaagaaa agaaaagaaa   5640
agaaaagaaa cagtctcact gtcatgtccc tcacacacta tactccagac atgctgaaac   5700
tacttaaaat tgcctaaatc aactattctg tcaagagttt gtgcctttgc tcctgtcaga   5760
ttaccctctc ctagaccctg tactggagaa tctcatactt ctcatttgac actaagcttg   5820
gccatcatct cctctgcaaa gcctgcttag acctccaaac tgtctaattc caattctggc   5880
tcatttcccc tccctcttct ggacttctgt agcccatgta cttcctctat cccagcactg   5940
ttcacaatgt gtcttcagtg tatgccattc ccaccagttt agtagctccc ctagcacagg   6000
gaccagactc atctatctct gtgtctctac aatagcctga gatagggctt taggggtaca   6060
ttagatctca gcaattattg ttgagctgaa cttatgacta gaaatgcacc ccaaattact   6120
ctcttacctt tgcatagatt ctccatcttg ggcgaagggc cactgtccct tcatgctgtc   6180
ggaactccag gatgggaaga gcaagattgt gcagaaggca gccccagaag tccaggaaga   6240
tgtgaaggct ttcaagacag gttggagtca agttccacct tatgcaacct ttactcctaa   6300
tgcttgaaca cactacgtca cagtcctgag ctaggctaat acaaaagcag ccagtacaca   6360
tcccatgatg agaagtccag tctttccagg ggagccatgg taggcaacag tttaggctgt   6420
atgctgaagc acaccatacc tgacaaacac atatgtacgg gctcctgaaa cttttagtca   6480
ttattctaag atgagccctc tagaattttg actcctcttt ttcaggtggc taaactgatc   6540
ccaacaggct ggggtcccac atttcagcaa gaccactcta tgagaatatg gatttgcatg   6600
aaagagaaag agctgggagt aggtacctcc tttaaccagg gtgcagatcc ccaggtcaac   6660
ttaattagtg cagaccaccc aagataatca ccccttgagat atggccacac tgttgacatc   6720
tttcataggc ccctttggga tatcattaag gacaaaaact tcaaaattga aatttaatga   6780
tgtttagaaa agaagagtaa ggtacattat cctgcatcta ctttctaaat gcaggaccca   6840
gggtggctgc tccagttacc tgagccaagg gaaaatccta gtggagagaa gtatgattca   6900
ccttatagaa ggtttcctaa caatgtaata gtctccattc ggggggataa atagaagctc   6960
accttggaga agatttcttc tcgctgtaga agctgccctt accttataaa cttgaatttt   7020
catgtgttgc attgagctta aagaggacaa cacatgcttt ctttttcccc cattctcttc   7080
acggccaatg aatctcacat tccgtctcag atctgcctag ctccctggtc tcagtcagcc   7140
```

```
taaggaagcc attttccggt ccccaggagc aggagcagat ctctgggaag gtcacacacc   7200
tgattcagaa caatatgcct ggtgagtttg ctgaggtgga aaaaaagggg accggaatag   7260
ggaaggcatt ctgaaagggc ctctgtcaca gtaggggaaa cagtacagaa gggccttgga   7320
accaaaggaa atttgagttt aaaatttaat gctggcactt gctggatcta ggtgttttgg   7380
caagtaagac actttccttc agtggcattt aatacctacc tcaataggtt accatgagaa   7440
gaaagtgaaa ttacatttat ggaagtgttt ctaatgaggc ttcattaaat attaggctta   7500
tttccattat ttcttctcta tgcttccctc aaaaactttc acccttcata cagcaccttt   7560
tccccattct tatatgtgtt tatattcctt tccataatga catttacatt attttctaat   7620
gtaaaaggaa tatgattcat ggtaaaatat ttttcaacat atacaggaaa gtataaggag   7680
ggaaatttaa gtcatgcaga gttccaccat taagtttttg ttatattttc tcccagatat   7740
ttttctatgg ctacacacac acacacacac acacacacac acacaccctc tgctctcttc   7800
accacaccca tgcttttgtt agaagtgtga tcttatttta cctggagttc gttatgctgt   7860
tttgttcact taaaaatatg tcatgggtat agtatggatt caatatcatt cagttaatca   7920
agcatctata atttaagttg tttccaattt tttgtattct ctcagtttag attgtaggtt   7980
ggttttacat acatacaaat gtactcaaag aaaatgtata gtattacttt tttcaatttt   8040
tatttttacc taataatatc ttgctatata ttttactctg tgcccttttt tcactcaaca   8100
atatactgtg gaaatgcttc cactttaaca catatgtatc taccttattt ttcaatgctt   8160
caaaatattt tgtagtatag atataataga gattatttgg ctactcctct atttggttgc   8220
ttccaatttt ttctattaca aacagtggtg caacaaacat ccttgaatgt atctccttgt   8280
gtacacaggc aagtgtttct ccaggataaa cactcagtgg tggaaattct tgggatgtaa   8340
ggatgtgtac atttttgata ttaatacatt ttgtcaatta gccctccaac atggctgtac   8400
cagttatcaa ggagggtatc catagtctca taccottacc agcccttgat attatcaaac   8460
tttaaatctt tatcaattga taggtgaaat tttgttttcc cagttttatt tttcctgatt   8520
aagaatcttt ttctacattt attgaattgt ctgttcatat tctatgccca tttttctact   8580
gagttgaaat ttttcatgtt aatttttcag agattatata ataaattctg agtatcaatc   8640
atttgtctgt taagtatgct gcaaatattt ctctagatat gtcagtatgt gcatttaaaa   8700
aactttttgat atgtatttcc aaacatctct gcagcaagga tgttaccagt ttgcacctcc   8760
agcagccata taaattgctg tctgcaacat gatttctgtc tcacgtaaag agttctagag   8820
tttaacaagc tctttggcaa acgttatttc aatttatcct agaaataaag ttaccccatt   8880
ttgtagtggt aatggttaaa gaagtgggct ctgagttact tacttgatga acacttactt   8940
gctgcatgac cctggtcaag ttgtctaaca cttaatgccc cagttccctc atctgtaaaa   9000
tggagatact aatagaactg tccatggagc attgttgtga ggaataaatt aaatatttat   9060
aaagttccta ggaaagaact tacatgtact aggcattcat taaatgttag ctataatgat   9120
gtaattgaat attagctatc tttattagta ttattatgac tactaatact atagcagtaa   9180
taatactact attaccatgt gccatttatt agtttgaata tattacatgt tgttggttgt   9240
cagatgctca caactctcca aggaaagtat tattagcctc attctacaaa taaagaaatt   9300
taaagtaaga aagaagattc atgacttgtt caaggccaca cagctaggaa gtggcaaaga   9360
gatcgctaga aacaagatct gttgatactc cttccagtga gactgaaagc agtgattcta   9420
gtaaggaggc tgccacacca acccgggaag agagatgagg ccataagaaa gtctaaatga   9480
atgtgtgaat gaactactga gtgaatgagt gaatgagtaa gcaaaaggat ggctgaatga   9540
```

```
agtagtagag agttaatgtg gtccataagt caatgactga gcaaataaat gaatatgtgg   9600
aaaaagagtt ggagaactca aaatcagcaa catgggtaaa atacagacta gccagggaga   9660
gacttaaaac gaattctttt catcctcata tctgctcctg caggaaacta tgtcttcagt   9720
tatgaccagt ttttcaggga caagatcatg gagaagaaac aggatcacac ctaccgtgtg   9780
ttcaagactg tgaaccgctg ggctgatgca tatccctttg cccaacattt ctctgaggca   9840
tctgtggcct caaaggatgt gtccgtctgg tgtagtaatg attacctggg catgagccga   9900
caccctcagg tcttgcaagc cacacagtga gtagtaggct ttcagccatc agcagtggcc   9960
agaggagatg aaaaaccaca catggaaaaa aaaaaaaggc agagctggca gtggaaactt  10020
gggttctatc accacttctt ttgtccaagg tcctccatca tatctattcc ttggatatga  10080
aataagtcaa cacaccatgt ttcccaaact cttcggtgtc caatgctatg gaggggaagg  10140
atgggagacc aagcaaggcc cactctgcct gagtttttaa tctagctgca gaattagtat  10200
tgccagagat ggagtgtgac ttcctctagg tcttccaaac tactcaagct caacctagct  10260
tctccctctc tccctgagta cctccagtcc tagaaggaag gcacatgtct ccctatcctc  10320
cccatccttc cctctacttt gtctcatagg acacagttta tataggatca ctaactcaac  10380
attgactccc atcaaggaag agaaacctac ccagttcctc gatgcctgac aagagtttct  10440
ttttctcctt ttctcctgtt ttctcctggc cagggagacc ctgcagcgtc atggtgctgg  10500
agctggtggc acccgcaaca tctcaggcac cagtaagttt catgtggagc ttgagcagga  10560
gctggctgag ctgcaccaga aggactcagc cctgctcttc tcctcctgct ttgttgccaa  10620
tgactctact ctcttcacct tggccaagat cctgccaggt aagcctgagg cctgagcttt  10680
gttcagggct ggtatcctgc aatacagcat ccagtttcac tggttccatc actccttccc  10740
tgtatttgga gttccctcac tcccattgtt cttccttctt atccaccttg catatcctca  10800
acactggata attatatccc tctgctttct ctccttctgc acgtagagag gaccattacc  10860
ggggaacatt accccacctc acagaaagga aacactataa attcatcacc tcccaactca  10920
actgagctct taacacacat acatagttat tttatgtctc cacaggagct ttttcaaact  10980
tcttctcctc ttctaaaacc tctgactacc ttctcctcca cacttagcaa ataacctcac  11040
atcttacttc acaataaaaa cagaagcccc agacagagaa tccttattta ttgccaccaa  11100
acctacgaac ttatctaatt gtttatctag ccttgcctca ttctttcctt ttacaatgga  11160
aggcatatct ctccttctgc ctaaaaccaa tcccttcact tgtacactgg ttcccatatt  11220
cccagtctcc tactctctag tctgtaatgt cctcacctca tacgccttgt tgtccttccg  11280
ccaaggccca atccagaatg aatacaaccc tccatcttca ctatatcaat tccgggctca  11340
tacagttgct cagacaggag tcactaaaaa ttcatactct taacctctac tgggttctcc  11400
atggtctctg acaatcccat ttccctggtc agttctcgaa gtttatgggg cagttttgcc  11460
aaaccaccat tatcctcagc cttcccacac cccctcctcc ccatctccct cagcagacaa  11520
cttcatgttc tactacattc aaaatagaag ataccagaca gcaatgtcct tgactcccag  11580
ccacaaagca cctacaaact cataagcatc ttcaaatgtc ctctcctcac tccttctctt  11640
ctgtcatagt ggaagaagta tcctttttct tgtgactaat ccttccactg ttgctctgtg  11700
ccccattccc ctctaccacc ttaggaatct tgacctattg gctctctcct cctctcctgt  11760
atcttcagcc tctccctctc tttaaacatg ttttcaagtc tcttgtatct tataaaaaaa  11820
cattgcctca acccctgatc actctctagc tactgccctc tttcctccct ataacaggca  11880
```

aactgcttga gagaagtctt cgctcttact atctacttcc tcacctcctg ctgattcttc 11940
agcacagcaa aaatattacc accacttctc agaaactttt tttgagtcca cccataagcc 12000
ccaactaaac tcaacatctt taagttgttt ttagtccatc ccctcctcaa ccattaaact 12060
tctttccatc tctactgcca gcatcctagc ctgatccaac atcatttttt aaagaaaatt 12120
ttacctttgc cctccgataa tctattcttt acaacagtca gaattttttt taatgcaaaa 12180
ctatctttgt caccccaccc tcagccctgg tcaaaaccct ttagtggacc cccattcccc 12240
caggaccaaa tccaaatttc ttatcacagc ttctaaagtt ctcaataatc tggcttctat 12300
gtatctcttc ggtctcacct ttttgcatcc ctcctctcac tatttcattc agtaatacat 12360
tcattcatat actcattcac ttacttataa atctgtcatc agtttattta tccattcatt 12420
taataaatgt ttacttagca tctactgtgt gcttactctt atactggaca ccagagacag 12480
agagataata agatgttttt gctcccatgc aactcccagt ctgcttgtct ttcaagccat 12540
tttctccaga aagccataac tcattttctc aggtggaagt tatcccttaa tcttataata 12600
aggccacagt tccttgatgg cagtgcagtt ggtggcaggg gttggggagg tccaggaatc 12660
aactccctct accaatttca catgcccacc tgccccacca ggattgccca gtaaaaagcc 12720
ctgcattctt caaatctttc tggaccttag ctttctcact tgtatagtaa agggatgaat 12780
cccatgatca ctaacagccc tgccagctct gacatgccat aagcttatga ttccaacagt 12840
aaaagcctga taaatatcca tccctgtaac cacaagcaga tgctacctgg aatggatgga 12900
atttcatcta gactaggaac aatctagcat cagtccgagt caacaaacat tccctggggt 12960
aatccctttt tcaagtcttg atcttatata ttggggagaa ggaaaatagg tcccgtcctc 13020
aaaaaactct gaagcttctt gggaaattaa atgttcttcc accccaaggc agtcagaggc 13080
tagaccaggg ttacaaatga ctggagggaa ggatgtaggg gtcagaattt gggaacagtg 13140
aagtccttcc aagggagaaa gaagtgtcac aaaagttccc agagaaggaa gaagcagagc 13200
aaggtcttca aagggaagaa agggttggcc cttttctttg ccaggtcaaa cctgaaggtt 13260
gaagtgggag tactgggaca gaagcttaag gattatacat ctgcttcctc agggtgcgag 13320
atttactcag acgcaggcaa ccatgcttcc atgatccaag gtatccgtaa cagtggagca 13380
gccaagtttg tcttcaggca caatgaccct gaccacctaa agaaacttct agagaagtct 13440
aaccctaaga tacccaaaat tgtggccttt gagactgtcc actccatgga tggtatgtat 13500
atgagtgagt gtatgtttac tagtgttggt ctcacaaaaa ccatgatgat catgatgatg 13560
atgatgacga taacattata acagctaata tttatagtgt ttattatgtg ccaagcaaaa 13620
ttattagtat tttacatgta ttaattcatt taattttctg aacaattcta tgtgataggt 13680
gttattatta ttttgatttt ttacatgagg aaactgagac ataagagtaa tttgtccaag 13740
gtcacacagc tagtaaatgc caaagaatgg aggcagctat tacattcatc ttataggtaa 13800
agaaactaaa gttcagagtt ggcatccaat tcatcttgag tggctcagca agttggtgct 13860
aaagtgagta tctgcaccct aacacatata actccaattc ctcgagtaac acttctcttg 13920
ttagaaatga tatgtaaatc aataatccca gtgtttggtt tttatgaagg aaatttcaaa 13980
aaccattgcc taggattttt ttcaaggtcc agtatgaagc attggggtca aaacaggttt 14040
tcaagtcaga gagacctggg ttcaaatccc acctttgaca gttactggct atgaccatgg 14100
gtaactcttt aactgtctaa gcctcaattt tcccaaaggt aaaatatctg gttgtaagaa 14160
ttagagatga tagaaaccat tctagttatt atgctttagt agaattaaat gatcttcaca 14220
ctcctacctc ctttctttgc tcaattgaaa caatgtccaa agctttctat tgctggccct 14280

```
gttgtgtaga aatcatgtgt tttaggcatc ctcttatgga tttatttaag ggaagaggtc  14340
ctcaactcat ttcagtttgt ccctttttcca actgaaacaa aagagtccat agtattccct  14400
gatttaggta tcttaagtgg catgtaatga ctatacacac aggctctaaa accagactat  14460
ccatgttcaa atcctagcat gaccatttac tagcttgggc aagcttctta attgctctgt  14520
gtctcagttc tcagttgctt atttgaaaaa tgtaagtgat aataattaaa taggtatgca  14580
aattaaatga gttaatatat gtaagaaact tactattatg cccactccca catttctaac  14640
actagcaata aagtaaaact atcctatccc ttttgtatat ttctaccact gagactattc  14700
aaattcatta tttctctagt ggaaactatg ttggtaccat tctacctcgt tacatttgca  14760
aataaatagt tatttaccta tttttggggt gcaaactctg cccaaactgt tgatccttag  14820
gctgaatctc tcccattgaa atgatgctag gctgaacaca gcagaaacag gaaaatagac  14880
attgtcagaa tgaagtaaaa acagaaagac aaagagtcaa gccttgatcc caggctgggg  14940
aacacacaca catgcgcaca cacacgtaca cacacacaca cacacacaca cacacacaca  15000
cacacacaca cacacacaga gagacagaga gagagagaga gaaggcaggg atgagataca  15060
ggcaatcgat ccatacacag aggtttgtaa tagttctaaa tgaaggcgca catcctcctt  15120
cctctctaca acaccctttt ccaacccaaa gtaggcatgt atgggaaatt ccacattgga  15180
gatggagctg gggaagggtt atgatgtcct acctctatcc cttggctttg ctcaggtgcc  15240
atctgtcccc tcgaggagtt gtgtgatgtg tcccaccagt atggggccct gaccttcgtg  15300
gatgaggtcc atgctgtagg actgtatggg tcccggggcg ctgggattgg ggagcgtgat  15360
ggaattatgc ataagattga catcatctct ggaactcttg gtaagtgaat gctttgggcc  15420
ttcttatata ccctccagag aggaggccct tacaaaattc ttttctgcct cctccccaaa  15480
gctatagggg ttgtttggac agaattcaca gccccaggct gctgccatcc tggactccct  15540
ctctccactc gcatcccact gcagagttga tgagaaagtc tggtagagtt ttttgaaaag  15600
accttgaact aggccaaata gttagattca acttgagtat gtgaagagct gtgtttctaa  15660
acccctcccc caccctagcc ccaagcttca tcttagctcc actcctgacc ctatccagct  15720
aaaggtcccc acccagctcc tgcctatcta gtcattgcat atggcaagac ttgaaagtcc  15780
tatctcaaag cagcagaatt atcagctacg actgccttgt catggacaga tgagcagagg  15840
cctgggaaga cagcctggag ccccaacttc tggtgcaccc ccttgtgtta tctggcacat  15900
gatcctgttg ctctgggact gattatggga tctgtgtata tcttattcct ttctgtctcc  15960
aggcaaggcc tttggctgtg tgggcggcta cattgccagc acccgtgact tggtggacat  16020
ggtgcgctcc tatgctgcag gcttcatctt taccacttct ctgcccccca tggtgctctc  16080
tggagctcta gaatctgtgc ggctgctcaa gggagaggag ggccaagccc tgaggcgagc  16140
ccaccagcgc aatgtcaagc acatgcgcca gctactcatg gacaggggcc ttcctgtcat  16200
cccctgcccc agccacatca tccccatccg ggtgagagcc ccaccatgcc cattgccctc  16260
tccacctatt tattctggga gcctcacgct cccaacaaac ctacatctgt tgctgtcttc  16320
aattatttgc tttcctgcta accattccct ttattgccag ctttgtttcc ctttttgaaa  16380
aattatcagc cattctggat taaccagtct tttccttgca tcagccatta cctcatgctt  16440
attagattat cctaacccta acaatagcga gtgctcacag cctataattc agagtttttc  16500
aaactggatc aagacaatta atgggtcaca aaatcagctt agtgggttat cattagcatt  16560
aaaaaaagaa aagaaacaga aaatgttgga gtacatcaca tactaagggt atcatcaatt  16620
```

tgtgaaaaat ttgtatgcat tttgggtatt tgcatataca catgtatgtg tatgtgtgcg 16680
tttatggtca cggtgtaaaa cgtacttctt attgagaaat gagggcagaa aaataaaatc 16740
aaaagccata ggattagctg ctactttgga tcctcaatat gagcatttac tgcctttaaa 16800
aatgaactgc tacttctttc ttaaataaca cgtatttgtg tgagtcagta agccagggca 16860
gggaaaggac acttatttgt gacaattttg tggatgagaa atagtcactg ctctttagac 16920
taacctagta tttcctttaa acactcattt tatgaattaa tttagtgaca gcaccccaga 16980
attggcttgg cgggggttcc agaattggct tggtgggggg tatcttctca cccagaacca 17040
tcccaaacta agatattagc taagtaaaat cagtgtgctt gctctgcaaa cagcttccaa 17100
acagggctcc tggtaccacc tctgctccat ccttttcaaa ccaaattgct agctctgagc 17160
tcctccttga tagaaattct ggagctgcca ctaagcccct aatggaaaaa aaaaatctat 17220
cccaaaattc agtgatgttc cctcatctag ttccctccat ctgcttaatg gagctagtga 17280
tggtggagcc agagtggcag gtactgatta gcctttctcc tgagtccagg tgggcaatgc 17340
agcactcaac agcaagctct gtgatctcct gctctccaag catggcatct atgtgcaggc 17400
catcaactac ccaactgtcc cccggggtga agagctcctg cgcttggcac cctcccccca 17460
ccacagccct cagatgatgg aagattttgt gggtaagttc tcaacatggg tgcctacagg 17520
acctccctcc cctcagcccc aggatctgaa agagaagctg agaggacaga gaccactgag 17580
tttacaaaat atttctggaa catctaatgt gtgccagcac ctatactagg gtcacaaata 17640
aatgagaagc agcccctaca cttgtagggc tccagtttgg ttggggatac catagtgaac 17700
acaaacaatg acactaaggg atgatcaaag ctccacaagg cagtgcatga tagagttgtc 17760
ggagcagaga ggaggggcct gactcagcct gagggatgca agacccactt cctagtagag 17820
gtgacacctg agctgagtct tgcaaagtga gtggtattaa aagaaagagg gcatggaaga 17880
agtattccta ccagagggaa gagcatgaag ataggtgagg agaatgagaa gcagccaggg 17940
atatatcaag aacaataagc aggtggtatt ggaatgtagg gtcataggaa tggagtgggg 18000
caggggagta tcaatctatg agtctacaaa gacaacatga gatagagact ggattgagag 18060
gcttgtagag ctgagtagtt tgagatttac cctgaaaatg ccagtttagt caattcacct 18120
aatgtttgtt ggatttctgt tgggtagttt tgtttttgtt tgtttgtttt tgtttttgtt 18180
tttttgagac agagtctggc tctgtagccc aggctggagt gcagtggcac gatcttggct 18240
cactgctacc tctgcctccc gggtcctggc tcaagcaatt ctcctgcctc agcctcccaa 18300
gtagctggga ttacaggcac gtgccaccat gcctagctaa tttctgtatt tttagtagag 18360
atggggtttc accatgttgg ccaggctagt ctcgaactcc tgacctcgta atccacctgc 18420
ctaggcctcc caaagtgctg ggattacagg cgtgagccac catgcccggc ctgggtagtt 18480
tttaatgcag ggcctgacat tgaataggtg ctcattccag gcctgttgga tgaaagacat 18540
gtaggcagtt gatggtctag cagaggagcc agatatagat ggtactggtc cagtatgatg 18600
agctccagta ttctgggagc tagagggagt ggacacatta tggagagaga gggtgggaag 18660
gatgaaattg gagaggcttt gtgagtaagg aagtttttat gatgcatgtt gaagtacatg 18720
tgaatatgtt gtaagaatat tccagaataa gggaattcca cgagcaatga cctagagata 18780
ggaaagcagt gggtatgtat tgacaacata attctgtttg tctgaagcat gggcagtatg 18840
agaattcaag gaagacaagc taggtaggcg ccattcattc attcaaaaac attaaataat 18900
gctggctaac attaagtact taccatgtgc caagcactgt tctaaacact ttacacgtat 18960
taactcatct aatccccaca acaacctcaa gagttagaga tcctcttatc atttccattt 19020

```
tgtacatgtg gaaattgagg cacaaaaata tatagtcgct gatccaaggt cacacagctt  19080
ctaagttgca actgggaggt ctgtctctac ctccatggtc ataactgcta ggtctaccac  19140
ctctctgagc tgatgaccca gactcctggg ccttttgttc agtattctct tttgctctgg  19200
gcttcaattg tagagctctc agtattcttg gttctctgaa tgtccaccta ggctaggctt  19260
ttgtaagaat atatgaggca tccacgatgg ctccaccagt ccctaagttc catagccaat  19320
ccatcctgaa atcctgcaaa agttatctat aatctctctc aaacctattt gcttttctcc  19380
cctgccactt ctttaatcca tgtcaacatg atttttttcc taatttctct gcttctctct  19440
tgctcctctc aaatcctttc tcgatgatga ccactagagg gatttttcta aaattctgac  19500
tatattgctc ccttgcttaa accccttcat gtttccctct agactctaaa gcagtgacct  19560
ccaaggggta tgcaaaatga ttacagggtg aaggaacaga atatgtatta gaattttatg  19620
tttttttatc ttaaaaatag gaaatcaagc atcactgata ctgatcttta atatacagac  19680
tgacagttat acatgtatat aatatataaa caaatataga gattggaggt acatgctaaa  19740
acatttgtac tgatagggat gtatagtcca aaatttggaa acattgacat ataggacaga  19800
gttgaagctc ttcagcatag cattcaatgc cttccacatg gtgatctcta tgccctcacc  19860
tcctccccac atgcatttg tttttcagc tacactgaag gacttgtcgt tccctcattt  19920
ttttctgctc tcttacctct gggactttgc tcatgctgct ctcttttgat tggaatgccc  19980
tccctcacac tttcctctgg cttactttcc ttcatcttgt agacttaact taggcattct  20040
ttcaacaaat atttattgag taccaactgt gtactagata ctgttctagg cactggggat  20100
gcagtagcaa acaaatcaga cacaaaattc ctaccctctg gagcttacat tctagtggaa  20160
ggggtagtaa aaaaaattac caaaaataag caaattaagt agcacattag ttctaagtgc  20220
tatgggaaaa aataaagcag gataaggaga atgggataag gggccagggg cgagttcaga  20280
gaagggttgt agtattagag tggcaagggt agaagacgct gaggtgaaac ttgagcaaaa  20340
atttgaagga ggtgaagtta gtgaggcaga tatctaaggg aatggcatcg caggcagagg  20400
gaacatccta aggcagggaa gacacaggag tattcctttt atatttgagg aacagtaaga  20460
agatgggtgt gggtggaatg gtataagcaa gtgggagaca gaaaaattga gtacatagag  20520
gcaatgtggg accagattgt atagggtatg gtaggccatt agaaggagtt tggcttttac  20580
tctgagagcc cttgaaagga tttgaacaca ggactgatat ttctgactcg ggttttaaca  20640
aaattgctcc aacttctatg tagagaatac actaaaaggg agcaagggtg gaagcaggga  20700
gacccaagag tgggctacag taatatccca ggtgagagat gatggtggct cagacttgat  20760
cataatgaag gcaataagaa gtggtcagat tttgaaggta gagccaaggg tctttgctga  20820
tagatgggat atagggtaag agagaaagag aaaaataaag gatagctctg aaatttttgg  20880
actgagcaac tggaattgcc atccactgag atgggaaaag ctaaaagtag aatagcttgg  20940
tggagggtag ggacatgagt agctcagttg tactcctaag ttagaaatgc atattagaca  21000
tctaggtgga gatggagaaa agccattgga tatacaagat tggaaaccag tagagtggcg  21060
tgagctggag attaaaattt ctgaaccatc agcatataga tggtctttaa agtcatgtga  21120
ctagacaaga tcaacaaggg catgaacaca gaaaaggcca agaacagagc cctggaacgt  21180
acctggggta cttcctccag ctaggtcagg ttcccttctc tgggttttca cacccccagg  21240
tggacccccct accccaggtt tcctggtcat agcaccaatg acacagtata gttactgtca  21300
ttatcattgt cctcataggg cttagagttc ccaagcagac agtcattctt gggccacagc  21360
```

```
acatcctata cttagggagt ggtccaggcc aggacagtat ggcttcaaat tgtgtcaaag  21420
gagagcttcc aaatctttta taatatatat cccagcatcc agatacaaat ggtaatattc  21480
acggcacaca cagaagcaaa cagtaggcta cttctggccc tgaggtatct tgaagggttg  21540
agggggatca atatcttggc tcatctgtac tgtgacagat ttggaagatc tagtctaacc  21600
catttttcc ctcccctccc cctaccacct tcagagaagc tgctgctggc ttggactgcg  21660
gtggggctgc ccctccagga tgtgtctgtg gctgcctgca atttctgtcg ccgtcctgta  21720
cactttgagc tcatgagtga gtgggaacgt tcctacttcg ggaacatggg gccccagtat  21780
gtcaccacct atgcctgaga agccagctgc ctaggattca caccccacct gcgcttcact  21840
tgggtccagg cctactcctg tcttctgctt tgttgtgtgc ctctagctga attgagccta  21900
aaaataaagc acaaaccaca gca                                          21923
```

<210> SEQ ID NO 42
<211> LENGTH: 31438
<212> TYPE: DNA
<213> ORGANISM: Homo sapiens

<400> SEQUENCE: 42

```
gcaggaaggt gggcctggaa gataacagct agcaggctaa ggtcagacac tgacacttgc     60
agttgtcttt ggtagttttt ttgcactaac ttcaggaacc agctcatgat ctcaggatgt    120
atggaaaaat aatctttgta ttactattgt caggtaagtg attttatttc atcttggttc    180
tgttatattg ggtatgagat catagaataa aatatgaact accctatttt agttctatct    240
tatttaaatc aataaatgag tagtatttcc tcttccagtc tggtggatgg attttactgg    300
aactcagcta ccaatgtggg ggaaatggca caagggagcc cagtatttat ggccaaatcc    360
agttttctag tatgagaagc ttacttcaat tctaagtcta gctagaatta aaataatttt    420
atcaaatgct atgagaaata cctctctgtg aataaatgta ttgctttgtt tgagttataa    480
ggagattcat ttccaaacta aagagttatt aacgaagatg ttggtagcta tatggctttt    540
agttttcaaa aggtataatt tcctatttct gccaaatggc gagaagccaa aagcatgaac    600
actgaaaccg tggggagttg ttcgcttctc tgtgggtcca ttactaaagt gtcacatagg    660
aagaaaaaaa acaaaaacaa ctcttactgg cttaggtatc ctgtgaattt taggagaaat    720
ttaaatccat taaaataaag aaatatcata gggttattat taaattgtat taattcaata    780
atttgaattt aacttagttt aaatttaatt attaatttag tgtcttaaat taacatgatt    840
ttggcctctt tctgagaata ttatagttaa acatcctctc aagtgcagtg cttatgtgtt    900
agcaatacta gtgcccagca cacagcgggc aggcagttgc ttgaaacatt ctgagtctat    960
tagacattgc tgtatcccaa gtgagagcaa gtatcaagga gctactgagc actctgtagc   1020
acacagggag gagagatcag cattttctaa gataccctag gggaggataa aatagtgcaa   1080
tagttaagag cacaggcatg aggaacagac agaactgggt tcaaatctac ttttacttct   1140
caaggctggg gaacattaag gcaaattatg tgcccacatt tttatgtgtc ctcgtcttta   1200
aaatgcaggc agtgttggta cttacctcat aataattgca taaagattaa acaaaatatt   1260
taatggaata cacttactga tgcctgaaac aaagtaaaat gttaagatta ctatgcattt   1320
tctgtgatta gaattaacta tcatgattaa aaagtattaa taatatatta ttaaaataag   1380
cagtagctat caatagttac agactaggga acaaacctac gtatgtgatt ggtgatttct   1440
gaaaagtcag agagaaaaga aaattacaga aagaaaacag aaaacaaaca tagctactct   1500
aatttttttaa gcagaaaagt atgaaaacat ttagtttgaa gaaaagaaaa caaatgaaag   1560
```

```
ggatgtagtg taatatttgt atatatattc atatatttga agtgctatta cacagaaaaa   1620
aagatgtatt ctttgtgttg ctccatgggg caaaccaaac tggatgtaac tcaagcaaaa   1680
ttagacactg catactctac tggggggtgtg cccagcattt gggaaaactc tgtgtgactt   1740
acaagtgccc caaatttgga aagggttcct ggcaaagaaa tgattttttt tttaaatttc   1800
tacaactaca caagcagata gtgtattaaa gccttaaatg gcacttggtc actggggcaa   1860
gatgaccctg aaagctacaa tggtctccag tacccaagct gttatcatct ttgtagcttc   1920
agaaaccctc caaggaaact ctcttgatgt ggctacttta tagtataaca gaaaggtgta   1980
agatcaagtt tttcccccat actgattagc tgaagagtaa acatggtgaa gtctttttct   2040
ttttctttta tgttgctata aaaaaaaaga tgattgcctt gctttctcca ggaatcttaa   2100
gaataaagcc aatatttcta attctaaact taccagagat ctccttccaa atggagaatc   2160
catttttttct aatatgactt gattcccagt ccctgaattc ctgcactcat ttgatgattc   2220
agtcattaca tgtcagattg tgaaccagac actgagccca cagcaggaag aaaaatgggc   2280
tcccatggag gatacacgga gggtaggcgc agtggatgat gggagggaac gcagataata   2340
aatggaacaa caactatctt attaaaataa gataaaaaca gtcaaaacta atacaaagca   2400
tataaaacca ggtaagatga taaacatgaa tgccgaaagc tgcttaagaa aagggtagca   2460
gggagttatt ttctgagtag atgacattta tgctaaatgt ggaacaagga gacggagcca   2520
accctgaaaa ttctgggaaa agaggacaga aggcagaggg aagagcaaga gcaaaaattc   2580
tgaaacagca ggtaagttag tgttttcaag gaaaagctgg agcttttatc tgaaaatcag   2640
attctgaagc taagaaccaa tttgaaaata caatacaata tcacttcgac taggaaatta   2700
tggcataaac caggagtctc caaaagcttt ttgtgtttac ttaaaaattc atacaaaatt   2760
tgcattctag gtcataatat actaatttaa ttggaggaaa caaaggcact ggtatgatat   2820
catcatgcct actttattca tccgtgtatc cccagaatct agcacagttc ccgattggta   2880
tttatagtag catattggtt gaataagcaa ggaaggaggt gaagggaggg agaaggagag   2940
agaagcagag agggagagga aggaagaaag aaaaggaaaa agggaaggaa agaagagagg   3000
agggagagag ggagggaggc aagaagggag aagagagaag ggaagggaag agacaggagg   3060
aaggggagga ggaaaggaaa gaggaaatat ttgttttcat ctggttagac acagtgagtg   3120
ctccgcatag acagatcatt attaccctgt gcatctgact catacccctg caagtacatc   3180
agtctgagaa gcacatgtta agtgaagaaa caaggcatct cttttttttt tttttttcag   3240
ggatccaaga agagagcctt gctagctgct atttaattgg cacaggaaag agttacagga   3300
actgtatgcc agggaataca tgactataaa ttctttaaaa gcaaaacctg tgtcttcgct   3360
tatgtgtccc acacattgtc agccacatag taggcagtca atatcaacta ctcaaaatga   3420
caaatgacaa atgaccagaa ttctgcggca gactagttta gccatgaaaa atcatttaac   3480
acccgtgggc ctcagttttc ttgtgcctat tcaataaagc gccgagtaga tggtatctac   3540
aagcattttt caactgtaaa ccccaatgaa tccccaaaat tcagcctgag atgagctgga   3600
ctagttgcca aacctataaa tatctttagc atggtgtgaa atagggtttt tagaaagaaa   3660
cagacaccca ctgtgaactc ctttgcagaa aaggtctgaa tagaggggaa agtagggatg   3720
gtatctcaaa cttactttgt agtgatttta aattaggaaa tttagcttca cattcttgtg   3780
ataaatttct tttcaccttg gtttctagaa gattattcaa aacatctgtg agactatttg   3840
agaagtatac ttttggggaa tttccccaag ttatctttat agattatatt ttgacatcaa   3900
```

ctgcaaatgt aatatctttt actcaaaaaa aacccaatcc tacttacatg gtgctgacaa 3960
aatcaggctg gacctacatt tttacatcat agatttccag ccattattat catatccaca 4020
tctttagtaa gtacctatct gtgtagtttt ctgtgataaa tgaactaaac taaaactaaa 4080
gcaaaaatgt tgaaaaaaaa ttccaggttt atctctgagt gttgggattg caaggttttt 4140
ttttctcatt ttaaatactt tctaaatttt ctgcaaagag aaccatataa tctaatcagg 4200
acaagtttta atatatttta aaaagtaaac cgaacaaaca caatctctgc tttctaagaa 4260
gtctttaatt tttgtacgtt ggtcatagac tatgactata caatttattt gtgatatgta 4320
ttaagaattt ctgtctaacc caaattatta tatgtaagca cgggaaaaat gatgtcatct 4380
ttgtttgtag tgtacaaagt tctataaaca gctatttgat caactttggt atttccatcc 4440
ctagatttat atacagcagg ttaggttcca tacagaggca ggttctgaat aataataacc 4500
aacactgata atagcactta ctttgtgccg tgcactgttc taagcaattt acatacactt 4560
aatttttaaa attgtagtaa aatacacata atataaattt accatttgaa ccattttaaa 4620
gtgtacaatg ggtagcattt aatgcagtca aaatgatgca cacccatcac cattatgtag 4680
ctccagaaca ttttcatcac tccaaaagga aacctcttac ccattagcag ccacttccaa 4740
ttcctccagc ccctggaaac cactaatttg ttttctacat ctacagatat acccattgta 4800
gatatttcat ataaatggaa tcatataata ggtagccttt tgtgtatgtc ctctttcact 4860
taaaataatg tgtttaaagt tcatccatat tgtagcatgt atcagtattt cattcctttt 4920
ataattgtgt tggtatatct cattttgttt atccacccat catttgatta aaatttgggt 4980
tggcatatca cattttgctt atcgatccat catttgatta aaatttgtgt tgtttccacc 5040
ttttggctat tgtgaatagt gctgctataa atattcctgt actagttttg tttgaaccca 5100
cttttaatac tcaaagatgt ataggggtag aattgctggg tcatagtaat tttatgttta 5160
acttactaag gaactgctca actcttttcc acaggagctg caccttttga ccttttcacc 5220
agggtgtatg aggtgccaat ttctccacaa tcttgccaga aattgtactt tttcattttt 5280
ttaattatag ccatttcaga gggtatgaaa tggtttttca ctgtggtttc ttgcattttc 5340
ctaataacta atgacgctga gaatcttctc atgtaattgt tggtaactgc attttgcata 5400
tctttggaga aatgttggta ctagtccttc acccattttt caatctattt ttctttttgt 5460
gttgctaagt tgtaagagtt ctttctatgt tctggataaa gagtcttatc agatatacta 5520
tttgcaaatc ttttccttca ttctgtagat ttttgttttt acttttgata gtgtcctttg 5580
atgcacaaat gtttttcatt ttcaagtcca atttattttt ttttcttttg ctgcttacgc 5640
ttttgatatc atatctaaaa ataattgcca aatttaaagt cataaaaatt tctccctatg 5700
ttttcttcta agagttttgt atttcttctc ttatatttag atctttggtt tattatcagt 5760
taatttttct atatgatgta tgataagagt ccacctttat tattttgcag ctgtcccagc 5820
accatttgtt gaagagacta tcctttgccc attgaatggt cttgacaccc ttcttgaaag 5880
ttaattggcc atggatatat gagtttattt ctggagtctc aattctatcc taagaatatg 5940
tctgttcttg gggcaaaatc acacagtttt tattgctgtt acttggttat acgtttttaa 6000
ttcatgaagt gtgattcacc aaactttgtt cttcaagatt gttttgccta tttagatccc 6060
taacaatttc atagaaattt taggattagg ttttccattc ttgcaaaaaa ataattatgt 6120
gcattttaac ttaacctgtt caataactct ataaggtaga gactaatcca tgtataatga 6180
tggaacaaaa atatagagat taagtaaatt ttgcaaggtc tcaggtagtt gctagaggaa 6240
ttagtttgag cctaggcagt tccactgcag aatctgtgca cttagagaat atgtcatgtt 6300

```
gcctgtacca tacctagtga tgttccagga ttggctcctt tactcttaca acattgtcac   6360
tcagtgttct gcctgtgctt tcaccaagct gaagacttta atgaaggttg acggtctgtc   6420
ttcctcacgt ggtgcagcta aggaactcta actgtgtggc tgttatgtta gccttttgct   6480
ccttttttata tgggctatag aaaatgtttt taaatcctgg aggcctcctt ttgatgttat   6540
cacttatttc ccagtcatca ctatattttt aaaagccaaa atagaaggaa ataaatacaa   6600
aacataaaac atgaatagta cagctatttg aggcaactga gaatagagat catggcactg   6660
aaattgcatt ttgctaggaa aaagaccaca aaagttctcc ccttgctacc tttcctgaac   6720
tattctgcta gattcagact tcaaaaacat tgtatcagga aatacagaaa tgttctttca   6780
aaatgagtgt atgggaatgt gggaatgcct aataaaatct gtcctcattg attcgttagc   6840
aaaaatcata taaatcaata ccttgtgatt gcaagcagat atatttcaga tcctttctgt   6900
gtttgttttt ttgctttctt gatctatcac aattggagaa aacttaaaat ttctcaatgg   6960
tattgtattt ttgccaattt cttattctgc tttatgtttc tcgttgctat attattgggc   7020
tataatggtc cataattact taagaatcac tgtgaaatat attgcttaat gacacaagta   7080
aatctttttc attgtttgta atgtctttgc tcttaattct actttgccta agattaatac   7140
ggttattcct gtttagtttt atatgtattt atttatttat tttgaagatg gagtctcgtt   7200
ctgtcgccca ggctggagtg cagttgcatg atctcggctc actgcaacct ctgcctcccg   7260
ggttcaagca attctcctgc ctcagcctcc caagtagctg agaatacagg cgcacaccat   7320
cgcgcccagt taatttttg tattttagta gagacggggt ttcactgtgt tgcccatgct   7380
ggtctccaac tcctgagctc aggcaatcca cctgcctcgg cctcccaaag tgttgggatt   7440
acaggcatga gccattgcac cagtcctaac ctatctcttt tgactcaatc taaaagtttc   7500
tgtcttttaa tacaaaacca caatccatat gcattcatta attcacaact gacatttagt   7560
atcttatttc tgttatccta tttcatattt tatgattcct tgtttctgct cttttgatat   7620
ataaattatg ttttatttgc ccttatcctt tcatgtgttt ctaaagtata tagcctacgt   7680
gtaattgtcc cattagctaa ctttatgttt ttgaaagcat tctctctcag aattcccatt   7740
ttagtggtgc agcacacata gaaagtctaa gtgctttctg gagctagata agctggataa   7800
aggtgtgcat gagccactgg tcaatggctt gtgcaggcgg tgagtgcatt tctggtattt   7860
catatgctat tgatctggca gccaggtatt cagatagggt ataaccaggt tcatcaggct   7920
caaaacataa tcaagtatta ttgagacata gttaatgtgc actacaactc acagcacaca   7980
ggctcacaca cacacttgtc tgaaataaaa ttccacaaaa taataccttc ccttattctg   8040
tgtgatgtac tttgatatat tctctcctgt tttatacaac ttaatttttt ttagagaaaa   8100
gattttgctc tgtggcctaa gctggactgc aacggcacag tcatagctta cttcagtctt   8160
gaactgctgg attcaagtga ttctccagct tctgcctctc aagtagctga gacttcaggt   8220
gtgctcaacc acacctgact aatttttttgg ttatttaatt tgtaaatatg gggtcttgct   8280
atgttgccca ggctggtctc gagctcctgg cctcaagcga tcctcctgcc ttggcctccc   8340
aaagcactgg ggttacaggc atgagccacc acacctagaa tacaacttaa ttttttagtg   8400
ccagtgacaa cccactggac tgatttcata acccattagt agaggaatgc accatcttga   8460
ctgaaggttg gaattttctc agggaatcta tgtagcactg atgattgggt ttcatatcca   8520
gagattctag ttatgctaat acagaggcca agcaaactat agcctgtgaa tggccggccc   8580
cctggttttg tataccttac aagttacaaa tgatttttac tttttaagt gcttaaaaaa   8640
```

```
accaaaatag gccgggtgca gtggttcaag cctgtaatcc catcactttg ggaggctgag   8700
gcaggcggat cacgaggtca gaggatcgag atcgtcctgg ctaacacagt gaaaccccat   8760
ctctcctaaa aatacaaaaa attagccagg cttggtggtg ggcgcctgta gtcctagcta   8820
cttgggaggc tgaggcagga gaatggagtg aacccgggag gcagagcttg cagtgagcca   8880
agatcatgcc acttcactct agcctgggca acagagcaag cctctgtctc aaagaaaaaa   8940
aaaaagaaag acacaaaaaa aatcaaaata ataataataa tatgtgaata ttatatgaaa   9000
ttcaaattct actgcccaca aatcattatt ggaacatagt catactcatt tatttatgct   9060
ttggtttaca tattgtctgt agctgctttt gcacagtgac agagttgaat atttgtaata   9120
gatggtccac aaagcctaaa gtagttgtgg cccacaaatc ctaaagtagt tactctctct   9180
ccctttacat aggaagttta ctaatacttg tgctaaggga tctcaacaga caatctgaaa   9240
aacttaagtt ttagactaaa gatttccaat ctaaattcct gtggagcttt ctgaagctgc   9300
caggtggaga tgggaacagg ttgtgaggct gcaggccaaa cactcaggcc agcttccacc   9360
aagcagttca actctgtctg tttcacacac tgatgagctt atccttggaa agtgattaaa   9420
gtaaaattaa atgcgaattg agggaggaag tgagggagac tgtggctcta aaacaaaacc   9480
ctaagaaaca ccaacattta agatggcaaa tgatgttatt tctaaagtcg ttcaggctaa   9540
tatcacatac tatagctgtt cactttatag ataaaggtga cactacaacc atagaaaatg   9600
taagagtgga cctcgaaact caggaagatg aagtttacat atattaatct atattaccaa   9660
ctggagcagt tgttctcact gctggccgca catcagaatc caattcctgg gatatcacag   9720
atgattctac catgcagtca aggatgagaa caaactaggt tcatttctgc aatttttta    9780
ttgttcaacc agtgaaaagg aagtaccagt ggtgtgagaa ctttgggata aagtttttgt   9840
tttcaattaa aattattttc atccagccca acttccttaa gcccaaattt aatgtgtgtg   9900
aagttcagct acagaaatac caaaccttag actaaagcgg acacaggtaa aatatgtgaa   9960
atcctctttt gttctgagga ttctttagta ggcaggagtg accagatagg aatatgcttg  10020
gctggaaaaa ttaagattca agttaacaaa ctgttaataa ccaggaccat ctgctcttcc  10080
gtaatgtgga tttgccactg caggtcaccc tacaatgcta tgttagaggt acaacactct  10140
taccctcagg ctataaacaa ggtgaattat tatctttata tctcttcatt tagccctgat  10200
ttgctgaagt gaaggctcgc ttgagagttg gttgcattat aatttggtga gaatttaatc  10260
tctcaatgac aacttacttg attccctcat tctctttctg ctacatagat cacagtagac  10320
cttggcagac agttctgtag ttacataggt ctgaattcaa aatccaggtc tgccacttgg  10380
tggctgtgtg aacttaagca agtcaggcaa tgcttctgat gtttttttcc tcctccacaa  10440
agaataatta acatataaca atagggtctc agctagttgt tttaaaaatg gttagagaga  10500
tgtgtggaat gaagtaagtg tgcagtaagt gttaactaca aatattatta tcttagacat  10560
acagatttcc atgattcatg aatggtgaag catcttagaa gacatccatt ccaggccagg  10620
catggtggtg tgcacctata gtccaagttg ctcagtagaa tgaggcagga gaattgcttg  10680
agcctaggag tttgaggcta gtatgggcaa tatggtgaaa ccctatctca agaaaaaagc  10740
aaaacatttt ttaaagttta aaaagagaga catctgttcc actactctca tcttagaggc  10800
cataaaactg aggctcagat aatttcagag acttgcacag atcccccaac catttggtgg  10860
caaagccagg aagagaactc tgctctcctt tcccactggg acagtggaag aaattcgtct  10920
tgatttccat ctgtccaggc tgaagaatgt gcactggctg gaatgacaga ctgaccgact  10980
ttttttctcc acctctgctg tctcagcaat ggtttgggac agtgtggatg accagaagct  11040
```

```
ggatagtaca gagccaggct aaagagttca ggcttcctga agggaagctg cagtcctcct  11100
aggccacaac accttcgaga tagaatacat aaagcaccct tctctaccaa gttaggaaag  11160
gaagaagtgt gaccaattag ctgtatgggg actgccaaag catgccagtc tgaagatgag  11220
cagaaactgg ctcattccat ttggcaccta gcacactaac tgcatccgtt aataggccat  11280
gcttttctcc agagccattg gctgaagaga tcaaataaaa agtattgaga ataggctacc  11340
caaaacagta ggctcagatg ctatcacaca aagcacttta tccttaagtt caatttttct  11400
aaattgtagt tggctgcttt ggcttaataa aaacttccaa aaaagaaaaa cgaatggcca  11460
cagacagtat gggtatctaa ctatattatc acaacttgac caagattgaa cttgccaatc  11520
ctttggttca agagccaaac aaaatcgttc ccttaaaata ttgcttcatg ggaacagtct  11580
tcttcaaaca tcttttagca caggcaagat tcccatttat acattaattc tgttcaagac  11640
aatgagattg ggcagaaaag gcattgagtt ggaagtcaat ggatatgagt ttttatccca  11700
gttttaccac aaattagctg agcataactt ccacagatgc atttatcaag tagttttcat  11760
ggtcattgca atgccaaaaa actgtagcat ttagaaaatt tagttttcag acttggaaac  11820
tatttaaggc atttcatatg aagggtgtgt ccttgtgaga gtttgcttat gcaagataag  11880
gcttctttca gctgcaagtc aggagcgaac caaaactcaa agcagcagct gcatgagctg  11940
actttatcac atcttgacaa gagctcagcc actggaagtt ttggcataca gcgaaactga  12000
agcgtactta tacaatatca cattttattt ttattgtttc taatagcatt ccaggttaga  12060
aatgtcaatt atttgggaaa gctgagggtc tggtagataa agcatgcagc agagagctag  12120
gaggctggct atttccagtc gttatcctaa catgtcttgg gcccccaagt caccccacct  12180
ccatggtaca atgggaactg tggcagaagt ccacgctctc tcccccaaca catggggata  12240
agagacaaga gaggtgaaat gttctggaac atatccgatg ttatacaagt ataagctgtg  12300
agatgatcca aacgcaaata ttgaatattt cattttctag aaagtatacc aattcattcc  12360
acccttctca aacctaaatt acagaattca attcaggtca cacagattta ctttgtacta  12420
agtaccatag caaatgccat ttcagtgcct gaaaactgaa aaacataaat ttaaagtagg  12480
agtttgaggc ctcactaata tgacaaaaca tacctttata ttttattttg cagtaatttg  12540
ccacttaatc attaaactct tatcaatctg agagatttgc caacacttgc ctgctaggtg  12600
acctaagcct ccacatcaat gcatgttata ctccccttc tccatatgtt aggcccatgc  12660
tatttcttta tccctcctcc tctgcatctt cacctaaaac tctgcccatc cttcagggtt  12720
catccagtga ttcatttgca agcaggcatg gggtaaggtc ttcagagtat gtttctcaga  12780
ggcccatgca gctaagaaaa tgtgcagtgt tggcacaagg tctgtctatt cctgggtagc  12840
cagatgctgg acacatcttt cataacacca caaggtaaat atacttcact tggagagaga  12900
ggtgaaattt tgcaggtata gactggatgt gttcctgcca gaagatgtga agggattaag  12960
aaactgactc tcatctccgt attgctagag caaaacataa tttctcatag tggctatagt  13020
ataaggacac tgaggggtaa gagatataat ctaagtaata caataaatta gtgtggaaaa  13080
atcatcaaaa tgaagactac atggttttta ctaaaattct agcttttagg atgtccaggg  13140
agctcaggaa tttagctgtc cttttttgta tgtacaatat gccccaatgc ttgctgacta  13200
atgtactaaa acattagaga aatcttgctg acaagatctc aaccagtcag cgagatccgg  13260
aaggtgagac taatattgag ggtcagcaga attaagtctc agttctgctg cttaccagat  13320
atgctgatct gagctagtca tttaattttt atgagaccaa atgtctatct gtaaagtcgg  13380
```

caatttggat tagatgtgct gcaagtggtt ttctagctta aatgtacctt ctgaattcaa 13440
caggacaata cttaaactga cctttaatct aggaatgaca caagtagatt tttgaaagct 13500
actttagcta cagaaagctg agagcaccaa aggcaaagag ataaaaataa caggagagcc 13560
ttcccttaat ccagtcccta agcagttttg gcaaactaaa gtttgttgtt caatggttac 13620
gagtttgctt caatgctttc tacccagttt actgaactaa atagtatata gctatagtaa 13680
aaagtcctat tcaaaaacca gcttctcaca gatattttgc agctttgcag aattgaatat 13740
gtccacagac gtctattagc tggttagggt cttaggaatc taggagagcc aagtagttgt 13800
gtgagctgtt gttatcaaat gtagttttga acattcttgg tgattttaag ggatcatatt 13860
gtggaaattt ggtttcctta ccttgaattt tgaatgaagc tttagaattt gaggatgttt 13920
ctttggtttc tccttccagg taagtgattt tttttttttt caaccagatg ctggtttatt 13980
taatttgaag gtattgatga aattctttaa attgccccca tgtgattcta ctctggaata 14040
actacgaaat tatttaaaag ttaattaata caagaaaata tgaaaactca tttttatggg 14100
agctattgtt ccttcaagat gacactgttt tgtaaactat agacttccag taacaagcct 14160
ctgtgccttc ttcttaccac taagcatgca tgggtattaa ttcctactga aagacttatg 14220
ctatcttttt tccagaaatg gaagaaaaat gaactatgaa aaaggtcatt tttataggtca 14280
gctaccacta tgagattgtt gaggaaatga tataaaaaac aatttttatc aaattatctt 14340
tagggcattt atatgtttat tttcttacta tgttgactta ggtgactata agaagttgta 14400
tcagagcaac tgattctggt gaattaaagc aagtatttct aagaacataa gtggcaactt 14460
tcagtctcaa atcaatttgg ccaccaatca gtttttgtaa gggtacaaat aggacataac 14520
atgctcagat gggacttgga taaagtgtat acaattttac atcgaggaaa ttgtgtcaat 14580
gtgttacctt caatgttaga aattcccaag ttctgacaat agttcagagc cttgttaaaa 14640
gccagagtgg aggcatgtag atccagctgg aaagagaggc attatggtct aacttaggac 14700
aaattttaaa gccagtgtta gggtctgagt ccagctttgt aaacttgagt acagtgtttg 14760
atctctgggg tttcagcctt cacttcagaa caaaatttcc accaagtgct cttttactgt 14820
gaggagtagc tgttgaagaa gaaagaagtc tacttatttg ctagagtgtt acaattgttt 14880
tgataaagct caaaacttat ctaaataagc tctctctccc taagcatgtt ttcattttta 14940
taaaaaagtt acatatactt tgcttataaa tttaaaatac ttttcacctc ctctgacttc 15000
atttaaaatt aaaataatta aagtgccaat tttaagagat gttagctccc attattggtt 15060
ctttgccata ttcttttgac aacctgctgt aattttctgc cccctttaaa gcctcaggct 15120
ataggccttc tccaccaaag gaatattaag aagtgataag gaccttctgt gagcagaagt 15180
ggcttgtttg caaagggact gcttatcttg gccactcttg aacacaagat gggaccctct 15240
actgcaaagc tctggcatgt tttttttttcc cctaagttat cctccatact actgacagtg 15300
attttcccta aataaaaaac tgcttcaaac cattcattgt ctttccactg ccttaaagat 15360
aaagtccaaa ttctagaaca tggcccacag catttggtgc ctcaccacct cttcagcctc 15420
tcagttgctg ttcacccatt tctctattcc tctccttctc acaccttgtg ctgcagccac 15480
atagataacc tgcagttttt gtaacgtgca atgatgtctc aaattccaag gcattgctgg 15540
taccacacag cctgcctggt aaaatcctag acttctttca agataaattc aaagacacct 15600
ccatgaggtc tttctacctc tccaagtaga gttgaccgct gtctcctttg tgtccccact 15660
tccaccacca tcctaaaata cttattatac ttagattaat aattgtcgct cttactgcac 15720
tggaattacc ctgaaaggaa aggccatgta ttatttatca ttgtcttcct agtacatagc 15780

```
ccacagccta tacctcccac cccaaaaaaa accttttgta aataattgaa caaattaaga  15840
aacacccaag gcccccagta aacatcaagg cctaaggaat gcatatctgg attctaaata  15900
atcataaggt tttacaacac catgttaagc accagggact tcagagagct tttagtctaa  15960
atcttattag agaggccagc gaagacctcc caaaggaagt ggcattgaac tgagacttga  16020
aaagccagta gttaggcaaa gatagggagg gaaatatttc agacgaaggg aggagatggc  16080
acaagattta ggacacggaa aagggtatgg tgcagtcata gagaaaacag atgtgcagaa  16140
tggctggagc cccaagaggg aagggaaggg cgaagcaatg aagatgtgag gcaagcagga  16200
ctggaccatg cagagtcttg cagatgttca caaagaaaat tgcagcaggt agtccctaac  16260
atcgtgctga acagttaggc aacttggagg aatatgtata tttgtactca tagtcaaaac  16320
cactagatgg catttacaga ctacgttttg tgtattttta ttttttactt tttgtttttt  16380
ttttcttatg ttagcaaaag tatgctcgct attgaaatgt tgaaaatatt tcattggtct  16440
taaaatgatg cttatttttc cagatgcttg cattcattct gcatgtgcta ttttgtcatg  16500
tggtttgctt aatttattaa acaattgtat taattaaata tattaattat aaattgatta  16560
atttataatt aattatgtgt tataattaag ttaaatttat taattactta aattattata  16620
ttcacattca gatgcaatct gaaaacccat ttgttctcac actgctataa agaaataact  16680
gatactgggt aatttataaa gaaaagaggt tccatttgac ccagccatcc cattactggg  16740
tatataccca aaggactata aatcatgctg ctataaagac acatggacgt gtatgtttat  16800
tgcggcacta ttcataatat caaagacttg gaaccaatcc aaatgtccaa caatgataga  16860
ctggattaag aaaatgtggc aaatatacac catggaatac tatgcagcca taaaaaatga  16920
tgagttcatg tcctttgtag gaacagggat gaaattggaa atcatcattc tcagtaaact  16980
gtcgcaagaa caaaaaacca aacaccgcat attctcactc ataggtggga attgaacagt  17040
gagaacacat ggacacagga aggggaacat cacactctgg agactgttgt ggggtggggg  17100
gagggggag ggatagcatt aggagatata cctaatgcta aatgacgagt taatgggtgc  17160
agcacaccag catggcacat gtatacatat gtaactaacc tgcacattgt gcacaggtac  17220
ccaaaaactt aaagtataat aataataaaa taaaataaaa taaaataaaa taaaataaaa  17280
taaaataaaa taaaataaaa gaggtttaat tgcctcatgg ttctgcaggc tatacaagaa  17340
gcatagtgct tctgcttctg gggaggcctc aggaaacaat catggcaaaa gacgaaggga  17400
aagtaggcac gtcttacatg gttggaacaa gagcaagaga gagagtgggg agagagagcc  17460
ttggagcagg agcaagagag agtggggagg tgccacacac ttttaaacaa ccagatctta  17520
tgagaaatca ctatctccca gacagcatca agggggatga tgttaagcaa tgagaaacca  17580
gccccatgat tcaattacca cccaccagtc cccacttcca acattgggga ttacatttcc  17640
ccatgagatt tggatgatgc cacagatcca aaccatacca ctcacctaat tctttctacg  17700
taagaatttg tccaagcatt tataacaatt agcatttcat ttaacatctt ttatgaataa  17760
agcactattc tcatgctgag aagattcaaa ataatgggaa attgaagtcc taggaacaag  17820
ttttatgttt cagaagagcc catttggtat ccacagggct aagaaatgtg caccctaaat  17880
gtaagtggat tacactgaac tgaaaggtgt aaagaaggag tggaagatta aagggagaag  17940
cttggagagg atgaaagtta gaaatggaag tgacgagcac acctgagtga aggatgagag  18000
ctccagctgc attttccagt tgtattccca tgttgctgag ccaaaggctg atctcaagtt  18060
tattgttaca tgcccattta aggcttctgg ccattaacac ttttgatttt ttttggcttg  18120
```

ttgttttact agctattttc acaacacttt catagctaaa cctattttac tcagattgta 18180
tgccttttca aaaatacaat agaaggtcca tattccatta tctagaaata agccaaagct 18240
catatctaac atttattaag agagatggat tatttttgtt cattagttat ctttataaat 18300
aatttttacg tactttagtt gactcataaa gatgtttctt tctgtaattt taatcttaat 18360
atttgttgaa cttcaaaatc cctatcacca ggttattgtt taaaagcatt ggtttttata 18420
ttatcttaaa agccattata cctgagtgct gaacaactta gaaacattca gtaattgttt 18480
tgcatgctat ttagtgaatt catatggcaa tcgtttatac atacatgatg gaatcaggtg 18540
gcaggccaag ttaaagagca aggccagaaa agaacttaaa agagaagaga aaaaatagac 18600
agtttaggaa caatagatca tgtcttctcc atgatttgga ggtaaactga ttacctatca 18660
gctgataaat agaggaaggt tttagaagtc ttcagttggg tagactaatg agaggtgtca 18720
gagaagatgt tttctgttgt ttgtgggttc tccaggaaac tttgagcatt cagctgaggg 18780
gccaagttgg ctgcctctga gaagaagccc ttccacctcc actccattgc acttgggtgc 18840
cattcccctc agttgaatat ctccaagaga tgagcaaatg tacatctaca gagttcaggg 18900
tactgacttt tatcataatg atttataact ctcagaagag tgaaaaacac atgaatgcac 18960
agaataggag attgaaatat aaaccacaga acattcatac aatggaatac tctgcagtca 19020
taaaaatctt ctcatagaag aatatttgac agcataggga tatctgtggc atattaagta 19080
gaaagtcaga cttgtaaaca ttatatacat attcacgtat atttaaacac catgatccca 19140
tatttagata taacaactaa aagttcagat ggctatatat caaaatgtgt caaatgttca 19200
accttgcata ggctgactgt agatgaattt tatattattc tttgtgcttt cttgtagttc 19260
ccaaattttc tttactgaat ctatattact tttgcaattt aaagaattta atttataaaa 19320
ttttataaaa taacttataa atttgaaatg tattgcattt aagaataaaa agtgtttaat 19380
tacaaaaata attcacaatt tatttaatga gattttaaaa ggatatatgt gagtctacat 19440
tctgatttca tgtttgcatg catggttttt tttttctttt gagacagagt ctcgctctgt 19500
cgcccaggct ggagtgcagt ggcgtgatct cggctcactg caagctttgc ctcctgggtt 19560
cacacaatgt aatagtgttt tattattgtt tccattttta ttgaagaagt aagattgtcc 19620
ctagcagatg gagacactga gatatgggac agaagttttg ttctatataa ttattatgcg 19680
cttccacctt tcttagcata gacagtttcc aaaatgcaac ttcaagttac ccctttataa 19740
gcataataac aataataccc aacatatatg taatgctctt tatgtgccaa gtactatact 19800
aacacatgca cattacatac acacacacca catacacaca catatttaaa ctaatttcgt 19860
tctcacaatg acattttgag gcaagtatta ttattgtaca gatgagaaaa ccaaggcacg 19920
ctttatctgt aaacctctgc tatgcagaaa ttctggaggg gcttctggcc ccttaatttt 19980
aaaataaggc caataataca atacttacca catagcaatt ctctaaacat tatgtaagat 20040
atataccaaa gcgcttagct cagggactgg agggatgtga gggaatttgt cttttgcaat 20100
atgctttatg gtccgctcag tcacctcgtt cttaatccct ttctcaactt ctattttata 20160
cagcaattgt gagcatatca gcatcaagta ccactggtgt ggcaatgcac acttcaacct 20220
cttcttcagt cacaaagagt tacatctcat cacagacaaa tggtttgttt tcatttttat 20280
ttttaaattg tggctccgaa atcatttttg tgatgtaacc cattttaggg gacctgtcac 20340
tgcagagaaa ctgacaaaca ctgagaaatg cgagctaagt agacacagcc tactaagtag 20400
acacaattcc tactatggag gaattcttgc ctctgaaata tctcacagaa ataatactgt 20460
gagttaaaga aattaaaaca atgtggcaaa gcacagaaat gatgcacgtg accatgaaat 20520
agtgggccag ataaagggga cctaatagtg cggtggtgcg gagggtctgt gggcaaactg 20580
agttcagctc agacccgggc tcagctctat gccagctgct gacccagggt gagttgccct 20640
gcagggtttc tatcccatta attttaaaat ggggccaata acacagtact tatctcacag 20700
catttctcta aaggctaaat aagaagatgt atctaaaagt tattagctca gagcctcaca 20760
cattctcagt gactgataaa caataagcaa agctgggtgc tgagataaga gtaatctggt 20820
ggcagtctct cttgttagtt ttcaggggag aagaagaaat tctggagccg ctgctgggag 20880
ggatgtggga gagtttgtct ttcataatac gctctatgtc cacgcagtca cctcattctt 20940
gtgccctttc tcaacttctc ttatatgcag atacgcacaa acgggacaca tatgcagcca 21000
ctcctagagc tcatgaagtt tcagaaattt ctgttagaac tgtttaccct ccagaagagg 21060
aaaccggtat gttcttagtt ttaaatagtt gctctggagt cattgttgtg attgaactct 21120
atttacacga gctgtaactc atgacagttc tcaagctttc gtgacagaaa acccatctct 21180
tttactccaa agcccatata gcacccacaa ctattaactg tgaccaagaa agagaaggca 21240
agccccaatt aacctttgta cgtaaagcct aaagaatgaa aaaatatacc tgaatcctca 21300
atcatcaaac agcatagtat atactaagta atttgtaata attaaactct agaaaattgt 21360
gtggcttcgg tagtaagaga gcttcatgat gtaaaatggc aagtggagac agagacaaaa 21420
gtaggatgtg gactgagagg gaaggttagc acaggtggaa cagtaaggca accatactat 21480
caattgctgc tgacatagaa tccagagaga ctattggcaa aagctcaaat gagacacagt 21540
aacagtttag attcagacag tggctgtggc ataaatcaga aaattgatag tcgcatgatc 21600
cctctttgca tgggactggc atctgtgtgg agtaatggtt ccatatgcct cctttcttct 21660
ccttattttt aaatttttta aaaatgcatt gcttcttgtg gaagtcaata agtgattctt 21720
ccaatacttt ctcattcctt ccccctcagt tatgagacaa tttgcttatt tctcatccat 21780
gaatacttgt tgggtcatta aaagtagata ctgaaattac taatggtacg actgacatat 21840
tacctcataa atgttactag ctagatgttg aaagttgacc aacaactctc aaaatatgat 21900
taagaaaagg aaacccacag aacagtttga ttccaaaatg atttttttct ttgcacatgc 21960
cttacttatt tggacttaca ttgaaatttt gctttatagg agaaagggta caacttgccc 22020
atcatttctc tgaaccaggt atgttaatat ttgacaaaga ataaaagtca ttccatttta 22080
aactatccat tgcttgtttc aaatgcctaa gaaaatgtgt ctatcttaga agagcatatg 22140
ttgttaactt tattcacaca aaattgtaaa ggcaaagaaa atattctctt tttaaaatta 22200
aaataggcat ttcttatttt taaaaacatt ttgggggcca ggggccgtgg ctcatgccta 22260
taatcccaga actttgggag gctgagcctg gctaatcgct tgagcccagg aatttgagaa 22320
cagcctgggc aatatggcga aatccatctc tacaaaaaat acaaaaatta gctggcatgg 22380
ggcacgcacc tgtagtctca gctacttggg aggctggctg aggtgggagg atcggatcca 22440
ttgcctgagt ctgggagttt aaggctgcag tgagctatga ctgtgccact gtactctagc 22500
cttggtaaga ccctgtctca aaaacaaata cataagtaaa taaaaataaa taaaaacatt 22560
ttggaaatag aaatacataa tttggtaata gtttttctct taagttagat gttttacctt 22620
tctaaccaag cctgagtact tgaaaaaagc ctcataagag cttataaaac aaatgaactt 22680
ccctcatata aaaagcaagg catttaaaat catctaatta actggtactg tatttcaagg 22740
gtaaatctca gccttgattc atttttggcc caatgcaacc acttagggac catcttgaca 22800
acctctgctg aagggacatc ccttcccctc acttgagtat cactgtgtgt gctcatttgc 22860
tattctgcat tccaaccctc ccttcacact tggctgtgtc cacggctcac agggtaaaaa 22920
gcacatcata gaacttcatc actatcgcat acattcaagc taagtggtca agaaggctgg 22980
gcaacaccag caagaggaaa tgctactttt actttttatc aacaataggg cttttaaata 23040
ttaattaggc aaataaatga gccattttac ctttatgtct agccttccat tctatttact 23100
tcaactggaa gcactacaaa tatgctataa atatggaaat atctcttaat tgatttcaat 23160
tgtttcattc ccaacatata aatgactcaa caagcatttt tagtgactac attggagact 23220
atgcataaga atactatgga aggaataaag cttagaacat agatgacctg cattataatt 23280
ataattctac ttttaactag ttgtctgacc aaggctaagt taaccttatt cagcttcttt 23340
tcttcatttg taaactgttt ataccagttt ctttccaaaa ttatgattct atgatctgtt 23400
caatgctctt ttatacatta agacattatt ttctctcata acttccaaac tatgggagaa 23460
tttgtggttt tttccccata tctgaggaga acgtccactg agttcttatc tacagttaca 23520
ctagtgaaga acgctgggtc tggaatcaga agcttcaggt cttagttctg tcatcaacta 23580
ttttgcgacc ttggacaaaa gacttgatca ctcacagtcc cagtttccca caaggttact 23640
gtaaagcaca caatttaaaa aaagacaaaa tctacataat agtatattaa ttgtgctttc 23700
tattaaaagg caaggtgatg gtatgctgat gttatctgtc ttatttttca gttgctatat 23760
ggtcatttat ttcagacttt cataattttg ctgctctctt tatctcctgt agagataaca 23820
ctcattattt ttggggtgat ggctggtgtt attggaacga tcctcttaat ttcttacggt 23880
attcgccgac tgataaaggt gagaattcag tttttaattt tgctgtaaat accaatgtga 23940
acagctctaa gagggtttat tcctctgagt tcagttaaac tcaaaagaga aacagaactg 24000
cataaaattc catatttttc aactggacac atagaagtca ctgtgtttct ctagcagaat 24060
ttttctttgc atttgcccaa ttaaagggaa cctctaaata taaatctgtc ccccattttc 24120
ccaatgaaag atctccctaa gtttttgtct aacttgctgt cacatatttt gatggatatt 24180
gaggaaatat taagattcta cttatagtat ttaccctatt agtgtataaa atatttaaaa 24240
taatatattt acatatgttt aaaactttga gggaagccaa ggcaggagga ttgcttgagc 24300
tcaggagttt gagaccagcc tgagcaaaaa ggtgaaacct agtctataca aaaaatatga 24360
aaattagaaa ggcgtggtgg tgcacatgtg tagtatcagc tactcagggg gctgaagtgg 24420
gaggattgct tgagcctggg aaatcaaggc tgcagtgagc tgtgatcatg ctactgcact 24480
ccagcctggg caacagagtg agaccctgtc tcaataatta tataaataaa taaataaaaa 24540
taaacaaaat aaaacttttg cctttcttaa ttctcacata ttctgaaaca gatttttcaa 24600
atttccaccc atgaattctt aacatcagtg attttttttg aatcattaat gcttttttta 24660
attttttttt tttttttga gacaagagtt tccctctgtc acccaggctc gagtgcaaag 24720
tggtgcaatc tctgctcact gcagcctctg cctccctggt ttaagtgatt ctcgtgcttc 24780
agcctccgca gtagttggga ctacaggtgc gggacaccat gcctgactaa tttttgtatt 24840
tttttaatag cagagatggg gtttcgctgt gttggccagg ctggtttcaa actcctgacc 24900
tcaagtgatc catctgccct tggcctccaa agtgctggga ttacaagcat gagccaccac 24960
gcccagccca ctaatgctat ttttacatcc atacaacaca gcttatcgaa gtgcataact 25020
tttgctatca ctttctattc acgatattta agacataata tgtgtgtgtg tatttatgat 25080
gctgtcactg tctctgtaat cctagatcag aagtacttag tcacatgaga ttggtacagt 25140
tgtgttttca ttcatcctct attcttaatc tctctttgtg atttttgaga ccataaccac 25200
tatataattc ttttaaaaag gctgagaggt gtgacagcac tgcaattgtg gggccatcag 25260

```
aagatatgat agtaatatct acattaagtt cctttgcctc ttttcttttt taactacttc  25320
taacagttaa cttctaccat catccaatcc tataattgat tttcagtatt ccatgtaaat  25380
atatcttcct taaataatac tttttgttaa tcaaagaaaa gtaactgaaa atgcctactc  25440
ttgtgtgaga tattttgtaa ggactttaat ataagatagc ttttttgcc tggagtataa  25500
aagagaaaag tcatcttctt acatgggcat atatggcaaa gtgggttgtc ttctctcttc  25560
gtcaatgttc taaaacctga aaaagccaag gaaatattta gttggcaaag ttcagagaat  25620
tttctaagtg tatatggatg aattttgtcc tggtcaacat gatgcagaga tcacacactt  25680
tatttttatt tttatttca ctttcactat ttattacagc agggaaatat gtaagtatca  25740
gtgtttgagg tgatatttct cctactgaaa taccaaatac tatagaggaa cacaaataca  25800
agtttaaatc aatgcttata ccagtaacta gtaacaacaa caataacaaa atctctgcaa  25860
aggggatttc aaccaaaaga aaaaaaattt tagaaaaaaa tatttttaag ctgaagcatt  25920
ttacttttta ctgtcttaag actagaaaat tgtgttatta atattttatg gtatttcttc  25980
atagaaaagc ccatctgatg taaaacctct cccctcacct gacacagacg tgcctttaag  26040
ttctgttgaa atagaaaatc caggttggtg ttaatatttg cagttccttt tgccttttag  26100
gaaaaaaaaa tcaaaccagt gagttacttc tttctgattt gagggaggag ggaaccagtt  26160
atgattcatt tctattctat ctcattaatt ctacttcttt gactttttag aaatgtctgc  26220
agcatagtga gattctcctt tggacacaaa gtgttttgtt ttgttttgtt tttttaacaa  26280
aaaaaaaaaa actcaatcaa atagtaaaag caaaagagaa aaccaagtgt acttcgtatt  26340
tcccaaactg caaagttatg tgtataggag actctatggt cagtatggtg tagcatagtg  26400
aattagcccc agatctgaaa tcagacttgg atttgaatcc atgctccaac acctattagc  26460
tgtgtaaccc tgagcaagct actaaacctc ttttaatatg gggataatga tagtatcaac  26520
ctcacaaagt ttaatgagaa ttaaatgagc tacaaccggt aaagcattta aaaccatttg  26580
tggccatcat aagtcctcat gcctgttagc tgttatcaat atagcactga catcaatgct  26640
atatcaatat agcatgttat caatatagtg tcattcccaa atgacctcct gtgcacactg  26700
gcaagccatc tggcacatgc tttcatctcc actcccaggt gctaagcaga tacaaaacat  26760
gtgaaaggcc atggatatat tttgtttatc cagaacagta ttaaaccaca tagtgctttt  26820
tgaaaagaat atttattgtc aacctttaaa agtcggaaat tgttacattt taaaaatcaa  26880
gtattgctat tcctctgggg aaaaatgtaa actcccaaaa tgctgagagc cttcatacca  26940
gcatgagacc aattcctaag agctgagtag tggctgctac ctgtactgtc tgtctaaatc  27000
cctagccaat tgcatttgtt ttattcaccg tggcccctgg tatgaactca ctaagaaagc  27060
atatagtttc tattaaactt tgcctgaagc ataaacccaa atgacatcta ttttgggaga  27120
tagttactaa gaacaagtct ctggaatgag ctttatttct caagcaaaag agatttcatt  27180
ctgccttcta caaaatcaac tgattttact cccataattt tcagaaatca tgacagatca  27240
gaggtcctgt atgcttctgg atttcgattt taaccctggg ccagtctagg ttttctagac  27300
tttagagtca cagaacacag agttttcaag atccatcaca gctacacagg ttatatgcag  27360
gatttgccac atcacattat catgtgaatt cttaaagctt aagagtaatt gttacataag  27420
tttataatcc taagacattc ctgctatgtg gaaatgaatg gcatagatat gattctcagc  27480
taaaaggatt aataaaatcc aatctgcaga tacttgaaac aacggaagtt tttgagtcat  27540
atgccagatt cacttcattt actaaggtta tcttgttatt ggactggcag ctggaacaag  27600
```

tatctgtaaa atattcattt tatctgcatt ctgccttgtt ccacaaaaaa gtcttgatgt 27660
agtttttcaa gtggagcaat tacaacctaa agcctatttt tcgaactgaa atttatatac 27720
atttttagct acttatttat tctagagaca aatttattgt ttagagtttc ccctgccatt 27780
tttttcatac aattttaagc atctcaaatg tttggcacaa tttaatacgc cacagtgcat 27840
caagatgtcc ttgtagttta attcagttaa gtgcaacaaa catttgctaa atgcatacag 27900
tggggtaggc accacactca cattagatat accaatatga gtcttcgtcc tttagaagct 27960
gagagactaa tggaaaaaac agaatgtcat tgcagtgaac aagttctaca gtagtggagg 28020
caatagctcc acttgtccca gagactgaga caggtatcaa aggcttctga agatgaaatc 28080
acctgggatt agccttaaaa gacagataga tattagctag ggcagggtag ttttagcaga 28140
agggcagcct gagtgagtaa aagcatggaa gacagaatat gtttacttaa agaattgtat 28200
gcatttccac attagcagga ttgctgcttt ggttctctgt tcacatctca aatatgtgta 28260
atggcagtgg aaagtcagaa gaaccaaact ttaggctcac tttatttccc cacatttgtg 28320
caagtgaagt tattaaatgt cttagtatgt tagtgagaca agttatgaat tctgactgca 28380
cctcacagaa aacataggaa aacacattat taaagattat ttaaaatgct ttatttctac 28440
ttttatagaa tatggctcta aattagttta taagccaaag gcataagagg ttaaaatgac 28500
agtaccatct caacaagaac taatgatgta aaggagtaat tagagtataa attgttttaa 28560
ccttctaaaa gtgcacatga tctgtgattg gtgaaaaatg agaataagcg aatctgagtc 28620
agctggccac tgtggcatgc atatgtgacc cactagccta tttcccacag gagaatgttt 28680
gagatgcaca gttcctgtgg tgcccaaata gaagaaggct ggaaaagctc tgcttctgga 28740
agagcaaggg ctcccctctc cctttcatgc agtttctagg agcaacataa attcaacctt 28800
ccaaccagga aaagtggagc atcgggttta ctggagaaaa ctagcccagt gcccttcttt 28860
tacaccctag aaccagagag gaacttggcc ataagctttt gtgcagactt ctccttgggg 28920
gaaaaaaaaa gtcattattt aaaaagacat gacagactta gacacatgcc ttaaatttta 28980
acatgcatat gtgattcaac ttatcattta ctggcttcac attatatttt gcctctatac 29040
aagtttggct gtttgtttct tatctctgta gaaactagga gcagagcaat tatatttatt 29100
ctttacctaa ggcttttaga atagatattc taagaaattc tgtatttttc tttacacaaa 29160
acttgacaat agagctaata tgtaaggaga gtcctttcgt ttcctactaa ttacattcaa 29220
gaacaactct gcaagaatgt agaatcctaa aatgtatact gtgcattaat ttcctgttgt 29280
gtttaaacat aactatgtct catatttcgg tcttgtattt tttttactat aatccttcta 29340
gagacaagtg atcaatgaga atctgttcac caaaccaaat gtggaaagaa cacaaagaag 29400
acataagact tcagtcaagt gaaaaattaa catgtggact ggacactcca ataaattata 29460
tacctgccta agttgtacaa tttcagaatg caattttcat tataatgagt tccagtgact 29520
caatgatggg gaaaaaaatc tctgctcatt aatatttcaa gataaagaac aaatgtttcc 29580
ttgaatgctt gcttttgtgt gttagcataa tttttagaat tgtttgagaa ttctgatcca 29640
aaactttagt tgaattcatc tacgtttgtt taatattaac ttaacctatt ctattgtatt 29700
ataatgatga ttctgtcaaa tgaaaggctt gaaataccta gatgaagttt agattttctt 29760
cctattgtaa actttttgagt ctggtttcat tgttttaaat aaattaaggg gacactaaag 29820
tcctatcatt catttccttc attgctgaac aggcaagata taatattaca tgaatgatta 29880
ctatattttg ttcacactaa taaagcttat gctcagaaat gccatacaca cacacaaaca 29940
cacacattta tcatttaatg cataaatcaa cacaaaaggt tttcccatta atatgaaata 30000

```
ttacatatat ataagtgcca tatttaaaat aatttgtcta acagtagaac tatgtcggag  30060

cactcactga agcttgcatt ccactgaaag agttatttgt gtaagtagag tatccggaga  30120

aggaaaagaa cttacgacct ttctttataa cagaaactca actctaaatt caacaagatg  30180

tgcaaaccgg acatgcaggt gaatatttta ataggttact ataaggttct caattaaatt  30240

ctttaatctg tccagtccca gtttctctta ttaataaaac tttggaaatt gctttaaacc  30300

atttaaagga aatttctaga tatagaaact aaggactgtg actatacagc tgtcactcat  30360

ttgtagtaaa acttaaaaag caaaaacaaa aaacaaaaaa gaccttcctg tgatacttta  30420

tttccgaact aataaaaatc tatatgactt tttattattg tgtgataacc aagtaaatgt  30480

tttctatttt gcatattttc aggcatggta acagaaattt accttttaat aaattaaaaa  30540

atctaaattt taacctactt gtatgttcgg agagtgtttt tgtactatat tgactactta  30600

aaatagagaa tgagactaag aagggaacat ttctgttgat acatgttttt taaaagaaat  30660

tttaagagca ttattaggtt aattttaatc caattaatga cccaaatgcc aaggtaattt  30720

taaatttaca tttttaataa aagcaacatg ttgaaacaag agagggtgag attaaccttt  30780

ttgctaaagt aatttacaag tcaaagacag gaagagatca gagtgaatgt gccttcttaa  30840

ccagagctac agaatttagt gaataattaa agtacaaact gctttgacct ccttgaactt  30900

ttccaagcaa tttctctgta cttctatata tgaatgtctt agccaatttt ctgctactat  30960

aacagaatac gacagactgg gtaatttaaa aagaaaagaa atttattttc ttcctagttc  31020

tggaggctgg gaaggcgaag ggcatggcac tgacatctgc cttgtaactg atgagaacct  31080

tcttactgca tgataacaaa gcagcaaggc aagcaaaagc gtaagatgaa gagagaggaa  31140

atgaagccaa acacatcctt tcatcagaag cccattccct ctataaggcg ttactacatt  31200

tatgagaatg gagtcctcat gacctaatcg tgaccttaaa ggcccctccc aacactgtta  31260

caatggcaat taaatttcaa caaaggttcc agaggtgaca ttcgaatcag caatgaaatt  31320

ttcatagtta aatttggtat tcgtggggga agaaatgacc atttcccttg tatttttata  31380

attaaatcag caaaatattg taataaagaa atctttcctg tgaagatacc atgacccc    31438
```

<210> SEQ ID NO 43
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 43 ugucca 7

<210> SEQ ID NO 44
<211> LENGTH: 7
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 44 augccca 7

<210> SEQ ID NO 45
<211> LENGTH: 7
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 45 gaguccc 7

<210> SEQ ID NO 46
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46 gccaugc 7

<210> SEQ ID NO 47
<211> LENGTH: 6
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47 cguaau 6

<210> SEQ ID NO 48
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48 acuuaca 7

<210> SEQ ID NO 49
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49 ccgguca 7

<210> SEQ ID NO 50
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50 ugaugga 7

<210> SEQ ID NO 51
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51 uugacug 7

<210> SEQ ID NO 52
<211> LENGTH: 6
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52 aggggc 6

<210> SEQ ID NO 53
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53 ggcauau 7

<210> SEQ ID NO 54
<211> LENGTH: 8
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 54 aacgugac 8

<210> SEQ ID NO 55
<211> LENGTH: 7
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 55 ugaaaua 7

<210> SEQ ID NO 56
<211> LENGTH: 80
<212> TYPE: DNA
<213> ORGANISM: Woodchuck hepatitis virus

<400> SEQUENCE: 56
gccacggcgg aactcatcgc cgcctgcctt gcccgctgct ggacaggggc tcggctgttg 60
ggcactgaca attccgtggt 80

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(3)
<223> OTHER INFORMATION: May or may not be present

<400> SEQUENCE: 57

Gly Ser Gly Glu Gly Arg Gly Ser Leu Leu Thr Cys Gly Asp Val Glu
1 5 10 15

Glu Asn Pro Gly Pro
20

<210> SEQ ID NO 58
<211> LENGTH: 22
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(3)
<223> OTHER INFORMATION: May or may not be present

<400> SEQUENCE: 58

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 59
<211> LENGTH: 23
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(3)
<223> OTHER INFORMATION: May or may not be present

<400> SEQUENCE: 59

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MISC_FEATURE
<222> LOCATION: (1)..(3)
<223> OTHER INFORMATION: May or may not be present

<400> SEQUENCE: 60

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 61

<211> LENGTH: 7683
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg gccgctgatc ttcagacctg gaggaggaga   1560
tatgagggac aattggagaa gtgaattata taaatataaa gtagtaaaaa ttgaaccatt   1620
aggagtagca cccaccaagg caaagagaag agtggtgcag agagaaaaaa gagcagtggg   1680
aataggagct ttgttccttg ggttcttggg agcagcagga agcactatgg gcgcagcgtc   1740
aatgacgctg acggtacagg ccagacaatt attgtctggt atagtgcagc agcagaacaa   1800
tttgctgagg gctattgagg cgcaacagca tctgttgcaa ctcacagtct ggggcatcaa   1860
gcagctccag gcaagaatcc tggctgtgga aagataccta aaggatcaac agctcctggg   1920
gatttggggt tgctctggaa aactcatttg caccactgct gtgccttgga atgctagttg   1980
gagtaataaa tctctggaac agatttggaa tcacacgacc tggatggagt gggacagaga   2040
aattaacaat tacacaagct taatacactc cttaattgaa gaatcgcaaa accagcaaga   2100
```

-continued

```
aaagaatgaa caagaattat tggaattaga taaatgggca agtttgtgga attggtttaa   2160
cataacaaat tggctgtggt atataaaatt attcataatg atagtaggag gcttggtagg   2220
tttaagaata gtttttgctg tactttctat agtgaataga gttaggcagg gatattcacc   2280
attatcgttt cagacccacc tcccaacccc gaggggaccc gacaggcccg aaggaataga   2340
agaagaaggt ggagagagag acagagacag atccattcga ttagtgaacg gatcggcact   2400
gcgtgcgcca attctgcaga caaatggcag tattcatcca caattttaaa agaaaagggg   2460
ggattggggg gtacagtgca ggggaaagaa tagtagacat aatagcaaca gacatacaaa   2520
ctaaagaatt acaaaaacaa attacaaaaa ttcaaaattt tcgggtttat tacagggaca   2580
gcagagatcc agtttggtta gtaccgggcc cgctctagcg tgaggctccg gtgcccgtca   2640
gtgggcagag cgcacatcgc ccacagtccc cgagaagttg gggggagggg tcggcaattg   2700
aaccggtgcc tagagaaggt ggcgcggggt aaactgggaa agtgatgtcg tgtactggct   2760
ccgccttttt cccgagggtg ggggagaacc gtatataagt gcagtagtcg ccgtgaacgt   2820
tctttttcgc aacgggtttg ccgccagaac acaggtaagt gccgtgtgtg gttcccgcgg   2880
gcctggcctc tttacgggtt atggcccttg cgtgccttga attacttcca cctggctgca   2940
gtacgtgatt cttgatcccg agcttcgggt tggaagtggg tgggagagtt cgaggccttg   3000
cgcttaagga gccccttcgc ctcgtgcttg agttgaggcc tggcctgggc gctggggccg   3060
ccgcgtgcga atctggtggc accttcgcgc ctgtctcgct gctttcgata agtctctagc   3120
catttaaaat ttttgatgac ctgctgcgac gctttttttc tggcaagata gtcttgtaaa   3180
tgcgggccaa gatctgcaca ctggtatttc ggtttttggg gccgcgggcg gcgacggggc   3240
ccgtgcgtcc cagcgcacat gttcggcgag gcggggcctg cgagcgcggc caccgagaat   3300
cggacggggg tagtctcaag ctggccggcc tgctctggtg cctggcctcg cgccgccgtg   3360
tatcgccccg ccctgggcgg caaggctggc ccggtcggca ccagttgcgt gagcggaaag   3420
atggccgctt cccggccctg ctgcagggag ctcaaaatgg aggacgcggc gctcgggaga   3480
gcgggcgggt gagtcaccca cacaaaggaa aagggccttt ccgtcctcag ccgtcgcttc   3540
atgtgactcc acggagtacc gggcgccgtc caggcacctc gattagttct cgagcttttg   3600
gagtacgtcg tctttaggtt ggggggaggg gttttatgcg atggagtttc cccacactga   3660
gtgggtggag actgaagtta ggccagcttg gcacttgatg taattctcct tggaatttgc   3720
cctttttgag tttggatctt ggttcattct caagcctcag acagtggttc aaagtttttt   3780
tcttccattt caggtgtcgt gagcggccgc tgagttaact attctagacc cgggctagga   3840
tccgcccctc tccctccccc ccccctaacg ttactggccg aagccgcttg gaataaggcc   3900
ggtgtgcgtt tgtctatatg ttattttcca ccatattgcc gtcttttggc aatgtgaggg   3960
cccggaaacc tggccctgtc ttcttgacga gcattcctag gggtctttcc cctctcgcca   4020
aaggaatgca aggtctgttg aatgtcgtga aggaagcagt tcctctggaa gcttcttgaa   4080
gacaaacaac gtctgtagcg accctttgca ggcagcggaa ccccccacct ggcgacaggt   4140
gcctctgcgg ccaaaagcca cgtgtataag atacacctgc aaaggcggca caaccccagt   4200
gccacgttgt gagttggata gttgtggaaa gagtcaaatg gctctcctca agcgtattca   4260
acaaggggct gaaggatgcc cagaaggtac cccattgtat gggatctgat ctggggcctc   4320
ggtacacatg ctttacatgt gtttagtcga ggttaaaaaa acgtctaggc cccccgaacc   4380
acggggacgt ggttttcctt tgaaaaacac gatgataata tggccacaac catggtgagc   4440
aagggcgagg agctgttcac cggggtggtg cccatcctgg tcgagctgga cggcgacgta   4500
```

aacggccaca agttcagcgt gtccggcgag ggcgagggcg atgccaccta cggcaagctg 4560
accctgaagt tcatctgcac caccggcaag ctgcccgtgc cctggcccac cctcgtgacc 4620
accctgacct acggcgtgca gtgcttcagc cgctaccccg accacatgaa gcagcacgac 4680
ttcttcaagt ccgccatgcc cgaaggctac gtccaggagc gcaccatctt cttcaaggac 4740
gacggcaact acaagacccg cgccgaggtg aagttcgagg gcgacaccct ggtgaaccgc 4800
atcgagctga agggcatcga cttcaaggag gacggcaaca tcctggggca caagctggag 4860
tacaactaca acagccacaa cgtctatatc atggccgaca agcagaagaa cggcatcaag 4920
gtgaacttca agatccgcca caacatcgag gacggcagcg tgcagctcgc cgaccactac 4980
cagcagaaca cccccatcgg cgacggcccc gtgctgctgc ccgacaacca ctacctgagc 5040
acccagtccg ccctgagcaa agaccccaac gagaagcgcg atcacatggt cctgctggag 5100
ttcgtgaccg ccgccgggat cactctcggc atggacgagc tgtacaagta aagcggccgc 5160
atcgataccg tcgacctcga tcgagaccta gaaaaacatg gagcaatcac aagtagcaat 5220
acagcagcta ccaatgctga ttgtgcctgg ctagaagcac aagaggagga ggaggtgggt 5280
tttccagtca cacctcaggt acctttaaga ccaatgactt acaaggcagc tgtagatctt 5340
agccactttt taaaagaaaa ggggggactg gaagggctaa ttcactccca acgaagacaa 5400
gatatccttg atctgtggat ctaccacaca caaggctact tccctgattg gcagaactac 5460
acaccagggc cagggatcag atatccactg acctttggat ggtgctacaa gctagtacca 5520
gttgagcaag agaaggtaga agaagccaat gaaggagaga acacccgctt gttacaccct 5580
gtgagcctgc atgggatgga tgacccggag agagaagtat tagagtggag gtttgacagc 5640
cgcctagcat ttcatcacat ggcccgagag ctgcatccgg actgtactgg gtctctctgg 5700
ttagaccaga tctgagcctg ggagctctct ggctaactag ggaacccact gcttaagcct 5760
caataaagct tgccttgagt gcttcaagta gtgtgtgccc gtctgttgtg tgactctggt 5820
aactagagat ccctcagacc cttttagtca gtgtggaaaa tctctagcag catgtgagca 5880
aaaggccagc aaaaggccag gaaccgtaaa aaggccgcgt tgctggcgtt tttccatagg 5940
ctccgccccc ctgacgagca tcacaaaaat cgacgctcaa gtcagaggtg gcgaaacccg 6000
acaggactat aaagatacca ggcgtttccc cctggaagct ccctcgtgcg ctctcctgtt 6060
ccgaccctgc cgcttaccgg atacctgtcc gcctttctcc cttcgggaag cgtggcgctt 6120
tctcatagct cacgctgtag gtatctcagt tcggtgtagg tcgttcgctc caagctgggc 6180
tgtgtgcacg aaccccccgt tcagcccgac cgctgcgcct tatccggtaa ctatcgtctt 6240
gagtccaacc cggtaagaca cgacttatcg ccactggcag cagccactgg taacaggatt 6300
agcagagcga ggtatgtagg cggtgctaca gagttcttga agtggtggcc taactacggc 6360
tacactagaa gaacagtatt tggtatctgc gctctgctga agccagttac cttcggaaaa 6420
agagttggta gctcttgatc cggcaaacaa accaccgctg gtagcggtgg tttttttgtt 6480
tgcaagcagc agattacgcg cagaaaaaaa ggatctcaag aagatccttt gatcttttct 6540
acggggtctg acgctcagtg gaacgaaaac tcacgttaag ggattttggt catgagatta 6600
tcaaaaagga tcttcaccta gatcctttta aattaaaaat gaagttttaa atcaatctaa 6660
agtatatatg agtaaacttg gtctgacagt taccaatgct taatcagtga ggcacctatc 6720
tcagcgatct gtctatttcg ttcatccata gttgcctgac tccccgtcgt gtagataact 6780
acgatacggg agggcttacc atctggcccc agtgctgcaa tgataccgcg agacccacgc 6840
tcaccggctc cagatttatc agcaataaac cagccagccg gaagggccga gcgcagaagt 6900
ggtcctgcaa ctttatccgc ctccatccag tctattaatt gttgccggga agctagagta 6960
agtagttcgc cagttaatag tttgcgcaac gttgttgcca ttgctacagg catcgtggtg 7020
tcacgctcgt cgtttggtat ggcttcattc agctccggtt cccaacgatc aaggcgagtt 7080
acatgatccc ccatgttgtg caaaaaagcg gttagctcct tcggtcctcc gatcgttgtc 7140
agaagtaagt tggccgcagt gttatcactc atggttatgg cagcactgca taattctctt 7200
actgtcatgc catccgtaag atgcttttct gtgactggtg agtactcaac caagtcattc 7260
tgagaatagt gtatgcggcg accgagttgc tcttgcccgg cgtcaatacg ggataatacc 7320
gcgccacata gcagaacttt aaaagtgctc atcattggaa aacgttcttc ggggcgaaaa 7380
ctctcaagga tcttaccgct gttgagatcc agttcgatgt aacccactcg tgcacccaac 7440
tgatcttcag catcttttac tttcaccagc gtttctgggt gagcaaaaac aggaaggcaa 7500
aatgccgcaa aaaagggaat aagggcgaca cggaaatgtt gaatactcat actcttcctt 7560
tttcaatatt attgaagcat ttatcagggt tattgtctca tgagcggata catatttgaa 7620
tgtatttaga aaaataaaca aataggggtt ccgcgcacat ttccccgaaa agtgccacct 7680
gac 7683

<210> SEQ ID NO 62
<211> LENGTH: 7503
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900
aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020
gcccgaacag ggacttgaaa gcgaaaggga aaccagagga gctctctcga cgcaggactc 1080
ggcttgctga agcgcgcacg gcaagaggcg aggggcggcg actggtgagt acgccaaaaa 1140

-continued

```
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg gccgctgatc ttcagacctg gaggaggaga   1560
tatgagggac aattggagaa gtgaattata taaatataaa gtagtaaaaa ttgaaccatt   1620
aggagtagca cccaccaagg caaagagaag agtggtgcag agagaaaaaa gagcagtggg   1680
aataggagct ttgttccttg ggttcttggg agcagcagga agcactatgg gcgcagcgtc   1740
aatgacgctg acggtacagg ccagacaatt attgtctggt atagtgcagc agcagaacaa   1800
tttgctgagg gctattgagg cgcaacagca tctgttgcaa ctcacagtct ggggcatcaa   1860
gcagctccag gcaagaatcc tggctgtgga aagataccta aaggatcaac agctcctggg   1920
gatttggggt tgctctggaa aactcatttg caccactgct gtgccttgga atgctagttg   1980
gagtaataaa tctctggaac agatttggaa tcacacgacc tggatggagt gggacagaga   2040
aattaacaat tacacaagct taatacactc cttaattgaa gaatcgcaaa accagcaaga   2100
aaagaatgaa caagaattat tggaattaga taaatgggca agtttgtgga attggtttaa   2160
cataacaaat tggctgtggt atataaaatt attcataatg atagtaggag gcttggtagg   2220
tttaagaata gtttttgctg tactttctat agtgaataga gttaggcagg gatattcacc   2280
attatcgttt cagacccacc tcccaacccc gaggggaccc gacaggcccg aaggaataga   2340
agaagaaggt ggagagagag acagagacag atccattcga ttagtgaacg gatcggcact   2400
gcgtgcgcca attctgcaga caaatggcag tattcatcca caattttaaa agaaaagggg   2460
ggattggggg gtacagtgca ggggaaagaa tagtagacat aatagcaaca gacatacaaa   2520
ctaaagaatt acaaaaacaa attacaaaaa ttcaaaattt tcgggtttat tacagggaca   2580
gcagagatcc agtttggtta gtaccgggcc cgctctagcg tgaggctccg gtgcccgtca   2640
gtgggcagag cgcacatcgc ccacagtccc cgagaagttg gggggagggg tcggcaattg   2700
aaccggtact ggcctggcca acatagtgaa accccatctc tcctaataat acaaaaatta   2760
gccaggcatg gtggcgggtg cctgtaatcc cagctactca ggagactgag gcaggataat   2820
cacttgaacc cagcaggtgg aggctgcagt gagccaagat cgtgccactg cactccagcc   2880
tgggtgacag agcaagacta catctcaaaa aaaaaaaaaa aaaaaaaaag aagatagatg   2940
accaacaagt ttatgaaaat atgctcaaca tcagtggtca cagggaaatg caaatcaaaa   3000
ccataacaag ataccacttc acacccacac ccagtaggat ggcgcgatcg cagaacccca   3060
gaagatgcca ggagggagtg agccagtcag ggaaggcttc cgagaagaga ggacattgaa   3120
gaagagtctc aaacttaggc ctgacggaga agacgcgcgg ccaggacacc ccaccccccgc  3180
cctcgtctcc cccaaagcct gatctggccc cactgattcc cttatctgcc cactcccagc   3240
tgcctccttg ctggctgaac tgtcgccgca gacttctgag cctgcgcccc ctccacgggg   3300
atgggggagg gaatggggtg aggcctggcc tcacagcctc ggggtttcca gctcttgctg   3360
gaggcagggc tctggggcgc cctactcctc acccttggct tctcttcctg agcgctctgt   3420
gctctccaga gctagcatgg cgggcaagaa gttgaggcca ctgtccctgg gtgttcctac   3480
ccccacaccc tcaccccaag acagcctgtt actgcggcgc caacagccac ggtcgcctac   3540
```

atctgataag acttatctgc tgccccaggg caggccggag ctggcgtaag ccccagtggg 3600
gcgctaagtg agtgtgcccc tgcctcccgc cagcactggc ctggcctgca ggcttagcct 3660
gggtcatcaa ggtatcccac aggctctagt tcaaatccag cagaacctct ctgagcctca 3720
ctcttctcac ctgcaaaatg ggtacagcca catcccttct ctccctgcag ccaggaagac 3780
gcacatacac aggagtctag cccacaccgg ccccgcacaa attaagggct ttactctctg 3840
aaaagcccag tgaagtcatg aaaccatatc tgctattttc atttatcttg gtttcagcct 3900
attttgcttg tctggacact acagtccacg ggagcctagg tcgagcgagg tccaagaatc 3960
cccagggtgg gcagggaggg tggaagaggg cctccagtgc ccaagaggtg ccccacaagc 4020
atgggacccg ccccctcccc tggactgccc cacccactgg ggcaccagcc actccctggg 4080
gaggagggag gagggagaag ggagggaggg agggagggag gaagggagcc tcaaaggcca 4140
aggccagcca ggacaccccc tgggatcaca ctgagcttgc cacatcccca aggcggccga 4200
accctccgca accaccagcc cagagatcta gagttaatcc ccagaggctc catggtgagc 4260
aagggcgagg agctgttcac cggggtggtg cccatcctgg tcgagctgga cggcgacgta 4320
aacggccaca agttcagcgt gtccggcgag ggcgagggcg atgccaccta cggcaagctg 4380
accctgaagt tcatctgcac caccggcaag ctgcccgtgc cctggcccac cctcgtgacc 4440
accctgacct acggcgtgca gtgcttcagc cgctaccccg accacatgaa gcagcacgac 4500
ttcttcaagt ccgccatgcc cgaaggctac gtccaggagc gcaccatctt cttcaaggac 4560
gacggcaact acaagacccg cgccgaggtg aagttcgagg gcgacaccct ggtgaaccgc 4620
atcgagctga agggcatcga cttcaaggag gacggcaaca tcctggggca caagctggag 4680
tacaactaca acagccacaa cgtctatatc atggccgaca agcagaagaa cggcatcaag 4740
gtgaacttca agatccgcca caacatcgag gacggcagcg tgcagctcgc cgaccactac 4800
cagcagaaca cccccatcgg cgacggcccc gtgctgctgc ccgacaacca ctacctgagc 4860
acccagtccg ccctgagcaa agaccccaac gagaagcgcg atcacatggt cctgctggag 4920
ttcgtgaccg ccgccgggat cactctcggc atggacgagc tgtacaagta aagcggccgc 4980
atcgataccg tcgacctcga tcgagaccta gaaaaacatg gagcaatcac aagtagcaat 5040
acagcagcta ccaatgctga ttgtgcctgg ctagaagcac aagaggagga ggaggtgggt 5100
tttccagtca cacctcaggt acctttaaga ccaatgactt acaaggcagc tgtagatctt 5160
agccactttt taaaagaaaa ggggggactg gaagggctaa ttcactccca acgaagacaa 5220
gatatccttg atctgtggat ctaccacaca caaggctact tccctgattg gcagaactac 5280
acaccagggc cagggatcag atatccactg acctttggat ggtgctacaa gctagtacca 5340
gttgagcaag agaaggtaga agaagccaat gaaggagaga acacccgctt gttacaccct 5400
gtgagcctgc atgggatgga tgacccggag agagaagtat tagagtggag gtttgacagc 5460
cgcctagcat ttcatcacat ggcccgagag ctgcatccgg actgtactgg gtctctctgg 5520
ttagaccaga tctgagcctg ggagctctct ggctaactag ggaacccact gcttaagcct 5580
caataaagct tgccttgagt gcttcaagta gtgtgtgccc gtctgttgtg tgactctggt 5640
aactagagat ccctcagacc cttttagtca gtgtggaaaa tctctagcag catgtgagca 5700
aaaggccagc aaaaggccag gaaccgtaaa aaggccgcgt tgctggcgtt tttccatagg 5760
ctccgccccc ctgacgagca tcacaaaaat cgacgctcaa gtcagaggtg gcgaaacccg 5820
acaggactat aaagatacca ggcgtttccc cctggaagct ccctcgtgcg ctctcctgtt 5880
ccgaccctgc cgcttaccgg atacctgtcc gcctttctcc cttcgggaag cgtggcgctt 5940
tctcatagct cacgctgtag gtatctcagt tcggtgtagg tcgttcgctc caagctgggc 6000
tgtgtgcacg aaccccccgt tcagcccgac cgctgcgcct tatccggtaa ctatcgtctt 6060
gagtccaacc cggtaagaca cgacttatcg ccactggcag cagccactgg taacaggatt 6120
agcagagcga ggtatgtagg cggtgctaca gagttcttga agtggtggcc taactacggc 6180
tacactagaa gaacagtatt tggtatctgc gctctgctga agccagttac cttcggaaaa 6240
agagttggta gctcttgatc cggcaaacaa accaccgctg gtagcggtgg tttttttgtt 6300
tgcaagcagc agattacgcg cagaaaaaaa ggatctcaag aagatccttt gatcttttct 6360
acggggtctg acgctcagtg gaacgaaaac tcacgttaag ggattttggt catgagatta 6420
tcaaaaagga tcttcaccta gatcctttta aattaaaaat gaagttttaa atcaatctaa 6480
agtatatatg agtaaacttg gtctgacagt taccaatgct taatcagtga ggcacctatc 6540
tcagcgatct gtctatttcg ttcatccata gttgcctgac tccccgtcgt gtagataact 6600
acgatacggg agggcttacc atctggcccc agtgctgcaa tgataccgcg agacccacgc 6660
tcaccggctc cagatttatc agcaataaac cagccagccg gaagggccga gcgcagaagt 6720
ggtcctgcaa ctttatccgc ctccatccag tctattaatt gttgccggga agctagagta 6780
agtagttcgc cagttaatag tttgcgcaac gttgttgcca ttgctacagg catcgtggtg 6840
tcacgctcgt cgtttggtat ggcttcattc agctccggtt cccaacgatc aaggcgagtt 6900
acatgatccc ccatgttgtg caaaaaagcg gttagctcct tcggtcctcc gatcgttgtc 6960
agaagtaagt tggccgcagt gttatcactc atggttatgg cagcactgca taattctctt 7020
actgtcatgc catccgtaag atgcttttct gtgactggtg agtactcaac caagtcattc 7080
tgagaatagt gtatgcggcg accgagttgc tcttgcccgg cgtcaatacg ggataatacc 7140
gcgccacata gcagaacttt aaaagtgctc atcattggaa aacgttcttc ggggcgaaaa 7200
ctctcaagga tcttaccgct gttgagatcc agttcgatgt aacccactcg tgcacccaac 7260
tgatcttcag catcttttac tttcaccagc gtttctgggt gagcaaaaac aggaaggcaa 7320
aatgccgcaa aaaagggaat aagggcgaca cggaaatgtt gaatactcat actcttcctt 7380
tttcaatatt attgaagcat ttatcagggt tattgtctca tgagcggata catatttgaa 7440
tgtatttaga aaaataaaca aataggggtt ccgcgcacat ttccccgaaa agtgccacct 7500
gac 7503

<210> SEQ ID NO 63
<211> LENGTH: 592
<212> TYPE: DNA
<213> ORGANISM: Woodchuck hepatitis virus

<400> SEQUENCE: 63
aatcaacctc tggattacaa aatttgtgaa agattgactg gtattcttaa ctatgttgct 60
ccttttacgc tatgtggata cgctgcttta atgcctttgt atcatgctat tgcttcccgt 120
atggctttca ttttctcctc cttgtataaa tcctggttgc tgtctcttta tgaggagttg 180
tggcccgttg tcaggcaacg tggcgtggtg tgcactgtgt ttgctgacgc aacccccact 240
ggttggggca ttgccaccac ctgtcagctc ctttccggga ctttcgcttt ccccctccct 300
attgccacgg cggaactcat cgccgcctgc cttgcccgct gctggacagg ggctcggctg 360
ttgggcactg acaattccgt ggtgttgtcg gggaagctga cgtcctttcc atggctgctc 420
gcctgtgttg ccacctggat tctgcgcggg acgtccttct gctacgtccc ttcggccctc 480
aatccagcgg accttccttc ccgcggcctg ctgccggctc tgcggcctct tccgcgtctt 540
cgccttcgcc ctcagacgag tcggatctcc ctttgggccg cctccccgcc tg 592

<210> SEQ ID NO 64
<211> LENGTH: 333
<212> TYPE: PRT
<213> ORGANISM: Homo sapiens

<400> SEQUENCE: 64

Met Glu Gly Ile Pro Gly Gly Ser Pro Tyr Ala Gly Trp Ala Tyr Gly
1 5 10 15

Lys Thr Gly Leu Tyr Pro Ala Ser Thr Val Cys Pro Thr Arg Glu Asp
20 25 30

Ser Pro Pro Gln Ala Val Glu Asp Leu Asp Gly Lys Gly Ser Thr Ser
35 40 45

Phe Leu Glu Thr Leu Lys Thr Glu Arg Leu Ser Pro Asp Leu Leu Thr
50 55 60

Leu Gly Pro Ala Leu Pro Ser Ser Leu Pro Val Pro Asn Ser Ala Tyr
65 70 75 80

Gly Gly Pro Asp Phe Ser Ser Thr Phe Phe Ser Pro Thr Gly Ser Pro
85 90 95

Leu Asn Ser Ala Ala Tyr Ser Ser Pro Lys Leu Arg Gly Thr Leu Pro
100 105 110

Leu Pro Pro Cys Glu Ala Arg Glu Cys Val Asn Cys Gly Ala Thr Ala
115 120 125

Thr Pro Leu Trp Arg Arg Asp Arg Thr Gly His Tyr Leu Cys Asn Ala
130 135 140

Cys Gly Leu Tyr His Lys Met Asn Gly Gln Asn Arg Pro Leu Ile Arg
145 150 155 160

Pro Lys Lys Arg Leu Ile Val Ser Lys Arg Ala Gly Thr Gln Cys Thr
165 170 175

Asn Cys Gln Thr Thr Thr Thr Thr Leu Trp Arg Arg Asn Ala Ser Gly
180 185 190

Asp Pro Val Cys Asn Ala Cys Gly Leu Tyr Tyr Lys Leu His Gln Pro
195 200 205

Pro Phe Trp Gln Val Asn Arg Pro Leu Thr Met Arg Lys Asp Gly Ile
210 215 220

Gln Thr Arg Asn Arg Lys Ala Ser Gly Lys Gly Lys Lys Lys Arg Gly
225 230 235 240

Ser Ser Leu Gly Gly Thr Gly Ala Ala Glu Gly Pro Ala Gly Gly Phe
245 250 255

Met Val Val Ala Gly Gly Ser Gly Ser Gly Asn Cys Gly Glu Val Ala
260 265 270

Ser Gly Leu Thr Leu Gly Pro Pro Gly Thr Ala His Leu Tyr Gln Gly
275 280 285

Leu Gly Pro Val Val Leu Ser Gly Pro Val Ser His Leu Met Pro Phe
290 295 300

Pro Gly Pro Leu Leu Gly Ser Pro Thr Gly Ser Phe Pro Thr Gly Pro
305 310 315 320

Met Pro Pro Thr Thr Ser Thr Thr Val Val Ala Pro Leu
325 330

<210> SEQ ID NO 65
<211> LENGTH: 330

<212> TYPE: PRT
<213> ORGANISM: Homo sapiens

<400> SEQUENCE: 65

```
Met Glu Gly Ile Pro Gly Gly Ser Pro Tyr Ala Gly Trp Ala Tyr Gly
1               5                   10                  15

Lys Thr Gly Leu Tyr Pro Ala Ser Thr Val Cys Pro Thr Arg Glu Asp
            20                  25                  30

Ser Pro Pro Gln Ala Val Glu Asp Leu Asp Gly Lys Gly Ser Thr Ser
        35                  40                  45

Phe Leu Glu Thr Leu Lys Thr Glu Arg Leu Ser Pro Asp Leu Leu Thr
    50                  55                  60

Leu Gly Pro Ala Leu Pro Ser Ser Leu Pro Val Pro Asn Ser Ala Tyr
65                  70                  75                  80

Gly Gly Pro Asp Phe Ser Ser Thr Phe Phe Ser Pro Thr Gly Ser Pro
                85                  90                  95

Leu Asn Ser Ala Ala Tyr Ser Ser Pro Lys Leu Arg Gly Thr Leu Pro
            100                 105                 110

Leu Pro Pro Cys Glu Ala Arg Glu Cys Val Asn Cys Gly Ala Thr Ala
        115                 120                 125

Thr Pro Leu Trp Arg Arg Asp Arg Thr Gly His Tyr Leu Cys Asn Ala
    130                 135                 140

Cys Gly Leu Tyr His Lys Met Asn Gly Gln Asn Arg Pro Leu Ile Arg
145                 150                 155                 160

Pro Lys Lys Arg Leu Ile Val Ser Lys Arg Ala Gly Thr Gln Cys Thr
                165                 170                 175

Asn Cys Gln Thr Thr Thr Thr Thr Leu Trp Arg Arg Asn Ala Ser Gly
            180                 185                 190

Asp Pro Val Cys Asn Ala Cys Gly Leu Tyr Tyr Lys Leu His Gln Val
        195                 200                 205

Asn Arg Pro Leu Thr Met Arg Lys Asp Gly Ile Gln Thr Arg Asn Arg
    210                 215                 220

Lys Ala Ser Gly Lys Gly Lys Lys Lys Arg Gly Ser Ser Leu Gly Gly
225                 230                 235                 240

Thr Gly Ala Ala Glu Gly Pro Ala Gly Gly Phe Met Val Val Ala Gly
                245                 250                 255

Gly Ser Gly Ser Gly Asn Cys Gly Glu Val Ala Ser Gly Leu Thr Leu
            260                 265                 270

Gly Pro Pro Gly Thr Ala His Leu Tyr Gln Gly Leu Gly Pro Val Val
        275                 280                 285

Leu Ser Gly Pro Val Ser His Leu Met Pro Phe Pro Gly Pro Leu Leu
    290                 295                 300

Gly Ser Pro Thr Gly Ser Phe Pro Thr Gly Pro Met Pro Pro Thr Thr
305                 310                 315                 320

Ser Thr Thr Val Val Ala Pro Leu Ser Ser
                325                 330
```

<210> SEQ ID NO 66
<211> LENGTH: 587
<212> TYPE: DNA
<213> ORGANISM: Unknown
<220> FEATURE:
<223> OTHER INFORMATION: Description of Unknown:
      Internal ribosome entry site sequence

<400> SEQUENCE: 66

-continued

```
ccccctctccc tccccccccc ctaacgttac tggccgaagc cgcttggaat aaggccggtg      60

tgcgtttgtc tatatgttat tttccaccat attgccgtct tttggcaatg tgagggcccg     120

gaaacctggc cctgtcttct tgacgagcat tcctaggggt ctttcccctc tcgccaaagg     180

aatgcaaggt ctgttgaatg tcgtgaagga agcagttcct ctggaagctt cttgaagaca     240

aacaacgtct gtagcgaccc tttgcaggca gcggaacccc ccacctggcg acaggtgcct     300

ctgcggccaa aagccacgtg tataagatac acctgcaaag gcggcacaac cccagtgcca     360

cgttgtgagt tggatagttg tggaaagagt caaatggctc tcctcaagcg tattcaacaa     420

ggggctgaag gatgcccaga aggtacccca ttgtatggga tctgatctgg ggcctcggta     480

cacatgcttt acatgtgttt agtcgaggtt aaaaaaacgt ctaggccccc cgaaccacgg     540

ggacgtggtt ttcctttgaa aaacacgatg ataatatggc cacaacc                   587


<210> SEQ ID NO 67
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67

gagtccatct gataagactt atctgctgcc ccccagagca ggccagagct ggcgta          56


<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

ccgctgattc ccttatctat gccttcccag                                       30


<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

cggcacaccc cctcccctgc actgccccac ccactg                                36
```

COMPOSITIONS AND METHODS FOR THE TREATMENT OF DBA USING GATA1 GENE THERAPY

CROSS-REFERENCE TO RELATED APPLICATIONS

This application is a 35 U.S.C. § 371 National Phase Entry Application of International Application No. PCT/US2020/036600 filed Jun. 8, 2020, which designates the U.S. and claims benefit under 35 U.S.C. § 119(e) of U.S. Provisional Application No. 62/859,369 filed Jun. 10, 2019, the contents of which are incorporated herein by reference in their entireties.

GOVERNMENT SUPPORT

This invention was made with government support under Grant Nos: R1 DK103794 and R33 HL120791 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 3, 2020, is named 701039-094470WO-PT_SL.txt and is 188,598 bytes in size.

TECHNICAL FIELD

The technology described herein relates to compositions and methods of GATA-1 gene therapy for the treatment of Diamond-Blackfan anemia and uses thereof.

BACKGROUND

Diamond-Blackfan anemia (DBA) is one of a rare group of inherited bone marrow failure syndromes (IBMFSs) and is characterized by red cell failure, the presence of congenital anomalies, and cancer predisposition. DBA is usually diagnosed in children during their first year of life. Children with DBA do not make enough red blood cells, the cells that carry oxygen to all other cells in the body. In children with DBA, many of the cells that would have become red blood cells die before they develop. In addition to being an inherited bone marrow failure syndrome, DBA is also categorized as a ribosomopathy as, in more than 50% of cases, the syndrome appears to result from haploinsufficiency of either a small or large subunit-associated ribosomal protein.

DBA is characterized by a specific reduction in the production of red blood (erythroid) cells and their precursors without defects in other hematopoietic lineages. Over the past decade, the elucidation of mutations in the ribosomal protein gene RPS19, followed by the discovery of mutations in 9 other ribosomal protein genes, has led to the hypothesis that DBA is a disorder of ribosomal biogenesis. However, approximately 50% of DBA cases have as-yet-unidentified molecular mutations, despite systematic sequencing of all ribosomal protein and other candidate genes in these cases.

The GATA-1 gene is located on the X-chromosome and encodes a transcription factor that regulates the development of erythrocytes. Recently, loss-of-function mutations in GATA-1 have been found in patients with Diamond-Blackfan anemia (DBA). However, no treatment targeting GATA-1 augmentation specifically in erythroid cells is currently available. Thus, therapeutic approaches that directly target GATA-1 dysfunction in erythroid cells are necessary in order to provide effective treatment.

SUMMARY

Recent studies have shown that GATA-1 augmentation in erythroid cells may have therapeutic effects in Diamond-Blackfan anemia (DBA). However, increasing the lineage-specific expression of therapeutic proteins including GATA-1 in vivo remains challenging. Attempting to increase GATA1 expression with existing technology necessarily increased GATA1 expression in cells (e.g. HSCs) where it is overwhelming deleterious to the subject, negating any possible therapeutic effect.

As described herein, the inventors have identified compositions and methods to increase lineage-specific expression of GATA1 specifically in early erythroid progenitors but not in hematopoietic stem cells as a gene therapeutic approach for the treatment of Diamond-Blackfan anemia. DBA is characterized by a specific reduction in the production of red blood (erythroid) cells and their precursors without defects in other hematopoietic lineages.

In one aspect of any of the embodiments, described herein is a nucleic acid sequence comprising at least one heterologous regulatory sequence selected from a hematopoietic enhancer element and miRNA binding site for a HSC restricted miRNA; and a sequence encoding a GATA-binding factor 1 (GATA1) polypeptide.

In some embodiments of any of the aspects, the nucleic acid sequence comprises at least one hematopoietic enhancer element.

In some embodiments of any of the aspects, the enhancer element comprises a sequence of at least 80% homology to a nucleotide sequence that is selected from the group consisting of: SEQ ID NO: 10, SEQ ID NO: 11, SEQ ID NO: 12, SEQ ID NO: 38 and/or SEQ ID NO: 39.

In some embodiments of any of the aspects, the enhancer element comprises an enhancer element of a gene selected from the group consisting of: Kell metalloendopeptidase (KEL); 5' aminolevulinate synthase 2 (ALAS2); and glycophorin A (GYPA).

In some embodiments of any of the aspects, the nucleic acid comprises at least one miRNA binding site for at least one HSC-restricted miRNA.

In some embodiments of any of the aspects, the at least one miRNA binding site for at least one HSC-restricted miRNA is selected from the group consisting of miR binding sites for miR10aT, miR125, miR155, miR130aT, miR142T, miR196bT, miR99, miR126miR126, miR181, miR193, miR223T, miR542, and let7e.

In some embodiments of any of the aspects, the nucleic acid comprises at least one hematopoietic enhancer element and at least one miRNA binding site for at least one HSC-restricted miRNA.

In some embodiments of any of the aspects, comprising: a heterologous 5' UTR comprising: a 5'UTR sequence of a hematopoietic transcription factor other than GATA1; ii. a sequence of at least 20 nucleotide acids; and/or iii. 1-25 upstream codons uAUGs; and/or b. a hematopoietic enhancer minigene.

In one aspect of any of the embodiments, described herein is a nucleic acid sequence comprising a 5' UTR comprising; i. a 5'UTR sequence of a hematopoietic transcription factor other than GATA1; ii. a sequence of at least 20 nucleotide acids; and/or iii. 1-25 upstream codons uAUGs and a sequence encoding a GATA-binding factor 1 (GATA1) polypeptide.

In some embodiments of any of the aspects, the 5'UTR comprises a 5'UTR of a gene selected from the group consisting of: Runt-related transcription factor 1 (RUNX1), LIM Domain Only 2 (LMO2), or ETS Variant 6 (ETV6).

In some embodiments of any of the aspects, the nucleic acid further comprises at least one hematopoietic enhancer element, miRNA binding site for a HSC restricted miRNA and/or a hematopoietic enhancer minigene (G1HEM).

In one aspect of any of the embodiments, described herein is a nucleic acid sequence comprising an hematopoietic enhancer minigene (G1HEM); a sequence encoding a GATA-binding factor 1 (GATA1) polypeptide.

In some embodiments of any of the aspects, the hematopoietic enhancer minigene (mG1HEM) comprises a sequence of at least 80% homology to a nucleotide sequence of: SEQ ID NO: 13.

In some embodiments of any of the aspects, the nucleic acid further comprises a 5' UTR comprising; i. a 5'UTR sequence of a hematopoietic transcription factor other than GATA1; ii. a sequence of at least 20 nucleotide acids; and/or iii. 1-25 upstream codons uAUGs; and/or at least one hematopoietic enhancer element; and/or at least one miRNA binding site for a HSC restricted miRNA.

In some embodiments of any of the aspects, the nucleic acid further comprises a 5' UTR comprising; a 5'UTR of a gene selected from the group consisting of: Runt-related transcription factor 1 (RUNX1), at least one hematopoietic enhancer element; and/or at least one miRNA binding site for a HSC restricted miRNA.

In some embodiments of any of the aspects, the nucleic acid the sequence comprises a promoter operably linked to the elements of a. and b.

In some embodiments of any of the aspects, the promoter is not a GATA1 promoter.

In some embodiments of any of the aspects, the promoter comprises a promoter sequence of Elongation factor 1-alpha 1 (eEF1a1).

In some embodiments of any of the aspects, the sequence encoding a GATA-binding factor 1 (GATA1) polypeptide comprises at least 60% sequence identity to a nucleotide sequence encoding a human GATA1 polypeptide.

In some embodiments of any of the aspects, the nucleic acid sequence comprises: a posttranscriptional regulatory element operably linked to the sequence encoding the GATA1 polypeptide.

In some embodiments of any of the aspects, the posttranscriptional regulatory element comprises a Woodchuck Hepatitis Virus Posttranscriptional Regulatory Element (WPRE).

In some embodiments of any of the aspects, the nucleic acid sequence further comprises: an internal ribosome entry site.

In some embodiments of any of the aspects, the internal ribosome entry site is operably linked to a marker gene and wherein the marker gene encodes an optically visible protein or an enzyme.

In some embodiments of any of the aspects, the sequence comprises a sequence selected from SEQ ID NOs 8, 9 and 62.

In some embodiments of any of the aspects, the nucleic acid sequence is a vector.

In some embodiments of any of the aspects, the vector is a plasmid, or an adenoviral, lentiviral or retroviral vector.

In one aspect of any of the embodiments, described herein is a lentiviral particle comprising the nucleic acid sequence.

In one aspect of any of the embodiments, described herein is a composition comprising a nucleic acid sequence or particle and a pharmaceutically acceptable carrier.

In one aspect of any of the embodiments, described herein is a method of treating Diamond-Blackfan Anemia in a subject in need thereof, the method comprising administering a therapeutically effective amount of a nucleic acid sequence, particle, or composition to the patient.

In one aspect of any of the embodiments, described herein is a method of restoring early erythroid progenitor cell-specific GATA1 expression, the method comprising contacting a population of cells comprising early erythroid progenitor cells with a nucleic acid sequence, particle, or composition.

In some embodiments of any of the aspects, the early erythroid progenitor cells comprise a DBA-associated gene mutation.

In one aspect of any of the embodiments, described herein is a nucleic acid sequence, particle, or composition described herein for use in the treatment of Diamond-Blackfan Anemia in a subject in need thereof.

BRIEF DESCRIPTION OF THE DRAWINGS

FIG. 4A. The three patients shown have mutations in RPS19 (Patient 2 and 3) and RPL35A (Patient 1).

FIG. 5 discloses SEQ ID NOS 67-69, respectively, in order of appearance.

FIG. 8A demonstrates the chromatin accessibility upstream of human GATA1. FIG. 8B. Two vectors to achieve developmentally faithful expression of GATA1 in early erythroid progenitors but not in hematopoietic stem cells.

FIG. 9A. R18 EF-1α IRES GFP Control. FIG. 9B. R21 EF-1α IRES GFP miR126. FIG. 9C. R49 EF-1α 1 peak enhancer GFP. FIG. 9D. R50 3 Peak Enhancer GFP. FIG. 9E. GATA1 vector with enhancer and miR126 binding site.

FIG. 27 shows a schemata depicting key features and a summary of experimental validation of a GATA1 gene therapy vector to cure DBA.

FIG. 28A. Accessible chromatin upstream of human GATA1 in descending order from HSPCs to reticulocytes (top) and schematic of lentiviral vector to achieve regulated GATA1 expression (bottom). FIG. 28C. Erythroid differentiation of murine G1E cells is achieved with regulated GATA1 expression. FIG. 28D. GFP ratio in erythroid progenitors compared to HSCs shows developmentally regulated expression.

FIG. 29A, FIG. 29B, and FIG. 29C shows exogenous GATA1 expression during erythroid differentiation. FIG. 29A. differentiating erythroid precursors first express CD71 followed by CD235 and finally loss of CD71 during terminal erythroid differentiation. FIG. 29B. Percentage of erythroid progenitors that express CD71 (dark grey) or both CD71 and CD235 (light grey) on day 4 is higher after infection with GATA1 virus. FIG. 29C. Ratio of GFP expression of CD71−CD235+ cells compared to CD71+CD235+ cells reveals decreased expression from hG1E during terminal erythroid differentiation, mimicking endogenous GATA1 expression.

FIG. 30A. Proportion of CD71+ cells that also express CD235 is higher after GATA1 infection. FIG. 30B. Regulated GATA1 promotes erythroid colony formation.

DETAILED DESCRIPTION

Figure 1:
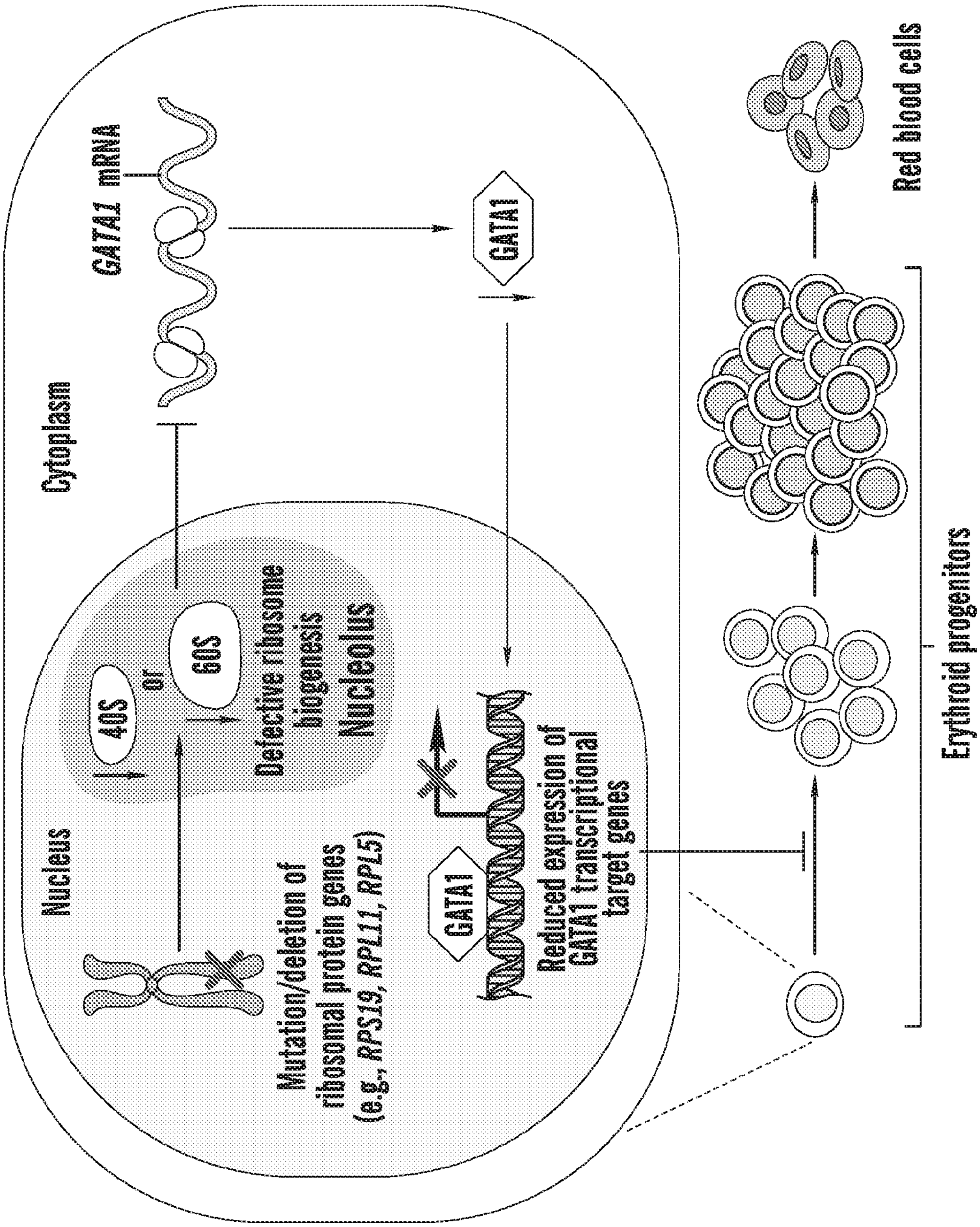
FIG. 1 depicts a schematic of the molecular pathways involved in Diamond-Blackfan anemia (DBA) pathogenesis.
Figure 2B:
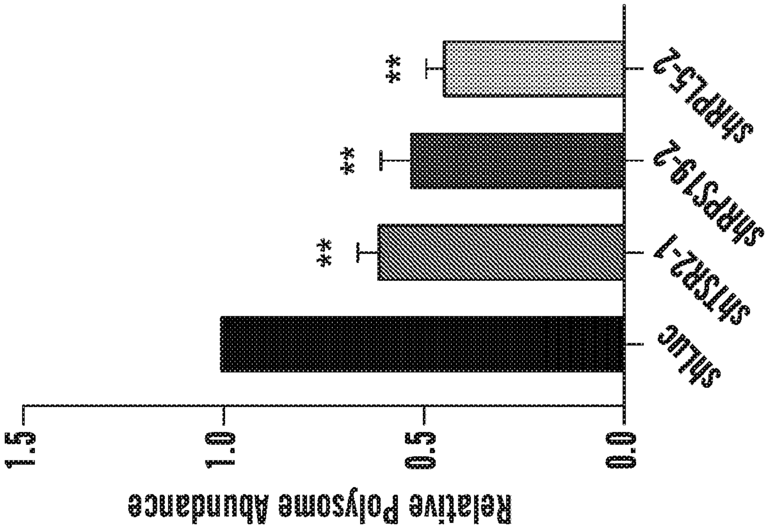
FIG. 2A, FIG. 2B, and FIG. 2C demonstrate reduced ribosome levels with DBA-molecular lesions.
Figure 2A:
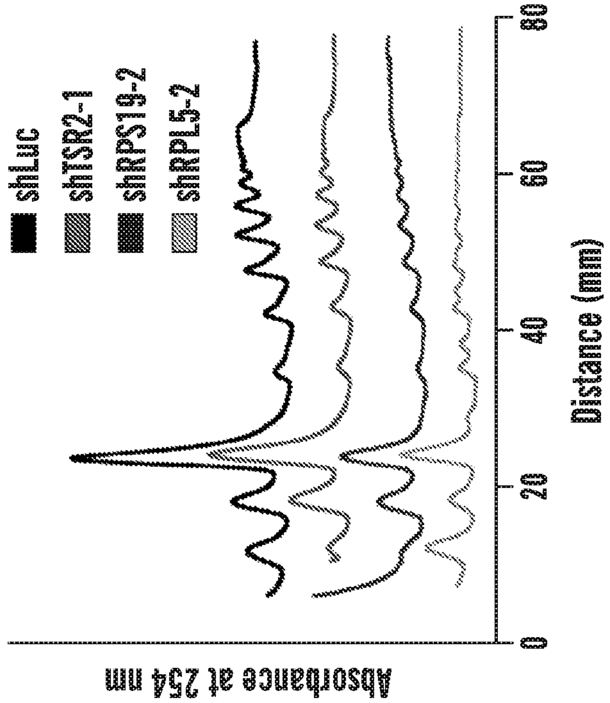
Figure 2C:
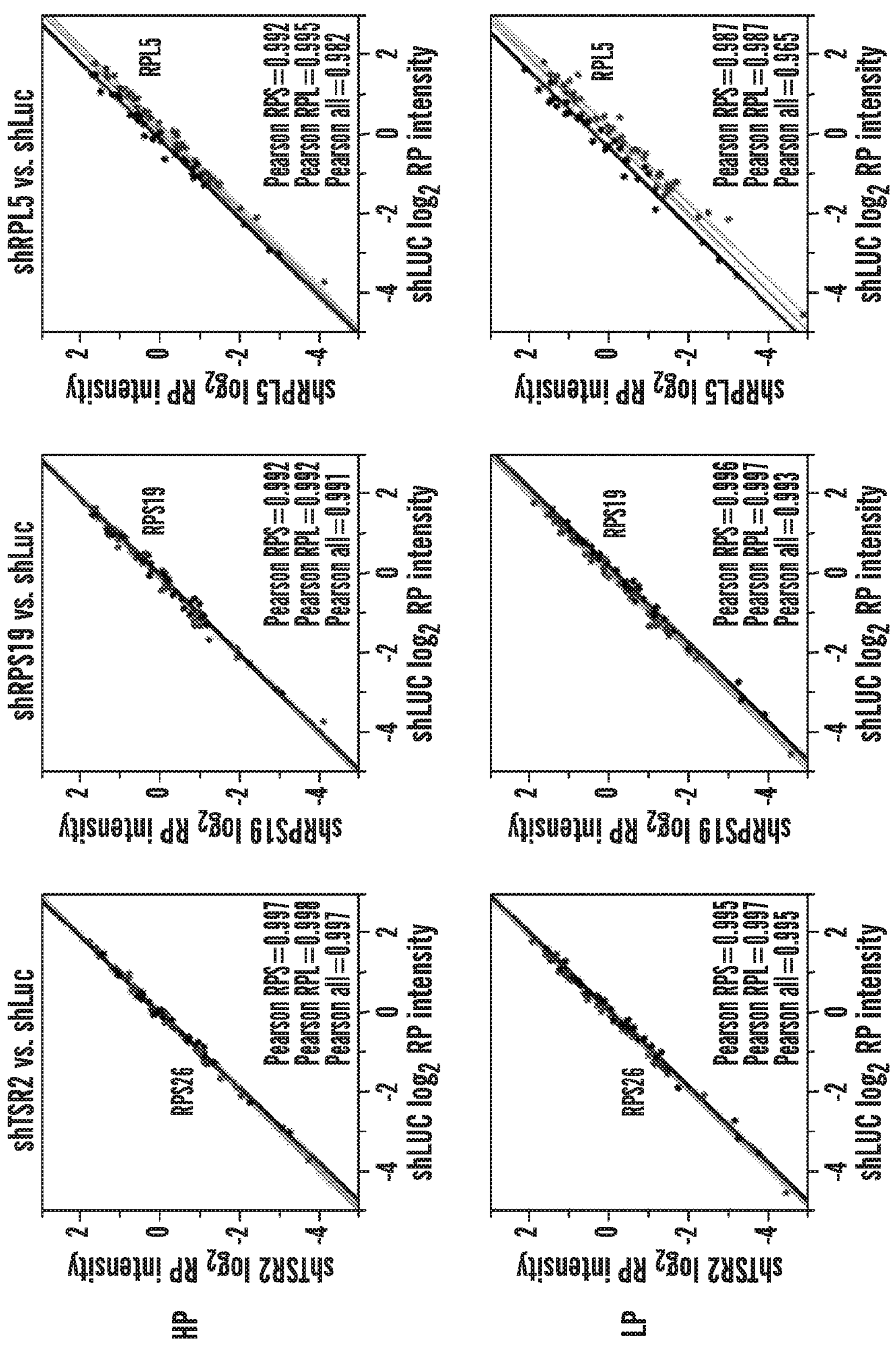
Figure 2C:
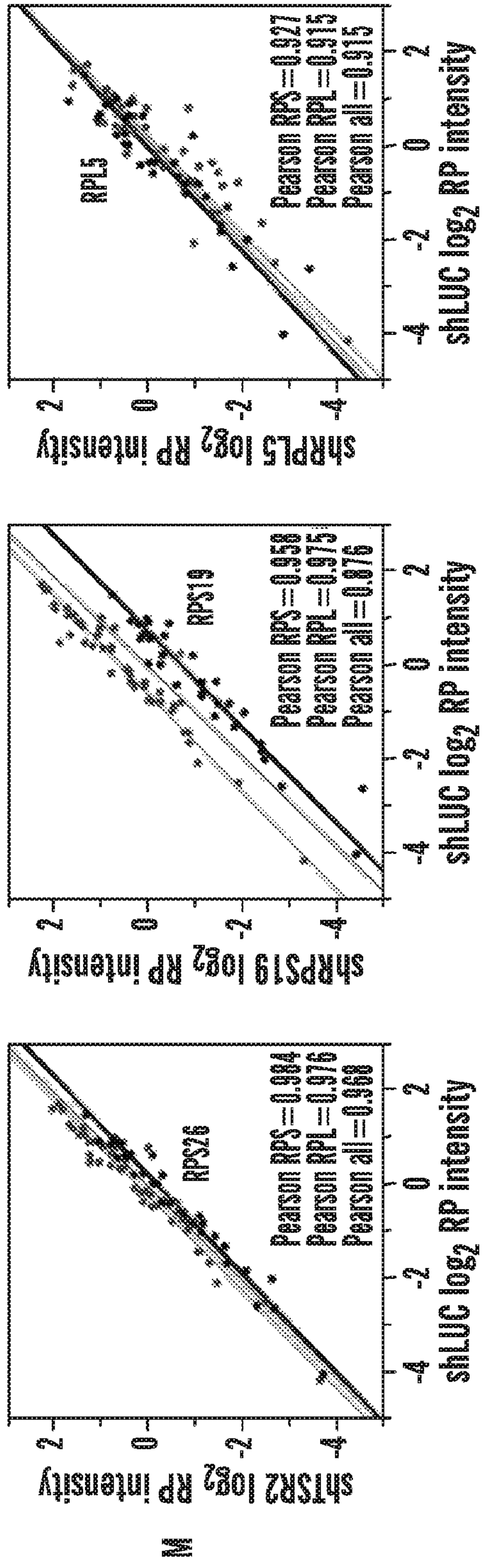

As described herein, GATA-1 augmentation in erythroid cells can have therapeutic effects in Diamond-Blackfan anemia (DBA). However, existing methods of increasing GATA-1 expression in erythroid cells also necessarily increase expression in other cell types, e.g., in hematopoietic stem cells. These off-target effects can lead to damaging side effects and must be avoided in order to provide an actual treatment to subjects. That said, increasing the lineage-specific expression of therapeutic proteins including GATA-1 in vivo has proven challenging and has not yet been successfully done.

As described herein, the inventors have identified nucleic acid sequences comprising regulatory sequences that can restore early erythroid progenitor cell-specific GATA1 expression, thereby permitting a therapeutic approach for DBA. Briefly, the methods described herein relate to compositions and methods to increase lineage-specific expression of GATA1 in early erythroid progenitors but not in hematopoietic stem cells as a therapy for DBA. More specifically, described herein are methods of restoring early erythroid progenitor cell-specific GATA1 expression by contacting a population of early erythroid progenitor cells, including but not limited to cells that comprise a DBA-associated gene mutation with a nucleic acid sequence, particle, or composition as described herein.

DBA is characterized by a specific reduction in the production of red blood (erythroid) cells and their precursors without defects in other hematopoietic lineages. Provided herein are methods of treating Diamond-Blackfan Anemia in a subject in need thereof, the method comprising administering a therapeutically effective amount of a nucleic acid sequence, particle, or composition including but not limited to vectors with specific gene regulatory elements for the development of broadly applicable hematopoietic gene therapy approaches for DBA patients, as described herein.

Furthermore, provided herein are methods of restoring early erythroid progenitor cell-specific GATA1 expression, the method comprising contacting a population of cells comprising early erythroid progenitor cells with a nucleic acid sequence, particle, or composition as described herein.

Diamond-Blackfan anemia (DBA) is a congenital erythroid aplasia that usually presents in infancy. DBA causes low red blood cell counts (anemia), without substantially affecting the other blood components (the platelets and the white blood cells). About 47% of affected individuals also have a variety of congenital abnormalities, including craniofacial malformations, thumb or upper limb abnormalities, cardiac defects, urogenital malformations, and cleft palate. Low birth weight and generalized growth delay are sometimes observed. DBA patients have a modest risk of developing leukemia and other malignancies.

DBA is characterized by a specific reduction in the production of red blood (erythroid) cells and their precursors without defects in other hematopoietic lineages. In more than 50% of cases, DBA is caused by heterozygous loss-of-function mutations (haploinsufficiency) in one of 11 genes encoding ribosomal proteins, including the RPL5, RPL11, RPL35A, RPS10, RPS17, RPS19, RPS24, and RPS26 genes. These and other genes associated with Diamond-Blackfan anemia provide instructions for making ribosomal proteins. Approximately 25 percent of individuals with Diamond-Blackfan anemia have mutations in the RPS19 gene. About another 25 to 35 percent of individuals with this disorder have mutations in the RPL5, RPL11, RPL35A, RPS10, RPS17, RPS24, or RPS26 gene. Mutations in any of these genes are believed to cause problems with ribosome function. It is striking that mutations of such ubiquitously expressed ribosomal proteins result in such specific human disorders. Studies indicate that a shortage of functioning ribosomes may increase the self-destruction of blood-forming cells in the bone marrow, resulting in anemia. Abnormal regulation of cell division or inappropriate triggering of apoptosis may contribute to the other health problems that affect some people with Diamond-Blackfan anemia. Numerous theories have been proposed for the pathogenesis underlying these diseases. However, these models are unable to explain the exquisite cell-type specificity of DBA and the other ribosomal disorders.

Haploinsufficiency of ribosomal proteins can contribute to other cell-type specific diseases in humans, including congenital asplenia and T-cell lymphocytic leukemia. It is striking that mutations of such ubiquitously expressed ribosomal proteins result in such specific human disorders. Numerous theories have been proposed for the pathogenesis underlying these diseases. However, these models are unable to explain the exquisite cell-type specificity of DBA and the other ribosomal disorders.

In various embodiments described herein are methods of restoring early erythroid progenitor cell-specific GATA1 expression, comprising contacting a population of cells comprising early erythroid progenitor cells with a nucleic acid sequences, particles, or compositions as described herein. Furthermore, it is contemplated that the nucleic acid sequences, particles, or compositions described herein can be used to treat DBA by administering a therapeutically effective amount of a nucleic acid sequence, particle, or composition as described herein to a patient in need of treatment for DBA.

As used herein, "GATA-1", "GATA1", or "GATA binding protein 1" is a protein that is encoded by the GATA1 gene. The protein encoded by this gene is a protein of the GATA family of transcription factors. The protein plays an important role in erythroid development by regulating the switch of fetal hemoglobin to adult hemoglobin. The GATA1 gene is located on the X-chromosome (Xp11.23) and encodes a transcription factor that regulates the development of erythrocytes. Loss-of-function mutation in GATA-1 are linked to hematopoietic disorders, including DBA.

The GATA-1 polypeptide has three functional domains: a N-terminal transactivation domain (TD), essential for transcriptional activation activity, a N-terminal zinc finger (NF), and a C-terminal zinc finger (CF) responsible for the binding to DNA. Exon 4 mutations have been identified in families with dyserythropoietic anemia, thrombocytopenia, thalassemia, and erythropoietic porphyria. Related germline mutations have also been described. The loss-of-function mutations of GATA-1 in DBA occur at the donor splice site of exon 2 in the GATA-1 gene and result in exon skipping.

Sequences for GATA1 are known for a number of species, e.g., human GATA1 (the GATA1 NCBI Gene ID is 2623) mRNA sequences (e.g., NM_002049.3, XM_011543897.2, XM_011543898.2, and XM_024452363.1) and polypeptide sequences (e.g., NP_002040.1, XP_011542199.1, XP_011542200.1, XP_024308131.1) are known in the art. These, together with any naturally occurring allelic, splice variants, and processed forms thereof that catalyze the same reaction are contemplated for use in the methods and compositions described herein.

In some embodiments of any of the aspects, the GATA1 nucleic acid includes or is derived from human GATA1 having the following nucleic acid sequence CCDS14305.1 (SEQ ID NO: 1).

ATGGAGTTCCCTGGCCTGGGGTCCCTGGGGACCTCAGAGCCCCTCCCCCA

GTTTGTGGATCCTGCTCTGGTGTCCTCCACACCAGAATCAGGGGTTTTCT

TCCCCTCTGGGCCTGAGGGCTTGGATGCAGCAGCTTCCTCCACTGCCCCG

AGCACAGCCACCGCTGCAGCTGCGGCACTGGCCTACTACAGGGACGCTGA

GGCCTACAGACACTCCCCAGTCTTTCAGGTGTACCCATTGCTCAACTGTA

TGGAGGGGATCCCAGGGGGCTCACCATATGCCGGCTGGGCCTACGGCAAG

ACGGGGCTCTACCCTGCCTCAACTGTGTGTCCCACCCGCGAGGACTCTCC

TCCCCAGGCCGTGGAAGATCTGGATGGAAAAGGCAGCACCAGCTTCCTGG

AGACTTTGAAGACAGAGCGGCTGAGCCCAGACCTCCTGACCCTGGGACCT

GCACTGCCTTCATCACTCCCTGTCCCCAATAGTGCTTATGGGGGCCCTGA

CTTTTCCAGTACCTTCTTTTCTCCCACCGGGAGCCCCCTCAATTCAGCAG

CCTATTCCTCTCCCAAGCTTCGTGGAACTCTCCCCCTGCCTCCCTGTGAG

GCCAGGGAGTGTGTGAACTGCGGAGCAACAGCCACTCCACTGTGGCGGAG

GGACAGGACAGGCCACTACCTATGCAACGCCTGCGGCCTCTATCACAAGA

TGAATGGGCAGAACAGGCCCCTCATCCGGCCCAAGAAGCGCCTGATTGTC

AGTAAACGGGCAGGTACTCAGTGCACCAACTGCCAGACGACCACCACGAC

ACTGTGGCGGAGAAATGCCAGTGGGGATCCCGTGTGCAATGCCTGCGGCC

TCTACTACAAGCTACACCAGGTGAACCGGCCACTGACCATGCGGAAGGAT

GGTATTCAGACTCGAAACCGCAAGGCATCTGGAAAAGGGAAAAAGAAACG

GGGCTCCAGTCTGGGAGGCACAGGAGCAGCCGAAGGACCAGCTGGTGGCT

TTATGGTGGTGGCTGGGGGCAGCGGTAGCGGGAATTGTGGGGAGGTGGCT

-continued

TCAGGCCTGACACTGGGCCCCCCAGGTACTGCCCATCTCTACCAAGGCCT

GGGCCCTGTGGTGCTGTCAGGGCCTGTTAGCCACCTCATGCCTTTCCCTG

GACCCCTACTGGGCTCACCCACGGGCTCCTTCCCCACAGGCCCCATGCCC

CCCACCACCAGCACTACTGTGGTGGCTCCGCTCAGCTCATGA

In some embodiments of any of the aspects, the GATA1 mRNA sequences includes or is derived from human GATA1 having the following sequence NM_002049.3 (SEQ ID NO: 2):

GACACCCCCTGGGATCACACTGAGCTTGCCACATCCCCAAGGCGGCCGAA

CCCTCCGCAACCACCAGCCCAGGTTAATCCCCAGAGGCTCCATGGAGTTC

CCTGGCCTGGGGTCCCTGGGGACCTCAGAGCCCCTCCCCCAGTTTGTGGA

TCCTGCTCTGGTGTCCTCCACACCAGAATCAGGGGTTTTCTTCCCCTCTG

GGCCTGAGGGCTTGGATGCAGCAGCTTCCTCCACTGCCCCGAGCACAGCC

ACCGCTGCAGCTGCGGCACTGGCCTACTACAGGGACGCTGAGGCCTACAG

ACACTCCCCAGTCTTTCAGGTGTACCCATTGCTCAACTGTATGGAGGGGA

TCCCAGGGGGCTCACCATATGCCGGCTGGGCCTACGGCAAGACGGGGCTC

TACCCTGCCTCAACTGTGTGTCCCACCCGCGAGGACTCTCCTCCCCAGGC

CGTGGAAGATCTGGATGGAAAAGGCAGCACCAGCTTCCTGGAGACTTTGA

AGACAGAGCGGCTGAGCCCAGACCTCCTGACCCTGGGACCTGCACTGCCT

TCATCACTCCCTGTCCCCAATAGTGCTTATGGGGGCCCTGACTTTTCCAG

TACCTTCTTTTCTCCCACCGGGAGCCCCCTCAATTCAGCAGCCTATTCCT

-continued

CTCCCAAGCTTCGTGGAACTCTCCCCCTGCCTCCCTGTGAGGCCAGGGAG

TGTGTGAACTGCGGAGCAACAGCCACTCCACTGTGGCGGAGGGACAGGAC

AGGCCACTACCTATGCAACGCCTGCGGCCTCTATCACAAGATGAATGGGC

AGAACAGGCCCCTCATCCGGCCCAAGAAGCGCCTGATTGTCAGTAAACGG

GCAGGTACTCAGTGCACCAACTGCCAGACGACCACCACGACACTGTGGCG

GAGAAATGCCAGTGGGGATCCCGTGTGCAATGCCTGCGGCCTCTACTACA

AGCTACACCAGGTGAACCGGCCACTGACCATGCGGAAGGATGGTATTCAG

ACTCGAAACCGCAAGGCATCTGGAAAAGGGAAAAAGAAACGGGGCTCCAG

TCTGGGAGGCACAGGAGCAGCCGAAGGACCAGCTGGTGGCTTTATGGTGG

TGGCTGGGGGCAGCGGTAGCGGGAATTGTGGGGAGGTGGCTTCAGGCCTG

ACACTGGGCCCCCCAGGTACTGCCCATCTCTACCAAGGCCTGGGCCCTGT

GGTGCTGTCAGGGCCTGTTAGCCACCTCATGCCTTTCCCTGGACCCCTAC

TGGGCTCACCCACGGGCTCCTTCCCCACAGGCCCCATGCCCCCCACCACC

AGCACTACTGTGGTGGCTCCGCTCAGCTCATGAGGGCACAGAGCATGGCC

TCCAGAGGAGGGGTGGTGTCCTTCTCCTCTTGTAGCCAGAATTCTGGACA

ACCCAAGTCTCTGGGCCCCAGGCACCCCCTGGCTTGAACCTTCAAAGCTT

TTGTAAAATAAAACCACCAAAGTCCTGAAAAAAAAAAAAAAAAAAAAAAA

A

In some embodiments of any of the aspects, the GATA1 mRNA sequences includes or is derived from human GATA1 having the following sequence XM_011543898.2 (SEQ ID NO: 3):

GACACCCCCTGGGATCACACTGAGCTTGCCACATCCCCAAGGCGGCCGAACCCTCCGCAACCACCAGCCC

AGGTTAATCCCCAGAGGCTCCATGGAGTTCCCTGGCCTGGGGTCCCTGGGGACCTCAGAGCCCCTCCCCC

AGTTTGTGGATCCTGCTCTGGTGTCCTCCACACCAGAATCAGGGGTTTTCTTCCCCTCTGGGCCTGAGGG

CTTGGATGCAGCAGCTTCCTCCACTGCCCCGAGCACAGCCACCGCTGCAGCTGCGGCACTGGCCTACTAC

AGGGACGCTGAGGCCTACAGACACTCCCCAGTCTTTCAGGTGTACCCATTGCTCAACTGTATGGAGGGGA

TCCCAGGGGGCTCACCATATGCCGGCTGGGCCTACGGCAAGACGGGGCTCTACCCTGCCTCAACTGTGTG

TCCCACCCGCGAGGACTCTCCTCCCCAGGCCGTGGAAGATCTGGATGGAAAAGGCAGCACCAGCTTCCTG

GAGACTTTGAAGACAGAGCGGCTGAGCCCAGACCTCCTGACCCTGGGACCTGCACTGCCTTCATCACTCC

CTGTCCCCAATAGTGCTTATGGGGGCCCTGACTTTTCCAGTACCTTCTTTTCTCCCACCGGGAGCCCCCT

CAATTCAGCAGCCTATTCCTCTCCCAAGCTTCGTGGAACTCTCCCCCTGCCTCCCTGTGAGGCCAGGGAG

TGTGTGAACTGCGGAGCAACAGCCACTCCACTGTGGCGGAGGGACAGGACAGGCCACTACCTATGCAACG

CCTGCGGCCTCTATCACAAGATGAATGGGCAGAACAGGCCCCTCATCCGGCCCAAGAAGCGCCTGATTGT

CAGTAAACGGGCAGGTACTCAGTGCACCAACTGCCAGACGACCACCACGACACTGTGGCGGAGAAATGCC

AGTGGGGATCCCGTGTGCAATGCCTGCGGCCTCTACTACAAGCTACACCAGGTGAACCGGCCACTGACCA

TGCGGAAGGATGGTATTCAGACTCGAAACCGCAAGGCATCTGGAAAAGGGAAAAAGAAACGGGGCTCCAG

TCTGGGAGGCACAGGAGCAGCCGAAGGACCAGCTGGTGGCTTTATGGTGGTGGCTGGGGGCAGCGGTAGC

GGGAATTGTGGGGAGGTGGCTTCAGGCCTGACACTGGGCCCCCCAGGTACTGCCCATCTCTACCAAGGCC

TGGGCCCTGTGGTGCTGTCAGGGCCTGTTAGCCACCTCATGCCTTTCCCTGGACCCCTACTGGGCTCACC

CACGGGCTCCTTCCCCACAGGCCCCATGCCCCCCACCACCAGCACTACTGTGGTGGCTCCGCTCAGCTCA

-continued

TGAGGGCACAGAGCATGGCCTCCAGAGGAGGGGTGGTGTCCTTCTCCTCTTGTAGCCAGAATTCTGGACA

ACCCAAGTCTCTGGGCCCCAGGCACCCCCTGGCTTGAACCTTCAAAGCTTTTGTAAAATAAAACCACCAA

AGTCCTGAAAAAAAAAAAAAAAAAAAA

In some embodiments of any of the aspects, the GATA1 mRNA sequences includes or is derived from human GATA1 having the following sequence XM_024452363.1 (SEQ ID NO: 4):

GGAAGGGAGCCTCAAAGGCCAAGGCCAGCCAGGACACCCCCTGGGATCACACTGAGCTTGCCACATCCCC

AAGGCGGCCGAACCCTCCGCAACCACCAGCCCAGTCTTTCAGGTGTACCCATTGCTCAACTGTATGGAGG

GGATCCCAGGGGGCTCACCATATGCCGGCTGGGCCTACGGCAAGACGGGGCTCTACCCTGCCTCAACTGT

GTGTCCCACCCGCGAGGACTCTCCTCCCCAGGCCGTGGAAGATCTGGATGGAAAAGGCAGCACCAGCTTC

CTGGAGACTTTGAAGACAGAGCGGCTGAGCCCAGACCTCCTGACCCTGGGACCTGCACTGCCTTCATCAC

TCCCTGTCCCCAATAGTGCTTATGGGGGCCCTGACTTTTCCAGTACCTTCTTTTCTCCCACCGGGAGCCC

CCTCAATTCAGCAGCCTATTCCTCTCCCAAGCTTCGTGGAACTCTCCCCCTGCCTCCCTGTGAGGCCAGG

GAGTGTGTGAACTGCGGAGCAACAGCCACTCCACTGTGGCGGAGGGACAGGACAGGCCACTACCTATGCA

ACGCCTGCGGCCTCTATCACAAGATGAATGGGCAGAACAGGCCCCTCATCCGGCCCAAGAAGCGCCTGAT

TGTCAGTAAACGGGCAGGTACTCAGTGCACCAACTGCCAGACGACCACCACGACACTGTGGCGGAGAAAT

GCCAGTGGGGATCCCGTGTGCAATGCCTGCGGCCTCTACTACAAGCTACACCAGGTGAACCGGCCACTGA

CCATGCGGAAGGATGGTATTCAGACTCGAAACCGCAAGGCATCTGGAAAAGGGAAAAAGAAACGGGGCTC

CAGTCTGGGAGGCACAGGAGCAGCCGAAGGACCAGCTGGTGGCTTTATGGTGGTGGCTGGGGGCAGCGGT

AGCGGGAATTGTGGGGAGGTGGCTTCAGGCCTGACACTGGGCCCCCCAGGTACTGCCCATCTCTACCAAG

GCCTGGGCCCTGTGGTGCTGTCAGGGCCTGTTAGCCACCTCATGCCTTTCCCTGGACCCCTACTGGGCTC

ACCCACGGGCTCCTTCCCCACAGGCCCCATGCCCCCCACCACCAGCACTACTGTGGTGGCTCCGCTCAGC

TCATGAGGGCACAGAGCATGGCCTCCAGAGGAGGGGTGGTGTCCTTCTCCTCTTGTAGCCAGAATTCTGG

ACAACCCAAGTCTCTGGGCCCCAGGCACCCCCTGGCTTGAACCTTCAAAGCTTTTGTAAAATAAAACCAC

CAAAGTCCTGAAA

In some embodiments of any of the aspects, the GATA1 mRNA sequences includes or is derived from human GATA1 having the following sequence XM 011543897.2 (SEQ ID NO: 5):

GACACCCCCTGGGATCACACTGAGCTTGCCACATCCCCAAGGCGGCCGAACCCTCCGCAACCACCAGCCC

AGGTTAATCCCCAGAGGCTCCATGGAGTTCCCTGGCCTGGGGTCCCTGGGGACCTCAGAGCCCCTCCCCC

AGTTTGTGGATCCTGCTCTGGTGTCCTCCACACCAGAATCAGGGGTTTTCTTCCCCTCTGGGCCTGAGGG

CTTGGATGCAGCAGCTTCCTCCACTGCCCCGAGCACAGCCACCGCTGCAGCTGCGGCACTGGCCTACTAC

AGGGACGCTGAGGCCTACAGACACTCCCCAGTCTTTCAGGTGTACCCATTGCTCAACTGTATGGAGGGGA

TCCCAGGGGGCTCACCATATGCCGGCTGGGCCTACGGCAAGACGGGGCTCTACCCTGCCTCAACTGTGTG

TCCCACCCGCGAGGACTCTCCTCCCCAGGCCGTGGAAGATCTGGATGGAAAAGGCAGCACCAGCTTCCTG

GAGACTTTGAAGACAGAGCGGCTGAGCCCAGACCTCCTGACCCTGGGACCTGCACTGCCTTCATCACTCC

CTGTCCCCAATAGTGCTTATGGGGGCCCTGACTTTTCCAGTACCTTCTTTTCTCCCACCGGGAGCCCCCT

CAATTCAGCAGCCTATTCCTCTCCCAAGCTTCGTGGAACTCTCCCCCTGCCTCCCTGTGAGGCCAGGGAG

-continued

TGTGTGAACTGCGGAGCAACAGCCACTCCACTGTGGCGGAGGGACAGGACAGGCCACTACCTATGCAACG

CCTGCGGCCTCTATCACAAGATGAATGGGCAGAACAGGCCCCTCATCCGGCCCAAGAAGCGCCTGATTGT

CAGTAAACGGGCAGGTACTCAGTGCACCAACTGCCAGACGACCACCACGACACTGTGGCGGAGAAATGCC

AGTGGGGATCCCGTGTGCAATGCCTGCGGCCTCTACTACAAGCTACACCAGGTGAACCGGCCACTGACCA

TGCGGAAGGATGGTATTCAGACTCGAAACCGCAAGGCATCTGGAAAAGGGAAAAAGAAACGGGGCTCCAG

TCTGGGAGGCACAGGAGCAGCCGAAGGACCAGCTGGTGGCTTTATGGTGGTGGCTGGGGGCAGCGGTAGC

GGGAATTGTGGGGAGGTGGCTTCAGGCCTGACACTGGGCCCCCCAGGTACTGCCCATCTCTACCAAGGCC

TGGGCCCTGTGGTGCTGTCAGGGCCTGTTAGCCACCTCATGCCTTTCCCTGGACCCCTACTGGGCTCACC

CACGGGCTCCTTCCCCACAGGCCCCATGCCCCCCACCACCAGCACTACTGTGGTGGCTCCGCTCAGCTCA

TGAGGGCACAGAGCATGGCCTCCAGAGGAGGGGTGGTGTCCTTCTCCTCTTGTAGCCAGAATTCTGGACA

ACCCAAGTCTCTGGGCCCCAGGCACCCCCTGGCTTGAACCTTCAAAGCTTTTGTAAAATAAAACCACCAA

AGTCCTGAAAAAAAAAAAAAAAAAAAAAAAA

In some embodiments of any of the aspects, the GATA1 polypeptide includes or is derived from human GATA1 having the following amino acid sequence NP_002040.1 (SEQ ID NO: 6):

MEFPGLGSLGTSEPLPQFVDPALVSSTPESGVFFPSGPEGLDAAASSTAPSTATAAAAALAYYRDAEAYR

HSPVFQVYPLLNCMEGIPGGSPYAGWAYGKTGLYPASTVCPTREDSPPQAVEDLDGKGSTSFLETLKTER

LSPDLLTLGPALPSSLPVPNSAYGGPDFSSTFFSPTGSPLNSAAYSSPKLRGTLPLPPCEARECVNCGAT

ATPLWRRDRTGHYLCNACGLYHKMNGQNRPLIRPKKRLIVSKRAGTQCTNCQTTTTTLWRRNASGDPVCN

ACGLYYKLHQVNRPLTMRKDGIQTRNRKASGKGKKKRGSSLGGTGAAEGPAGGFMVVAGGSGSGNCGEVA

SGLTLGPPGTAHLYQGLGPVVLSGPVSHLMPFPGPLLGSPTGSFPTGPMPPTTSTTVVAPLSS

In some embodiments of any of the aspects, the GATA1 polypeptide includes or is derived from human GATA1 having the following amino acid sequence XP_011542199.1 (SEQ ID NO: 7):

MEFPGLGSLGTSEPLPQFVDPALVSSTPESGVFFPSGPEGLDAAASSTAPSTATAAAAALAYYRDAEAYR

HSPVFQVYPLLNCMEGIPGGSPYAGWAYGKTGLYPASTVCPTREDSPPQAVEDLDGKGSTSFLETLKTER

LSPDLLTLGPALPSSLPVPNSAYGGPDFSSTFFSPTGSPLNSAAYSSPKLRGTLPLPPCEARECVNCGAT

ATPLWRRDRTGHYLCNACGLYHKMNGQNRPLIRPKKRLIVSKRAGTQCTNCQTTTTTLWRRNASGDPVCN

ACGLYYKLHQPPFWQVNRPLTMRKDGIQTRNRKASGKGKKKRGSSLGGTGAAEGPAGGFMVVAGGSGSGN

CGEVASGLTLGPPGTAHLYQGLGPVVLSGPVSHLMPFPGPLLGSPTGSFPTGPMPPTTSTTVVAPLSS

In some embodiments of any of the aspects, the GATA1 polypeptide includes or is derived from human GATA1 having the following amino acid sequence XP_011542200.1 (SEQ ID NO 64)

MEGIPGGSPYAGWAYGKTGLYPASTVCPTREDSPPQAVEDLDGKGSTSFLETLKTERLSPDLLTLGPALP

SSLPVPNSAYGGPDFSSTFFSPTGSPLNSAAYSSPKLRGTLPLPPCEARECVNCGATATPLWRRDRTGHY

LCNACGLYHKMNGQNRPLIRPKKRLIVSKRAGTQCTNCQTTTTTLWRRNASGDPVCNACGLYYKLHQPPF

WQVNRPLTMRKDGIQTRNRKASGKGKKKRGSSLGGTGAAEGPAGGFMVVAGGSGSGNCGEVASGLTLGPP

GTAHLYQGLGPVVLSGPVSHLMPFPGPLLGSPTGSFPTGPMPPTTSTTVVAPL

In some embodiments of any of the aspects, the GATA1 polypeptide includes or is derived from human GATA1 having the following amino acid sequence XP_024308131.1 (SEQ ID NO: 65):

```
MEGIPGGSPYAGWAYGKTGLYPASTVCPTREDSPPQAVEDLDGKGSTSFLETLKTERLSPDLLTLGPALP

SSLPVPNSAYGGPDFSSTFFSPTGSPLNSAAYSSPKLRGTLPLPPCEARECVNCGATATPLWRRDRTGHY

LCNACGLYHKMNGQNRPLIRPKKRLIVSKRAGTQCTNCQTTTTTLWRRNASGDPVCNACGLYYKLHQVNR

PLTMRKDGIQTRNRKASGKGKKKRGSSLGGTGAAEGPAGGFMVVAGGSGSGNCGEVASGLTLGPPGTAHL

YQGLGPVVLSGPVSHLMPFPGPLLGSPTGSFPTGPMPPTTSTTVVAPLSS
```

In some embodiments of any of the aspects, the sequence encoding a GATA-binding factor 1 (GATA1) polypeptide comprises at least 60% sequence identity to a nucleotide sequence encoding a human GATA1 polypeptide. In some embodiments of any of the aspects, the sequence encoding a GATA-binding factor 1 (GATA1) polypeptide comprises a nucleotide sequence encoding a human GATA1 polypeptide.

In some embodiments of any of the aspects, a sequence encoding a GATA1 polypeptide is comprises, consists of, or consists essentially of a nucleic acid sequence selected from any of SEQ ID NOs. 1-5. In some embodiments of any of the aspects, a sequence encoding a GATA1 polypeptide comprises, consists of, or consists essentially of a nucleic acid sequence with at least 60%, at least 80%, at least 85%, at least 90%, at least 95%, at least 98% or greater sequence identity to one of SEQ ID NOs. 1-5. In some embodiments of any of the aspects, a sequence encoding a GATA1 polypeptide comprises, consists of, or consists essentially of a nucleic acid sequence with at least 60%, at least 80%, at least 85%, at least 90%, at least 95%, at least 98% or greater sequence identity to one of SEQ ID Nos. 1-5, which encodes a polypeptide which retains the GATA1 wild-type activity, e.g., it has transcription factor activity as described herein.

In some embodiments of any of the aspects, a GATA1 polypeptide comprises, consists of, or consists essentially of an amino acid sequence selected from any of SEQ ID NOs. 6, 7, 64 and/or 65. In some embodiments of any of the aspects, a GATA1 polypeptide comprises, consists of, or consists essentially of an amino acid sequence with at least 60%, at least 80%, at least 85%, at least 90%, at least 95%, at least 98% or greater sequence identity to one of SEQ ID NOs. 6, 7, 64 and/or 65. In some embodiments of any of the aspects, a GATA1 polypeptide comprises, consists of, or consists essentially of an amino acid sequence with at least 60%, at least 80%, at least 85%, at least 90%, at least 95%, at least 98% or greater sequence identity to one of SEQ ID NOs. 6, 7, 64 and/or 65, which retains the GATA1 wild-type activity, e.g., it has transcription factor activity as described herein.

Hematopoietic stem cells (HSCs) are the stem cells that give rise to other blood cells. This process is called haematopoiesis. This process occurs in the red bone marrow, in the core of most bones. In embryonic development, the red bone marrow is derived from the layer of the embryo called the mesoderm. Hematopoiesis is the process by which all mature blood cells are produced. It must balance enormous production needs with the need to precisely regulate the number of each blood cell type in the circulation. In vertebrates, the vast majority of hematopoiesis occurs in the bone marrow and is derived from a limited number of HSCs that are multipotent and capable of extensive self-renewal. HSCs are found in the bone marrow of adults, especially in the pelvis, femur, and sternum. They are also found in umbilical cord blood and, in small numbers, in peripheral blood. Mammalian hematopoiesis produces approximately 10 distinct cell types, the most abundant of which belongs to the erythroid lineage. Erythropoiesis results in the production of large numbers of red blood cells that are responsible for supplying oxygen to the developing embryonic, fetal, and adult tissues. They also help maintain blood viscosity and provide the shear stress required for vascular development and remodeling.

As used herein, the term "Hematopoietic stem cell" or "HSC" refers to a clonogenic, self-renewing pluripotent cell capable of ultimately differentiating into all cell types of the hematopoietic system, including B cells T cells, NK cells, lymphoid dendritic cells, myeloid dendritic cells, granulocytes, macrophages, megakaryocytes, and erythroid cells. As with other cells of the hematopoietic system, HSCs can be defined by the presence of a characteristic set of cell markers. In some embodiments of any of the aspects, a HSC can be a cell which expresses CD34, CD90, or the combination thereof. Other marker signatures used to identify HSCs include, but are not limited to: $EMCN^+$, $CD34^+$, $CD59^+$, $CD90^+$, $CD117^+$, $CD133^+$, $CD38^-$, $lin^-$, $CD150^+$, $CD48^-$, and $CD244^-$.

GATA1 protein levels are suppressed in HSCs from DBA patients and increasing GATA1 expression specifically in those cells can ameliorate the erythroid lineage commitment defect characteristic of DBA. The expression of GATA1 during terminal erythropoiesis needs to be regulated.

In one aspect of any of the embodiments, described herein is a nucleic acid sequence comprising a) at least one heterologousheterologous regulatory sequence selected from i) a hematopoietic enhancer element and/or ii) a binding site for for a HSC-restricted miRNA; and b) a sequence encoding a GATA-binding factor 1 (GATA1) polypeptide.

Regulatory sequences as disclosed herein include but are not limited to promoters, enhancers and other expression control elements (e.g., polyadenylation signals) that control the transcription or translation of a gene they are operably linked to. Such regulatory sequences are described, for example, in Goeddel; Gene Expression Technology. Methods in Enzymology 185, Academic Press, San Diego, Calif. (1990). Examples of regulatory sequences for mammalian host cell expression include viral elements that direct high levels of protein expression in mammalian cells, such as promoters and/or enhancers derived front cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter, Elongation factor 1-alpha 1 (eEF1a1) promoter or β-globin promoter. A eukaryotic promoter is a regulatory region of DNA located upstream of a gene that binds transcription factor II D (TFIID) and allows the subsequent coordination of components of the transcription initiation complex, facilitating recruitment of RNA polymerase II and initiation of transcription.

In some embodiments of any of the aspects, disclosed herein are heterologous regulatory sequences or combinations thereof that permit carefully regulated expression of GATA1 in hematopoietic progenitors to improve erythropoiesis in DBA without unwanted effects on hematopoiesis.

As used herein, "HSC-restricted", e.g., as used in reference to regulatory sequences, is an activity or element which preferentially occurs or exists in HSCs as compared to other cells of the hematopoietic lineage (e.g. erythrocytes or erythroid precursors). In some embodiments of any of the aspects, the activity or element occurs or exists at a level in HSCs which is at least 10×, at least 100×, or higher than in other cells of the hematopoietic lineage (e.g. erythrocytes or erythroid precursors). More specifically, an HSC-restricted miRNA is a miRNA that is expressed at higher (e.g., 10×, 100×, or higher) levels in HSCs than in other cells of the hematopoietic lineage (e.g. erythrocytes or erythroid precursors).

The term "heterologous" refers to a combination of elements which is not naturally occurring. For example, a heterologous regulatory sequence is one that is not naturally found operably connected to the coding sequence being considered. In some embodiments of any of the aspects, the heterologous regulatory sequence can be a regulatory sequence not naturally found in that species.

As used herein, "regulatory sequence" refers to a nucleic acid sequence that is capable of increasing or decreasing the expression of specific genes, nucleic acid sequences or polypeptides.

In some embodiments of any of the aspects, the heterologous regulatory sequence is a hematopoietic enhancer element. A Hematopoietic enhancer element is an enhancer element which is active in hematopoetic cells, e.g., in HSCs and/or in other cells in the erythroid lineage. In some embodiments, the hematopoietic enhancer element is active in cells undergoing erythropoiesis. A hematopoietic enhancer element is not necessarily exclusively active in any of the foregoing cells. Alternatively, in some embodiments of any of the aspects, the hematopoietic enhancer element can be HSC-restricted and or restricted to erythroid precursors/progenitors. In some embodiments, the enhancer element is located distal to the sequence encoding GATA1, e.g., it is a distal enhancer element. Suitable enhancer elements can readily be identified by one of skill in the art by consulting, e.g., expression data freely available on the world wide web for one or more cell types in the erythroid lineage and identifying genes which are expressed or highly expressed in those cells.

In some embodiments of any of the aspects, the heterologous enhancer element comprises the following nucleic acid sequence: NC_000023.11:48638900-48639300 on *Homo sapiens* chromosome X, GRCh38.p12 Primary Assembly (SEQ ID NO: 10):

```
ACTTTCATGAAATTACTGACATAATTTTGGGTCCAAAATTTCAAAATTTTAAATATTTTTATTTGGAATT
TTAAAATAATTTATATGCTCTTTTTACTGGCTAATAATGCTATTCATTATAATCTGATATTCAAACTGTC
TAAAAAAGTTAACAATCATTGATTTATTTGTTGTATATACAGTTTATTTCTATGACAGTTTTAATGTCAC
CTAATATTATTTTTAATGTTTCAATTTCTCATTTAAATACATTTTGTGTTGTTTATTTTAATCTCATTCA
ATCTGTATGTGCAAATGGCTTAGAAAAAAAGGCCATATATGACAAGCCCACAGCTAACATCATATAGTCA
ACAGTGAAAAACTAAAAGCTTCTCCTTTAAGATCAGGAACAAGGCAAGGAT
```

In some embodiments of any of the aspects, the heterologous enhancer element comprises the following nucleic acid sequence: NC_000023.11:48641200-48641700 on *Homo sapiens* chromosome X, GRCh38.p12 Primary Assembly (SEQ ID NO: 11):

```
TTTTATTATTTATTTATTTTTTTGAGACAGATTCTCACTCTGTCGCCTAGGCTGGAATGCAATGGCGTGA
TCCCGGCTCACTGCAACCTCTGCCTCCCAGGTTCAAGCGATTCTCCTGCCTCAGCCTCCCGAGTAGCTGG
GATTACAGGCATGCGCCACCACGCCTGGCTAATTTTTTGTATTTTTAGTAGAGACAGGGTTTCTCCATGT
TGGTCAGGCTGGTCTCGAACTACCGACCTTAGGTAATCCTCCCACCTCGGCCTCCGAAAGTGCTGGGATT
ACAGGCGTGAGCCACTGCGCCCGGCCTACATTTATTTTTAAATAAATGGATTTAAATGTTAAGACCTGAA
CCTATAAAAATGGGACACCTGCATAGGGCATTAACCATGAGTAGAGCTTGCAGGACTGGAAGTTGCTATG
GGTGAGTCAGTGTGTGAGTGGTGAGTGAATGGGAAGGCCTAGGACATTCCTGTACACTACCATGGACTTT
ATAAATTCTGT
```

In some embodiments of any of the aspects, the heterologous enhancer element comprises the following nucleic acid sequence: NC_000023.11:48644250-48645100 on *Homo sapiens* chromosome X, GRCh38.p12 Primary Assembly (SEQ ID NO: 12):

```
TCATAGAAACAAAACACTAGGATGGTGGTTGCCAGGGGCTGAGAGGATGGGGAAATGGGGAGTTGCTGTT
CAATGGATATTGCGCCCGGCCAGCCACACCAATTCTTACACCAAGAAGTGATGGAGCACAAGTGCTGATG
```

-continued

```
GGCCTTAACACCATCATAAACATCTTTTGTTTGTCCCGGGGAAGAAATTCCCAACTCCTTCCAAAGGTCT
GCCAAAGTCTACCAGTATCCCAAGCTGATTTCCTTATCCCCTCAGCAGATGCTGGAAAGCTGGAAGTCTC
CTTCCTTCTCACTCTCCTGCTTGACATCTGCACAGCCATTCTTCTTCCTCCCCTTGCTCCCCTTCCTCCC
CTTCTCCTTCTCCTACTTATTGAGACAGAGTCTCGCTCTGTCGCCGAGGCTGGAGTGCAGTGGTGTCATC
TCGGCTCACTGCAACCTCTGCCTCCTGGGTTCAAGCAATTCTCTTGCCTCCACCTCCTGAGTAGGTGGGA
TTACAGGTGTGTGCCACCACAGCAGGCTAATTTTTGTATTTTTAGTAGAGACGGGGTTTCACCATATTGG
CCAGGATGGTCTCGAACTCCTGACCTCAGGTGATCTGCCTGTCTTGGCCTCCCAAAGTGCCGGGATTACA
GGCATGAGCCACCGGCGCCCGGCCCTTTTTATTATTATATATTATTTTTGAGACTGGGTCTCACTCTGTA
ATCCAGGCTGGAGGGCAGTGGCGTGATCACAGCTCACTGCAGCCCTGACCTCTTGGGCACAAGCAGTCCT
CCCGCGTCAGCCACCCAAAGTGCTGGGTCTACAGGCATGAGCTACTGTGCCCAGTCTACGATTTTTTTAA
AATTTATAATT
```

In some embodiments of any of the aspects, the heterologous enhancer element comprises the following nucleic acid sequence (SEQ ID NO: 38):

```
ATGAAACCATATCTGCTATTTTCATTTATCTTGGTTTCAGCCTATTTTGCTTGTCTGGACACTACAGTCCACGGGAGCCTAGG
TCGAGCGAGGTCCAAGAATCCCCAGGGTGGGCAGGGAGGGTGGAAGAGGGCCTCCAGTGCCCAAGAGGTGCCCCACAAGCATG
GGACCCGCCCCCTCCCCTGGACTGCCCCACCCACTGGGGCACCAGCCACTCCCTGGGGAGGAGGGAGGAGGGAGAAGGGAGGG
AGGGAGGGAGGGAGGAAGGGAGCCTCAAAGGCCAAGGCCAGCCAGGACACCCCCTGGGATCACACTGAGCTTGCCACATCCCC
AAGGCGGCCGAACCCTCCGCAACCACCAGCCCAGAGATCTAGAGTTAATCCCCAGAGGCTCCATGGTGAGCAAGGGCGAGGAG
CTGTTCACCGGGGTGGTGCCCATCCTGGTCGAGCTGGACGGCGACGTAAACGGCCACAAGTTCAGCGTGTCCGGCGAGGGCGA
CCACCCTGACCTACGGCGTGCAGTGCTTCAGCCGCTACCCCGACCACATGAAGCAGCACGACTTCTTCAAGTCCGCCATGCCC
GAAGGCTACGTCCAGGAGCGCACCATCTTCTTCAAGGACGACGGCAACTACAAGACCCGCGCCGAGGTGAAGTTCGAGGGCGA
CACCCTGGTGAACCGCATCGAGCTGAAGGGCATCGACTTCAAGGAGGACGGCAACATCCTGGGGCACAAGCTGGAGTACAACT
ACAACAGCCACAACGTCTATATCATGGCCGACAAGCAGAAGAACGGCATCAAGGTGAACTTCAAGATCCGCCACAACATCGAG
GACGGCAGCGTGCAGCTCGCCGACCACTACCAGCAGAACACCCCCATCGGCGACGGCCCCGTGCTGCTGCCCGACAACCACTA
CCTGAGCACCCAGTCCGCCCTGAGCAAAGACCCCAACGAGAAGCGCGATCACATGGTCCTGCTGGAGTTCGTGACCGCCGCCG
GGATCACTCTCGGCATGGACGAGCTGTACAAGTAAAGCGGCCGCATCGATACCGTCGACCTCGATCGAGACCTAGAAAAACAT
GGAGCAATCACAAGTAG
```

In some embodiments of any of the aspects, the heterologous enhancer element comprises the following nucleic acid sequence (SEQ TD NO 39)

```
ATGGCGGGCAAGAAGTTGAGGCCACTGTCCCTGGGTGTTCCTACCCCCACACCCTCACCCCAAGACAGCCTGTTACTGCGGCG
CCAACAGCCACGGTCGCCTACATCTGATAAGACTTATCTGCTGCCCCAGGGCAGGCCGGAGCTGGCGTAAGCCCCAGTGGGGC
GCTAAGTGAGTGTGCCCCTGCCTCCCGCCAGCACTGGCCTGGCCTGCAGGCTTAGCCTGGGTCATCAAGGTATCCCACAGGCT
CTAGTTCAAATCCAGCAGAACCTCTCTGAGCCTCACTCTTCTCACCTGCAAAATGGGTACAGCCACATCCCTTCTCTCCCTGC
AGCCAGGAAGACGCACATACACAGGAGTCTAGCCCACACCGGCCCCGCACAAATTAAGGGCTTTACTCTCTGAAAAGCCCAGT
GAAGTCATGAAACCATATCTGCTATTTTCATTTATCTTGGTTTCAGCCTATTTTGCTTGTCTGGACACTACAGTCCACGGGAG
CCTAGGTCGAGCGAGGTCCAAGAATCCCCAGGGTGGGCAGGGAGGGTGGAAGAGGGCCTCCAGTGCCCAAGAGGTGCCCCACA
AGCATGGGACCCGCCCCCTCCCCTGGACTGCCCCACCCACTGGGGCACCAGCCACTCCCTGGGGAGGAGGGAGGAGGGAGAAG
```

-continued

```
GGAGGGAGGGAGGGAGGGAGGAAGGGAGCCTCAAAGGCCAAGGCCAGCCAGGACACCCCCTGGGATCACACTGAGCTTGCCAC

ATCCCCAAGGCGGCCGAACCCTCCGCAACCACCAGCCCAGAGATCTAGA
```

In some embodiments of any of the aspects, hematopoietic enhancer element comprises, consists of, or consists essentially of a sequence of at least 80% homology to a nucleotide sequence that is selected from the group consisting of: SEQ ID NO: 10, SEQ ID NO: 11, SEQ ID NO: 12, SEQ ID NO: 38 and/or SEQ ID NO: 39. In some embodiments of any of the aspects, a hematopoietic enhancer element comprises, consists of, or consists essentially of a sequence of at least with at least 60%, at least 80%, at least 85, at least 90%, at least 95, at least 98 or greater sequence identity to one of SEQ ID 10, SEQ ID NO: 11, ID NO: 12, SEQ ID NO: 38 and/or SEQ ID NO: 39. In some embodiments of any of the aspects, the nucleic acid sequence described herein comprises at least one, or at least 2, or at least 3, or at least 4, or at least 5, or at least 6, or at least 7, or at least 10, or at least 11, or at least 12, or at least 13, or at least 14, or at least 15, or at least 16, or at least 17, or at least 20, or at least 25, or at least 30 Hematopoietic enhancer elements. Where a subset of the three foregoing Hematopoietic enhancer elements is used, any combination of the Hematopoietic enhancer elements can be used in each of various embodiments of the aspects described herein. For example, it is specifically contemplated herein that any pairwise combination of the 3 Hematopoietic enhancer elements can be used, e.g., any combination shown in Table 1.

TABLE 1

Contemplated exemplary combinations of enhancer elements are indicated by "X"

| | Enhancer element (SEQ ID NO: 10) | Enhancer element (SEQ ID NO: 11) | Enhancer element (SEQ ID NO: 12) | Enhancer element (SEQ ID NO: 38) | Enhancer element (SEQ ID NO: 39) |
|---|---|---|---|---|---|
| Enhancer element (SEQ ID NO: 10) | | X | X | X | X |
| Enhancer element (SEQ ID NO: 11) | X | | X | X | X |
| Enhancer element (SEQ ID NO: 12) | X | X | | X | X |
| Enhancer element (SEQ ID NO: 38) | X | X | X | | X |
| Enhancer element (SEQ ID NO: 39) | X | X | X | X | |

In some embodiments of any of the aspects, the hematopoietic enhancer element can be an enhancer element of a gene selected from the group consisting of: Kell metallo-endopeptidase (KEL), 5-aminolevulinate synthase 2 (ALAS2), glycophorin A (GYPA).

As used herein, "KEL", "ECE3"; "CD238", or "Kell metallo-endopeptidase" is a type II transmembrane glycoprotein that is the highly polymorphic Kell blood group antigen. Sequences for KEL are known for a number of species, e.g., human KEL (the KEL NCBI Gene ID is 3792), the nucleic acid sequence (e.g. NG_007492.2), mRNA sequences (e.g. NM_000420.3) and polypeptide sequences (e.g., NP_000411.1) are known in the art. These, together with any naturally occurring allelic, splice variants, and processed forms thereof that catalyze the same reaction are contemplated for use in the methods and compositions described herein.

In some embodiments of any of the aspects, the KEL enhancer elements includes or is derived from human KEL sequences having the following nucleic acid sequence NG_007492.2 (SEQ ID NO: 40):

NG_007492.2: 5001-26303 *Homo sapiens* Kell metallo-endopeptidase (Kell blood group) (KEL), RefSeqGene on chromosome 7

```
GGGAGGAGAAGCCTGGGTGCCCCCCACTGATAAGCAGGCTCCACCCAGAGGCCAGTCCTGTGTGTCTGGG

GACAAGGCGAAAGAGCAGCAGAAGTGCCCCTTCTCCAGGATCAAGGAACTGGGGCGGGGGGTGTTTCCTG

GACCCCAGTCCTCCGAATCAGCTCCTAGAGTGGAACCAGGAAGGATTCTGGAGCCACAGAAGATAGACAG

ATGGTAAGTCCCCTTTTGGAGTCAGAGGCTTAGCGGGGAGGGGTGAGGGTGGCTGTGTGCAAAAGTCCTG

CCCCCACTGGAGGGGAGGGAATGTAAGGCTTACAGAGTAGAAAGGTGGGGAGAGAGGGAGGTAATGGGAG

AGGGATCGAGAAATGGCACATTCAGGGGACAGGTT GTTCTGAAGCCCATCTGGGAACACTGCTCCGAGA

TAAAAATATGTGTGTGGGGGCAGGGCAGGCAGCGAGGGTATCAAAATGGCCTGATAAAACTCTCTTCAAT

GCACCATTTCCTGAACCAGCTTCTCTCTCCTCCTTCTCCCTCCACTCACTTCAGGAAGGTGGGGACCAAA

GTGAGGAAGAGCCGAGGGAACGCAGCCAGGCAGGTGGAATGGGAACTCTCTGGAGCCAAGAGGTAAGTGG

CCTCCTCTCCTGGGTCTGGAATACACTGATGTTGTCACTCTCGGCTCTAAAATCCCACAAACACTCATCT

ACTAACTGTCTGCTTCATCCTCACCCAAAACAGTTGACATTCCTTGTTTTCTCATCTCCCAGGAGTTAAA
```

-continued

GTAGGGCTGGGTTTAGGAAGAATTGGGATAATTATTTCTGTATAAAGGGACTGTAGCACCAACAGATTCA

TTCTCTCTCCTCTTCTTCCCATCCCTGTCTCTCAACCCCCATCTTGTATCTTTCACCTCTTGGTTCCTCC

CACAGAGCACTCCAGAAGAGAGGCTGCCCGTGGAAGGGAGCAGGCCATGGGCAGTGGCCAGGCGGGTGCT

GACAGCTATCCTGATTTTGGGCCTGCTCCTTTGTTTTTCTGTGCTTTTGTTCTACAACTTCCAGAACTGT

GGCCCTCGTAAGCAAGATCCCAGACCCCCTAACCTAGTCAGCCCTCCCCCAGCCCTGGGGCCCAGGCCCA

GTCCCTGCTCCTGGGGCTTCTGCCCACCCTGACCCTTGGGGTCCCCATGGTTCTTCTTCCTCCCTGCATC

CTAACCATTTCTTTTTCATCAGCTCCCCACTTAGTTACTCACCTGATGTTCTTTGCCTAGCCCCTTGGGG

GAGCCCTTGTCTTTTTGCCTCTTCTTTCCCAGCTCTGAGCTTTTCCCCACAGGCCCCTGTGAGACATCTG

TGTGTTTGGATCTCCGGGATCATTACCTGGCCTCTGGGAACACAAGTGTGGCCCCCTGCACCGACTTCTT

CAGCTTTGCCTGTGGAAGGGCCAAAGAGACCAATAATTCTTTTCAGGAGCTTGCCACAAAGAACAAAAAC

CGACTTCGGAGAATACTGGGTGAGGAAAGCAGGGTGGAAGATGCTCTGTGCAAGTGGGTGACTCTGTGCC

TAAAATGACCATGACTGCTCCAAACCCTGTGTAGTTGTGGAACAACTGATTTGCACCATCCCAGGTGGGA

TTATACGGGTGGATGATTGGAGATGATGGGGGAGTAAAAGAGGCAGGATGGCGGGAGCTGCCTGGGTTTG

CTCATCTCTCACTGTTTCCTGTTGCCTTGCCTTGGGTACCCTTCTTCCGTTTCTCTTGGTCCCTTTCTGC

ATTTTTTTCTTTATCTAATTTCCATCTTCTTTGCTTCTCCATGTATCCATAATTACTCCATTCTCTCCAA

CTTGTCCCTTTTAGCAAGCTCCATCTTTGTTGCTTCCTCCAAATGTTCAGTTTCTATCCTATGCATGGTG

TTTTCCTCCACAAGCATCTCTTCAGCATCTCCTGCATTTCAATTCTTTTGTCCATCACTCTCATTCTCTA

ACCTCCAAAACCTCAGTCTCCCAATGACTCCTTGTCAACATTACCCTCTCCCTCTCACCATGCCGGAGCT

CCCCTCTCTCACAATGATCTCTTGCTTCTTGCTTCTCCATTGAAACCTTGAACCATGGCAAGCAAGTTGA

CCTGGAACAAGTGGGATGTTAGAGATGGATGATTGGAGATGATGGATGATGGTGGAATGAAAGGGGTAGG

ATGGTGGGGTGAGAAGTGAGAGAGGGCTTCATCACTGTGCATAAGAGAAAAAGTGGGTAAGTACAAAGGA

TATGCTGGAAGAAGAGGAGAGCTGAGTTAATTGGCAGTGGAAGTAAAGTTCCTGCAGATGGAGGCTGGAG

AGGAAAACTGCCAGGACTGAGAGGAAAACCAGAAGGATGAGCTGAAACTGAGTAGGAGGTTGGAAGTGCG

TCCCAGGAAGTTGGTGGATGGTGGTGAGGATTTGGGAATAAGAACATATAAGATAGACATGCATTTCCAG

TGCAAGGGAACCTAAAGAATGTGTTGACACTATCAATTAGAATCTGGGAAAAGTAAATGCACCCCTCTGC

CCTCTTTTTTTGATGGGGAAAGAGTGGGAGGGGGCCTCTCTTTGGGTAAATGGATACTTTCAGGGAAGGC

ACAGAGATAAAAAGAAAAAATATGCTCAGGATAAATTATATTGCCTACAATGGGATGAATAGATATCAGG

GGGACTGAGGGTGAAAAGAGTGTTAGATATTAGAGGGTGGATGATTCAGAGAGACTTGCATTTGATTATT

GTAGTGTGTTTGTTTCCTGGGATCAATGGATGAGGAGTCTGGACTAGAAGAGTCTTCCCCTGTTTCTTCT

CTTTGCTAAACCTTTCCTTATGAGTTTTCTTCTCTCCAAATCCTTAAAGTTCTCTAGTTCCCTGAATTTG

TCTAATTTCTTCAATCATTTCTTTTGTCTTTCATTTCTCTCTTTTCTCCTTTGCCCATATCCCACTTATT

GCTACCTTTCTCCTTTCTTCCCTGTCTTTTCCTTCTTGGTTTCTTCCCCACATTTCTTTTATTTTCCATA

TTGTCTTCTTCTCCTCATTCTCTTTCCCTGCTTTCATCATTTCATCAAGTTGATCCATTCCAAATTGGGC

AGTCCTCTCATCTTTCTTATTTTCCTCATCTCTATTCCTCCCCCTCCTTCCATATTCTGTGGGAGTCTTT

CTTTCCTGTAAGCTCCCTGTCTCCCACCCTCCCTCTTTGCCTCTATACCAGTTGCCACTCCTTTAATTCT

CCTGCCGACAAAAAGAGTCAAACTCTGTAAAATATTTGAAAAGATTTATTTTGAGCCAAATATGAGTGAC

CATGGCCCATGATACAGTCCTCAGGAGATCCTGAGAACATGTGCCCAAGGTGGCTGGGGCACAGCTTGGT

TTTATACATTTTAGAGAGTCATGAGACATCAATCAAATACATTTAAGAAATACATTGGTTTGGTCCAGAA

AGGTGGAACAACTCAAAGGGGTGGGGGTGGCTTCCAGGGTACAGGTGAATTTAAACATTTCCGGATTGAC

AGTTGCTTGAGTTTGTCTAAAGATCTGGGATAGATAGAAAGGGAATGTTCAGGGTAAGATAAAGATTGCG

GAGACCGAAGTTCTTTTGAAGTCTTATAGTGGCTGCCCTTAGAGACAATAGGTGACAAATGTTTCCTATT

-continued

CAGATCTTAGTTAATCAAAAGATCTAGCTATGTTAATGAGATATGTTAATAGCTAATAGAGATGCTTTAC

AGATGCAAATTTTCCTCCACAAAGAACAGCTTTGCAGGGCCATTTCAAAATGTGGCAAAGAAACATGTTT

TGGGGTAAAATATTTTTGTTTTCTTCTTTGTCTCGTAATGTTATGCCAGAATCAGGTTAGAAAGTAAATC

ATGTTACATGGGTTAAATAAAACCCATCTGATGAGAACTTATGATATAGGGCATGACTCCCCAGACCCCT

TTGATAGGAATTTGGGGCAAGATAAAAAAAATCAGAGTTTAGTCCTCACTCCCATGCTTCCTTTCTAGAG

GTCCAGAATTCCTGGCACCCAGGCTCTGGGGAGGAGAAAGCCTTCCAGTTCTACAACTCCTGCATGGATA

CACTTGCCATTGAAGCTGCAGGGACTGGTCCCCTCAGACAAGTTATTGAGGAGGTGAGAAAAGTTGGGAT

ATTAACTTTTCTGGATACATAACATATGGGACCAATGCATGCTTAGGGCTGCCATTTTTTTTTCTAGAGG

GTGGGTCTTCTTCCTAGGGCCCCCCAATTTCTAGGAGGGAGATGGAGATGGAAATGGTTATGCCCTATGA

AAGTATCAGGACCTTGGGAGAAGGCAGATAAAAAAGGATAGATGTGGCTTCCTAGAGGAATCGAAGGGCG

CAGGGCAGAGGTCAGGCAGTAGCAGCTGTGTAAGAGCCGATCCAGACAATGGGGGATGGGCTCCACGGAT

CCTTATGCTCAGCCCCCTCTCTCTCCTTTAAAGCTTGGAGGCTGGCGCATCTCTGGTAAATGGACTTCCT

TAAACTTTAACCGAACGCTGAGACTTCTGATGAGTCAGTATGGCCATTTCCCTTTCTTCAGAGCCTACCT

AGGACCTCATCCTGCCTCTCCACACACACCAGTCATCCAGGTGAGGGATGCACTGGCGAAGACACAGTTG

GACCTGGCCTGCCTCCAACTCTAGCCAATCATCCCTTAGAGGAAGGTTGCAGGTTGGGAAGAGAGGACAC

CTGTGTGATATAGGAAACAACCCTACCTTAAGGGAAAATTATTGATGTGAAAGTCAGGGACATTAGCTGG

GGGTGGGAAATGGAGCAGCAGAGCCAGTGCTGGGAAGACAGAAGTAGGCCTGGTCTTTCTTACTGTTAAT

CTGGATTAGTCTCAGAGCCCCTTAACCAGTCCTCCTATCTCTAGGATTGCCCTCATTTTATTTACTCTTT

ATTTTTACTAGAGGGAACTTTTCTAAACCAAGGGCTAACTAACTATGCTACTGTCTGTATTTAAATGCTT

GTCAGTGACCCAGTGGCTTGCCAGGTCATCAGAATCTAGTCCCTAATCTTTAGTAAAGCTTTGCAAGCAC

CTTGTGATCTGACCCCTACACACTTCTCCAGCCTTATCTCCCGTACATTCCTTCTCTCCCTTACCCCCAA

GCCATGCTGACTCACTGCTGCTTCCAGGAATATTCCTCAGTTCTTTGCCTATGCTGCTCCCTGTGCCTGC

AACCATCCCCCACACTGAACCTGGAAAACTTACATGTTTTTCAAATGTTGGCTTTATTATCTCTTCCAGG

AAGTCTTCACCGACACCCTAGTTATGAGTTAGGTGAAGCCCTGCTCTCCCTACTTTCGTTTCCTCATGCT

CTCAGCATTTATCACTCTGTGTTGAAGATTGTGAGCCTCTTTAGAACAGGACCATGCTTTATTCACCTTT

GTTTCTCAGGACCTATCACAGGGCCAGGCAGCTAGAAGTTTTGCCAGGTATTTGTAGTGAGTGAGTAACT

AAATAAAAACACTGGAGCTATCACTCTTGTGGTTAAACAATGTAATGCTATCTGCATATTTGGGCCCTAC

TGTCAAAAGAGCCACAAAATTACCAAAGGATAAGTACAAAAGAAGAATTGATTATCATTATGAGGTGTTC

TAAAATTTAGTTTTAAACAGTCTGCTCAGGAGTTTAACTGATGTGGCCTTTAGGGGCCGGTTAAGATCTG

GTTAAGGAGAGGCTCAGAGAGGAGAGAATGAGAGAAGGTGAGCTAAGCCAGCCTTGAAACATGGTTAATT

CACACAAGTGGAGGTGAAGCTATGGGGCGTTGGAAATGCTGAGCCAGGGGGAGGACCTGGAATGGTGTGA

TTCCTTCGTGGAGTCAGTGAGGAGGCTGATCTATTTAATTGAGGATTTGGGAGGCAAGGTGGGGTGCAGT

GGGAGGTAAAAGTGAGACTGAAGACATAAGGTTGAGCCTGATTATTTCTAAGAAGCCAGGCGAAGGTGAA

ACATTTGACATAATAGAAAAAAAAAAAAAGAGCTACTGAGGCCATCCAACTCTTATGACAATTGTGCATAG

AGCAAGTATTTTGATGGTTGTGCGTAGAGTCAGCAGTTTTGAAGGTCAGTCTGGGGGTGTTGAGGAAACT

AAATGAGCATTTTTGAGGCCCTGAGATAGAGGTAGAAATGGAAAGGAAGAGCCAGGCACAAGGATTTAGG

CAACTTCACCCTAGTGATGATAGTTCATGCTGTTTCTAGAGGATTTGGTGACTGATTGGATATAAAGAAA

GAAAGTGGGGGATTACACAGTGATCCCATTGTTTTGATTTAGTGTGAGTGGGAGGAGGGTGATTATCATC

AGTGTGAGCCTGGATAGTCTCTTGGGTTAAAAGCAGGTAGGAAGAATGGACTACAGAAAGAGAAGTCCAA

AGACTGAGGGCAGAAGGGAGCCAGGGAAGAGAGAGTACTATTGGAGAGATGGGAGCTAGACCAGTATGGT

-continued

GGGCCACAAAGGAAAGAAAAGGAGCTTCAGGAAGGAGGGGTCAGCTCAGAGAAGAAGGAATGAGAAGACA

CCCTTGGATACCTAGAGATACTTTCCAAACAGTTATGGCAGTGGACACAGACTGCACAGAGCTTAGGAGG

AAGATAAGAAAGTGGAAACAATGGGCATAGATGCTTTTTTGTTCTTTGAACTGTGGACATACAATGTAGC

AAAAGGGTCAAGTGAAAGTTTTTTTCGAGACAGAAGGAAAAGTATATGGCTCAAGATAAGAGTGGGATAT

TGAAATTGGAGAAGAAAAGGGAAAGAGTAGAAGCAAAGATCTTCAGAATAGAAACAAGGGTTCATCAGGG

CCAGACTAAGGTGAAATATACATGGTGCTTACCTGGGGTGCTAATTTAAGAAGGTCCCCAAAACTCAGTA

TCATGATAAATAGTATTTTATTAAATATTCCTAAAAAATCAAAATCAATGCAACAATACATGATGGAACA

AAATATCAAACTTTTCTTCATTATGAATTTTTTTGAAAAAAGATTATGCTTTTTTTCCCAAAAAATGGGA

CAAAATTCTGTGTGAATCTTTTTGAAAATACTAATTTTTTTATTCAAAATGAATCAAAAATACATTGAGG

ACTTTTCTTGAACACATCATGATTCTTTTCAAAATTGACTAAAAGTATGTTTTTTTGGGGAAAAAAAGTC

CATGATAAGCAAAGTTTTGAGATTTTATTTATCATACATTTTTGGTAGTAATTTTGATTTTTTAAAATGT

TAATTATTTATCTTGATTACTGAGTTTTTTTAAAAAAGAGTTTATTTGAGCAAAGACTGATTTATGAATT

GGGCAGCATCCTGAAGCAGTAGAGGTTCAGAGAGCTCCACCCAACAATGCAGGCAGGCAGTATTTACAGA

AAGAGGAAGTGACACCCAGAAACAGCTTGATTGGTTACAGCTTAGCAATTGTCTTTAATGGGCATGGTCT

GATCACTTGACAGCCTGTGGTTGCCTGAAGATCAGCTGGTATGGCTGGCTGAGATGGAGCTACCTGTTGC

AAGAATATACTCCTAAGTTAGGTTGCAGTTTGATTACTGAGTTTTTGGTACCTCTTAGATTTTGTACCTG

GGACAGGTTCCTCACCTCACTCACCCTGGCCCTGTTCCTGAGACAAGGAATAGCTCCTTTTAAGATGCTG

ATTATCATGCTTCTGCCTTGCTGGGCACACCCACACTGGTTGTAATACTCACCATCTCTTCCCATTTTCA

CATCTGGACTCTTCTTCTCATGCCCCTCAACCCTTAATCCCTCCCTTTCTTTGTACTCTTGCTTCTCTTC

TGTCCAATCTTTGTGTCCATCTCCCAAGGCCATCTCCCATGGTATATTCCCCACCTCCCCACACCTGCCC

TCTCCATCCGCCATGCTCCCTGCTTCTCTCCAGTCTCTCTTGTGCCCAGATAGACCAGCCAGAGTTTGAT

GTTCCCCTCAAGCAAGATCAAGAACAGAAGATCTATGCCCAGGTAAGATGGCACATGGACAAAGGCCCTG

CCCTCTGAGGCCAGGAGAAAAGCAGGGACCTCTGGCACCTGTGACTGACATTTCCTTCCTCCAGATCTTT

CGGGAATACCTGACTTACCTGAATCAGCTGGGAACCTTGCTGGGAGGAGACCCAAGCAAGGTGCAAGAAC

ACTCTTCCTTGTCAATCTCCATCACTTCACGGCTGTTCCAGTTTCTGAGGCCCCTGGAGCAGCGGCGGGC

ACAGGGCAAGCTCTTCCAGATGGTCACTATCGACCAGCTCAAGGTGCCTGGAACTGGGGGCCAGAAGACT

GTGGGCATGGGGATCTTCCTCTCAAACATTACCTCCTTTCCTTCTTCCTCCTAGTGCCCTTAATACCTTT

TCATTCTGTCTCTGACTCCATCCCCTCCCCCAGTTAGCCTGTTCTCTTCTTTTTCTCACACCCAAGGGGA

AGCCCTTTCCCCTTCCTTCTCTTTTCCTTTTCCCCCTCAGCTTTGTGTCCCTCCTCTAAGGAAATGGCCC

CCGCCATCGACTGGTTGTCCTGCTTGCAAGCGACATTCACACCGATGTCCCTGAGCCCTTCTCAGTCCCT

CGTGGTCCATGACGTGGAATATTTGAAAAACATGTCACAACTGGTGGAGGAGATGCTGCTAAAGCAGAGG

TTCGCCGCAGGTGGGATTGGGGAGATCATGGAAATGGAGGAGAGCCTGAGCACCGTAGATCTTGGGGGCA

AAGGAAACCTTGGGGAAGGCAGGCTGGTAAGGGCCTCCCAGGAGGATAAGAGGAACCTGCCACCTGTGCG

GGCAGAGAAGCGTGGGGTGGGTGGCACAGAGAGGATGGAGGGATCAAGAAGGATGTGTCTTGGGAGCACG

AGTAAGGGAGGATACACACGACATGAGGAACGCAGGGTCAGCCAAGACACGGGGTTTCCTGAGAGTAGAA

CACCAGCCAGTCAAGAGCCTCTGAGCTGTAGAAGATGCTGGAAGACCCAGACACAGAAGACAGTTAAGTG

TATGTATGTCTTTTTAGCAGCTGAGGACTGTGGGCAGGAGGAGGAGGCACATGAGATGAGGAGATGAAGA

TGGTGAAGGCTGGGGATGCTTAGGGGAAGAAAGGAAGAGGAGGGGCCATTCCTCAGGTGTGGTGTGAAGA

TGCTGGAGCTCTTATGGGAAACAATGTCTAAGAGCATTTCTGCTGGTGTCAGGAAATCAAGGGGGTGTTG

GGGTTGGGGACATGAAAGAGTGGCTCTTTGTTGGGCTCTCTGCCTCCCCTGATACCTGGGTGGCTACCAC

CTGAAAGCAGTGGCTTTCTTCCAGGGGCTTGGACCTAAGGGCCTTCTTCATGGTGGCAGCAGCATCTGGA

-continued

AATCCTTTTTGAGGGAGGTAGCTGCCCATTCACATGGCAGTGAGCAGGCTTACATAAGGGTGCAATGCAG

CCCTGGCAGGAGCATTGCTGGTGGAGGAGAGAGCAGTCACAGAGACCAGCTTACTTATGCTTATGAGATA

CATCTGAGGATAACCAGAGATATCTTGACTGTGGAAGCAGAATCTGTTTCATGACATGAGTCCAGACTCC

ATCTAGCCCAGAACTTTCTTTCCCTGTGACTTTGAAGGCTGCCTCTTCATCTAGTTTCTTTTACTAAGGA

GCTAGATCCCACCCCAACCTACATCATGAAAAGCTCTTTTTGACTTGGGTGCATGTTAAAACACTTATTA

ATACAGAGGAGAAGGAGCTGCCTTCACGAGTATCAAGGTGACTTACACAAGGAGAGGCTCTTCTTGAAGC

ATCCCCAGATTCCTGGGGTATATGTGTGGGTCTCTTTTGTCTCCATAGGGACTTTCTGCAGAGCCACATG

ATCTTAGGGCTGGTGGTGACCCTTTCTCCAGCCCTGGACAGTCAATTCCAGGAGGCACGCAGAAAGCTCA

GCCAGAAACTGCGGGAACTGACAGAGCAACCACCCATGGTGAGGAGAGGAGCGGGTGTATTTGCCCAGAT

ACTCGAAAGGAGTATCTACTCTTTTGAGGGGTAAATGTCGGCATCTCTCTCTCAGGGAGGGGGCCGTGAT

GGTAGATGCCCCTCCATGTCTTGGCTTTCCATAGAAGCAGGCAAGTTGGACAGACAAAGTTTAACTTGAA

AACCAAGATGCCACGTGCCAGACCTTCAGGCACACATCTCCCAGCCTGACTACCTCTCTGGCTTCTTGCT

GGGTGTTTGAGCTCAAATATAAAACTCTGATATTATCAAAACTGCCCTTTCTTTGTCATGATGCTTACAC

TATTTGCTCAGGATAACTTGGACTTAGAGCTTACAATTTATTGGGATGACAGAGAGATATGTTACGCAGT

GGCCTTCCTTATGTCTAGTTGATTCCATGTTCAAACGTGCTTCACAAAGAGTTTATCTCTGACATCCAGT

GGGATCCACTGGGCCACATGTAGACTTTGTGGCACAGATGTGGATATATCTGAGGAGGGGCCTGGGTAGA

AAATGCACTTCACTAACCAGAGTCTACTTATTACATAAGATGCAGAGATGCTCCTTTGCTGAGAATCTTG

AAATCCCAAGTTGGATATATCCAAATGCAAGCAGAAGAGTCTAGTACATTGGATACATCCCAACCTCAGT

GAAGGCCTCAGTTTAGTCTTAAAAATCACTGGATTTTTTTTCTTAGTAATTTGTGGTCCATTTCCCTGCC

TTGGAGAAACTCTCTGCTTTGGCAACCTAAAATTGCTGTGGAATTCAGAGAAGATAAATGTATTCACAGG

GACTGGAATGTAGTTATTGCTTATCAAGAGCTAATGGTGTGCTAGACACTCTGAAATCCTTTAGATCTAA

ATCTAGATTTAGATTTAATCTTTACAATTCCATGAGGTACCATGGATGCCATTTGGTTCCTATTTTAAAG

AGGAGGAGACAGAGGCACGAAAGATAAGGAAGTTGCTCAGGTATGACAGTAAGTTAGTGGGGTGAGGATT

TGAACCCTGGCAGTCTGGCTCCAGGGTCTGTGTTGTTTACTCATTGTGCTAAAAAAGCAGTCTTCCTGAG

GAACATCACTTGGGTTGGAGAGTGGCCAAGAAGCTTCTGCCCAGCTTTTCTCTTGATTCAGATGAAGCAG

ACCAGAGCCCCAAGTTATCTTAATTGGGGTTGCTACAAAATCCTGGCAACAAACAGCTACCTATAAATGC

CAGCACCATGGCCTCATGGCACTTCTTGGAGGCTGTAAGAGTGCTAATGTTGAGGCTTAGGCTTAAAGAA

TGCAGAAGGCTTAGATGTCCTGAAGCCATTATCTTTTCCACTAGGGCACATAATTGTCCTTGGGCTTAAA

AGCTGAACTAATCTCTGCCAACAAATAGTTGTGTGACCTTGGGGACGCCACTTCACCTTTCTGGAACAAT

AGTATAAAAGATGGCACTTAATAATAATGATAATAGCTGCTATACATGGAGTAGTCACTGTCTGTCAGCA

CTTGGGACAGGTTATTCATTTAAATCTTCCAGAAACACTTGGAGGTTTTTAATCCCCATTTTGCAGAAGC

AAAAATAGGCTCAGAAAGGTCAAGAAACTTTCTCAAGACCACACAGCTCACAAGTAAGTGAACAGACTCC

AAAACAGATGTTTTGGCTCATAAAGTCATGTTTTTAACCACACACTATACAGGATTGAGAAACAAGTAGG

TGCTACAAACAAAGGTTAGAAAACTTTTTTATAAAGGGCAACATAGTAAATATCGACTTCGTGATCCATA

AATGGTTGGTGTTACAAACTACTCAACTCTGTCCCTGTAGTGCAAAAACAACTGTACACTAAGTAAATGC

TGTGTTCCCAGGGGATCCTGGTTGAGACAGCAGATATTCTTGGAGTTCCCAAGAGGGAGAGATCAGGGAG

CATTTGAAGGATCAGTGGCATCTCTGTGCAGGAGGCAGAACTGACAAAATGTCTAGAGAGAGGAAGGAGT

TTTCTGGTGAAGAAAGGGGTATCATCTCATGGGGACAGGGCAGGAGGCAGGCTGGCTAAAACTTGGTGCA

GGGTGAGGGATCCTCCTGGTGGCTCTGGTTGAGAGGAGAAGACTAGGCTTGCTGTGTCCACTGATGCCCC

TGGAGCATGCTCCAGGTGTTTGAGAATCAGCAAGGGAGCCAGGGCACCTGGATCAGAGTGACTAGGACAA

-continued

TAGTGGGGAGGGAATCAGAGCAGGAAGGAGAGAACCATACAAGGTCTGGTAGGTTGCTGAAGGACTTTTG

CTTCTCTCTGTATGAAATAAAGACATGCAGAGGGATTTATCTCATTTATGTTTTAAAAGAACATATTTTA

AGGTTAGTAATGGGATGTCCTGATGATGAGTGATGTGAGAAGGAGAATGGAATCAAAGACATCACCTAGA

GTTTGGCCTTGATATGATCAAAATGTTTGGTTTTATTCAGTGGCCATTAATTACCGACTTCTGATCATAT

TCTTTTGAATGAATTATAATTTATAGTGCCCTTATACAGAAAGATTTCTAAATCTCATTATTGGCCCATC

TTTGGATGATTAGTTTTGAATAGAGTTATAGTCAATGAAAATGGCTGTTAAGTCAGGTTTTCTTTTATGA

AACTTGGGAAGGTGGGTTTTGAGAAGTAAAAGCAGAACTTCACATTTGTGATGATTAAATGTGAATGATT

TATATTCAGCCCAACATCTCAATTTATTCAGGTCTTCCAGCTTTGGATCATTTGCAATTTTATTCAGTGT

ATCTTCGTCCAGACTACTGTTAAGATCCTGAAGGGAGAAGGGCATCGGGTCAGGTTATTGAAGACCTAGA

TATGGATTTATGCATTCATTTATGTAACAAACATTTATTGAGAACCTAGTGTACTTCAGGTACTTCTCCA

GGCACTTGGAATGCAGCAATGAACAAAAAAGACAAATAAATAATCCTGCCTTCAGCCACATATCCTGGTG

AAAGAAGAAAGACAATAAACAAACTAATAAAATAATAAAATATGTTAGGAGGTGTTATGAAGAAAAGCAA

AACAGGAAATGAGGAAAGGAAATGCTAAGTGAGTGGTAGTTAGGATTCTTAGTAGGAATGTCACTGGAGG

TCAAGTTAACTTGAAATCATTCACCATTGATGTTTACTTTTGATTCAGCCAGATGAGACTCCACTCAAAT

TGCACTATCATTCAACATCAGTTTCTCTATCTAATTCACGAGGACTCAATCTGTGTTTTTCAAGCCTGGC

TAAATCAAGATAATGCCAACAGAGTGGGGTAGTGCCTTAGAGTACTTGAAAGGTATTATTTCACCTGATC

CCCAAACCTGTGAGGAAGGTAGACTAGATATTGTTTTCATTTCGACAACTGGTGTCACTGAACCACAGGG

GTTTAAGTTAATAACTCAAACTTAGTAAGTGCTAATACTCTATTCAGTGGTAGGATGGTAGTGGTGCTTG

AGGATGTATTTCGTCTATAGATGTGTTTTGTTAGCCTGTAGAATCTTTTGCAAACTTTGAATTAATCACC

AACATTCAAAAACTAGGATATGGCATGCCAGCATTCAGGTTTCTAGTGTGTGTGTGTGTGTGTGTGTGTG

TGTGTGTCTGTGAAGCTTGGGAAACACTGGGCTACCCTTCTCCTGTGGCAACAACTGACTGTCGCTACAT

GATGCAGCTCAGGGCTGGGTGCGCTCTCTGAAGCCCCACCACAGCCTGTAGCTCTGATGTTGCACTGCTG

TTCTCTGTTATGCCTCTGCATGGCCCCTATTGGAGTTTGCGGCTTCCGGTCTTTCATATGCCTCAGTTAC

ATAAGCCTTTTAGCCAGAAGAATTTTTATCATTTTGGCATTATTTTTCTTCAGTGATCCTATCATAGCCC

TTAGTAGTTACACATTATTTTCCAAGTGTTAAAAAACTGTTTAATGATTCGTTCCACAATTTTGTTTAGA

AATTAACATTAAGGATTCCTGGTTGGCTCGTAATCCCTAAAATTTCCTTTCATCCTATAGAAGATTGGTC

AAATTTTTGCTTCCCTCCGGACTCTTAGAATCTGTCCTGATTTCTATCATTTCTCAAATACTATCTGTGG

TTCTGAGGTTGTATATGGAACTTTTTTTTTCTGGTGCCCTAAAATTAGTCCACTGAGTTTCATTATCTTG

GGTTTGAAGTATTTCTTCTATTGTTTATATTTTGGAGACTTTTTTTTCTCGAATTCTATTTCTCTCCCTC

TCTTTCTCTCTCTGACTCTCCCTTTGCAGTCAATGTGGTATACACTACCATTCCACATCTTGAGAGAGAG

CTGTAGTAGTGGTCTGAGGTGGCGATTGTATTATCCAGTAGTCAGGTCCCACGGCAAAGCATGTTGGAGA

AATGATCAGGCTCCAGCAAAGGGCATCAGGAAACAAATCAAGAATGAGAAGGGGTGAGAAGAATAGGCAG

ATCTACACTTCCAAGCTCAAGTGGTCTCCCTGCTGATGCTGGTTGCTGCTCCACATGTAGCAACTGTCTG

GTAAGAGGTATTCCTGGAGCCAAGCTTGTCCAGCAGAATGTGGCTGGCAGATTCTCAACTTGGCCTATAA

TTGCTTTCAGACCCGGACTTCTTTTTAGTTCCTGTTGTTTCAGAGCTCCAACTCATGCAGCATGAGAAGA

ATCTGAGCCTCTTCTCTTTATCAGAGACAAGGTTGGCCAGGTGCGGTGGCTCTTGCCTGCAATCCCAGCA

CTTTGGGAGGCCAAGGCAGATGGACCACTTGAGCCCAGGAGTTTGAGACCAGCCTGGCCAACATGGCAAA

ACTTCATCTCTGGTGGTAGCCACCTGTAATCCCAGCTACTTGGGAGACTGAAGCAGAAGACTCACTTGAA

CCCGGGAGGTGAAAGTTGCAGTGAGCCGAGATTGCACCACTGCACTCCAGCCTGGGTCACAGAGTGAGAC

TCTGTTACAAAATAAAAATAAAAATAAGACTCAAGGTTAGCAGACCTCAAGGTTCAATAGAACACAGATG

TGGACAGCCAGGCCTGCAGCAACCTCCAAAATGATAACCTCTTTAACTGGTGGGTTCGGGAGTTTTTTCT

-continued

TCGGTGACTACCAGACTGGCCTCTTTGGTCTGTTTCCTGTAGTGGGATGCACATAAACCCCCTCCATTCC
CAGGACCAGCCTAGCTCCTGCGGGGAGAGTATTAGTGGCAGCCTTCCTACCTTCCCCGTGGGCAGGTCTT
TGGGAAGTAAAAAAATCACAGGAATAAAGTTTTGAGGCTTCATCCTGCCTAACCCAAATTAGCATATTAG
CTGGTATTTATCAGTTCCAGCTCAGCTTTCCCTCAGGCCAGCTACCTCCTCCTGTCCCTGGGTTCCTTGA
GTGTGTGTCTCCATTTACCGTGTCATCTCTGGGTTTATGCCTTGGTCAAGTTTTTAAAGCCATGCAAGCC
CACCGCCAAGACCTTCTCAGCATCTGTCTCTTCTGTTTCTCATTCTTGAGGTCCTCAGCTGGCACTGCCC
TCTTGGATGTTTGTCCATGGCCTCCTGCCTCTGCAGTGAAAGCCCTCCACCTTCCTGTTCTATTCTCTCC
TCTCTGACTTGGCTGGAAGTCTTCCAGCTCTATGAATTTATACACTGAGTCTTGTCTTGTGTCCTCTTTT
CCTAGCAAACAATATGGCATCTAAAACCCAGTTCTACTCTGATAATTTTTTCTTTACAAGATGCTACAGT
ATGATACACCATGCCCACCTGGAGAGAGGATAAAGGTGATGGTGGTAGGACAGAATTTCCATCCGCAATC
TCCGTTTTGAGCAAAGAAGCATGGAGGATGGAAGTCATTGCTGGGACCCCGGAGTAGAGTGGTGGTGGGG
GAACAGGGGGAACATCAGACTGCCGAGGTATGAGTTTGGGTTCTCATCTTCTTCCCAGGAGGCTTTTGAA
ACCCCAGGATGATGCCTCCTAGAGGCCTTGCTGTCAAATTCAATAGGCAATAACATGAAGGATTTACTCA
GCCAGGCTCATGAGACCAGCTCTGAGGAAGCTGTGCTTTTCTTGTACTGATCGGTGATGTGCATCACCCT
AAGGGATAGTAAACAGATGAAACCCAGAAAGTCCAGTCAAAAGAGCACCCTCTGGGAATGAAGATCTAGT
GAAGACTGGGGAGACAGATGAGGAAAGAGTCCTGAACAGGAGCCACTCATTCCAGCTTTGTCTCCATAGC
CTGCCCGCCCACGATGGATGAAGTGCGTGGAGGAGACAGGCACGTTCTTCGAGCCCACGCTGGCGGCTTT
GTTTGTTCGTGAGGCCTTTGGCCCGAGCACCCGAAGTGCTGTATGTGAGAGCTCTTCCCAGCCCACATCC
CTCCACCCCTTCCTACCCAAAGCAGCCTTCCCTCTTCTATTAACTTTGACTTTCTCAGTGGTGTGTGTGA
TTGGGGAATTGGGCAGTCAGAGAAGGGCCACTGAGAGAGGGAACCCAAAGGCCTGCTCCATCCCTGGTGT
GGAAACAGTTCAGCTTCAGGCCACAAATTCTCCATGACATGCTCTCACTTGGACAAGTCACCCAACTTTC
CTGGTCTTGTGTTTCTTCAACCATCAAATGAGAAAATCGAGCCAGGCTCGGTGGCTCACACCTGTAATCC
CAGCACTTTGGGAGGCTGAGGTGGGCGGATCACCTGAGGTCAGGAGTTCAAGACCAGCCTGACCAACATG
GAGAAACCCCATCTCTACTAAAAATACAAAATTAGCTGGGCGTGGTGGTGCATGCCTGTAATCCCAGCTA
CTCGGGAGGCCGAGGCAGGCGAATCGCTTGAACCTGGGCGGCAGAGGTTGCAGTGAGCCGAGATCACGCC
ATTGTACTCTAGCCTGGGTGACAAGAGTGAAACTCCATCTCCAAAAAAAAAAAAGGAAAATTGAACACTA
TCATCTCTAAGTCTCCTCCCTGTTGTAGCTAAGATTTTTTTAACAACACATGACGTGACATCAGAACAGA
TGACATAATCTTGAAGAGGGCAAATAAATCAAATAAATCACCACTGAATACTTTCTGAGTACCTACCACA
TGCCTGGGACTCCTTCAAGAACTTTGCATGAACTACGTCATTTAGTTCCTATTATGATCCTGATTTTATA
CAAGAGGGAACTGAAGCAAAGAGAGGTTAAGTGACTTGCCCAAAGTCACACAGTTACCAAAAAGCAGAGA
CAGGGTTTGAACTCAGGCATTCTGATGCCAGAGCCCAGGCTCTCGATATTGCCTTTCATTTTCCTCCAGG
AAAGGATTTACATGAGATGGCAGGTGGCTGGGGAAGCAGTGAGTACACACTCACGTTGTGAAGGCAGGGA
GACTTGTGGGGGACTTGCTGGGAAGCTGAAGAGCTCAGGAGGATGAGGAGAGGGAGTGGACGGTTTAAAA
AAGACAGTGTGAGAACAAGAGCCCTGAGCCAGAGGAGAAAATGACAGCCCTCTCCTCCCTCTGATTTCTG
AGAGGTGTTCCTGCCCCCAGGAGTGAGGACACTGTCTTTCTCCTGTGTCAGGCTATTTCCCCATGGAAAG
GAACTATATCTCCCTGATGGCCCTCACGGATGGCCAGGCCCCACCTTCCCTTTGTGGGCTTGGCACTGCC
TTCCTTTCTCCACAGATCCTTTAGTTGCTTTAGTTGAGCTGCTCCTCTAGCAGCAGCTCCAGCCCAGGCA
GCTCCTTGGGGCCAAGCCCTTTTCCAAGGGTCAGAAGCTGTGGGCAGGGCCAGGCTGAGGCCTCTCCTGA
TCCTGTCCCCCTGTCCCTGGACCTCACTCCCACAGGCCATGAAATTATTCACTGCGATCCGGGATGCCCT
CATCACTCGCCTCAGAAACCTTCCCTGGATGAATGAGGAGACCCAGAACATGGCCCAGGACAAGGTCAGG

-continued

CCAGGCGTCCTGGCTGGTGTGGGAGCCTGTGCAGGGAATGGAGTATTGGAACAAGCGAGATGGGGATTGG

AAGCAAATGCCAAAGGCCCCCCCAGGCACATGCTAAGTAGGGAAGCCACTGGGCTGTATACTCACACTGG

CAACAATGTGAGAGGCTGGGACAGGGCAACGAGTGGGAGAAATTTCCTCTGGTAGACTCGGAGAGTATTC

CTAGCCTCTTCTGTGTCTCTCTCCAGGTTGCTCAACTGCAGGTGGAGATGGGGGCTTCAGAATGGGCCCT

GAAGCCAGAGCTGGCCCGACAAGAATACAACGATGTGGGTCCCTGTGTTTTCCAGCTCCTTTTCAGTCCT

TGACTTCTCGTCACTTCTCTGACCCTCCTAAGTCTTTGTTGGACAATCAGTTTTCCCTGGGTGACTTAGC

TCTGTCCTTACTCTGGTGCTGGCTGGGGTTGATGGGGAAATATCCACACTGTACGTCTTGCTGGCAGAAG

AACAGAATCTTTTCAGGTCCCAACGCATGTGCCAACACACATGCATGCATCCTGTGACTTGTCTGGGCGT

GTTCATCTGTGTGCTGATATGTGTAAAGCCTGGGTGTGCTGTGTAGTGATGCCATTGGGCTGCTCTCTCC

TAATCCCTGGATGCCTGCCTGTCAGGGCTTGCCTGTTTGGGGTCAAATGGTCCCATTGGTGTTTGTCAGC

GTGCATCTATAGAAGTCTCTGTGTGCCCAAGTCACCTCCTGCCTCTTCCCCAGATACAGCTTGGATCGAG

CTTCCTGCAGTCTGTCCTGAGCTGTGTCCGGTCCCTCCGAGCTAGAATTGTCCAGAGCTTCTTGCAGCCT

CACCCCCAACACAGGTATGACAGCAGGGGAGACACAGGCACTCCATCCCAGAGAGACCCATCCATGATTC

ACAGGAAAGGAAGCCAGGGCTCAGGGCAGGCAGCATGAACAGTAATGGTAGTTGGGAGGGACTGTGTAGG

TCTCAGGGTGGCAGGGCAATACGTGGTGGGGGCTGGAGTTCACATGTCCTCTTCCCACAGGTGGAAGGTG

TCCCCTTGGGACGTCAATGCTTACTATTCGGTATCTGACCATGTGGTAGTCTTTCCAGCTGGACTCCTCC

AACCCCCATTCTTCCACCCTGGCTATCCCAGGTATGGGTCACTCTGTAAGGGTAGGTAGGGAGTTTCCCA

AGAGGGGCCGACAGGTGTTATGATGGATGGGACTTACGGTTGGAGAATTGGGGTCACAAATGCTGAGAGA

TTCTGGGGGTCAAATAAGCCCTTGTCTCCCTAGAGCCGTGAACTTTGGCGCTGCTGGCAGCATCATGGCC

CACGAGCTGTTGCACATCTTCTACCAGCTCTGTGGGTAACAGGGGCCACTGGGAGGTGGGATAATAGGGA

ACCTAAGGGAAGACCACAAGGGAGGCCTGGAGGGGAAAGGGAGGTTATTTGAGGGTTTGAGGTGGGGCAG

TCCTGGGAACTTTGCCATGCTCCTGGGAGCTGATTCAGTCTGTGGTACCACCCACATCCTCACCTAGGCA

GCACCAACCCTATGTTCTCTTGCTGTATGTTCTCTTGTCCCATTTTCAACAGTACTGCCTGGGGGCTGCC

TCGCCTGTGACAACCATGCCCTCCAGGAAGCTCACCTGTGCCTGAAGCGCCATTATGCTGCCTTTCCATT

ACCTAGCAGAACCTCCTTCAATGACTCCCTCACATTCTTAGAGAATGCTGCAGACGTTGGGGGGCTAGCC

ATCGCGCTGCAGGTATGCAAGTGTCAAGGGCCACAGTTTATGTGTACTGGCAGACTAGAAAACATGTCCT

CAAGTTTTCCTTCCACCATTCCTGACACAAGTACAGTTGCATGGCTTTCTGCCCTTCGCATCCCCACTGA

ATAGACGGCAACTTGGGGATCCCCCTCCTACCCCAGAGATCCTCCATTTTAGGACATCTATAGGTCTTCT

GGGAAGTACTCTTTCTTCTGGCTCAGATCAACTAGTCAGTGCAGAACCAGTGAGCAAGGGCCATGGGTTT

TGGGTACTGTGTGGAGGGACTTTCAAATGGCCACAGGTCTAGAGCCTGATGGCCCTTCTCTACCCACCCC

TACCCAGGCATACAGCAAGAGGCTGTTACGGCACCATGGGGAGACTGTCCTGCCCAGCCTGGACCTCAGC

CCCCAGCAGATCTTCTTTCGAAGCTATGCCCAGGTAGGCAGCGGCCACCTCCCGCCACAGCTTGCTTTAT

GTCAGTTGAACGCCTTATTACTGAAGCTCATGGAAGTCCCCTCTTCAGACACTCCGTCAAATACCCCAAA

CCCTCTTCTGCAGATGTCCTCACTGTTATCTTTTCTCTTCCCTCCCTACCCCTTGGAATCACCCCTCAGA

TGACTACAGGTTCTTCTACCTAATTCAGCACCCCCACAACTCAAAAGGTAGAAAAAACTCTATTCCCAAG

TTCCTCCAGGAGAGGAGGAGACCAACTTTTTTTTCCTCTCATACCCCCAAAATACAGATGCCTTAAAAAT

GAGCCTGTGGTTGGGCACAGTGGCTCACACCTGTAATCCTGGCACTCTAGGAGGCCGAGGTGGGCGGATC

ACTTGAGATCAGGAGTTTAAGACCAGCCTGGCCAATATGGTGAAACCCCGTCTCTACTAAAAATACAAAA

CTTAGCTGGGCTTGGTGGCGGGCGCCTGTAATCCCAGCTACTTGAGAGGCTGAGGCACGAGAATCGCTTG

AACCTGGGAGGCGGAGGTTGCAGTGAGCCAAGATCATGCCACTGCACTCCAGGCTGGGTGGTAGAGCAAG

ACTCAGTCTCACAAAAAAAAAAAAAAAAGCCTGCGACAGGCTGACTGTGTGCCACATTCCTCTTCAGACAC

-continued

CTGACCTTAGGTGTGGCGCCCACTTGACATCACCTCCTTAAGCACCCTGTACTCCCTCAACAGACTCAGG

TGCCAGGTCTTCAACACGCTTAGATTAGACTTCACCCCAGAGCTCCTGCGCTAGACCCTGCCTCTCTGTC

ATTGATAAATGGTATCATTACACAGCCCAGGCCCTCCTCCTGGACTCCTATTGCCAGATTAAATGAACTA

TACATTTCAAATGCTCCATGTGGCCCTTGGGGCACTTGATCCCCTGGTTCCCCTCTTTGTCTGCTGTCCC

TGATCACCCCTTGTCACCGGGTCAGCTTTGTCCTGTGGACCCTCCCCCTTCAATGACCTCTCTTCCTGCT

CAGGTGATGTGTAGGAAGCCCAGCCCCCAGGACTCTCACGACACTCACAGCCCTCCACACCTCCGAGTCC

ACGGGCCCCTCAGCAGCACCCCAGCCTTTGCCAGGTATTTCCGCTGTGCACGTGGTGCTCTCTTGAACCC

CTCCAGCCGCTGCCAGCTCTGGTAACTTGGTTACCAAAGATGCCACAGCACAGAAATATCGACCAACACC

TCCCTGGTCACATCCATGGAATCAGAGCAAGATTTCCTTTCTGCTTCTGTTCCAAAAATAAAAGCTGGCA

CTTGGCTTCCGCTTGTCTCTTAA

As used herein, "ALAS2", "ASB"; "ANH1", or "5'-aminolevulinate synthase 2" is an erythroid-specific mitochondrially located enzyme. Sequences for ALAS2 are known for a number of species, e.g., human ALAS2 (the ALAS2 NCBI Gene ID is 212), the nucleic acid sequence (e.g. NG_008983.1), mRNA sequences (e.g. NM_001037967.3) and polypeptide sequences (e.g. NP_001033056.1) are known in the art. These, together with any naturally occurring allelic, splice variants, and processed forms thereof that catalyze the same reaction are contemplated for use in the methods and compositions described herein.

In some embodiments of any of the aspects, the ALAS2 enhancer element includes or is derived from human ALAS2 sequences having the following nucleic acid sequence NG_008983.1 (SEQ ID NO: 41):

NG_008983.1: 5088-27010 *Homo sapiens* 5'-aminolevulinate synthase 2 (ALAS2), RefSeqGene (LRG_L163) on chromosome X

ACCTGTCATTCGTTCGTCCTCAGTGCAGGGCAACAGGTAAGAGCTGCTTTCAGCCTGGCACCCTATCTCT

GGTCTGCCAGCTGGTCTCTCAGGGCTGTACACACTGACTCTCTGGTCTGAGTAGATCTGACTTTTTCCTT

TGTTTGTTTCTTAGAATCTGTCTCTTTTTCATTTTCTTTTTATCTCCCATGTCTCTTTCTGTCTTTCCTC

ATTTTCAGCTTTTTTCTCTCTTTTTCCCTTCGTTACTTTCTTTTGTTAGTTTTCAAGATCATTCATTTCA

TTTCATCATTCTCTGACACTCTTGCTTTCTCTTATTTTTCCCTCTGAATTCTAACTATCTTTTTCTCTAA

ATTTCTTTCTCTCCCCCTTTTTGTCTCTTTCCTCGGCTTTGTATCTCTCCGTCTCTGTGTTTCTGTCTCT

CTCTTCCTCTCTATCAAGAACGATGGCTTAATATTTCTTCCTGCAATTCCCCATTCCTCTCTCCCTTTGA

CTCCCTCTACCTGCTGGGCTGACAGCAGAGCTCAGTGGGTCAGAGCCCATGGGGAGCCTAGGGGTGGGGG

AAGAGCTAGGGAGGGAAACTAAGAGGATGTGGGGGTGATGGGAATGATGAATTGGGTAAGGAGAGATTTG

GGGAATTGAGAGATGAATAATTAGCAGAAATAAGTGAAGAAAGTGGAAGAGGAATGTAGTGTCACTATAC

AGAAAGTAAACAGATTTCTATTCTCATCCTAATTCACTGTGAGACCCTAGGCAAGTCATTCACTCTCTGA

AAAAAAGGCTTGGCCTGTAATTTCCACCACCCTTTCTAGTTTTGATTTTGTGATCTTCTAAATTTTCCTG

TTTCTAAGAATTTCTGATTCTCTGATTACAGTTATCTAAAGTTCTGTATGATTCTTTCATGGTGGGAAAG

GGGTACTAGGAAGAGAAGTAAGGCCTGATGTTTCCAACTCCTGAAGAGAAATTACCACTTCCCTTCCAGA

CCTAATTGACTTTTGCAAAGCAGGCCACAAAAGGGGTGGGGGGGTGGGGGACAAGGAATGCTGCAATGAG

TGTTTTCTGGCTGTCTGCTGGGGTAGAGTTGCAGTTGGCCCTTTTCACCTCTGGGAGTACAGATTGGGTG

CTGACACAAGAGAGGATTTTAAAGTCGTAGGGAAAAACTTTCAGTAATGATCTGTTACTTGGTCTCAAAT

TTCACCATCATCTCTTTGGTTAAAAGTATTGTTTTAAGAAGATGCCTGGCAAGCATTATCACACATTAGG

TACATAAGTTATTGAATGGTAGAGTAAATGAATATTCAACAGTACCTGAAATTCCACTGTAGTTACAGAT

CTGTTCCTTTGGTAAGGCATTGGTGACAAATGGCATATGACCTGGAAAGAGGCCTATGTTAGTGCAGCAG

AGGAGATAAATGTCTAGAGTCAGGCCCTCAGTCAAGAAAAAAAGGTAGTAATATTTGAATCACAGATCCA

TAATGGTTAAGTTAGGAATCTCTGGAAACAGATTGCCTAGGTTCAAATCCTGCTTCTCCTATGTACTAGC

TTTCTGATCTAGACAGGTTACTTAATCTTTTTGGGATTCAGTTTCCCTATCATCACAGGGTTGACATGAG

-continued

AACACGGCCTGGCACAGAGGGCTCTGTAAGTGTTTGACTATCAGAACTAGGCGGAATCTATGAAATTATC

TAGTCCAATGTCAGTGGAGAAACGGAAGCCCAGAGAGGGGAATTACAGAGCCCAAGTTCACACAATAAAT

TGTAACAGGATTGGGACAAGAATCAATTCTCTAGCTTCCCAAACCCAGCCTGGTATATTCATGTGACTTC

CCTTGGCTGTACGTTCATTTTTTCTACATGGGAAATGGAGAAAATAAAAATAATAAAGTCTATCAATTAA

ATATAATATTTAACACTTTTTTACTGTTTACTCTGGGATAGGTACTCTGCTAAATGCTTTATATGGATTA

TCTTACTGAATCTTCACAACATTCCTGTGATGCAGATTGTCCTTGTTATTACCAACATTTTCCAGATATA

AGATGTACAGCAGGGAAGTGACTTTTCTAAGGTCCCAAAGCTAGTGAGTGGTGGAGCCAGGATTCAAACC

CAAGTAGTTTGGCTCTAGAGCCTATACTCTTTATACCCTAAATTGACTAAAATGCTTCCTTGATTCAATT

TTACTCACTCTAGTCTCTTGGTAGGTAATGAGATGGAATAGAAACAGAGCCCATGGTAACTAGACTACAA

GGTCATGGGTATAATGATGGCCAGGCAGAGTGAGGCAGAGCAAATTTCAGGAAAGGAGTAACAGAACAAG

AGAAATGAGAACAGGAGCTTGAAAGAACTTGAGAATTCAACAAATTCCAAGAAGTGGTCTATATTTTCCC

AGGACCCTGAGCATATCATGGCCAAAAGCCCCCTAGTAATGATGTGTGTTAATTTCTCCTGTTTTTATAT

ACAGGAGGTAGGTCTTCTCCACCATCCCAAGGCAGGACTGGACTTTGCCTCCAATATTGGGGGCTTTCCT

TCCCACTACATACCCCAATGTTGTTGGCATTATTGTTGCCAGTATTGATGTTAGGGGAGTTTACAGGAGC

CTGGAGCCTTGTCATCTGCCTTGCCTGCACTTCTGGGCCATCCATTTCTTACCACCAATAGCCAGGGCCA

GCTCTAGCCAGATGCTCAGACGTGATTCCAGGAAGGGGCTCCTCTTCTCTCCCACGCCCTGGTCTCAGCT

TGGGGAGTGGTCAGACCCCAATGGCGATAAACTCTGGCAACTTTATCTGTGGTCTGCAGGCTCAGCCCCA

AGTGCTTTAGCTTTCACAAGCAGGCAGGGGAAGGGAAACACATATCTCCAGATATGAGGTAGGCACTGGA

TCCAATTCCTTACCTACCTTGTGAAGTGGCCATAATTACCTCACGTTTGACAGCTGATGAAGGCCAAGAT

CCAGAGAGGGGAAGTGATTTGAACAAGAACATCCAACAATGAAATTGGAGAGCTGGAATTTTAATAAGAA

AAGCTAACATTTATTGAAGATTTACTATGTGCCAAAAACTATACTAAAGGCTTAACTTGGATTGTTTCAT

TTAGTCCCTCCAACAACCCTTCTGTCTTTTCCAATTTCAGGGCCCACATGCCTTGGCCCCACATACCAAC

CCAGGCTGCTGTGACAGCCCATGAGAGGGGGAGAGGTTGCTCTGGGATGGAACAAGAAAAAGAGGTTGTT

TTGTGAGGTACGGGGAGGGTGCTTGTTCTATGAGATCAGGAAGGGAGGGAGATGAAGGAGGTTGCCATAT

GAGGGCAGGGCCATGAGCTGACCTGTCCCTCAAAACATAAGGCTGAGGGTGCTAGTAGATTCTACTCAGT

AACTTTCTTCACAGTGTCAGTGCTTTAGTCTTCTCACATTCTCCCATGTCTCTCCCATTGTACTGTCCCT

TATCTTGTCTCACTTTTTGACTCTGTCTTTCCAATTTGCCCTTTTTCTTTACATCTGTCTCTCCTTCTTG

CTCTCTCTAGCTGTCTTTCTCTTGGTGTCTCTCAGCTCTCACCCCTCTTAACCCTCATCCCCCTGCTTTA

GTCACCTCTCTGTCTCTATCCTTTGATCTTGTCATTTTCTCTACTCTCTTCTCTCTGTCCCTCAGTCTCT

CTCTCATCTCCCTCAATTAGGGCCATGATTCTCTTCCCTAAACTTACTTAGCCTTTTGCAATTTCTGGCA

GCATTTTTTTATGTTTGTGTCTGACTGACTCTCTACCCCTGCTGGATCCTCTCCACTCCTGTTCTCACTT

CTATGAATCTTTGTATAATCCTCTAGACTCATTGATCCCTCCTCATGTCCCTTTCGTGCCCCTTGGTCTA

TCTGTCTCTGCCTTTATCCCTGTGTGCACTATCACCACCCCCTTTTTCTTTTTTCATTTTCTCTTTCTCT

CGACTCAATCTCTGTTTTCATCTCTACCCTGCTCCCTTTCCCTCTACCTTTGATCTCTTTTTCCCCCTCA

ATTTCTGTTCTTTTAACTCTACCACCACCACCACATCTTTGTTCTCTCTCTACTTTCCTCCTTTTATCTT

TCCTAAATTTTCTTTTCTTCTGGCTTTTCTCCTAGTCCCTTCTCCTTCCTCAATTTCAGACTCTGTTCAT

TCATCAATTTACCCCAAAATTCAACAAATATTTATTGAGTGCCTGTGTGTCATTTGCTTTCTCTTTTTCT

GATCTCTTTGCCCCCTTTCTCTTCTCTGTCTTGGCCTCTGCCTGTTTCACTAATCCATAGACTATGTCTT

TGTCCCTGTTTTCCAGCCCCACTGGGACTTGCTTTCACCTCTTCCTATATCTGTGCTTATCCAAGAGACA

GGAGCAAATTCAAAGACAGCATAATATCAGGCTGGTGGTACACATTCTGTAGGACCTAGGGCCTACCCTT

-continued

CCTTCCGGATCCCTTGATTTCCTTAAACTGATACATGTGACCTCAAGCTCCTTCTCCCCTCTGGCTGATC

CTGCTTAGGAAACACCCTGGGCCAAGCCTCAGGAGCTCTACTCAATGACATATGTTTGCATTAGCAGGCT

GAATCTTCACTTGGCTAAGACCAACATTCTTAGAAAGATTCTTGGCCTTAAGTATTGATCAAAGGGTTAG

TGGGTTGGCAGTTCTCATCCTGCCACACAAAAACACATTTCAGTGATCCTCATCATCACAGAGGTAGTCA

GTGCCAGAATGTGAGTCAGAATCCAGGCTTTCTGACCTCCAGTTAGAACTGTTTCCTTCACCCCTTTGCC

CAGTAGTCAGTTTCCTATTTCTTCCTCCCTCATGTTTTATTGGTACATGTTAACATTGGGAAAGAAGTTC

TTTCCCTGGAAGGGCAATAAGAGCATCTCGGAGGCAGCAAGTTTTGGGTGGGAAGCTGAAGACGAGGATC

AAAGGCTTGGCTTTTTGCCAGGCCCTCATGATGGAACCTCATCTCTTCCATGTCTTCTGCAGGACTTTAG

GTTCAAGATGGTGACTGCAGCCATGCTGCTACAGTGCTGCCCAGTGCTTGCCCGGGGCCCCACAAGCCTC

CTAGGCAAGGTGGTTAAGACTCACCAGTTCCTGTTTGGTATTGGACGCTGTCCCATCCTGGCTACCCAAG

GACCAAACTGTTCTCAAATCCACCTTAAGGCAACAAAGGCTGGAGGAGGTAAGAAGAGGCTGCTAGCAAA

AGGGGAGAATGTTAGGGTCCTGGGGTAAAAGTTCCAAGTTATACTGGCCATCTTTGCCTAATAATTAGGA

CGGTTCATGTGAAAAGTGTCAAGATAGCATGAACTGGCCCCAAAATATACCCAGAATCTGTCTTCTGCCA

GGTTCTCTAGAAAGAGTCTCATTCTCGGCCAGGCACAGTGGCTCACGCCTGTAATCCCAGCACTTTGGGA

GGCCGAGGCGAGTGGATCACGAGGTCAGGAGTTCAAGACCACCCTGGCCAAGATGGTGAAATCCCATATC

TACTAAAAATAAAAAAATTAGCCAGGAGTGGTGGTGGGCGCCTGTAATCCCAGCTGCTTGGGAGGCTGAG

GCAGAGAATTGCTTGAACCCAGGAGGCGGAGGTTGCAGTGAGCCAAGATCATGCCACTGCACTCCAGCCT

GGGCAACAGAGCGAGAATCTGTCAAAGAAAAGAAAAGAAAAGAAAAGAAACAGTCTCACTGTCATGTCCC

TCACACACTATACTCCAGACATGCTGAAACTACTTAAAATTGCCTAAATCAACTATTCTGTCAAGAGTTT

GTGCCTTTGCTCCTGTCAGATTACCCTCTCCTAGACCCTGTACTGGAGAATCTCATACTTCTCATTTGAC

ACTAAGCTTGGCCATCATCTCCTCTGCAAAGCCTGCTTAGACCTCCAAACTGTCTAATTCCAATTCTGGC

TCATTTCCCCTCCCTCTTCTGGACTTCTGTAGCCCATGTACTTCCTCTATCCCAGCACTGTTCACAATGT

GTCTTCAGTGTATGCCATTCCCACCAGTTTAGTAGCTCCCCTAGCACAGGGACCAGACTCATCTATCTCT

GTGTCTCTACAATAGCCTGAGATAGGGCTTTAGGGGTACATTAGATCTCAGCAATTATTGTTGAGCTGAA

CTTATGACTAGAAATGCACCCCAAATTACTCTCTTACCTTTGCATAGATTCTCCATCTTGGGCGAAGGGC

CACTGTCCCTTCATGCTGTCGGAACTCCAGGATGGGAAGAGCAAGATTGTGCAGAAGGCAGCCCCAGAAG

TCCAGGAAGATGTGAAGGCTTTCAAGACAGGTTGGAGTCAAGTTCCACCTTATGCAACCTTTACTCCTAA

TGCTTGAACACACTACGTCACAGTCCTGAGCTAGGCTAATACAAAAGCAGCCAGTACACATCCCATGATG

AGAAGTCCAGTCTTTCCAGGGGAGCCATGGTAGGCAACAGTTTAGGCTGTATGCTGAAGCACACCATACC

TGACAAACACATATGTACGGGCTCCTGAAACTTTTAGTCATTATTCTAAGATGAGCCCTCTAGAATTTTG

ACTCCTCTTTTTCAGGTGGCTAAACTGATCCCAACAGGCTGGGGTCCCACATTTCAGCAAGACCACTCTA

TGAGAATATGGATTTGCATGAAAGAGAAAGAGCTGGGAGTAGGTACCTCCTTTAACCAGGGTGCAGATCC

CCAGGTCAACTTAATTAGTGCAGACCACCCAAGATAATCACCCTTGAGATATGGCCACACTGTTGACATC

TTTCATAGGCCCCTTTGGGATATCATTAAGGACAAAAACTTCAAAATTGAAATTTAATGATGTTTAGAAA

AGAAGAGTAAGGTACATTATCCTGCATCTACTTTCTAAATGCAGGACCCAGGGTGGCTGCTCCAGTTACC

TGAGCCAAGGGAAAATCCTAGTGGAGAGAAGTATGATTCACCTTATAGAAGGTTTCCTAACAATGTAATA

GTCTCCATTCGGGGGGATAAATAGAAGCTCACCTTGGAGAAGATTTCTTCTCGCTGTAGAAGCTGCCCTT

ACCTTATAAACTTGAATTTTCATGTGTTGCATTGAGCTTAAAGAGGACAACACATGCTTTCTTTTTCCCC

CATTCTCTTCACGGCCAATGAATCTCACATTCCGTCTCAGATCTGCCTAGCTCCCTGGTCTCAGTCAGCC

TAAGGAAGCCATTTTCCGGTCCCCAGGAGCAGGAGCAGATCTCTGGGAAGGTCACACACCTGATTCAGAA

CAATATGCCTGGTGAGTTTGCTGAGGTGGAAAAAAAGGGGACCGGAATAGGGAAGGCATTCTGAAAGGGC

-continued

CTCTGTCACAGTAGGGGAAACAGTACAGAAGGGCCTTGGAACCAAAGGAAATTTGAGTTTAAAATTTAAT

GCTGGCACTTGCTGGATCTAGGTGTTTTGGCAAGTAAGACACTTTCCTTCAGTGGCATTTAATACCTACC

TCAATAGGTTACCATGAGAAGAAAGTGAAATTACATTTATGGAAGTGTTTCTAATGAGGCTTCATTAAAT

ATTAGGCTTATTTCCATTATTTCTTCTCTATGCTTCCCTCAAAAACTTTCACCCTTCATACAGCACCTTT

TCCCCATTCTTATATGTGTTTATATTCCTTTCCATAATGACATTTACATTATTTTCTAATGTAAAAGGAA

TATGATTCATGGTAAAATATTTTTCAACATATACAGGAAAGTATAAGGAGGGAAATTTAAGTCATGCAGA

GTTCCACCATTAAGTTTTTGTTATATTTTCTCCCAGATATTTTTCTATGGCTACACACACACACACACAC

ACACACACACACACACCCTCTGCTCTCTTCACCACACCCATGCTTTTGTTAGAAGTGTGATCTTATTTTA

CCTGGAGTTCGTTATGCTGTTTTGTTCACTTAAAAATATGTCATGGGTATAGTATGGATTCAATATCATT

CAGTTAATCAAGCATCTATAATTTAAGTTGTTTCCAATTTTTTGTATTCTCTCAGTTTAGATTGTAGGTT

GGTTTTACATACATACAAATGTACTCAAAGAAAATGTATAGTATTACTTTTTTCAATTTTTATTTTTACC

TAATAATATCTTGCTATATATTTTACTCTGTGCCCTTTTTTCACTCAACAATATACTGTGGAAATGCTTC

CACTTTAACACATATGTATCTACCTTATTTTTCAATGCTTCAAAATATTTTGTAGTATAGATATAATAGA

GATTATTTGGCTACTCCTCTATTTGGTTGCTTCCAATTTTTTCTATTACAAACAGTGGTGCAACAAACAT

CCTTGAATGTATCTCCTTGTGTACACAGGCAAGTGTTTCTCCAGGATAAACACTCAGTGGTGGAAATTCT

TGGGATGTAAGGATGTGTACATTTTTGATATTAATACATTTTGTCAATTAGCCCTCCAACATGGCTGTAC

CAGTTATCAAGGAGGGTATCCATAGTCTCATACCCTTACCAGCCCTTGATATTATCAAACTTTAAATCTT

TATCAATTGATAGGTGAAATTTTGTTTTCCCAGTTTTATTTTTCCTGATTAAGAATCTTTTTCTACATTT

ATTGAATTGTCTGTTCATATTCTATGCCCATTTTTCTACTGAGTTGAAATTTTTCATGTTAATTTTTCAG

AGATTATATAATAAATTCTGAGTATCAATCATTTGTCTGTTAAGTATGCTGCAAATATTTCTCTAGATAT

GTCAGTATGTGCATTTAAAAAACTTTTGATATGTATTTCCAAACATCTCTGCAGCAAGGATGTTACCAGT

TTGCACCTCCAGCAGCCATATAAATTGCTGTCTGCAACATGATTTCTGTCTCACGTAAAGAGTTCTAGAG

TTTAACAAGCTCTTTGGCAAACGTTATTTCAATTTATCCTAGAAATAAAGTTACCCCATTTTGTAGTGGT

AATGGTTAAAGAAGTGGGCTCTGAGTTACTTACTTGATGAACACTTACTTGCTGCATGACCCTGGTCAAG

TTGTCTAACACTTAATGCCCCAGTTCCCTCATCTGTAAAATGGAGATACTAATAGAACTGTCCATGGAGC

ATTGTTGTGAGGAATAAATTAAATATTTATAAAGTTCCTAGGAAAGAACTTACATGTACTAGGCATTCAT

TAAATGTTAGCTATAATGATGTAATTGAATATTAGCTATCTTTATTAGTATTATTATGACTACTAATACT

ATAGCAGTAATAATACTACTATTACCATGTGCCATTTATTAGTTTGAATATATTACATGTTGTTGGTTGT

CAGATGCTCACAACTCTCCAAGGAAAGTATTATTAGCCTCATTCTACAAATAAAGAAATTTAAAGTAAGA

AAGAAGATTCATGACTTGTTCAAGGCCACACAGCTAGGAAGTGGCAAAGAGATCGCTAGAAACAAGATCT

GTTGATACTCCTTCCAGTGAGACTGAAAGCAGTGATTCTAGTAAGGAGGCTGCCACACCAACCCGGGAAG

AGAGATGAGGCCATAAGAAAGTCTAAATGAATGTGTGAATGAACTACTGAGTGAATGAGTGAATGAGTAA

GCAAAAGGATGGCTGAATGAAGTAGTAGAGAGTTAATGTGGTCCATAAGTCAATGACTGAGCAAATAAAT

GAATATGTGGAAAAAGAGTTGGAGAACTCAAAATCAGCAACATGGGTAAAATACAGACTAGCCAGGGAGA

GACTTAAAACGAATTCTTTTCATCCTCATATCTGCTCCTGCAGGAAACTATGTCTTCAGTTATGACCAGT

TTTTCAGGGACAAGATCATGGAGAAGAAACAGGATCACACCTACCGTGTGTTCAAGACTGTGAACCGCTG

GGCTGATGCATATCCCTTTGCCCAACATTTCTCTGAGGCATCTGTGGCCTCAAAGGATGTGTCCGTCTGG

TGTAGTAATGATTACCTGGGCATGAGCCGACACCCTCAGGTCTTGCAAGCCACACAGTGAGTAGTAGGCT

TTCAGCCATCAGCAGTGGCCAGAGGAGATGAAAAACCACACATGGAAAAAAAAAAAAAGGCAGAGCTGGCA

GTGGAAACTTGGGTTCTATCACCACTTCTTTTGTCCAAGGTCCTCCATCATATCTATTCCTTGGATATGA

-continued

AATAAGTCAACACACCATGTTTCCCAAACTCTTCGGTGTCCAATGCTATGGAGGGGAAGGATGGGAGACC

AAGCAAGGCCCACTCTGCCTGAGTTTTTAATCTAGCTGCAGAATTAGTATTGCCAGAGATGGAGTGTGAC

TTCCTCTAGGTCTTCCAAACTACTCAAGCTCAACCTAGCTTCTCCCTCTCTCCCTGAGTACCTCCAGTCC

TAGAAGGAAGGCACATGTCTCCCTATCCTCCCCATCCTTCCCTCTACTTTGTCTCATAGGACACAGTTTA

TATAGGATCACTAACTCAACATTGACTCCCATCAAGGAAGAGAAACCTACCCAGTTCCTCGATGCCTGAC

AAGAGTTTCTTTTTCTCCTTTTCTCCTGTTTTCTCCTGGCCAGGGAGACCCTGCAGCGTCATGGTGCTGG

AGCTGGTGGCACCCGCAACATCTCAGGCACCAGTAAGTTTCATGTGGAGCTTGAGCAGGAGCTGGCTGAG

CTGCACCAGAAGGACTCAGCCCTGCTCTTCTCCTCCTGCTTTGTTGCCAATGACTCTACTCTCTTCACCT

TGGCCAAGATCCTGCCAGGTAAGCCTGAGGCCTGAGCTTTGTTCAGGGCTGGTATCCTGCAATACAGCAT

CCAGTTTCACTGGTTCCATCACTCCTTCCCTGTATTTGGAGTTCCCTCACTCCCATTGTTCTTCCTTCTT

ATCCACCTTGCATATCCTCAACACTGGATAATTATATCCCTCTGCTTTCTCTCCTTCTGCACGTAGAGAG

GACCATTACCGGGGAACATTACCCCACCTCACAGAAAGGAAACACTATAAATTCATCACCTCCCAACTCA

ACTGAGCTCTTAACACACATACATAGTTATTTTATGTCTCCACAGGAGCTTTTTCAAACTTCTTCTCCTC

TTCTAAAACCTCTGACTACCTTCTCCTCCACACTTAGCAAATAACCTCACATCTTACTTCACAATAAAAA

CAGAAGCCCCAGACAGAGAATCCTTATTTATTGCCACCAAACCTACGAACTTATCTAATTGTTTATCTAG

CCTTGCCTCATTCTTTCCTTTTACAATGGAAGGCATATCTCTCCTTCTGCCTAAAACCAATCCCTTCACT

TGTACACTGGTTCCCATATTCCCAGTCTCCTACTCTCTAGTCTGTAATGTCCTCACCTCATACGCCTTGT

TGTCCTTCCGCCAAGGCCCAATCCAGAATGAATACAACCCTCCATCTTCACTATATCAATTCCGGGCTCA

TACAGTTGCTCAGACAGGAGTCACTAAAAATTCATACTCTTAACCTCTACTGGGTTCTCCATGGTCTCTG

ACAATCCCATTTCCCTGGTCAGTTCTCGAAGTTTATGGGGCAGTTTTGCCAAACCACCATTATCCTCAGC

CTTCCCACACCCCCTCCTCCCCATCTCCCTCAGCAGACAACTTCATGTTCTACTACATTCAAAATAGAAG

ATACCAGACAGCAATGTCCTTGACTCCCAGCCACAAAGCACCTACAAACTCATAAGCATCTTCAAATGTC

CTCTCCTCACTCCTTCTCTTCTGTCATAGTGGAAGAAGTATCCTTTTTCTTGTGACTAATCCTTCCACTG

TTGCTCTGTGCCCCATTCCCCTCTACCACCTTAGGAATCTTGACCTATTGGCTCTCTCCTCCTCTCCTGT

ATCTTCAGCCTCTCCCTCTCTTTAAACATGTTTTCAAGTCTCTTGTATCTTATAAAAAAACATTGCCTCA

ACCCCTGATCACTCTCTAGCTACTGCCCTCTTTCCTCCCTATAACAGGCAAACTGCTTGAGAGAAGTCTT

CGCTCTTACTATCTACTTCCTCACCTCCTGCTGATTCTTCAGCACAGCAAAAATATTACCACCACTTCTC

AGAAACTTTTTTTGAGTCCACCCATAAGCCCCAACTAAACTCAACATCTTTAAGTTGTTTTTAGTCCATC

CCCTCCTCAACCATTAAACTTCTTTCCATCTCTACTGCCAGCATCCTAGCCTGATCCAACATCATTTTTT

AAAGAAAATTTTACCTTTGCCCTCCGATAATCTATTCTTTACAACAGTCAGAATTTTTTTTAATGCAAAA

CTATCTTTGTCACCCCACCCTCAGCCCTGGTCAAAACCCTTTAGTGGACCCCCATTCCCCCAGGACCAAA

TCCAAATTTCTTATCACAGCTTCTAAAGTTCTCAATAATCTGGCTTCTATGTATCTCTTCGGTCTCACCT

TTTTGCATCCCTCCTCTCACTATTTCATTCAGTAATACATTCATTCATATACTCATTCACTTACTTATAA

ATCTGTCATCAGTTTATTTATCCATTCATTTAATAAATGTTTACTTAGCATCTACTGTGTGCTTACTCTT

ATACTGGACACCAGAGACAGAGAGATAATAAGATGTTTTTGCTCCCATGCAACTCCCAGTCTGCTTGTCT

TTCAAGCCATTTTCTCCAGAAAGCCATAACTCATTTTCTCAGGTGGAAGTTATCCCTTAATCTTATAATA

AGGCCACAGTTCCTTGATGGCAGTGCAGTTGGTGGCAGGGGTTGGGGAGGTCCAGGAATCAACTCCCTCT

ACCAATTTCACATGCCCACCTGCCCCACCAGGATTGCCCAGTAAAAAGCCCTGCATTCTTCAAATCTTTC

TGGACCTTAGCTTTCTCACTTGTATAGTAAAGGGATGAATCCCATGATCACTAACAGCCCTGCCAGCTCT

GACATGCCATAAGCTTATGATTCCAACAGTAAAAGCCTGATAAATATCCATCCCTGTAACCACAAGCAGA

TGCTACCTGGAATGGATGGAATTTCATCTAGACTAGGAACAATCTAGCATCAGTCCGAGTCAACAAACAT

-continued

TCCCTGGGGTAATCCCTTTTTCAAGTCTTGATCTTATATATTGGGGAGAAGGAAAATAGGTCCCGTCCTC

AAAAAACTCTGAAGCTTCTTGGGAAATTAAATGTTCTTCCACCCCAAGGCAGTCAGAGGCTAGACCAGGG

TTACAAATGACTGGAGGGAAGGATGTAGGGGTCAGAATTTGGGAACAGTGAAGTCCTTCCAAGGGAGAAA

GAAGTGTCACAAAAGTTCCCAGAGAAGGAAGAAGCAGAGCAAGGTCTTCAAAGGGAAGAAAGGGTTGGCC

CTTTTCTTTGCCAGGTCAAACCTGAAGGTTGAAGTGGGAGTACTGGGACAGAAGCTTAAGGATTATACAT

CTGCTTCCTCAGGGTGCGAGATTTACTCAGACGCAGGCAACCATGCTTCCATGATCCAAGGTATCCGTAA

CAGTGGAGCAGCCAAGTTTGTCTTCAGGCACAATGACCCTGACCACCTAAAGAAACTTCTAGAGAAGTCT

AACCCTAAGATACCCAAAATTGTGGCCTTTGAGACTGTCCACTCCATGGATGGTATGTATATGAGTGAGT

GTATGTTTACTAGTGTTGGTCTCACAAAAACCATGATGATCATGATGATGATGATGACGATAACATTATA

ACAGCTAATATTTATAGTGTTTATTATGTGCCAAGCAAAATTATTAGTATTTTACATGTATTAATTCATT

TAATTTTCTGAACAATTCTATGTGATAGGTGTTATTATTATTTTGATTTTTTACATGAGGAAACTGAGAC

ATAAGAGTAATTTGTCCAAGGTCACACAGCTAGTAAATGCCAAAGAATGGAGGCAGCTATTACATTCATC

TTATAGGTAAAGAAACTAAAGTTCAGAGTTGGCATCCAATTCATCTTGAGTGGCTCAGCAAGTTGGTGCT

AAAGTGAGTATCTGCACCCTAACACATATAACTCCAATTCCTCGAGTAACACTTCTCTTGTTAGAAATGA

TATGTAAATCAATAATCCCAGTGTTTGGTTTTTATGAAGGAAATTTCAAAAACCATTGCCTAGGATTTTT

TTCAAGGTCCAGTATGAAGCATTGGGGTCAAAACAGGTTTTCAAGTCAGAGAGACCTGGGTTCAAATCCC

ACCTTTGACAGTTACTGGCTATGACCATGGGTAACTCTTTAACTGTCTAAGCCTCAATTTTCCCAAAGGT

AAAATATCTGGTTGTAAGAATTAGAGATGATAGAAACCATTCTAGTTATTATGCTTTAGTAGAATTAAAT

GATCTTCACACTCCTACCTCCTTTCTTTGCTCAATTGAAACAATGTCCAAAGCTTTCTATTGCTGGCCCT

GTTGTGTAGAAATCATGTGTTTTAGGCATCCTCTTATGGATTTATTTAAGGGAAGAGGTCCTCAACTCAT

TTCAGTTTGTCCCTTTTCCAACTGAAACAAAAGAGTCCATAGTATTCCCTGATTTAGGTATCTTAAGTGG

CATGTAATGACTATACACACAGGCTCTAAAACCAGACTATCCATGTTCAAATCCTAGCATGACCATTTAC

TAGCTTGGGCAAGCTTCTTAATTGCTCTGTGTCTCAGTTCTCAGTTGCTTATTTGAAAAATGTAAGTGAT

AATAATTAAATAGGTATGCAAATTAAATGAGTTAATATATGTAAGAAACTTACTATTATGCCCACTCCCA

CATTTCTAACACTAGCAATAAAGTAAAACTATCCTATCCCTTTTGTATATTTCTACCACTGAGACTATTC

AAATTCATTATTTCTCTAGTGGAAACTATGTTGGTACCATTCTACCTCGTTACATTTGCAAATAAATAGT

TATTTACCTATTTTTGGGGTGCAAACTCTGCCCAAACTGTTGATCCTTAGGCTGAATCTCTCCCATTGAA

ATGATGCTAGGCTGAACACAGCAGAAACAGGAAAATAGACATTGTCAGAATGAAGTAAAAACAGAAAGAC

AAAGAGTCAAGCCTTGATCCCAGGCTGGGGAACACACACACATGCGCACACACACGTACACACACACACA

CACACACACACACACACACACACACACACACACACACAGAGAGACAGAGAGAGAGAGAGAGAAGGCAGGG

ATGAGATACAGGCAATCGATCCATACACAGAGGTTTGTAATAGTTCTAAATGAAGGCGCACATCCTCCTT

CCTCTCTACAACACCCTTTTCCAACCCAAAGTAGGCATGTATGGGAAATTCCACATTGGAGATGGAGCTG

GGGAAGGGTTATGATGTCCTACCTCTATCCCTTGGCTTTGCTCAGGTGCCATCTGTCCCCTCGAGGAGTT

GTGTGATGTGTCCCACCAGTATGGGGCCCTGACCTTCGTGGATGAGGTCCATGCTGTAGGACTGTATGGG

TCCCGGGGCGCTGGGATTGGGGAGCGTGATGGAATTATGCATAAGATTGACATCATCTCTGGAACTCTTG

GTAAGTGAATGCTTTGGGCCTTCTTATATACCCTCCAGAGAGGAGGCCCTTACAAAATTCTTTTCTGCCT

CCTCCCCAAAGCTATAGGGGTTGTTTGGACAGAATTCACAGCCCCAGGCTGCTGCCATCCTGGACTCCCT

CTCTCCACTCGCATCCCACTGCAGAGTTGATGAGAAAGTCTGGTAGAGTTTTTTGAAAAGACCTTGAACT

AGGCCAAATAGTTAGATTCAACTTGAGTATGTGAAGAGCTGTGTTTCTAAACCCCTCCCCCACCCTAGCC

CCAAGCTTCATCTTAGCTCCACTCCTGACCCTATCCAGCTAAAGGTCCCCACCCAGCTCCTGCCTATCTA

-continued

GTCATTGCATATGGCAAGACTTGAAAGTCCTATCTCAAAGCAGCAGAATTATCAGCTACGACTGCCTTGT

CATGGACAGATGAGCAGAGGCCTGGGAAGACAGCCTGGAGCCCCAACTTCTGGTGCACCCCCTTGTGTTA

TCTGGCACATGATCCTGTTGCTCTGGGACTGATTATGGGATCTGTGTATATCTTATTCCTTTCTGTCTCC

AGGCAAGGCCTTTGGCTGTGTGGGCGGCTACATTGCCAGCACCCGTGACTTGGTGGACATGGTGCGCTCC

TATGCTGCAGGCTTCATCTTTACCACTTCTCTGCCCCCCATGGTGCTCTCTGGAGCTCTAGAATCTGTGC

GGCTGCTCAAGGGAGAGGAGGGCCAAGCCCTGAGGCGAGCCCACCAGCGCAATGTCAAGCACATGCGCCA

GCTACTCATGGACAGGGGCCTTCCTGTCATCCCCTGCCCCAGCCACATCATCCCCATCCGGGTGAGAGCC

CCACCATGCCCATTGCCCTCTCCACCTATTTATTCTGGGAGCCTCACGCTCCCAACAAACCTACATCTGT

TGCTGTCTTCAATTATTTGCTTTCCTGCTAACCATTCCCTTTATTGCCAGCTTTGTTTCCCTTTTTGAAA

AATTATCAGCCATTCTGGATTAACCAGTCTTTTCCTTGCATCAGCCATTACCTCATGCTTATTAGATTAT

CCTAACCCTAACAATAGCGAGTGCTCACAGCCTATAATTCAGAGTTTTTCAAACTGGATCAAGACAATTA

ATGGGTCACAAAATCAGCTTAGTGGGTTATCATTAGCATTAAAAAAAGAAAAGAAACAGAAAATGTTGGA

GTACATCACATACTAAGGGTATCATCAATTTGTGAAAAATTTGTATGCATTTTGGGTATTTGCATATACA

CATGTATGTGTATGTGTGCGTTTATGGTCACGGTGTAAAACGTACTTCTTATTGAGAAATGAGGGCAGAA

AAATAAAATCAAAAGCCATAGGATTAGCTGCTACTTTGGATCCTCAATATGAGCATTTACTGCCTTTAAA

AATGAACTGCTACTTCTTTCTTAAATAACACGTATTTGTGTGAGTCAGTAAGCCAGGGCAGGGAAAGGAC

ACTTATTTGTGACAATTTTGTGGATGAGAAATAGTCACTGCTCTTTAGACTAACCTAGTATTTCCTTTAA

ACACTCATTTTATGAATTAATTTAGTGACAGCACCCCAGAATTGGCTTGGCGGGGGTTCCAGAATTGGCT

TGGTGGGGGGTATCTTCTCACCCAGAACCATCCCAAACTAAGATATTAGCTAAGTAAAATCAGTGTGCTT

GCTCTGCAAACAGCTTCCAAACAGGGCTCCTGGTACCACCTCTGCTCCATCCTTTTCAAACCAAATTGCT

AGCTCTGAGCTCCTCCTTGATAGAAATTCTGGAGCTGCCACTAAGCCCCTAATGGAAAAAAAAAATCTAT

CCCAAAATTCAGTGATGTTCCCTCATCTAGTTCCCTCCATCTGCTTAATGGAGCTAGTGATGGTGGAGCC

AGAGTGGCAGGTACTGATTAGCCTTTCTCCTGAGTCCAGGTGGGCAATGCAGCACTCAACAGCAAGCTCT

GTGATCTCCTGCTCTCCAAGCATGGCATCTATGTGCAGGCCATCAACTACCCAACTGTCCCCCGGGGTGA

AGAGCTCCTGCGCTTGGCACCCTCCCCCCACCACAGCCCTCAGATGATGGAAGATTTTGTGGGTAAGTTC

TCAACATGGGTGCCTACAGGACCTCCCTCCCCTCAGCCCCAGGATCTGAAAGAGAAGCTGAGAGGACAGA

GACCACTGAGTTTACAAAATATTTCTGGAACATCTAATGTGTGCCAGCACCTATACTAGGGTCACAAATA

AATGAGAAGCAGCCCCTACACTTGTAGGGCTCCAGTTTGGTTGGGGATACCATAGTGAACACAAACAATG

ACACTAAGGGATGATCAAAGCTCCACAAGGCAGTGCATGATAGAGTTGTCGGAGCAGAGAGGAGGGGCCT

GACTCAGCCTGAGGGATGCAAGACCCACTTCCTAGTAGAGGTGACACCTGAGCTGAGTCTTGCAAAGTGA

GTGGTATTAAAAGAAAGAGGGCATGGAAGAAGTATTCCTACCAGAGGGAAGAGCATGAAGATAGGTGAGG

AGAATGAGAAGCAGCCAGGGATATATCAAGAACAATAAGCAGGTGGTATTGGAATGTAGGGTCATAGGAA

TGGAGTGGGGCAGGGGAGTATCAATCTATGAGTCTACAAAGACAACATGAGATAGAGACTGGATTGAGAG

GCTTGTAGAGCTGAGTAGTTTGAGATTTACCCTGAAAATGCCAGTTTAGTCAATTCACCTAATGTTTGTT

GGATTTCTGTTGGGTAGTTTTGTTTTTGTTTGTTTGTTTTTGTTTTTGTTTTTTTGAGACAGAGTCTGGC

TCTGTAGCCCAGGCTGGAGTGCAGTGGCACGATCTTGGCTCACTGCTACCTCTGCCTCCCGGGTCCTGGC

TCAAGCAATTCTCCTGCCTCAGCCTCCCAAGTAGCTGGGATTACAGGCACGTGCCACCATGCCTAGCTAA

TTTCTGTATTTTTAGTAGAGATGGGGTTTCACCATGTTGGCCAGGCTAGTCTCGAACTCCTGACCTCGTA

ATCCACCTGCCTAGGCCTCCCAAAGTGCTGGGATTACAGGCGTGAGCCACCATGCCCGGCCTGGGTAGTT

TTTAATGCAGGGCCTGACATTGAATAGGTGCTCATTCCAGGCCTGTTGGATGAAAGACATGTAGGCAGTT

GATGGTCTAGCAGAGGAGCCAGATATAGATGGTACTGGTCCAGTATGATGAGCTCCAGTATTCTGGGAGC

-continued

TAGAGGGAGTGGACACATTATGGAGAGAGAGGGTGGGAAGGATGAAATTGGAGAGGCTTTGTGAGTAAGG

AAGTTTTTATGATGCATGTTGAAGTACATGTGAATATGTTGTAAGAATATTCCAGAATAAGGGAATTCCA

CGAGCAATGACCTAGAGATAGGAAAGCAGTGGGTATGTATTGACAACATAATTCTGTTTGTCTGAAGCAT

GGGCAGTATGAGAATTCAAGGAAGACAAGCTAGGTAGGCGCCATTCATTCATTCAAAAACATTAAATAAT

GCTGGCTAACATTAAGTACTTACCATGTGCCAAGCACTGTTCTAAACACTTTACACGTATTAACTCATCT

AATCCCCACAACAACCTCAAGAGTTAGAGATCCTCTTATCATTTCCATTTTGTACATGTGGAAATTGAGG

CACAAAAATATATAGTCGCTGATCCAAGGTCACACAGCTTCTAAGTTGCAACTGGGAGGTCTGTCTCTAC

CTCCATGGTCATAACTGCTAGGTCTACCACCTCTCTGAGCTGATGACCCAGACTCCTGGGCCTTTTGTTC

AGTATTCTCTTTTGCTCTGGGCTTCAATTGTAGAGCTCTCAGTATTCTTGGTTCTCTGAATGTCCACCTA

GGCTAGGCTTTTGTAAGAATATATGAGGCATCCACGATGGCTCCACCAGTCCCTAAGTTCCATAGCCAAT

CCATCCTGAAATCCTGCAAAAGTTATCTATAATCTCTCTCAAACCTATTTGCTTTTCTCCCCTGCCACTT

CTTTAATCCATGTCAACATGATTTTTTTCCTAATTTCTCTGCTTCTCTCTTGCTCCTCTCAAATCCTTTC

TCGATGATGACCACTAGAGGGATTTTTCTAAAATTCTGACTATATTGCTCCCTTGCTTAAACCCCTTCAT

GTTTCCCTCTAGACTCTAAAGCAGTGACCTCCAAGGGGTATGCAAAATGATTACAGGGTGAAGGAACAGA

ATATGTATTAGAATTTTATGTTTTTTTATCTTAAAAATAGGAAATCAAGCATCACTGATACTGATCTTTA

ATATACAGACTGACAGTTATACATGTATATAATATATAAACAAATATAGAGATTGGAGGTACATGCTAAA

ACATTTGTACTGATAGGGATGTATAGTCCAAAATTTGGAAACATTGACATATAGGACAGAGTTGAAGCTC

TTCAGCATAGCATTCAATGCCTTCCACATGGTGATCTCTATGCCCTCACCTCCTCCCCACATGCATTTTG

TTTTTCAGCTACACTGAAGGACTTGTCGTTCCCTCATTTTTTTCTGCTCTCTTACCTCTGGGACTTTGC

TCATGCTGCTCTCTTTTGATTGGAATGCCCTCCCTCACACTTTCCTCTGGCTTACTTTCCTTCATCTTGT

AGACTTAACTTAGGCATTCTTTCAACAAATATTTATTGAGTACCAACTGTGTACTAGATACTGTTCTAGG

CACTGGGGATGCAGTAGCAAACAAATCAGACACAAAATTCCTACCCTCTGGAGCTTACATTCTAGTGGAA

GGGGTAGTAAAAAAAATTACCAAAAATAAGCAAATTAAGTAGCACATTAGTTCTAAGTGCTATGGGAAAA

AATAAAGCAGGATAAGGAGAATGGGATAAGGGGCCAGGGGCGAGTTCAGAGAAGGGTTGTAGTATTAGAG

TGGCAAGGGTAGAAGACGCTGAGGTGAAACTTGAGCAAAAATTTGAAGGAGGTGAAGTTAGTGAGGCAGA

TATCTAAGGGAATGGCATCGCAGGCAGAGGGAACATCCTAAGGCAGGGAAGACACAGGAGTATTCCTTTT

ATATTTGAGGAACAGTAAGAAGATGGGTGTGGGTGGAATGGTATAAGCAAGTGGGAGACAGAAAAAATTGA

GTACATAGAGGCAATGTGGGACCAGATTGTATAGGGTATGGTAGGCCATTAGAAGGAGTTTGGCTTTTAC

TCTGAGAGCCCTTGAAAGGATTTGAACACAGGACTGATATTTCTGACTCGGGTTTTAACAAAATTGCTCC

AACTTCTATGTAGAGAATACACTAAAAGGGAGCAAGGGTGGAAGCAGGGAGACCCAAGAGTGGGCTACAG

TAATATCCCAGGTGAGAGATGATGGTGGCTCAGACTTGATCATAATGAAGGCAATAAGAAGTGGTCAGAT

TTTGAAGGTAGAGCCAAGGGTCTTTGCTGATAGATGGGATATAGGGTAAGAGAGAAAGAGAAAAATAAAG

GATAGCTCTGAAATTTTTGGACTGAGCAACTGGAATTGCCATCCACTGAGATGGGAAAAGCTAAAAGTAG

AATAGCTTGGTGGAGGGTAGGGACATGAGTAGCTCAGTTGTACTCCTAAGTTAGAAATGCATATTAGACA

TCTAGGTGGAGATGGAGAAAAGCCATTGGATATACAAGATTGGAAACCAGTAGAGTGGCGTGAGCTGGAG

ATTAAAATTTCTGAACCATCAGCATATAGATGGTCTTTAAAGTCATGTGACTAGACAAGATCAACAAGGG

CATGAACACAGAAAAGGCCAAGAACAGAGCCCTGGAACGTACCTGGGGTACTTCCTCCAGCTAGGTCAGG

TTCCCTTCTCTGGGTTTTCACACCCCCAGGTGGACCCCCTACCCCAGGTTTCCTGGTCATAGCACCAATG

ACACAGTATAGTTACTGTCATTATCATTGTCCTCATAGGGCTTAGAGTTCCCAAGCAGACAGTCATTCTT

GGGCCACAGCACATCCTATACTTAGGGAGTGGTCCAGGCCAGGACAGTATGGCTTCAAATTGTGTCAAAG

-continued

GAGAGCTTCCAAATCTTTTATAATATATATCCCAGCATCCAGATACAAATGGTAATATTCACGGCACACA

CAGAAGCAAACAGTAGGCTACTTCTGGCCCTGAGGTATCTTGAAGGGTTGAGGGGGATCAATATCTTGGC

TCATCTGTACTGTGACAGATTTGGAAGATCTAGTCTAACCCATTTTTTCCCTCCCCTCCCCCTACCACCT

TCAGAGAAGCTGCTGCTGGCTTGGACTGCGGTGGGGCTGCCCCTCCAGGATGTGTCTGTGGCTGCCTGCA

ATTTCTGTCGCCGTCCTGTACACTTTGAGCTCATGAGTGAGTGGGAACGTTCCTACTTCGGGAACATGGG

GCCCCAGTATGTCACCACCTATGCCTGAGAAGCCAGCTGCCTAGGATTCACACCCCACCTGCGCTTCACT

TGGGTCCAGGCCTACTCCTGTCTTCTGCTTTGTTGTGTGCCTCTAGCTGAATTGAGCCTAAAAATAAAGC

ACAAACCACAGCA

As used herein, "GYPA", "GPA"; "MN", or "glycophorin A" a sialoglycoprotein of the human erythrocyte membrane which bear the antigenic determinants for the MN and Ss blood groups. Sequences for are known for a number of species, e.g., human GYPA (the GYPA NCBI Gene ID is 2993), the nucleic acid sequence (e.g. NG_007470.3), mRNA sequences (e.g. NM_001308190.1) and polypeptide sequences (e.g. NP_001295119.1) are known in the art. These, together with any naturally occurring allelic, splice variants, and processed forms thereof that catalyze the same reaction are contemplated for use in the methods and compositions described herein.

In some embodiments of any of the aspects, the GYPA enhancer element includes or is derived from human GYPA sequences having the following nucleic acid sequence NG_007470.3 (SEQ ID NO: 42):

NG_007470.3: 5001-36438 *Homo sapiens* glycophorin A (MNS blood group) (GYPA), RefSeqGene on chromosome 4

GCAGGAAGGTGGGCCTGGAAGATAACAGCTAGCAGGCTAAGGTCAGACACTGACACTTGCAGTTGTCTTT

GGTAGTTTTTTTGCACTAACTTCAGGAACCAGCTCATGATCTCAGGATGTATGGAAAAATAATCTTTGTA

TTACTATTGTCAGGTAAGTGATTTTATTTCATCTTGGTTCTGTTATATTGGGTATGAGATCATAGAATAA

AATATGAACTACCCTATTTTAGTTCTATCTTATTTAAATCAATAAATGAGTAGTATTTCCTCTTCCAGTC

TGGTGGATGGATTTTACTGGAACTCAGCTACCAATGTGGGGGAAATGGCACAAGGGAGCCCAGTATTTAT

GGCCAAATCCAGTTTTCTAGTATGAGAAGCTTACTTCAATTCTAAGTCTAGCTAGAATTAAAATAATTTT

ATCAAATGCTATGAGAAATACCTCTCTGTGAATAAATGTATTGCTTTGTTTGAGTTATAAGGAGATTCAT

TTCCAAACTAAAGAGTTATTAACGAAGATGTTGGTAGCTATATGGCTTTTAGTTTTCAAAAGGTATAATT

TCCTATTTCTGCCAAATGGCGAGAAGCCAAAAGCATGAACACTGAAACCGTGGGGAGTTGTTCGCTTCTC

TGTGGGTCCATTACTAAAGTGTCACATAGGAAGAAAAAAAACAAAAACAACTCTTACTGGCTTAGGTATC

CTGTGAATTTTAGGAGAAATTTAAATCCATTAAAATAAAGAAATATCATAGGGTTATTATTAAATTGTAT

TAATTCAATAATTTGAATTTAACTTAGTTTAAATTTAATTATTAATTTAGTGTCTTAAATTAACATGATT

TTGGCCTCTTTCTGAGAATATTATAGTTAAACATCCTCTCAAGTGCAGTGCTTATGTGTTAGCAATACTA

GTGCCCAGCACACAGCGGGCAGGCAGTTGCTTGAAACATTCTGAGTCTATTAGACATTGCTGTATCCCAA

GTGAGAGCAAGTATCAAGGAGCTACTGAGCACTCTGTAGCACACAGGGAGGAGAGATCAGCATTTTCTAA

GATACCCTAGGGGAGGATAAAATAGTGCAATAGTTAAGAGCACAGGCATGAGGAACAGACAGAACTGGGT

TCAAATCTACTTTTACTTCTCAAGGCTGGGGAACATTAAGGCAAATTATGTGCCCACATTTTTATGTGTC

CTCGTCTTTAAAATGCAGGCAGTGTTGGTACTTACCTCATAATAATTGCATAAAGATTAAACAAAATATT

TAATGGAATACACTTACTGATGCCTGAAACAAAGTAAAATGTTAAGATTACTATGCATTTTCTGTGATTA

GAATTAACTATCATGATTAAAAAGTATTAATAATATATTATTAAAATAAGCAGTAGCTATCAATAGTTAC

AGACTAGGGAACAAACCTACGTATGTGATTGGTGATTTCTGAAAAGTCAGAGAGAAAAGAAAATTACAGA

AAGAAAACAGAAAACAAACATAGCTACTCTAATTTTTTAAGCAGAAAAGTATGAAAACATTTAGTTTGAA

GAAAAGAAAACAAATGAAAGGGATGTAGTGTAATATTTGTATATATATTCATATATTTGAAGTGCTATTA

CACAGAAAAAAAGATGTATTCTTTGTGTTGCTCCATGGGGCAAACCAAACTGGATGTAACTCAAGCAAAA

TTAGACACTGCATACTCTACTGGGGGTGTGCCCAGCATTTGGGAAAACTCTGTGTGACTTACAAGTGCCC

-continued
CAAATTTGGAAAGGGTTCCTGGCAAAGAAATGATTTTTTTTTAAATTTCTACAACTACACAAGCAGATA

GTGTATTAAAGCCTTAAATGGCACTTGGTCACTGGGGCAAGATGACCCTGAAAGCTACAATGGTCTCCAG

TACCCAAGCTGTTATCATCTTTGTAGCTTCAGAAACCCTCCAAGGAAACTCTCTTGATGTGGCTACTTTA

TAGTATAACAGAAAGGTGTAAGATCAAGTTTTTCCCCCATACTGATTAGCTGAAGAGTAAACATGGTGAA

GTCTTTTTCTTTTTCTTTTATGTTGCTATAAAAAAAAAGATGATTGCCTTGCTTTCTCCAGGAATCTTAA

GAATAAAGCCAATATTTCTAATTCTAAACTTACCAGAGATCTCCTTCCAAATGGAGAATCCATTTTTTCT

AATATGACTTGATTCCCAGTCCCTGAATTCCTGCACTCATTTGATGATTCAGTCATTACATGTCAGATTG

TGAACCAGACACTGAGCCCACAGCAGGAAGAAAAATGGGCTCCCATGGAGGATACACGGAGGGTAGGCGC

AGTGGATGATGGGAGGGAACGCAGATAATAAATGGAACAACAACTATCTTATTAAAATAAGATAAAAACA

GTCAAAACTAATACAAAGCATATAAAACCAGGTAAGATGATAAACATGAATGCCGAAAGCTGCTTAAGAA

AAGGGTAGCAGGGAGTTATTTTCTGAGTAGATGACATTTATGCTAAATGTGGAACAAGGAGACGGAGCCA

ACCCTGAAAATTCTGGGAAAAGAGGACAGAAGGCAGAGGGAAGAGCAAGAGCAAAAATTCTGAAACAGCA

GGTAAGTTAGTGTTTTCAAGGAAAAGCTGGAGCTTTTATCTGAAAATCAGATTCTGAAGCTAAGAACCAA

TTTGAAAATACAATACAATATCACTTCGACTAGGAAATTATGGCATAAACCAGGAGTCTCCAAAAGCTTT

TTGTGTTTACTTAAAAATTCATACAAAATTTGCATTCTAGGTCATAATATACTAATTTAATTGGAGGAAA

CAAAGGCACTGGTATGATATCATCATGCCTACTTTATTCATCCGTGTATCCCCAGAATCTAGCACAGTTC

CCGATTGGTATTTATAGTAGCATATTGGTTGAATAAGCAAGGAAGGAGGTGAAGGGAGGGAGAAGGAGAG

AGAAGCAGAGAGGGAGAGGAAGGAAGAAAGAAAAGGAAAAAGGGAAGGAAAGAAGAGAGGAGGGAGAGAG

GGAGGGAGGCAAGAAGGGAGAAGAGAGAAGGGAAGGGAAGAGACAGGAGGAAGGGGAGGAGGAAAGGAAA

GAGGAAATATTTGTTTTCATCTGGTTAGACACAGTGAGTGCTCCGCATAGACAGATCATTATTACCCTGT

GCATCTGACTCATACCCCTGCAAGTACATCAGTCTGAGAAGCACATGTTAAGTGAAGAAACAAGGCATCT

CTTTTTTTTTTTTTTTTCAGGGATCCAAGAAGAGAGCCTTGCTAGCTGCTATTTAATTGGCACAGGAAAG

AGTTACAGGAACTGTATGCCAGGGAATACATGACTATAAATTCTTTAAAAGCAAAACCTGTGTCTTCGCT

TATGTGTCCCACACATTGTCAGCCACATAGTAGGCAGTCAATATCAACTACTCAAAATGACAAATGACAA

ATGACCAGAATTCTGCGGCAGACTAGTTTAGCCATGAAAAATCATTTAACACCCGTGGGCCTCAGTTTTC

TTGTGCCTATTCAATAAAGCGCCGAGTAGATGGTATCTACAAGCATTTTTCAACTGTAAACCCCAATGAA

TCCCCAAAATTCAGCCTGAGATGAGCTGGACTAGTTGCCAAACCTATAAATATCTTTAGCATGGTGTGAA

ATAGGGTTTTTAGAAAGAAACAGACACCCACTGTGAACTCCTTTGCAGAAAAGGTCTGAATAGAGGGGAA

AGTAGGGATGGTATCTCAAACTTACTTTGTAGTGATTTTAAATTAGGAAATTTAGCTTCACATTCTTGTG

ATAAATTTCTTTTCACCTTGGTTTCTAGAAGATTATTCAAAACATCTGTGAGACTATTTGAGAAGTATAC

TTTTGGGGAATTTCCCCAAGTTATCTTTATAGATTATATTTTGACATCAACTGCAAATGTAATATCTTTT

ACTCAAAAAAAACCCAATCCTACTTACATGGTGCTGACAAAATCAGGCTGGACCTACATTTTTACATCAT

AGATTTCCAGCCATTATTATCATATCCACATCTTTAGTAAGTACCTATCTGTGTAGTTTTCTGTGATAAA

TGAACTAAACTAAAACTAAAGCAAAAATGTTGAAAAAAAATTCCAGGTTTATCTCTGAGTGTTGGGATTG

CAAGGTTTTTTTTTCTCATTTTAAATACTTTCTAAATTTTCTGCAAAGAGAACCATATAATCTAATCAGG

ACAAGTTTTAATATATTTTAAAAAGTAAACCGAACAAACACAATCTCTGCTTTCTAAGAAGTCTTTAATT

TTTGTACGTTGGTCATAGACTATGACTATACAATTTATTTGTGATATGTATTAAGAATTTCTGTCTAACC

CAAATTATTATATGTAAGCACGGGAAAAATGATGTCATCTTTGTTTGTAGTGTACAAAGTTCTATAAACA

GCTATTTGATCAACTTTGGTATTTCCATCCCTAGATTTATATACAGCAGGTTAGGTTCCATACAGAGGCA

GGTTCTGAATAATAATAACCAACACTGATAATAGCACTTACTTTGTGCCGTGCACTGTTCTAAGCAATTT

ACATACACTTAATTTTTAAAATTGTAGTAAAATACACATAATATAAATTTACCATTTGAACCATTTTAAA

-continued

GTGTACAATGGGTAGCATTTAATGCAGTCAAAATGATGCACACCCATCACCATTATGTAGCTCCAGAACA

TTTTCATCACTCCAAAAGGAAACCTCTTACCCATTAGCAGCCACTTCCAATTCCTCCAGCCCCTGGAAAC

CACTAATTTGTTTTCTACATCTACAGATATACCCATTGTAGATATTTCATATAAATGGAATCATATAATA

GGTAGCCTTTTGTGTATGTCCTCTTTCACTTAAAATAATGTGTTTAAAGTTCATCCATATTGTAGCATGT

ATCAGTATTTCATTCCTTTTATAATTGTGTTGGTATATCTCATTTTGTTTATCCACCCATCATTTGATTA

AAATTTGGGTTGGCATATCACATTTTGCTTATCGATCCATCATTTGATTAAAATTTGTGTTGTTTCCACC

TTTTGGCTATTGTGAATAGTGCTGCTATAAATATTCCTGTACTAGTTTTGTTTGAACCCACTTTTAATAC

TCAAAGATGTATAGGGGTAGAATTGCTGGGTCATAGTAATTTTATGTTTAACTTACTAAGGAACTGCTCA

ACTCTTTTCCACAGGAGCTGCACCTTTTGACCTTTTCACCAGGGTGTATGAGGTGCCAATTTCTCCACAA

TCTTGCCAGAAATTGTACTTTTTCATTTTTTTAATTATAGCCATTTCAGAGGGTATGAAATGGTTTTTCA

CTGTGGTTTCTTGCATTTTCCTAATAACTAATGACGCTGAGAATCTTCTCATGTAATTGTTGGTAACTGC

ATTTTGCATATCTTTGGAGAAATGTTGGTACTAGTCCTTCACCCATTTTTCAATCTATTTTTCTTTTTGT

GTTGCTAAGTTGTAAGAGTTCTTTCTATGTTCTGGATAAAGAGTCTTATCAGATATACTATTTGCAAATC

TTTTCCTTCATTCTGTAGATTTTTGTTTTTACTTTTGATAGTGTCCTTTGATGCACAAATGTTTTTCATT

TTCAAGTCCAATTTATTTTTTTTTCTTTTGCTGCTTACGCTTTTGATATCATATCTAAAAATAATTGCCA

AATTTAAAGTCATAAAAATTTCTCCCTATGTTTTCTTCTAAGAGTTTTGTATTTCTTCTCTTATATTTAG

ATCTTTGGTTTATTATCAGTTAATTTTTCTATATGATGTATGATAAGAGTCCACCTTTATTATTTTGCAG

CTGTCCCAGCACCATTTGTTGAAGAGACTATCCTTTGCCCATTGAATGGTCTTGACACCCTTCTTGAAAG

TTAATTGGCCATGGATATATGAGTTTATTTCTGGAGTCTCAATTCTATCCTAAGAATATGTCTGTTCTTG

GGGCAAAATCACACAGTTTTTATTGCTGTTACTTGGTTATACGTTTTTAATTCATGAAGTGTGATTCACC

AAACTTTGTTCTTCAAGATTGTTTTGCCTATTTAGATCCCTAACAATTTCATAGAAATTTTAGGATTAGG

TTTTCCATTCTTGCAAAAAAATAATTATGTGCATTTTAACTTAACCTGTTCAATAACTCTATAAGGTAGA

GACTAATCCATGTATAATGATGGAACAAAAATATAGAGATTAAGTAAATTTTGCAAGGTCTCAGGTAGTT

GCTAGAGGAATTAGTTTGAGCCTAGGCAGTTCCACTGCAGAATCTGTGCACTTAGAGAATATGTCATGTT

GCCTGTACCATACCTAGTGATGTTCCAGGATTGGCTCCTTTACTCTTACAACATTGTCACTCAGTGTTCT

GCCTGTGCTTTCACCAAGCTGAAGACTTTAATGAAGGTTGACGGTCTGTCTTCCTCACGTGGTGCAGCTA

AGGAACTCTAACTGTGTGGCTGTTATGTTAGCCTTTTGCTCCTTTTTATATGGGCTATAGAAAATGTTTT

TAAATCCTGGAGGCCTCCTTTTGATGTTATCACTTATTTCCCAGTCATCACTATATTTTTAAAAGCCAAA

ATAGAAGGAAATAAATACAAAACATAAAACATGAATAGTACAGCTATTTGAGGCAACTGAGAATAGAGAT

CATGGCACTGAAATTGCATTTTGCTAGGAAAAAGACCACAAAAGTTCTCCCCTTGCTACCTTTCCTGAAC

TATTCTGCTAGATTCAGACTTCAAAAACATTGTATCAGGAAATACAGAAATGTTCTTTCAAAATGAGTGT

ATGGGAATGTGGGAATGCCTAATAAAATCTGTCCTCATTGATTCGTTAGCAAAAATCATATAAATCAATA

CCTTGTGATTGCAAGCAGATATATTTCAGATCCTTTCTGTGTTTGTTTTTTTGCTTTCTTGATCTATCAC

AATTGGAGAAAACTTAAAATTTCTCAATGGTATTGTATTTTTGCCAATTTCTTATTCTGCTTTATGTTTC

TCGTTGCTATATTATTGGGCTATAATGGTCCATAATTACTTAAGAATCACTGTGAAATATATTGCTTAAT

GACACAAGTAAATCTTTTTCATTGTTTGTAATGTCTTTGCTCTTAATTCTACTTTGCCTAAGATTAATAC

GGTTATTCCTGTTTAGTTTTATATGTATTTATTTATTTATTTTGAAGATGGAGTCTCGTTCTGTCGCCCA

GGCTGGAGTGCAGTTGCATGATCTCGGCTCACTGCAACCTCTGCCTCCCGGGTTCAAGCAATTCTCCTGC

CTCAGCCTCCCAAGTAGCTGAGAATACAGGCGCACACCATCGCGCCCAGTTAATTTTTTGTATTTTAGTA

GAGACGGGGTTTCACTGTGTTGCCCATGCTGGTCTCCAACTCCTGAGCTCAGGCAATCCACCTGCCTCGG

-continued
CCTCCCAAAGTGTTGGGATTACAGGCATGAGCCATTGCACCAGTCCTAACCTATCTCTTTTGACTCAATC

TAAAAGTTTCTGTCTTTTAATACAAAACCACAATCCATATGCATTCATTAATTCACAACTGACATTTAGT

ATCTTATTTCTGTTATCCTATTTCATATTTTATGATTCCTTGTTTCTGCTCTTTTGATATATAAATTATG

TTTTATTTGCCCTTATCCTTTCATGTGTTTCTAAAGTATATAGCCTACGTGTAATTGTCCCATTAGCTAA

CTTTATGTTTTTGAAAGCATTCTCTCTCAGAATTCCCATTTTAGTGGTGCAGCACACATAGAAAGTCTAA

GTGCTTTCTGGAGCTAGATAAGCTGGATAAAGGTGTGCATGAGCCACTGGTCAATGGCTTGTGCAGGCGG

TGAGTGCATTTCTGGTATTTCATATGCTATTGATCTGGCAGCCAGGTATTCAGATAGGGTATAACCAGGT

TCATCAGGCTCAAAACATAATCAAGTATTATTGAGACATAGTTAATGTGCACTACAACTCACAGCACACA

GGCTCACACACACACTTGTCTGAAATAAAATTCCACAAAATAATACCTTCCCTTATTCTGTGTGATGTAC

TTTGATATATTCTCTCCTGTTTTATACAACTTAATTTTTTTTAGAGAAAAGATTTTGCTCTGTGGCCTAA

GCTGGACTGCAACGGCACAGTCATAGCTTACTTCAGTCTTGAACTGCTGGATTCAAGTGATTCTCCAGCT

TCTGCCTCTCAAGTAGCTGAGACTTCAGGTGTGCTCAACCACACCTGACTAATTTTTTGGTTATTTAATT

TGTAAATATGGGGTCTTGCTATGTTGCCCAGGCTGGTCTCGAGCTCCTGGCCTCAAGCGATCCTCCTGCC

TTGGCCTCCCAAAGCACTGGGGTTACAGGCATGAGCCACCACACCTAGAATACAACTTAATTTTTTAGTG

CCAGTGACAACCCACTGGACTGATTTCATAACCCATTAGTAGAGGAATGCACCATCTTGACTGAAGGTTG

GAATTTTCTCAGGGAATCTATGTAGCACTGATGATTGGGTTTCATATCCAGAGATTCTAGTTATGCTAAT

ACAGAGGCCAAGCAAACTATAGCCTGTGAATGGCCGGCCCCCTGGTTTTGTATACCTTACAAGTTACAAA

TGATTTTTACTTTTTTAAGTGCTTAAAAAAACCAAAATAGGCCGGGTGCAGTGGTTCAAGCCTGTAATCC

CATCACTTTGGGAGGCTGAGGCAGGCGGATCACGAGGTCAGAGGATCGAGATCGTCCTGGCTAACACAGT

GAAACCCCATCTCTCCTAAAAATACAAAAAATTAGCCAGGCTTGGTGGTGGGCGCCTGTAGTCCTAGCTA

CTTGGGAGGCTGAGGCAGGAGAATGGAGTGAACCCGGGAGGCAGAGCTTGCAGTGAGCCAAGATCATGCC

ACTTCACTCTAGCCTGGGCAACAGAGCAAGCCTCTGTCTCAAAGAAAAAAAAAAAGAAAGACACAAAAAA

AATCAAAATAATAATAATAATATGTGAATATTATATGAAATTCAAATTCTACTGCCCACAAATCATTATT

GGAACATAGTCATACTCATTTATTTATGCTTTGGTTTACATATTGTCTGTAGCTGCTTTTGCACAGTGAC

AGAGTTGAATATTTGTAATAGATGGTCCACAAAGCCTAAAGTAGTTGTGGCCCACAAATCCTAAAGTAGT

TACTCTCTCTCCCTTTACATAGGAAGTTTACTAATACTTGTGCTAAGGGATCTCAACAGACAATCTGAAA

AACTTAAGTTTTAGACTAAAGATTTCCAATCTAAATTCCTGTGGAGCTTTCTGAAGCTGCCAGGTGGAGA

TGGGAACAGGTTGTGAGGCTGCAGGCCAAACACTCAGGCCAGCTTCCACCAAGCAGTTCAACTCTGTCTG

TTTCACACACTGATGAGCTTATCCTTGGAAAGTGATTAAAGTAAAATTAAATGCGAATTGAGGGAGGAAG

TGAGGGAGACTGTGGCTCTAAAACAAAACCCTAAGAAACACCAACATTTAAGATGGCAAATGATGTTATT

TCTAAAGTCGTTCAGGCTAATATCACATACTATAGCTGTTCACTTTATAGATAAAGGTGACACTACAACC

ATAGAAAATGTAAGAGTGGACCTCGAAACTCAGGAAGATGAAGTTTACATATATTAATCTATATTACCAA

CTGGAGCAGTTGTTCTCACTGCTGGCCGCACATCAGAATCCAATTCCTGGGATATCACAGATGATTCTAC

CATGCAGTCAAGGATGAGAACAAACTAGGTTCATTTCTGCAATTTTTTTATTGTTCAACCAGTGAAAAGG

AAGTACCAGTGGTGTGAGAACTTTGGGATAAAGTTTTTGTTTTCAATTAAAATTATTTTCATCCAGCCCA

ACTTCCTTAAGCCCAAATTTAATGTGTGTGAAGTTCAGCTACAGAAATACCAAACCTTAGACTAAAGCGG

ACACAGGTAAAATATGTGAAATCCTCTTTTGTTCTGAGGATTCTTTAGTAGGCAGGAGTGACCAGATAGG

AATATGCTTGGCTGGAAAAATTAAGATTCAAGTTAACAAACTGTTAATAACCAGGACCATCTGCTCTTCC

GTAATGTGGATTTGCCACTGCAGGTCACCCTACAATGCTATGTTAGAGGTACAACACTCTTACCCTCAGG

CTATAAACAAGGTGAATTATTATCTTTATATCTCTTCATTTAGCCCTGATTTGCTGAAGTGAAGGCTCGC

TTGAGAGTTGGTTGCATTATAATTTGGTGAGAATTTAATCTCTCAATGACAACTTACTTGATTCCCTCAT

-continued

TCTCTTTCTGCTACATAGATCACAGTAGACCTTGGCAGACAGTTCTGTAGTTACATAGGTCTGAATTCAA

AATCCAGGTCTGCCACTTGGTGGCTGTGTGAACTTAAGCAAGTCAGGCAATGCTTCTGATGTTTTTTTCC

TCCTCCACAAAGAATAATTAACATATAACAATAGGGTCTCAGCTAGTTGTTTTAAAAATGGTTAGAGAGA

TGTGTGGAATGAAGTAAGTGTGCAGTAAGTGTTAACTACAAATATTATTATCTTAGACATACAGATTTCC

ATGATTCATGAATGGTGAAGCATCTTAGAAGACATCCATTCCAGGCCAGGCATGGTGGTGTGCACCTATA

GTCCAAGTTGCTCAGTAGAATGAGGCAGGAGAATTGCTTGAGCCTAGGAGTTTGAGGCTAGTATGGGCAA

TATGGTGAAACCCTATCTCAAGAAAAAAGCAAAACATTTTTTAAAGTTTAAAAAGAGAGACATCTGTTCC

ACTACTCTCATCTTAGAGGCCATAAAACTGAGGCTCAGATAATTTCAGAGACTTGCACAGATCCCCCAAC

CATTTGGTGGCAAAGCCAGGAAGAGAACTCTGCTCTCCTTTCCCACTGGGACAGTGGAAGAAATTCGTCT

TGATTTCCATCTGTCCAGGCTGAAGAATGTGCACTGGCTGGAATGACAGACTGACCGACTTTTTTTCTCC

ACCTCTGCTGTCTCAGCAATGGTTTGGGACAGTGTGGATGACCAGAAGCTGGATAGTACAGAGCCAGGCT

AAAGAGTTCAGGCTTCCTGAAGGGAAGCTGCAGTCCTCCTAGGCCACAACACCTTCGAGATAGAATACAT

AAAGCACCCTTCTCTACCAAGTTAGGAAAGGAAGAAGTGTGACCAATTAGCTGTATGGGGACTGCCAAAG

CATGCCAGTCTGAAGATGAGCAGAAACTGGCTCATTCCATTTGGCACCTAGCACACTAACTGCATCCGTT

AATAGGCCATGCTTTTCTCCAGAGCCATTGGCTGAAGAGATCAAATAAAAAGTATTGAGAATAGGCTACC

CAAAACAGTAGGCTCAGATGCTATCACACAAAGCACTTTATCCTTAAGTTCAATTTTTCTAAATTGTAGT

TGGCTGCTTTGGCTTAATAAAAACTTCCAAAAAAGAAAAACGAATGGCCACAGACAGTATGGGTATCTAA

CTATATTATCACAACTTGACCAAGATTGAACTTGCCAATCCTTTGGTTCAAGAGCCAAACAAAATCGTTC

CCTTAAAATATTGCTTCATGGGAACAGTCTTCTTCAAACATCTTTTAGCACAGGCAAGATTCCCATTTAT

ACATTAATTCTGTTCAAGACAATGAGATTGGGCAGAAAAGGCATTGAGTTGGAAGTCAATGGATATGAGT

TTTTATCCCAGTTTTACCACAAATTAGCTGAGCATAACTTCCACAGATGCATTTATCAAGTAGTTTTCAT

GGTCATTGCAATGCCAAAAAACTGTAGCATTTAGAAAATTTAGTTTTCAGACTTGGAAACTATTTAAGGC

ATTTCATATGAAGGGTGTGTCCTTGTGAGAGTTTGCTTATGCAAGATAAGGCTTCTTTCAGCTGCAAGTC

AGGAGCGAACCAAAACTCAAAGCAGCAGCTGCATGAGCTGACTTTATCACATCTTGACAAGAGCTCAGCC

ACTGGAAGTTTTGGCATACAGCGAAACTGAAGCGTACTTATACAATATCACATTTTATTTTTATTGTTTC

TAATAGCATTCCAGGTTAGAAATGTCAATTATTTGGGAAAGCTGAGGGTCTGGTAGATAAAGCATGCAGC

AGAGAGCTAGGAGGCTGGCTATTTCCAGTCGTTATCCTAACATGTCTTGGGCCCCCAAGTCACCCCACCT

CCATGGTACAATGGGAACTGTGGCAGAAGTCCACGCTCTCTCCCCCAACACATGGGGATAAGAGACAAGA

GAGGTGAAATGTTCTGGAACATATCCGATGTTATACAAGTATAAGCTGTGAGATGATCCAAACGCAAATA

TTGAATATTTCATTTTCTAGAAAGTATACCAATTCATTCCACCCTTCTCAAACCTAAATTACAGAATTCA

ATTCAGGTCACACAGATTTACTTTGTACTAAGTACCATAGCAAATGCCATTTCAGTGCCTGAAAACTGAA

AAACATAAATTTAAAGTAGGAGTTTGAGGCCTCACTAATATGACAAAACATACCTTTATATTTTATTTTG

CAGTAATTTGCCACTTAATCATTAAACTCTTATCAATCTGAGAGATTTGCCAACACTTGCCTGCTAGGTG

ACCTAAGCCTCCACATCAATGCATGTTATACTCCCCTTTCTCCATATGTTAGGCCCATGCTATTTCTTTA

TCCCTCCTCCTCTGCATCTTCACCTAAAACTCTGCCCATCCTTCAGGGTTCATCCAGTGATTCATTTGCA

AGCAGGCATGGGGTAAGGTCTTCAGAGTATGTTTCTCAGAGGCCCATGCAGCTAAGAAAATGTGCAGTGT

TGGCACAAGGTCTGTCTATTCCTGGGTAGCCAGATGCTGGACACATCTTTCATAACACCACAAGGTAAAT

ATACTTCACTTGGAGAGAGAGGTGAAATTTTGCAGGTATAGACTGGATGTGTTCCTGCCAGAAGATGTGA

AGGGATTAAGAAACTGACTCTCATCTCCGTATTGCTAGAGCAAAACATAATTTCTCATAGTGGCTATAGT

ATAAGGACACTGAGGGGTAAGAGATATAATCTAAGTAATACAATAAATTAGTGTGGAAAAATCATCAAAA

-continued

TGAAGACTACATGGTTTTTACTAAAATTCTAGCTTTTAGGATGTCCAGGGAGCTCAGGAATTTAGCTGTC

CTTTTTTGTATGTACAATATGCCCCAATGCTTGCTGACTAATGTACTAAAACATTAGAGAAATCTTGCTG

ACAAGATCTCAACCAGTCAGCGAGATCCGGAAGGTGAGACTAATATTGAGGGTCAGCAGAATTAAGTCTC

AGTTCTGCTGCTTACCAGATATGCTGATCTGAGCTAGTCATTTAATTTTTATGAGACCAAATGTCTATCT

GTAAAGTCGGCAATTTGGATTAGATGTGCTGCAAGTGGTTTTCTAGCTTAAATGTACCTTCTGAATTCAA

CAGGACAATACTTAAACTGACCTTTAATCTAGGAATGACACAAGTAGATTTTTGAAAGCTACTTTAGCTA

CAGAAAGCTGAGAGCACCAAAGGCAAAGAGATAAAAATAACAGGAGAGCCTTCCCTTAATCCAGTCCCTA

AGCAGTTTTGGCAAACTAAAGTTTGTTGTTCAATGGTTACGAGTTTGCTTCAATGCTTTCTACCCAGTTT

ACTGAACTAAATAGTATATAGCTATAGTAAAAAGTCCTATTCAAAAACCAGCTTCTCACAGATATTTTGC

AGCTTTGCAGAATTGAATATGTCCACAGACGTCTATTAGCTGGTTAGGGTCTTAGGAATCTAGGAGAGCC

AAGTAGTTGTGTGAGCTGTTGTTATCAAATGTAGTTTTGAACATTCTTGGTGATTTTAAGGGATCATATT

GTGGAAATTTGGTTTCCTTACCTTGAATTTTGAATGAAGCTTTAGAATTTGAGGATGTTTCTTTGGTTTC

TCCTTCCAGGTAAGTGATTTTTTTTTTTTTCAACCAGATGCTGGTTTATTTAATTTGAAGGTATTGATGA

AATTCTTTAAATTGCCCCCATGTGATTCTACTCTGGAATAACTACGAAATTATTTAAAAGTTAATTAATA

CAAGAAAATATGAAAACTCATTTTTATGGGAGCTATTGTTCCTTCAAGATGACACTGTTTTGTAAACTAT

AGACTTCCAGTAACAAGCCTCTGTGCCTTCTTCTTACCACTAAGCATGCATGGGTATTAATTCCTACTGA

AAGACTTATGCTATCTTTTTTCCAGAAATGGAAGAAAAATGAACTATGAAAAAGGTCATTTTATAGGTCA

GCTACCACTATGAGATTGTTGAGGAAATGATATAAAAAACAATTTTTATCAAATTATCTTTAGGGCATTT

ATATGTTTATTTTCTTACTATGTTGACTTAGGTGACTATAAGAAGTTGTATCAGAGCAACTGATTCTGGT

GAATTAAAGCAAGTATTTCTAAGAACATAAGTGGCAACTTTCAGTCTCAAATCAATTTGGCCACCAATCA

GTTTTTGTAAGGGTACAAATAGGACATAACATGCTCAGATGGGACTTGGATAAAGTGTATACAATTTTAC

ATCGAGGAAATTGTGTCAATGTGTTACCTTCAATGTTAGAAATTCCCAAGTTCTGACAATAGTTCAGAGC

CTTGTTAAAAGCCAGAGTGGAGGCATGTAGATCCAGCTGGAAAGAGAGGCATTATGGTCTAACTTAGGAC

AAATTTTAAAGCCAGTGTTAGGGTCTGAGTCCAGCTTTGTAAACTTGAGTACAGTGTTTGATCTCTGGGG

TTTCAGCCTTCACTTCAGAACAAAATTTCCACCAAGTGCTCTTTTACTGTGAGGAGTAGCTGTTGAAGAA

GAAAGAAGTCTACTTATTTGCTAGAGTGTTACAATTGTTTTGATAAAGCTCAAAACTTATCTAAATAAGC

TCTCTCTCCCTAAGCATGTTTTCATTTTTATAAAAAAGTTACATATACTTTGCTTATAAATTTAAAATAC

TTTTCACCTCCTCTGACTTCATTTAAAATTAAAATAATTAAAGTGCCAATTTTAAGAGATGTTAGCTCCC

ATTATTGGTTCTTTGCCATATTCTTTTGACAACCTGCTGTAATTTTCTGCCCCCTTTAAAGCCTCAGGCT

ATAGGCCTTCTCCACCAAAGGAATATTAAGAAGTGATAAGGACCTTCTGTGAGCAGAAGTGGCTTGTTTG

CAAAGGGACTGCTTATCTTGGCCACTCTTGAACACAAGATGGGACCCTCTACTGCAAAGCTCTGGCATGT

TTTTTTTTCCCCTAAGTTATCCTCCATACTACTGACAGTGATTTTCCCTAAATAAAAAACTGCTTCAAAC

CATTCATTGTCTTTCCACTGCCTTAAAGATAAAGTCCAAATTCTAGAACATGGCCCACAGCATTTGGTGC

CTCACCACCTCTTCAGCCTCTCAGTTGCTGTTCACCCATTTCTCTATTCCTCTCCTTCTCACACCTTGTG

CTGCAGCCACATAGATAACCTGCAGTTTTTGTAACGTGCAATGATGTCTCAAATTCCAAGGCATTGCTGG

TACCACACAGCCTGCCTGGTAAAATCCTAGACTTCTTTCAAGATAAATTCAAAGACACCTCCATGAGGTC

TTTCTACCTCTCCAAGTAGAGTTGACCGCTGTCTCCTTTGTGTCCCCACTTCCACCACCATCCTAAAATA

CTTATTATACTTAGATTAATAATTGTCGCTCTTACTGCACTGGAATTACCCTGAAAGGAAAGGCCATGTA

TTATTTATCATTGTCTTCCTAGTACATAGCCCACAGCCTATACCTCCCACCCCAAAAAAAACCTTTTGTA

AATAATTGAACAAATTAAGAAACACCCAAGGCCCCCAGTAAACATCAAGGCCTAAGGAATGCATATCTGG

ATTCTAAATAATCATAAGGTTTTACAACACCATGTTAAGCACCAGGGACTTCAGAGAGCTTTTAGTCTAA

-continued

ATCTTATTAGAGAGGCCAGCGAAGACCTCCCAAAGGAAGTGGCATTGAACTGAGACTTGAAAAGCCAGTA
GTTAGGCAAAGATAGGGAGGGAAATATTTCAGACGAAGGGAGGAGATGGCACAAGATTTAGGACACGGAA
AAGGGTATGGTGCAGTCATAGAGAAAACAGATGTGCAGAATGGCTGGAGCCCCAAGAGGGAAGGGAAGGG
CGAAGCAATGAAGATGTGAGGCAAGCAGGACTGGACCATGCAGAGTCTTGCAGATGTTCACAAAGAAAAT
TGCAGCAGGTAGTCCCTAACATCGTGCTGAACAGTTAGGCAACTTGGAGGAATATGTATATTTGTACTCA
TAGTCAAAACCACTAGATGGCATTTACAGACTACGTTTTGTGTATTTTTATTTTTTACTTTTTGTTTTTT
TTTTCTTATGTTAGCAAAAGTATGCTCGCTATTGAAATGTTGAAAATATTTCATTGGTCTTAAAATGATG
CTTATTTTTCCAGATGCTTGCATTCATTCTGCATGTGCTATTTTGTCATGTGGTTTGCTTAATTTATTAA
ACAATTGTATTAATTAAATATATTAATTATAAATTGATTAATTTATAATTAATTATGTGTTATAATTAAG
TTAAATTTATTAATTACTTAAATTATTATATTCACATTCAGATGCAATCTGAAAACCCATTTGTTCTCAC
ACTGCTATAAAGAAATAACTGATACTGGGTAATTTATAAAGAAAAGAGGTTCCATTTGACCCAGCCATCC
CATTACTGGGTATATACCCAAAGGACTATAAATCATGCTGCTATAAAGACACATGGACGTGTATGTTTAT
TGCGGCACTATTCATAATATCAAAGACTTGGAACCAATCCAAATGTCCAACAATGATAGACTGGATTAAG
AAAATGTGGCAAATATACACCATGGAATACTATGCAGCCATAAAAAATGATGAGTTCATGTCCTTTGTAG
GAACAGGGATGAAATTGGAAATCATCATTCTCAGTAAACTGTCGCAAGAACAAAAAACCAAACACCGCAT
ATTCTCACTCATAGGTGGGAATTGAACAGTGAGAACACATGGACACAGGAAGGGGAACATCACACTCTGG
AGACTGTTGTGGGGTGGGGGGAGGGGGGAGGGATAGCATTAGGAGATATACCTAATGCTAAATGACGAGT
TAATGGGTGCAGCACACCAGCATGGCACATGTATACATATGTAACTAACCTGCACATTGTGCACAGGTAC
CCAAAAACTTAAAGTATAATAATAATAAAATAAAATAAAATAAAATAAAATAAAATAAAATAAAATAAAA
TAAAATAAAAGAGGTTTAATTGCCTCATGGTTCTGCAGGCTATACAAGAAGCATAGTGCTTCTGCTTCTG
GGGAGGCCTCAGGAAACAATCATGGCAAAAGACGAAGGGAAAGTAGGCACGTCTTACATGGTTGGAACAA
GAGCAAGAGAGAGAGTGGGGAGAGAGAGCCTTGGAGCAGGAGCAAGAGAGAGTGGGGAGGTGCCACACAC
TTTTAAACAACCAGATCTTATGAGAAATCACTATCTCCCAGACAGCATCAAGGGGGATGATGTTAAGCAA
TGAGAAACCAGCCCCATGATTCAATTACCACCCACCAGTCCCCACTTCCAACATTGGGGATTACATTTCC
CCATGAGATTTGGATGATGCCACAGATCCAAACCATACCACTCACCTAATTCTTTCTACGTAAGAATTTG
TCCAAGCATTTATAACAATTAGCATTTCATTTAACATCTTTTATGAATAAAGCACTATTCTCATGCTGAG
AAGATTCAAAATAATGGGAAATTGAAGTCCTAGGAACAAGTTTTATGTTTCAGAAGAGCCCATTTGGTAT
CCACAGGGCTAAGAAATGTGCACCCTAAATGTAAGTGGATTACACTGAACTGAAAGGTGTAAAGAAGGAG
TGGAAGATTAAAGGGAGAAGCTTGGAGAGGATGAAAGTTAGAAATGGAAGTGACGAGCACACCTGAGTGA
AGGATGAGAGCTCCAGCTGCATTTTCCAGTTGTATTCCCATGTTGCTGAGCCAAAGGCTGATCTCAAGTT
TATTGTTACATGCCCATTTAAGGCTTCTGGCCATTAACACTTTTGATTTTTTTTGGCTTGTTGTTTTACT
AGCTATTTTCACAACACTTTCATAGCTAAACCTATTTTACTCAGATTGTATGCCTTTTCAAAAATACAAT
AGAAGGTCCATATTCCATTATCTAGAAATAAGCCAAAGCTCATATCTAACATTTATTAAGAGAGATGGAT
TATTTTTGTTCATTAGTTATCTTTATAAATAATTTTTACGTACTTTAGTTGACTCATAAAGATGTTTCTT
TCTGTAATTTTAATCTTAATATTTGTTGAACTTCAAAATCCCTATCACCAGGTTATTGTTTAAAAGCATT
GGTTTTTATATTATCTTAAAAGCCATTATACCTGAGTGCTGAACAACTTAGAAACATTCAGTAATTGTTT
TGCATGCTATTTAGTGAATTCATATGGCAATCGTTTATACATACATGATGGAATCAGGTGGCAGGCCAAG
TTAAAGAGCAAGGCCAGAAAAGAACTTAAAAGAGAAGAGAAAAAATAGACAGTTTAGGAACAATAGATCA
TGTCTTCTCCATGATTTGGAGGTAAACTGATTACCTATCAGCTGATAAATAGAGGAAGGTTTTAGAAGTC
TTCAGTTGGGTAGACTAATGAGAGGTGTCAGAGAAGATGTTTTCTGTTGTTTGTGGGTTCTCCAGGAAAC

-continued

TTTGAGCATTCAGCTGAGGGGCCAAGTTGGCTGCCTCTGAGAAGAAGCCCTTCCACCTCCACTCCATTGC

ACTTGGGTGCCATTCCCCTCAGTTGAATATCTCCAAGAGATGAGCAAATGTACATCTACAGAGTTCAGGG

TACTGACTTTTATCATAATGATTTATAACTCTCAGAAGAGTGAAAAACACATGAATGCACAGAATAGGAG

ATTGAAATATAAACCACAGAACATTCATACAATGGAATACTCTGCAGTCATAAAAATCTTCTCATAGAAG

AATATTTGACAGCATAGGGATATCTGTGGCATATTAAGTAGAAAGTCAGACTTGTAAACATTATATACAT

ATTCACGTATATTTAAACACCATGATCCCATATTTAGATATAACAACTAAAAGTTCAGATGGCTATATAT

CAAAATGTGTCAAATGTTCAACCTTGCATAGGCTGACTGTAGATGAATTTTATATTATTCTTTGTGCTTT

CTTGTAGTTCCCAAATTTTCTTTACTGAATCTATATTACTTTTGCAATTTAAAGAATTTAATTTATAAAA

TTTTATAAAATAACTTATAAATTTGAAATGTATTGCATTTAAGAATAAAAAGTGTTTAATTACAAAAATA

ATTCACAATTTATTTAATGAGATTTTAAAAGGATATATGTGAGTCTACATTCTGATTTCATGTTTGCATG

CATGGTTTTTTTTTTCTTTTGAGACAGAGTCTCGCTCTGTCGCCCAGGCTGGAGTGCAGTGGCGTGATCT

CGGCTCACTGCAAGCTTTGCCTCCTGGGTTCACACAATGTAATAGTGTTTTATTATTGTTTCCATTTTTA

TTGAAGAAGTAAGATTGTCCCTAGCAGATGGAGACACTGAGATATGGGACAGAAGTTTTGTTCTATATAA

TTATTATGCGCTTCCACCTTTCTTAGCATAGACAGTTTCCAAAATGCAACTTCAAGTTACCCCTTTATAA

GCATAATAACAATAATACCCAACATATATGTAATGCTCTTTATGTGCCAAGTACTATACTAACACATGCA

CATTACATACACACACACCACATACACACACATATTTAAACTAATTTCGTTCTCACAATGACATTTTGAG

GCAAGTATTATTATTGTACAGATGAGAAAACCAAGGCACGCTTTATCTGTAAACCTCTGCTATGCAGAAA

TTCTGGAGGGGCTTCTGGCCCCTTAATTTTAAAATAAGGCCAATAATACAATACTTACCACATAGCAATT

CTCTAAACATTATGTAAGATATATACCAAAGCGCTTAGCTCAGGGACTGGAGGGATGTGAGGGAATTTGT

CTTTTGCAATATGCTTTATGGTCCGCTCAGTCACCTCGTTCTTAATCCCTTTCTCAACTTCTATTTTATA

CAGCAATTGTGAGCATATCAGCATCAAGTACCACTGGTGTGGCAATGCACACTTCAACCTCTTCTTCAGT

CACAAAGAGTTACATCTCATCACAGACAAATGGTTTGTTTTCATTTTTATTTTTAAATTGTGGCTCCGAA

ATCATTTTTGTGATGTAACCCATTTTAGGGGACCTGTCACTGCAGAGAAACTGACAAACACTGAGAAATG

CGAGCTAAGTAGACACAGCCTACTAAGTAGACACAATTCCTACTATGGAGGAATTCTTGCCTCTGAAATA

TCTCACAGAAATAATACTGTGAGTTAAAGAAATTAAAACAATGTGGCAAAGCACAGAAATGATGCACGTG

ACCATGAAATAGTGGGCCAGATAAAGGGGACCTAATAGTGCGGTGGTGCGGAGGGTCTGTGGGCAAACTG

AGTTCAGCTCAGACCCGGGCTCAGCTCTATGCCAGCTGCTGACCCAGGGTGAGTTGCCCTGCAGGGTTTC

TATCCCATTAATTTTAAAATGGGGCCAATAACACAGTACTTATCTCACAGCATTTCTCTAAAGGCTAAAT

AAGAAGATGTATCTAAAAGTTATTAGCTCAGAGCCTCACACATTCTCAGTGACTGATAAACAATAAGCAA

AGCTGGGTGCTGAGATAAGAGTAATCTGGTGGCAGTCTCTCTTGTTAGTTTTCAGGGGAGAAGAAGAAAT

TCTGGAGCCGCTGCTGGGAGGGATGTGGGAGAGTTTGTCTTTCATAATACGCTCTATGTCCACGCAGTCA

CCTCATTCTTGTGCCCTTTCTCAACTTCTCTTATATGCAGATACGCACAAACGGGACACATATGCAGCCA

CTCCTAGAGCTCATGAAGTTTCAGAAATTTCTGTTAGAACTGTTTACCCTCCAGAAGAGGAAACCGGTAT

GTTCTTAGTTTTAAATAGTTGCTCTGGAGTCATTGTTGTGATTGAACTCTATTTACACGAGCTGTAACTC

ATGACAGTTCTCAAGCTTTCGTGACAGAAAACCCATCTCTTTTACTCCAAAGCCCATATAGCACCCACAA

CTATTAACTGTGACCAAGAAAGAGAAGGCAAGCCCCAATTAACCTTTGTACGTAAAGCCTAAAGAATGAA

AAAATATACCTGAATCCTCAATCATCAAACAGCATAGTATATACTAAGTAATTTGTAATAATTAAACTCT

AGAAAATTGTGTGGCTTCGGTAGTAAGAGAGCTTCATGATGTAAAATGGCAAGTGGAGACAGAGACAAAA

GTAGGATGTGGACTGAGAGGGAAGGTTAGCACAGGTGGAACAGTAAGGCAACCATACTATCAATTGCTGC

TGACATAGAATCCAGAGAGACTATTGGCAAAAGCTCAAATGAGACACAGTAACAGTTTAGATTCAGACAG

TGGCTGTGGCATAAATCAGAAAATTGATAGTCGCATGATCCCTCTTTGCATGGGACTGGCATCTGTGTGG

-continued

AGTAATGGTTCCATATGCCTCCTTTCTTCTCCTTATTTTTAAATTTTTTAAAAATGCATTGCTTCTTGTG

GAAGTCAATAAGTGATTCTTCCAATACTTTCTCATTCCTTCCCCCTCAGTTATGAGACAATTTGCTTATT

TCTCATCCATGAATACTTGTTGGGTCATTAAAAGTAGATACTGAAATTACTAATGGTACGACTGACATAT

TACCTCATAAATGTTACTAGCTAGATGTTGAAAGTTGACCAACAACTCTCAAAATATGATTAAGAAAAGG

AAACCCACAGAACAGTTTGATTCCAAAATGATTTTTTTCTTTGCACATGCCTTACTTATTTGGACTTACA

TTGAAATTTTGCTTTATAGGAGAAAGGGTACAACTTGCCCATCATTTCTCTGAACCAGGTATGTTAATAT

TTGACAAAGAATAAAAGTCATTCCATTTTAAACTATCCATTGCTTGTTTCAAATGCCTAAGAAAATGTGT

CTATCTTAGAAGAGCATATGTTGTTAACTTTATTCACACAAAATTGTAAAGGCAAAGAAAATATTCTCTT

TTTAAAATTAAAATAGGCATTTCTTATTTTTAAAAACATTTTGGGGGCCAGGGGCCGTGGCTCATGCCTA

TAATCCCAGAACTTTGGGAGGCTGAGCCTGGCTAATCGCTTGAGCCCAGGAATTTGAGAACAGCCTGGGC

AATATGGCGAAATCCATCTCTACAAAAAATACAAAAATTAGCTGGCATGGGGCACGCACCTGTAGTCTCA

GCTACTTGGGAGGCTGGCTGAGGTGGGAGGATCGGATCCATTGCCTGAGTCTGGGAGTTTAAGGCTGCAG

TGAGCTATGACTGTGCCACTGTACTCTAGCCTTGGTAAGACCCTGTCTCAAAAACAAATACATAAGTAAA

TAAAAATAAATAAAAACATTTTGGAAATAGAAATACATAATTTGGTAATAGTTTTTCTCTTAAGTTAGAT

GTTTTACCTTTCTAACCAAGCCTGAGTACTTGAAAAAAGCCTCATAAGAGCTTATAAAACAAATGAACTT

CCCTCATATAAAAAGCAAGGCATTTAAAATCATCTAATTAACTGGTACTGTATTTCAAGGGTAAATCTCA

GCCTTGATTCATTTTTGGCCCAATGCAACCACTTAGGGACCATCTTGACAACCTCTGCTGAAGGGACATC

CCTTCCCCTCACTTGAGTATCACTGTGTGTGCTCATTTGCTATTCTGCATTCCAACCCTCCCTTCACACT

TGGCTGTGTCCACGGCTCACAGGGTAAAAAGCACATCATAGAACTTCATCACTATCGCATACATTCAAGC

TAAGTGGTCAAGAAGGCTGGGCAACACCAGCAAGAGGAAATGCTACTTTTACTTTTTATCAACAATAGGG

CTTTTAAATATTAATTAGGCAAATAAATGAGCCATTTTACCTTTATGTCTAGCCTTCCATTCTATTTACT

TCAACTGGAAGCACTACAAATATGCTATAAATATGGAAATATCTCTTAATTGATTTCAATTGTTTCATTC

CCAACATATAAATGACTCAACAAGCATTTTTAGTGACTACATTGGAGACTATGCATAAGAATACTATGGA

AGGAATAAAGCTTAGAACATAGATGACCTGCATTATAATTATAATTCTACTTTTAACTAGTTGTCTGACC

AAGGCTAAGTTAACCTTATTCAGCTTCTTTTCTTCATTTGTAAACTGTTTATACCAGTTTCTTTCCAAAA

TTATGATTCTATGATCTGTTCAATGCTCTTTTATACATTAAGACATTATTTTCTCTCATAACTTCCAAAC

TATGGGAGAATTTGTGGTTTTTTCCCCATATCTGAGGAGAACGTCCACTGAGTTCTTATCTACAGTTACA

CTAGTGAAGAACGCTGGGTCTGGAATCAGAAGCTTCAGGTCTTAGTTCTGTCATCAACTATTTTGCGACC

TTGGACAAAAGACTTGATCACTCACAGTCCCAGTTTCCCACAAGGTTACTGTAAAGCACACAATTTAAAA

AAAGACAAAATCTACATAATAGTATATTAATTGTGCTTTCTATTAAAAGGCAAGGTGATGGTATGCTGAT

GTTATCTGTCTTATTTTTCAGTTGCTATATGGTCATTTATTTCAGACTTTCATAATTTTGCTGCTCTCTT

TATCTCCTGTAGAGATAACACTCATTATTTTTGGGGTGATGGCTGGTGTTATTGGAACGATCCTCTTAAT

TTCTTACGGTATTCGCCGACTGATAAAGGTGAGAATTCAGTTTTTAATTTTGCTGTAAATACCAATGTGA

ACAGCTCTAAGAGGGTTTATTCCTCTGAGTTCAGTTAAACTCAAAAGAGAAACAGAACTGCATAAAATTC

CATATTTTTCAACTGGACACATAGAAGTCACTGTGTTTCTCTAGCAGAATTTTTCTTTGCATTTGCCCAA

TTAAAGGGAACCTCTAAATATAAATCTGTCCCCCATTTTCCCAATGAAAGATCTCCCTAAGTTTTTGTCT

AACTTGCTGTCACATATTTTGATGGATATTGAGGAAATATTAAGATTCTACTTATAGTATTTACCCTATT

AGTGTATAAAATATTTAAAATAATATATTTACATATGTTTAAAACTTTGAGGGAAGCCAAGGCAGGAGGA

TTGCTTGAGCTCAGGAGTTTGAGACCAGCCTGAGCAAAAAGGTGAAACCTAGTCTATACAAAAAATATGA

AAATTAGAAAGGCGTGGTGGTGCACATGTGTAGTATCAGCTACTCAGGGGGCTGAAGTGGGAGGATTGCT

-continued

TGAGCCTGGGAAATCAAGGCTGCAGTGAGCTGTGATCATGCTACTGCACTCCAGCCTGGGCAACAGAGTG

AGACCCTGTCTCAATAATTATATAAATAAATAAATAAAAATAAACAAAATAAAACTTTTGCCTTTCTTAA

TTCTCACATATTCTGAAACAGATTTTTCAAATTTCCACCCATGAATTCTTAACATCAGTGATTTTTTTTG

AATCATTAATGCTTTTTTTAATTTTTTTTTTTTTTTTTGAGACAAGAGTTTCCCTCTGTCACCCAGGCTC

GAGTGCAAAGTGGTGCAATCTCTGCTCACTGCAGCCTCTGCCTCCCTGGTTTAAGTGATTCTCGTGCTTC

AGCCTCCGCAGTAGTTGGGACTACAGGTGCGGGACACCATGCCTGACTAATTTTTGTATTTTTTTAATAG

CAGAGATGGGGTTTCGCTGTGTTGGCCAGGCTGGTTTCAAACTCCTGACCTCAAGTGATCCATCTGCCCT

TGGCCTCCAAAGTGCTGGGATTACAAGCATGAGCCACCACGCCCAGCCCACTAATGCTATTTTTACATCC

ATACAACACAGCTTATCGAAGTGCATAACTTTTGCTATCACTTTCTATTCACGATATTTAAGACATAATA

TGTGTGTGTGTATTTATGATGCTGTCACTGTCTCTGTAATCCTAGATCAGAAGTACTTAGTCACATGAGA

TTGGTACAGTTGTGTTTTCATTCATCCTCTATTCTTAATCTCTCTTTGTGATTTTTGAGACCATAACCAC

TATATAATTCTTTTAAAAAGGCTGAGAGGTGTGACAGCACTGCAATTGTGGGGCCATCAGAAGATATGAT

AGTAATATCTACATTAAGTTCCTTTGCCTCTTTTCTTTTTTAACTACTTCTAACAGTTAACTTCTACCAT

CATCCAATCCTATAATTGATTTTCAGTATTCCATGTAAATATATCTTCCTTAAATAATACTTTTTGTTAA

TCAAAGAAAAGTAACTGAAAATGCCTACTCTTGTGTGAGATATTTTGTAAGGACTTTAATATAAGATAGC

TTTTTTTGCCTGGAGTATAAAAGAGAAAAGTCATCTTCTTACATGGGCATATATGGCAAAGTGGGTTGTC

TTCTCTCTTCGTCAATGTTCTAAAACCTGAAAAAGCCAAGGAAATATTTAGTTGGCAAAGTTCAGAGAAT

TTTCTAAGTGTATATGGATGAATTTTGTCCTGGTCAACATGATGCAGAGATCACACACTTTATTTTTATT

TTTATTTTCACTTTCACTATTTATTACAGCAGGGAAATATGTAAGTATCAGTGTTTGAGGTGATATTTCT

CCTACTGAAATACCAAATACTATAGAGGAACACAAATACAAGTTTAAATCAATGCTTATACCAGTAACTA

GTAACAACAACAATAACAAAATCTCTGCAAAGGGGATTTCAACCAAAAGAAAAAAAATTTTAGAAAAAAA

TATTTTTAAGCTGAAGCATTTTACTTTTTACTGTCTTAAGACTAGAAAATTGTGTTATTAATATTTTATG

GTATTTCTTCATAGAAAAGCCCATCTGATGTAAAACCTCTCCCCTCACCTGACACAGACGTGCCTTTAAG

TTCTGTTGAAATAGAAAATCCAGGTTGGTGTTAATATTTGCAGTTCCTTTTGCCTTTTAGGAAAAAAAAA

TCAAACCAGTGAGTTACTTCTTTCTGATTTGAGGGAGGAGGGAACCAGTTATGATTCATTTCTATTCTAT

CTCATTAATTCTACTTCTTTGACTTTTTAGAAATGTCTGCAGCATAGTGAGATTCTCCTTTGGACACAAA

GTGTTTTGTTTTGTTTTGTTTTTTTAACAAAAAAAAAAAAACTCAATCAAATAGTAAAAGCAAAAGAGAA

AACCAAGTGTACTTCGTATTTCCCAAACTGCAAAGTTATGTGTATAGGAGACTCTATGGTCAGTATGGTG

TAGCATAGTGAATTAGCCCCAGATCTGAAATCAGACTTGGATTTGAATCCATGCTCCAACACCTATTAGC

TGTGTAACCCTGAGCAAGCTACTAAACCTCTTTTAATATGGGGATAATGATAGTATCAACCTCACAAAGT

TTAATGAGAATTAAATGAGCTACAACCGGTAAAGCATTTAAAACCATTTGTGGCCATCATAAGTCCTCAT

GCCTGTTAGCTGTTATCAATATAGCACTGACATCAATGCTATATCAATATAGCATGTTATCAATATAGTG

TCATTCCCAAATGACCTCCTGTGCACACTGGCAAGCCATCTGGCACATGCTTTCATCTCCACTCCCAGGT

GCTAAGCAGATACAAAACATGTGAAAGGCCATGGATATATTTTGTTTATCCAGAACAGTATTAAACCACA

TAGTGCTTTTTGAAAAGAATATTTATTGTCAACCTTTAAAAGTCGGAAATTGTTACATTTTAAAAATCAA

GTATTGCTATTCCTCTGGGGAAAAATGTAAACTCCCAAAATGCTGAGAGCCTTCATACCAGCATGAGACC

AATTCCTAAGAGCTGAGTAGTGGCTGCTACCTGTACTGTCTGTCTAAATCCCTAGCCAATTGCATTTGTT

TTATTCACCGTGGCCCCTGGTATGAACTCACTAAGAAAGCATATAGTTTCTATTAAACTTTGCCTGAAGC

ATAAACCCAAATGACATCTATTTTGGGAGATAGTTACTAAGAACAAGTCTCTGGAATGAGCTTTATTTCT

CAAGCAAAAGAGATTTCATTCTGCCTTCTACAAAATCAACTGATTTTACTCCCATAATTTTCAGAAATCA

TGACAGATCAGAGGTCCTGTATGCTTCTGGATTTCGATTTTAACCCTGGGCCAGTCTAGGTTTTCTAGAC

-continued

TTTAGAGTCACAGAACACAGAGTTTTCAAGATCCATCACAGCTACACAGGTTATATGCAGGATTTGCCAC

ATCACATTATCATGTGAATTCTTAAAGCTTAAGAGTAATTGTTACATAAGTTTATAATCCTAAGACATTC

CTGCTATGTGGAAATGAATGGCATAGATATGATTCTCAGCTAAAAGGATTAATAAAATCCAATCTGCAGA

TACTTGAAACAACGGAAGTTTTTGAGTCATATGCCAGATTCACTTCATTTACTAAGGTTATCTTGTTATT

GGACTGGCAGCTGGAACAAGTATCTGTAAAATATTCATTTTATCTGCATTCTGCCTTGTTCCACAAAAAA

GTCTTGATGTAGTTTTTCAAGTGGAGCAATTACAACCTAAAGCCTATTTTTCGAACTGAAATTTATATAC

ATTTTTAGCTACTTATTTATTCTAGAGACAAATTTATTGTTTAGAGTTTCCCCTGCCATTTTTTTCATAC

AATTTTAAGCATCTCAAATGTTTGGCACAATTTAATACGCCACAGTGCATCAAGATGTCCTTGTAGTTTA

ATTCAGTTAAGTGCAACAAACATTTGCTAAATGCATACAGTGGGGTAGGCACCACACTCACATTAGATAT

ACCAATATGAGTCTTCGTCCTTTAGAAGCTGAGAGACTAATGGAAAAAACAGAATGTCATTGCAGTGAAC

AAGTTCTACAGTAGTGGAGGCAATAGCTCCACTTGTCCCAGAGACTGAGACAGGTATCAAAGGCTTCTGA

AGATGAAATCACCTGGGATTAGCCTTAAAAGACAGATAGATATTAGCTAGGGCAGGGTAGTTTTAGCAGA

AGGGCAGCCTGAGTGAGTAAAAGCATGGAAGACAGAATATGTTTACTTAAAGAATTGTATGCATTTCCAC

ATTAGCAGGATTGCTGCTTTGGTTCTCTGTTCACATCTCAAATATGTGTAATGGCAGTGGAAAGTCAGAA

GAACCAAACTTTAGGCTCACTTTATTTCCCCACATTTGTGCAAGTGAAGTTATTAAATGTCTTAGTATGT

TAGTGAGACAAGTTATGAATTCTGACTGCACCTCACAGAAAACATAGGAAAACACATTATTAAAGATTAT

TTAAAATGCTTTATTTCTACTTTTATAGAATATGGCTCTAAATTAGTTTATAAGCCAAAGGCATAAGAGG

TTAAAATGACAGTACCATCTCAACAAGAACTAATGATGTAAAGGAGTAATTAGAGTATAAATTGTTTTAA

CCTTCTAAAAGTGCACATGATCTGTGATTGGTGAAAAATGAGAATAAGCGAATCTGAGTCAGCTGGCCAC

TGTGGCATGCATATGTGACCCACTAGCCTATTTCCCACAGGAGAATGTTTGAGATGCACAGTTCCTGTGG

TGCCCAAATAGAAGAAGGCTGGAAAAGCTCTGCTTCTGGAAGAGCAAGGGCTCCCCTCTCCCTTTCATGC

AGTTTCTAGGAGCAACATAAATTCAACCTTCCAACCAGGAAAAGTGGAGCATCGGGTTTACTGGAGAAAA

CTAGCCCAGTGCCCTTCTTTTACACCCTAGAACCAGAGAGGAACTTGGCCATAAGCTTTTGTGCAGACTT

CTCCTTGGGGGAAAAAAAAAGTCATTATTTAAAAAGACATGACAGACTTAGACACATGCCTTAAATTTTA

ACATGCATATGTGATTCAACTTATCATTTACTGGCTTCACATTATATTTTGCCTCTATACAAGTTTGGCT

GTTTGTTTCTTATCTCTGTAGAAACTAGGAGCAGAGCAATTATATTTATTCTTTACCTAAGGCTTTTAGA

ATAGATATTCTAAGAAATTCTGTATTTTTCTTTACACAAAACTTGACAATAGAGCTAATATGTAAGGAGA

GTCCTTTCGTTTCCTACTAATTACATTCAAGAACAACTCTGCAAGAATGTAGAATCCTAAAATGTATACT

GTGCATTAATTTCCTGTTGTGTTTAAACATAACTATGTCTCATATTTCGGTCTTGTATTTTTTTTACTAT

AATCCTTCTAGAGACAAGTGATCAATGAGAATCTGTTCACCAAACCAAATGTGGAAAGAACACAAAGAAG

ACATAAGACTTCAGTCAAGTGAAAAATTAACATGTGGACTGGACACTCCAATAAATTATATACCTGCCTA

AGTTGTACAATTTCAGAATGCAATTTTCATTATAATGAGTTCCAGTGACTCAATGATGGGGAAAAAAATC

TCTGCTCATTAATATTTCAAGATAAAGAACAAATGTTTCCTTGAATGCTTGCTTTTGTGTGTTAGCATAA

TTTTTAGAATTGTTTGAGAATTCTGATCCAAAACTTTAGTTGAATTCATCTACGTTTGTTTAATATTAAC

TTAACCTATTCTATTGTATTATAATGATGATTCTGTCAAATGAAAGGCTTGAAATACCTAGATGAAGTTT

AGATTTTCTTCCTATTGTAAACTTTTGAGTCTGGTTTCATTGTTTTAAATAAATTAAGGGGACACTAAAG

TCCTATCATTCATTTCCTTCATTGCTGAACAGGCAAGATATAATATTACATGAATGATTACTATATTTTG

TTCACACTAATAAAGCTTATGCTCAGAAATGCCATACACACACACAAACACACACATTTATCATTTAATG

CATAAATCAACACAAAAGGTTTTCCCATTAATATGAAATATTACATATATATAAGTGCCATATTTAAAAT

AATTTGTCTAACAGTAGAACTATGTCGGAGCACTCACTGAAGCTTGCATTCCACTGAAAGAGTTATTTGT

-continued

```
GTAAGTAGAGTATCCGGAGAAGGAAAAGAACTTACGACCTTTCTTTATAACAGAAACTCAACTCTAAATT
CAACAAGATGTGCAAACCGGACATGCAGGTGAATATTTTAATAGGTTACTATAAGGTTCTCAATTAAATT
CTTTAATCTGTCCAGTCCCAGTTTCTCTTATTAATAAAACTTTGGAAATTGCTTTAAACCATTTAAAGGA
AATTTCTAGATATAGAAACTAAGGACTGTGACTATACAGCTGTCACTCATTTGTAGTAAAACTTAAAAAG
CAAAAACAAAAAACAAAAAAGACCTTCCTGTGATACTTTATTTCCGAACTAATAAAAATCTATATGACTT
TTTATTATTGTGTGATAACCAAGTAAATGTTTTCTATTTTGCATATTTTCAGGCATGGTAACAGAAATTT
ACCTTTTAATAAATTAAAAAATCTAAATTTTAACCTACTTGTATGTTCGGAGAGTGTTTTTGTACTATAT
TGACTACTTAAAATAGAGAATGAGACTAAGAAGGGAACATTTCTGTTGATACATGTTTTTTAAAAGAAAT
TTTAAGAGCATTATTAGGTTAATTTTAATCCAATTAATGACCCAAATGCCAAGGTAATTTTAAATTTACA
TTTTTAATAAAAGCAACATGTTGAAACAAGAGAGGGTGAGATTAACCTTTTTGCTAAAGTAATTTACAAG
TCAAAGACAGGAAGAGATCAGAGTGAATGTGCCTTCTTAACCAGAGCTACAGAATTTAGTGAATAATTAA
AGTACAAACTGCTTTGACCTCCTTGAACTTTTCCAAGCAATTTCTCTGTACTTCTATATATGAATGTCTT
AGCCAATTTTCTGCTACTATAACAGAATACGACAGACTGGGTAATTTAAAAAGAAAAGAAATTTATTTTC
TTCCTAGTTCTGGAGGCTGGGAAGGCGAAGGGCATGGCACTGACATCTGCCTTGTAACTGATGAGAACCT
TCTTACTGCATGATAACAAAGCAGCAAGGCAAGCAAAAGCGTAAGATGAAGAGAGAGGAAATGAAGCCAA
ACACATCCTTTCATCAGAAGCCCATTCCCTCTATAAGGCGTTACTACATTTATGAGAATGGAGTCCTCAT
GACCTAATCGTGACCTTAAAGGCCCCTCCCAACACTGTTACAATGGCAATTAAATTTCAACAAAGGTTCC
AGAGGTGACATTCGAATCAGCAATGAAATTTTCATAGTTAAATTTGGTATTCGTGGGGGAAGAAATGACC
ATTTCCCTTGTATTTTTATAATTAAATCAGCAAAATATTGTAATAAAGAAATCTTTCCTGTGAAGATACC
ATGACCCC
```

Enhancer elements use m the nucleic acids described herein can be single instances of an enhancer element sequence, or concatentations or repeats of one or more individual unique enhancer element sequences. Concatentations and repeats can comprise 2, 3, 4, 5, or more instances of a single sequence, or a collection of 2, 3, 4, 5 or more distinguishable enhancer element sequences (e.g., different elements from one gene or different elements from different genes).

In some embodiments of any of the aspects, the hematopoietic enhancer element is located at least about 5 kb from the boundary of the GATA-1 gene's open reading frame, e.g., at least about 5 kb, at least about 6 kb, at least about 7 kb, at least about 8 kb, at least about 9 kb, at least about 10 kb or further from the boundary of the GATA-1 gene's open reading frame. In some embodiments of any of the aspects, the hematopoietic enhancer element sequence is located at least 5 kb from the boundary of the GATA-1 gene's open reading frame, e.g., at least 5 kb, at least 6 kb, at least 7 kb, at least 8 kb, at least 9 kb, at least 10 kb or further from the boundary of the GATA-1 gene's open reading frame. In some embodiments of any of the aspects, the hematopoietic enhancer element sequence is located at about 5 kb from the boundary of the GATA-1 gene's open reading frame, e.g., at about 5 kb, at about 6 kb, at about 7 kb, at about 8 kb, at about 9 kb, or at about 10 kb from the boundary of the GATA-1 gene's open reading frame. In some embodiments of any of the aspects, the hematopoietic enhancer element sequence can be in intergenic sequence or in the sequence of an intervening gene. In some embodiments of any of the aspects described herein, the target sequence can be identified within from the sequence which is about 500 bp to about 10 kb from the end of the open reading frame, e.g., about 1 kb to about 9 kb, about 2 kb to about 8 kb, about 3 kb to about 7 kb, or about 4 kb to about 6 kb from the open reading frame. In some embodiments of any of the aspects described herein, the hematopoietic enhancer element sequence can be located within the sequence which is 500 bp to 10 kb from the end of the open reading frame, e.g., 1 kb to 9 kb, 2 kb to 8 kb, 3 kb to 7 kb, or 4 kb to 6 kb from the open reading frame.

In some embodiments of any of the aspects, the heterologous regulatory sequence is a GATA1 hematopoietic enhancer minigene (G1HEM). The G1HEM can permit lineage-specific expression of GATA1 specifically in early erythroid progenitors but not in hematopoietic stem cells, e.g., as a gene therapeutic approach for the treatment of Diamond-Blackfan anemia. GATA1 hematopoietic enhancer minigene (G1HEM) comprises a concatenation of 4 distinct regulatory elements to achieve lineage-specific expression of GATA1 specifically in early erythroid progenitors. G1HEM elements as disclosed herein include a −3 kb hematopoietic enhancer, an upstream double GATA motif, an upstream CACCC box, and a segment of the first intron of GATA1. Indeed, the 979 nucleotides present in this minigene are sufficient to drive Gata1 cDNA appropriately to rescue a Gata1 knockout mouse and allow for ostensibly normal erythropoiesis.

In some embodiments of any of the aspects, the GATA1 hematopoietic enhancer minigene (G1HEM) comprises the following nucleic acid sequence (SEQ ID NO: 13):

```
ACCGGTGGCGCGCCGATCCAAGGAAGAGAGGACATTAGCATGGGTCTCAA
ATGGAAGCCTGACAGAGAAGACGCTTCAACCCGGACACCCCACCCCCGCC
TGCAATGGGCTCCCCCAAGCCTAGCCTGGCCCCCGCTGATTCCCTTATCT
```

-continued

```
ATGCCTTCCCAGCTGCCTCCCTGCTGGCTGAACTGTGGCCACAGACTTCT
GGGCCTTGCACCCCCTCCACTGCCCCCCAGCCCCAAGACAGCCTGTTACT
GCGGCACCAACAGCCACAGTCGAGTCCATCTGATAAGACTTATCTGCTGC
CCCAGAGCAGGCCAGAGCTGGCGTAAGCCCCAGGCACGAGCCGAAGCACT
AAAGAAGTGTATGTACCCTTACCCACTAGTAGTAAAACATGAAACTTAGA
TCTTGACTAATTGCTCATATGACTTGACTGGACACTGGACTCCACAGAAG
CCAAAGGCAAAGGGGATCCAACAACCTGCAGGATAGACAGGAAGGGCGGA
GGGACTAGAGCCTAAAAGGTCCTCCACAAGGAGGCGGCACACCCCCTCCC
CTGCACTGCCCCACCCACTGGGGCACCAGCCACTCCCTGGGGAGGAAAGA
GGAGGGAGAAGGTGAGTGGGAGGGAGGGAGGGCGGGCGGGCTGGCAGGAG
GGAGAGAAGGGAGACTCAGAGGCCGAGCTCCAAGGATAAATTACTTGTTG
AATAAGGATCTAATGTGTAGAACCCATACTGACATGGTAGCAGGCACATC
AGCACAGTTTTAGGGAAATGGGAGATGGAGAAGACTCACTGGAGGCTCAC
AGGCCTGTCCTGGTACACACGGTGGAAAAATATGAGACCCTCTTTAAAAA
GGAAGTGGATGGTAAGGACCAACACCCATGTTTGTCCACTGACCTCCAGA
TAGATAGATAGATAGATAGATAGATAGATAGATAGATAGATAGATAGATA
GATAGACAGACTGACTGACTGACTGACTGACTGACTGACTGACTGACTGA
TTGACTGCAG
```

In some embodiments of any of the aspects, described herein is a GATA1 hematopoietic enhancer minigene (G1HEM) comprising, consisting of, or consisting essentially of a sequence of at least 80% homology to SEQ ID NO: 13. In some embodiments of any of the aspects, a GATA1 hematopoietic enhancer minigene (G1HEM) comprises, consists of, or consists essentially of a sequence of with at least 60%, at least 80%, at least 85%, at least 90%, at least 95%, at least 98% or greater sequence identity to SEQ ID NO: 13.

In some embodiments of any of the aspects, the nucleic acid sequence comprises at least one, or at least 2, or at least 3, or at least 4, or at least 5, or at least 6, or at least 7, or at least 10, or at least 11, or at least 12, or at least 13, or at least 14, or at least 15, or at least 16, or at least 17, or at least 20, or at least 25, or at least 30 GATA1 hematopoietic enhancer minigenes (G1HEM).

In some embodiments of any of the aspects, the GATA1 hematopoietic enhancer minigene is located at least about 5 kb from the boundary of the GATA-1 gene's open reading frame, e.g., at least about 5 kb, at least about 6 kb, at least about 7 kb, at least about 8 kb, at least about 9 kb, at least about 10 kb or further from the boundary of the GATA-1 gene's open reading frame. In some embodiments of any of the aspects, the GATA1 hematopoietic enhancer minigene sequence is located at least 5 kb from the boundary of the GATA-1 gene's open reading frame, e.g., at least 5 kb, at least 6 kb, at least 7 kb, at least 8 kb, at least 9 kb, at least 10 kb or further from the boundary of the GATA-1 gene's open reading frame. In some embodiments of any of the aspects, the GATA1 hematopoietic enhancer minigene is located at about 5 kb from the boundary of the GATA-1 gene's open reading frame, e.g., at about 5 kb, at about 6 kb, at about 7 kb, at about 8 kb, at about 9 kb, or at about 10 kb from the boundary of the GATA-1 gene's open reading frame. In some embodiments of any of the aspects, the GATA1 hematopoietic enhancer minigene sequence can be in intergenic sequence or in the sequence of an intervening gene. In some embodiments of any of the aspects described herein, the GATA1 hematopoietic enhancer minigene sequence can be located about 500 bp to about 10 kb from the end of the open reading frame, e.g., about 1 kb to about 9 kb, about 2 kb to about 8 kb, about 3 kb to about 7 kb, or about 4 kb to about 6 kb from the open reading frame. In some embodiments of any of the aspects described herein, the GATA1 hematopoietic enhancer minigene sequence is located s 500 bp to 10 kb from the end of the open reading frame, e.g., 1 kb to 9 kb, 2 kb to 8 kb, 3 kb to 7 kb, or 4 kb to 6 kb from the open reading frame.

In some embodiments of any of the aspects, disclosed herein are binding sites for HSC restricted miRNAs that permit regulated expression of GATA1 in hematopoietic progenitors to improve erythropoiesis in DBA without unwanted effects on hematopoiesis.

Non-limiting examples of HSC-restricted miRNAs include miR10aT, miR125, miR155, miR130aT, miR142T, miR196bT, miR99, miR126, miR181, miR193, miR223T, miR542, and let7e. Sequences for these miRNAs are known in the art for a number of species, e.g., human miR10aT, miR125, miR155, miR130aT, miR142T, miR196bT, miR99, miR126miR126, miR181, miR193, miR223T, miR542, and let7e.

Binding sites for each of these miRNAs are similarly known in the art and include those readily available on miRBase, miRDB, and/or TargetScan. Briefly, animal miRNA binding sites will be complementary to at least the "seed region" (6-8 nt in length) of the miRNA's sequence. Seed regions for each of the miRNAs described herein are publically available, e.g., at TargetScan and SEQ ID NOs: 43-55 provided herein at Table 2.

In some embodiments of any of the aspects, a binding site for a given miRNA described herein can be a sequence that comprises, consists of, or consists essentially of a sequence complementary to the seed region of that miRNA. In some embodiments of any of the aspects, a nucleic acid sequence described herein can comprise 2, 3, 4, or more repeats of a sequence complementary to the seed region of a single HSC restricted miRNA. Such a sequence can include repeats of an individual sequence and/or combinations of different sequences in series.

In some embodiments of any of the aspects, a binding site for a two or more miRNAs described herein can be a sequence that comprises, consists of, or consists essentially of sequences complementary to the seed region(s) of those miRNAs. In some embodiments of any of the aspects, a binding site for two or more miRNAs described herein can be a sequence that comprises, consists of, or consists essentially of sequences having 2, 3, 4, or more repeats of a sequences complementary to the seed region(s) of those miRNAs. Such a sequence can include repeats of an individual sequence and/or combinations of different sequences in series.

In some embodiments ofany of the aspects, a binding site for one or more miRNAs described herein can be a sequence that comprises, consists of, or consists essentially of a sequence or sequences selected from SEQ ID NOs: 31-37. In some embodiments ofany of the aspects, a binding site for one or more miRNAs described herein can be a sequence that comprises, consists of, or consists essentially of a sequence having 2, 3, 4, or more sequences selected from SEQ ID NOs: 31-37. Such a sequence can include repeats of an individual sequence and/or combinations of different sequences in series. In some embodiments of any of the aspects, the aspects, a nucleic acid sequence described herein can comprise a sequence that comprises, consists of, or consists essentially of 4 repeats of a sequence selected from SEQ ID NOs: 31-37.

sites for at least one HSC-restricted miRNA that is selected from the group consisting of miR binding sites for miR10aT, miR125, miR155, miR130aT, miR142T, miR196bT, miR99, miR126, miR181, miR193, miR223T, miR542, and let7e.

TABLE 2

Non-limiting examples of HSC-restricted miRNA names, miRBase accession number, nucleotide sequence, exemplary seed regions and exemplary nucleotide sequence of the miRNA binding site.

| miRNA name | miRBase accession number | Nucleotide sequence of the mature miRNA | Exemplary seed regions | Nucleotide sequence of exemplary miRNA binding site |
|---|---|---|---|---|
| miR10aT | MI0000266 | UACCCUGUAGAUCCGAAUU UGUG (SEQ ID NO: 18) | UGUCCCA (SEQ ID NO: 43) | CACAAAT TCGGATCTACAGG GTA (SEQ ID NO: 31) |
| miR99 | MI0000101 | AACCCGUAGAUCCGAUCUU GUG (SEQ ID NO: 19) | AUGCCCA (SEQ ID NO: 44) | |
| miR125 | MI0000469 | ACAGGUGAGGUUCUUGGGA GCC (SEQ ID NO: 20) | GAGUCCC (SEQ ID NO: 45) | |
| miR126 | MI0000471 | CAUUAUUACUUUUGGUACG CG (SEQ ID NO: 21) | GCCAUGC (SEQ ID NO: 46) | GCATTAT TACTCACGGTACG A (SEQ ID NO: 32) |
| miR155 | MI0000681 | CUGUUAAUGCUAAUCGUGA UAGGGGUUUUUGCCUCCAA CUGACUCCUACAUAUUAGC AUUAACAG (SEQ ID NO: 22) | CGUAAU (SEQ ID NO: 47) | |
| miR181 | MI0000289 | AACAUUCAACGCUGUCGGU GAGU (SEQ ID NO: 23) | ACUUACA (SEQ ID NO: 48) | |
| miR193 | MI0000487 | AACUGGCCUACAAAGUCCC AGU (SEQ ID NO: 24) | CCGGUCA (SEQ ID NO: 49) | |
| miR196bT | MI0000238 | CAACAACAUUAAACCACCC GA (SEQ ID NO: 25) | UGAUGGA (SEQ ID NO: 50) | CCAACAA CAGGAAACTACCT A (SEQ ID NO: 33) |
| miR223T | MI0000300 | UGUCAGUUUGUCAAAUACC CCA (SEQ ID NO: 26) | UUGACUG (SEQ ID No: 51) | TGTCAGT TTGTCAAATACCC C (SEQ ID NO: 34) |
| miR542 | MI0003686 | UGUGACAGAUUGAUAACUG AAA (SEQ ID NO: 27) | AGGGGC (SEQ ID NO: 52) | |
| let7e | MI0000066 | UGAGGUAGGAGGUUGUAU AGUU (SEQ ID NO: 28) | GGCAUAU (SEQ ID NO: 53) | AACTATA CAACCTACTACCT CA (SEQ ID NO: 35) |
| miR130aAT | MI0000448 | GCUCUUUUCACAU UGUGCUACU (SEQ ID NO: 29) | AACGUGA C (SEQ ID NO: 54) | CAGTGCA ATGTTAAAAGGGC AT (SEQ ID NO: 36) |
| miR142T | MI0000458 | CAUAAAGUAGAAA GCACUACU (SEQ ID NO: 30) | UGAAAUA (SEQ ID NO: 55) | TCCATAA AGTAGGAAACACT ACA (SEQ ID NO: 37) |

In one aspect of any of the embodiments, described herein is a nucleic acid sequence comprising at least one miRNA-binding site for at least one HSC-restricted miRNA that is selected from the group consisting of miR binding sites for miR10aT, miR125, miR155, miR130aT, miR142T, miR196bT, miR99, miR126, miR181, miR193, miR223T, miR542, and let7e. In one aspect of any of the embodiments, described herein is a nucleic acid sequence comprising at least one, or at least two, or at least three, or at least four, or at least five, or at least six, or at least seven, or at least eight, or at least ten, or at least eleven, or at least twelve binding Where a subset of the miRNA binding sites for the foregoing miRNAs is used, any combination of the miRNA binding sites can be used in each of various embodiments of the aspects described herein. For example, it is specifically contemplated herein that any pairwise combination of binding sites for the 12 miRNAs can be used, e.g., any combination shown in Table 3.

In one aspect of any of the embodiments, described herein is a nucleic acid sequence comprising at least one Hematopoietic enhancer element and at least miRNA binding site for at least one HSC-restricted miRNA. In one aspect of any of the embodiments, described herein is a nucleic acid sequence comprising at least one Hematopoietic enhancer element and at least one binding site for at least one HSC-restricted miRNA and a sequence encoding a GATA1 polypeptide.

TABLE 3

Contemplated exemplary combinations of miRNA binding sites are indicated by “X”

| | miR10aT | miR125 | miR155 | miR130aT | miR196bT | miR142T | miR99 | miR126 | miR181 | miR193 | miR223T | miR542 | Let7e |
|---|---|---|---|---|---|---|---|---|---|---|---|---|---|
| miR10aT | | X | X | X | X | X | X | X | X | X | X | X | X |
| miR125 | X | | X | X | X | X | X | X | X | X | X | X | X |
| miR155 | X | X | | X | X | X | X | X | X | X | X | X | X |
| miR130aT | X | X | X | | X | X | X | X | X | X | X | X | X |
| miR196bT | X | X | X | X | | X | X | X | X | X | X | X | X |
| miR142T | X | X | X | X | X | | X | X | X | X | X | X | X |
| miR99 | X | X | X | X | X | X | | X | X | X | X | X | X |
| miR126 | X | X | X | X | X | X | X | | X | X | X | X | X |
| miR181 | X | X | X | X | X | X | X | X | | X | X | X | X |
| miR193 | X | X | X | X | X | X | X | X | X | | X | X | X |
| miR223T | X | X | X | X | X | X | X | X | X | X | | X | X |
| miR542 | X | X | X | X | X | X | X | X | X | X | X | | X |
| Let7e | X | X | X | X | X | X | X | X | X | X | X | X | |

In some embodiments of any of the aspects, the miRNA binding site is located at least about 5 kb from the boundary of the GATA-1 gene’s open reading frame, e.g., at least about 5 kb, at least about 6 kb, at least about 7 kb, at least about 8 kb, at least about 9 kb, at least about 10 kb or further from the boundary of the GATA-1 gene’s open reading frame. In some embodiments of any of the aspects, the miRNA binding site sequence is located at least 5 kb from the boundary of the GATA-1 gene’s open reading frame, e.g., at least 5 kb, at least 6 kb, at least 7 kb, at least 8 kb, at least 9 kb, at least 10 kb or further from the boundary of the GATA-1 gene’s open reading frame. In some embodiments of any of the aspects, the miRNA binding site sequence is located at about 5 kb from the boundary of the GATA-1 gene’s open reading frame, e.g., at about 5 kb, at about 6 kb, at about 7 kb, at about 8 kb, at about 9 kb, or at about 10 kb from the boundary of the GATA-1 gene’s open reading frame. In some embodiments of any of the aspects, the miRNA binding site sequences can be in intergenic sequence or in the sequence of an intervening gene. In some embodiments of any of the aspects described herein, the target sequence located within the sequence which is about 500 bp to about 10 kb from the end of the open reading frame, e.g., about 1 kb to about 9 kb, about 2 kb to about 8 kb, about 3 kb to about 7 kb, or about 4 kb to about 6 kb from the open reading frame. In some embodiments of any of the aspects described herein, the miRNA binding site sequences are located about 500 bp to 10 kb from the end of the open reading frame, e.g., 1 kb to 9 kb, 2 kb to 8 kb, 3 kb to 7 kb, or 4 kb to 6 kb from the open reading frame.

In some embodiments of any of the aspects, disclosed herein are nucleic acid sequences comprising a sequence encoding a GATA1 polypeptide and a heterologous 5' UTR. Such combinations permit lineage-specific expression of GATA1 specifically in early erythroid progenitors Cap analysis of gene expression was used to define 5' untranslated regions (UTRs) for transcripts in HSPCs undergoing erythroid lineage commitment, a stage at which the functional defects in erythroid differentiation arise. Transcripts that were most highly translated at baseline and which had short and unstructured 5' UTRs tend to be the ones that were downregulated at the translational level in the setting of RP haploinsufficiency. The 5' UTR or “5' untranslated region” or 5' leader sequence refers to regions of an mRNA that are not translated. Described herein is the discovery that among all hematopoietic master transcript factors, only GATA1 has a short 5' UTR and that replacing this 5' UTR with those of other transcript factors (including but not limited to RUNX1, LMO2, or ETV6) alters the translation of the GATA1 hematopoietic transcription factor.

In one aspect of any of the embodiments, described herein is a nucleic acid sequence comprising i) a heterologous 5' UTR comprising a) a 5'UTR sequence of a hematopoietic transcription factor other than GATA1; b) a sequence of at least 20 nucleotide acids; and/or c) 1-25 upstream codons uAUGs and ii) a nucleic acid sequence encoding a GATA1 polypeptide. In some embodiments of any of the aspects, a nucleic acid sequence described herein can further comprise a) a heterologous 5' UTR comprising a) a 5'UTR sequence of a hematopoietic transcription factor other than GATA1; b) a sequence of at least 20 nucleotide acids; and/or c) 1-25 upstream codons uAUGs.

The length of the 5' UTR can be modified by mutation for example substitution, deletion or insertion of the 5' UTR. The 5' UTR can be further modified by mutating a naturally occurring start codon or translation initiation site such that the codon no longer functions as start codon and translation may initiate at an alternate initiation site.

In some embodiments of any of the aspects, the a 5'UTR sequence of a hematopoietic transcription factor other than GATA1 can be a 5'UTR of a gene selected from the group consisting of: Runt-related transcription factor 1 (RUNX1), LIM Domain Only 2 (LMO2), and ETS Variant 6 (ETV6).

As used herein, “RUNX1”, “ANL1”, or “Runt-related transcription factor 1” refers to the alpha subunit of the heterodimeric core binding factor (CBF) transcription factor which is thought to be involved in the development of normal hematopoiesis. RUNX1 is itself a transcription factor and complexes with CBFB cofactor to form CBF. Sequences for RUNX1 are known for a number of species, e.g., human RUNX1 (the RUNX1 NCBI Gene ID is 861) mRNA sequences (e.g., NM_001001890.2) and polypeptide sequences (e.g., NP 001001890.1) are known in the art. These, together with any naturally occurring allelic, splice variants, and processed forms thereof that catalyze the same reaction are contemplated for use in the methods and compositions described herein.

In some embodiments of any of the aspects, the RUNX1 5' UTR comprises a 5'UTR that comprises, consists of, consists essentially of or is derived from the following nucleic acid sequence: NG_011402.2:940414-1201911

*Homo sapiens* RUNX family transcription factor 1 (RUNX1), RefSeqGene (LRG 482) on chromosome 21, (SEQ ID NO: 14):

```
CACAGAACCACAAGTTGGGTAGCCTGGCAGTGTCAGAAGTCTGAACCCAG
CATAGTGGTCAGCAGGCAGGACGAATCACACTGAATGCAAACCACAGGGT
TTCGCAGCGTGGTAAAAGAAATCATTGAGTCCCCCGCCTTCAGAAGAGGG
TGCATTTTCAGGAGGAAGCG
```

As used herein, "LMO2", "TTG2", or "LIM Domain Only 2" refers to a cysteine-rich, two LIM-domain protein that is required for yolk sac erythropoiesis. Sequences for LMO2 are known for a number of species, e.g., human LMO2 (the LMO2 NCBI Gene ID is 4005) mRNA sequences (e.g., NM_001142315.1) and polypeptide sequences (e.g., NP 001135787.1) are known in the art. These, together with any naturally occurring allelic, splice variants, and processed forms thereof that catalyze the same reaction are contemplated for use in the methods and compositions described herein.

In some embodiments of any of the aspects, the LMO2 5' UTR comprises a 5'UTR that comprises, consists of, consists essentially of, or is derived from the following nucleic acid sequence: NC_000011.10:c33892289-33858576 *Homo sapiens* chromosome 11, GRCh38.p12, (SEQ ID NO: 15):

```
ACAAGGGCCTCTGGGTGTCCTGGCAGAGAGGGGAGATGGCACAGGCACCA
GGTGCTAGGGTGCCAGGGCCTCCCGAGAAGGAACAGGTGCAAAGCAGGCA
ATTAGCCCAGAAGGTATCCGTGGGGCAGGCAGCCTAGATCTGATGGGGGA
AGCCACCAGGATTACATCATCTGCTGTAACAACTGCTCTGAAAAGAAGAT
ATTTTTCAACCTGAACTTGCAGTAGCTAGTGGAGAGGCAGGAAAAAGGAA
ATGAAACCAGAGACAGAGGGAAGCTGAGCGAAAATAGACCTTCCCGAGAG
AGGAGGAAGCCCGGAGAGAGACGCACGGTCCCCTCCCCGCCCCTAGGCCG
CCGCCCCCTCTCTGCCCTCGGCGGCGAGCAGCGCGCCGCGACCCGGGCCG
AAGGTGCGAGGGGCTCCGGGCGGCCGGGCGGGCGCACACCATCCCCGCGG
GCGGCGCGGAGCCGGCGACAGCGCGCGAGAGGGACCGGGCGGTGGCGGCG
GCGGGACCGGG
```

As used herein, "ETV6", "TEL", or "ETS Variant 6" refers to a transcription factor with two functional domains: a N-terminal pointed (PNT) domain that is involved in protein-protein interactions with itself and other proteins, and a C-terminal DNA-binding domain. Sequences for ETV6 are known for a number of species, e.g., human ETV6 (the ETV6 NCBI Gene ID is 2120) mRNA sequences (e.g., NM_001987.4) and polypeptide sequences (e.g., NP 001978.1) are known in the art. These, together with any naturally occurring allelic, splice variants, and processed forms thereof that catalyze the same reaction are contemplated for use in the methods and compositions described herein.

In some embodiments of any of the aspects, the ETV6 5' UTR comprises a 5'UTR that comprises, consists of, consists essentially of, or is derived from the following nucleic acid sequence NG_011443.1:5001-250549 *Homo sapiens* ETS variant 6 (ETV6), RefSeqGene (LRG 609) on chromosome 12 (SEQ ID NO: 16):

```
CGTCAGTTTCTGCACTGAAACTCTCAAGATCAATGAGCAAAGAGCTTTCT
CAGTTCTGCCTTTCAGTTTCTCTCTTCCAGGAAGGAAAACATTCGAGAGA
GCGAGGGAGAGCCGCGGGAGGGCGGGGGGCGGGGGCGCCGGCTGCGGGTG
GGAGGAGAGACCGGGAGGCCGGCCGGGCTGCGTCCCGGGTCCCCGCGCCG
CGCCGCGACCTGCAGACCCCGCCGCCGCGCTCGGGCCCGTCTCCCACGCC
CCCGCCGCCCCGCGCGCCCAACTCCGCCGGCCGCCCCGCCCCGCCCCGCG
CGCTCCAGACCCCCGGGGCGGCTGCCGGGAGAGATGCTGGAAGAAACTTC
TTAAATGACCGCGTCTGGCTGGCCGTGGAGCCTTTCTGGGTTGGGGAGAG
GAAAGGAAAGTGGAAAAAACCTGAGAACTTCCTGATCTCTCTCGCTGTGA
GAC
```

The nucleic acid sequences/elements described herein can be operably linked so that they can interact either directly or indirectly to carry out an intended function, e.g. the mediation or modulation of expression of a nucleic acid sequence. "Operably linked" refers to an arrangement of elements wherein the components so described are configured so as to perform their usual function. Thus, control elements operably linked to an open reading frame are capable of effecting the expression of the open reading frame. The control elements need not be contiguous with the open reading frame, so long as they function to direct the expression thereof. Thus, for example, intervening untranslated yet transcribed sequences can be present between a promoter sequence and the open reading frame and the promoter sequence can still be considered "operably linked" to the open reading frame. The interaction of operatively linked sequences can, for example, be mediated by proteins that interact with the operatively linked sequences.

In some embodiments of any of the aspects, a promoter can be operably linked to any of the elements disclosed herein, e.g., a nucleic acid sequence comprising a heterologous 5'UTR, at least one distal hematopoietic stem cell (HSC) restricted enhancer element, a binding site for a HSC restricted miRNA, and/or a nucleic acid encoding a GATA1 polypeptide. In some embodiments of any of the aspects, the promoter is not a GATA1 promoter.

In some embodiments of any of the aspects, the promoter comprises a promoter sequence of Elongation factor 1-alpha 1 (eEF1a1). As used herein, "eEF1a1", "CCS-3", or "LENG7" refers to the alpha subunit of the elongation factor-1 complex, which is responsible for the enzymatic delivery of aminoacyl tRNAs to the ribosome. Sequences for eEF1a1 are known for a number of species, e.g., human eEF1a1 (the eEF1a1 NCBI Gene ID is 1915) are known in the art. In some embodiments of any of the aspects, the eEF1a1 promoter comprises a promoter that comprises, consists of, consists essentially of, or is derived from the following nucleic acid sequence NC_000006.12: c73521032-73515750 *Homo sapiens* chromosome 6, GRCh38.p12 Primary Assembly (SEQ ID NO: 17):

```
CTTTTTCGCAACGGGTTTGCCGCCAGAACACAGGTAAGTGCCGTGTGTGGTTCCCGCGGGCCTGGCCTCT
TTACGGGTTATGGCCCTTGCGTGCCTTGAATTACTTCCACGCCCCTGGCTGCAGTACGTGATTCTTGATC
```

-continued

CCGAGCTTCGGGTTGGAAGTGGGTGGGAGAGTTCGAGGCCTTGCGCTTAAGGAGCCCCTTCGCCTCGTGC

TTGAGTTGAGGCCTGGCTTGGGCGCTGGGGCCGCCGCGTGCGAATCTGGTGGCACCTTCGCGCCTGTCTC

GCTGCTTTCGATAAGTCTCTAGCCATTTAAAATTTTTGATGACCTGCTGCGACGCTTTTTTTCTGGCAAG

ATAGTCTTGTAAATGCGGGCCAAGATCTGCACACTGGTATTTCGGTTTTTGGGGCCGCGGGCGGCGACGG

GGCCCGTGCGTCCCAGCGCACATGTTCGGCGAGGCGGGGCCTGCGAGCGCGGCCACCGAGAATCGGACGG

GGGTAGTCTCAAGCTGGCCGGCCTGCTCTGGTGCCTGGCCTCGCGCCGCCGTGTATCGCCCCGCCCTGGG

CGGCAAGGCTGGCCCGGTCGGCACCAGTTGCGTGAGCGGAAAGATGGCCGCTTCCCGGCCCTGCTGCAGG

GAGCTCAAAATGGAGGACGCGGCGCTCGGGAGAGCGGGCGGGTGAGTCACCCACACAAAGGAAAAGGGCC

TTTCCGTCCTCAGCCGTCGCTTCATGTGACTCCACGGAGTACCGGGCGCCGTCCAGGCACCTCGATTAGT

TCTCGAGCTTTTGGAGTACGTCGTCTTTAGGTTGGGGGGAGGGGTTTTATGCGATGGAGTTTCCCCACAC

TGAGTGGGTGGAGACTGAAGTTAGGCCAGCTTGGCACTTGATGTAATTCTCCTTGGAATTTGCCCTTTTT

GAGTTTGGATCTTGGTTCATTCTCAAGCCTCAGACAGTGGTTCAAAGTTTTTTTCTTCCATTTCAGGTGT

CGTGAAAACTACCCCTAAAAGCCAAAATGGGAAAGGAAAAGACTCATATCAACATTGTCGTCATTGGACA

CGTAGATTCGGGCAAGTCCACCACTACTGGCCATCTGATCTATAAATGCGGTGGCATCGACAAAAGAACC

ATTGAAAAATTTGAGAAGGAGGCTGCTGAGGTATGTTTAATACCAGAAAGGGAAAGATCAACTAAAATGA

GTTTTACCAGCAGAATCATTAGGTGATTTCCCCAGAACTAGTGAGTGGTTTAGATCTGAATGCTAATAGT

TAAGACCTTACTTATGAAATAATTTTGCTTTTGGTGACTTCTGTAATCGTATTGCTAGTGAGTAGATTTG

GATGTTAATAGTTAAGATCCGACTTATAAAAGTTTGATTTTTGGTTGCTTCTGTAACCCAAAGTGACTAA

AATCACTTTGGACTTGGAGTTGTAAAGTGGAAACTGCCAATTAAGGGCTGGGGACAAGGAAATTGAAGCT

GGAGTTTGTGTTTTAGTAACCAAGTAACGACTCTTAATCCTTACAGATGGGAAAGGGCTCCTTCAAGTAT

GCCTGGGTCTTGGATAAACTGAAAGCTGAGCGTGAACGTGGTATCACCATTGATATCTCCTTGTGGAAAT

TTGAGACCAGCAAGTACTATGTGACTATCATTGATGCCCCAGGACACAGAGACTTTATCAAAAACATGAT

TACAGGGACATCTCAGGTTGGTGGGATTAATAATTCTAGGTTTCTTTATCCCAAAAGGCTTGCTTTGTAC

ACTGGTTTTGTCATTTGGAGAGTTGACAGGGATATGTCTTTGCTTTCTTTAAAGGCTGACTGTGCTGTCC

TGATTGTTGCTGCTGGTGTTGGTGAATTTGAAGCTGGTATCTCCAAGAATGGGCAGACCCGAGAGCATGC

CCTTCTGGCTTACACACTGGGTGTGAAACAACTAATTGTCGGTGTTAACAAAATGGATTCCACTGAGCCA

CCCTACAGCCAGAAGAGATATGAGGAAATTGTTAAGGAAGTCAGCACTTACATTAAGAAAATTGGCTACA

ACCCCGACACAGTAGCATTTGTGCCAATTTCTGGTTGGAATGGTGACAACATGCTGGAGCCAAGTGCTAA

CGTAAGTGGCTTTCAAGACCATTGTTAAAAAGCTCTGGGAATGGCGATTTCATGCTTACACAAATTGGCA

TGCTTGTGTTTCAGATGCCTTGGTTCAAGGGATGGAAAGTCACCCGTAAGGATGGCAATGCCAGTGGAAC

CACGCTGCTTGAGGCTCTGGACTGCATCCTACCACCAACTCGTCCAACTGACAAGCCCTTGCGCCTGCCT

CTCCAGGATGTCTACAAAATTGGTGGTAAGTTGGCTGTAAACAAAGTTGAATTTGAGTTGATAGAGTACT

GTCTGCCTTCATAGGTATTTAGTATGCTGTAAATATTTTTAGGTATTGGTACTGTTCCTGTTGGCCGAGT

GGAGACTGGTGTTCTCAAACCCGGTATGGTGGTCACCTTTGCTCCAGTCAACGTTACAACGGAAGTAAAA

TCTGTCGAAATGCACCATGAAGCTTTGAGTGAAGCTCTTCCTGGGGACAATGTGGGCTTCAATGTCAAGA

ATGTGTCTGTCAAGGATGTTCGTCGTGGCAACGTTGCTGGTGACAGCAAAAATGACCCACCAATGGAAGC

AGCTGGCTTCACTGCTCAGGTAACAATTTAAAGTAACATTAACTTATTGCAGAGGCTAAAGTCATTTGAG

ACTTTGGATTTGCACTGAATGCAAATCTTTTTTCCAAGGTGATTATCCTGAACCATCCAGGCCAAATAAG

CGCCGGCTATGCCCCTGTATTGGATTGCCACACGGCTCACATTGCATGCAAGTTTGCTGAGCTGAAGGAA

AAGATTGATCGCCGTTCTGGTAAAAAGCTGGAAGATGGCCCTAAATTCTTGAAGTCTGGTGATGCTGCCA

-continued

```
TTGTTGATATGGTTCCTGGCAAGCCCATGTGTGTTGAGAGCTTCTCAGACTATCCACCTTTGGGTAAGGA

TGACTACTTAAATGTAAAAAAGTTGTGTTAAAGATGAAAAATACAACTGAACAGTACTTTGGGTAATAAT

TAACTTTTTTTTTAATAGGTCGCTTTGCTGTTCGTGATATGAGACAGACAGTTGCGGTGGGTGTCATCAA

AGCAGTGGACAAGAAGGCTGCTGGAGCTGGCAAGGTCACCAAGTCTGCCCAGAAAGCTCAGAAGGCTAAA

TGAATATTATCCCTAATACCTGCCACCCCACTCTTAATCAGTGGTGGAAGAACGGTCTCAGAACTGTTTG

TTTCAATTGGCCATTTAAGTTTAGTAGTAAAAGACTGGTTAATGATAACAATGCATCGTAAAACCTTCAG

AAGGAAAGGAGAATGTTTTGTGGACCACTTTGGTTTTCTTTTTTGCGTGTGGCAGTTTTAAGTTATTAGT

TTTTAAAATCAGTACTTTTTAATGGAAACAACTTGACCAAAAATTTGTCACAGAATTTTGAGACCCATTA

AAAAAGTTAAATGAGAAACCTGTGTGTTCCTTTGGTCAACACCGAGACATTTAGGTGAAAGACATCTAAT

TCTGGTTTTACGAATCTGGAAACTTCTTGAAAATGTAATTCTTGAGTTAACACTTCTGGGTGGAGAATAG

GGTTGTTTTCCCCCCACATAATTGGAAGGGGAAGGAATATCATTTAAAGCTATGGGAGGGTTGCTTTGAT

TACAACACTGGAGAGAAATGCAGCATGTTGCTGATTGCCTGTCACTAAAACAGGCCAAAAACTGAGTCCT

TGTGTTGCATAGAAAGCTTCATGTTGCTAAACCAATGTTAAGTGAATCTTTGGAAACAAAATGTTTCCAA

ATTACTGGGATGTGCATGTTGAAACGTGGGTTAAAATGACTGGGCAGTGAAAGTTGACTATTTGCCATGA

CATAAGAAATAAGTGTAGTGGCTAGTGTACACCCTATGAGTGGAAGGGTCCATTTTGAAGTCAGTGGAGT

AAGCTTTATGCCAGTTTGATGGTTTCACAAGTTCTATTGAGTGCTATTCAGAATAGGAACAAGGTTCTAA

TAGAAAAAGATGGCAATTTGAAGTAGCTATAAAATTAGACTAATCTACATTGCTTTTCTCCTGCAGAGTC

TAATACCTTTTATGCTTTGATAATTAGCAGTTTGTCTACTTGGTCACTAGGAATGAAACTACATGGTAAT

AGGCTTAACAGGTGTAATAGCCCACTTACTCCTGAATCTTTAAGCATTTGTGCATTTGAAAAATGCTTTT

CGCGATCTTCCTGCTGGGATTACAGGCATGAGCCACTGTGCCTGACCTCCCATATGTAAAAGTGTCTAAA

GGTTTTTTTTTGGTTATAAAAGGAAAATTTTTGCTTAAGTTTGAAGGATAGGTAAAATTAAAGGACATGC

TTTCTGTTTGTGTGATGGTTTTTAAAAATTTTTTTTAAGATGGAGTTCTTGTTGCCCAGGCTAGAATGCA

ATGGCAAAATCTCACTGCAATCTCCTCCTCCTGGGTTCAAGCAATTCTCCTACTTCAGCCTCCCAAGTAG

CTGGGATTACAGGCATGTGCTAATTTGGTGTTTTTAATAGAGATGAGGTTTTTCCATGTTGGTCAGGCTG

GTCTCAAACTCCTGACCTTAGGTGATCGCCTCGGCCTCCTAAAGTGCTGGAATTACAGGCATGAGCCACC

ATGCCTGGCCAGGACATGTGTTCTTAAGGACATGCTAAGCAGGAGTTAAAGCAGCCCAAGAGATAAGGCC

TCTTAAAGTGACTGGCAATGTGTATTGCTCAAGATTCAAAGGTACTTGAATTGGCCATAGACAAGTCTGT

AATGAAGTGTTATCGTTTTCCCTCATCTGAGTCTGAATTAGATAAAATGCCTTCCCATCAGCCAGTGCTC

TGAGGTATCAAGTCTAAATTGAACTAGAGATTTTTGTCCTTAGTTTCTTTGCTATCTAATGTTTACACAA

GTAAATAGTCTAAGATTTGCTGGATGACAGAAAAAACAGGTAAGGCCTTTAATAGATGGCCAATAGATGC

CCTGATAATGAAAGTTGACACCTGTAAGATTTACCAGTAGAGAATTCTTGACATGCAAGGAAGCAAGATT

TAACTGAAAAATTGTTCCCACTGGAAGCAGGAATGAGTCAGTTTACTTGCATATACTGAGATTGAGATTA

ACTTCCTGTGAAACCCAGTGTCTTAGACAACTGTGGCTTGAGCACCACCTGCTGGTATTCATTACAAACT

TGCTCACTACAATAAATGAATTTTAAGCTTTAA
```

Complex cellular and developmental processes depend on precise spatiotemporal regulation of mRNA and protein levels and activities. Such regulation arises essentially at the transcriptional, posttranscriptional, and posttranslational levels. Post-transcriptional regulation is the control of gene expression at the RNA level, therefore between the transcription and the translation of the gene. Posttranscriptional regulation can be controlled through both protein-RNA and RNA-RNA interactions. As used herein, posttranscriptional regulatory elements include nucleotide sequences including but not limited Woodchuck Hepatitis Virus Posttranscriptional Regulatory Elements. In some embodiments of any of the aspects, the nucleic acid sequences described herein can further comprise a posttranscriptional regulatory element operably linked to the sequence encoding the GATA1 polypeptide.

In some embodiments of any of the aspects, the posttranscriptional regulatory element comprises a Woodchuck Hepatitis Virus Posttranscriptional Regulatory Element. Woodchuck Hepatitis Virus (WHP) Posttranscriptional Regulatory Element, abbreviated WPRE, is a DNA sequence that, when transcribed, creates a tertiary structure enhancing expression. WPRE is a tripartite regulatory element with gamma, alpha, and beta components.

In some embodiments of any of the aspects, the Woodchuck Hepatitis Virus Posttranscriptional Regulatory Element (WPRE) comprises, consists of, or consists essentially of the following nucleotide sequence (SEQ ID NO: 56):

```
GCCACGGCGGAACTCATCGCCGCCTGCCTTGCCCGCTGCTGGACAGGGGC
TCGGCTGTTGGGCACTGACAATTCCGTGGT
```

In some embodiments of any of the aspects, the Woodchuck Hepatitis Virus Posttranscriptional Regulatory Element (WPRE) comprises, consists of, or consists essentially of the following nucleotide sequence (SEQ ID NO: 63):

```
AATCAACCTCTGGATTACAAAATTTGTGAAAGATTGACTGGTATTCTTAA
CTATGTTGCTCCTTTTACGCTATGTGGATACGCTGCTTTAATGCCTTTGT
ATCATGCTATTGCTTCCCGTATGGCTTTCATTTTCTCCTCCTTGTATAAA
TCCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCT
ATTGCCACGGCGGAACTCATCGCCGCCTGCCTTGCCCGCTGCTGGACAGG
GGCTCGGCTGTTGGGCACTGACAATTCCGTGGTGTTGTCGGGGAAGCTGA
CGTCCTTTCCATGGCTGCTCGCCTGTGTTGCCACCTGGATTCTGCGCGGG
ACGTCCTTCTGCTACGTCCCTTCGGCCCTCAATCCAGCGGACCTTCCTTC
CCGCGGCCTGCTGCCGGCTCTGCGGCCTCTTCCGCGTCTTCGCCTTCGCC
CTCAGACGAGTCGGATCTCCCTTTGGGCCGCCTCCCCGCCTG
```

Alternative and/or optimized WPRE are also known in the art, e.g., as described in Patel and Olsen RNA Virus Vectors 11:S322 (2005), which is incorporated by reference herein in its entirety.

In some embodiments of any of the aspects, a WPRE comprises a sequence of at least 80% homology to a nucleotide sequence that is of: SEQ ID NO: 56 and/or SEQ ID NO: 63. In some embodiments of any of the aspects, a WPRE comprises a sequence of at least with at least 60%, at least 80%, at least 85%, at least 90%, at least 95%, at least 98% or greater sequence identity to SEQ ID NO: 56 and/or SEQ ID NO: 63. In some embodiments of any of the aspects, a WPRE comprises a sequence of at least with at least 60%, at least 80%, at least 85%, at least 90%, at least 95%, at least 98% or greater sequence identity to SEQ ID NO: 56 and/or SEQ ID NO: 63 and which retains the wild-type activity of SEQ ID NO: 56 and/or SEQ ID NO: 63. A nucleic acid sequence described herein can comprise multiple post-transcriptional regulatory elements, e.g., the nucleic acid sequence comprises at least one, or at least 2, or at least 3, or at least 4, or at least 5, or at least 6, or at least 7, or at least 10, or at least 11, or at least 12, or at least 13, or at least 14, or at least 15, or at least 16, or at least 17, or at least 20, or at least 25, or at least 30 post-transcriptional regulatory elements.

In some embodiments of any of the aspects, the posttranscriptional regulatory element is located at least about 5 kb from the boundary of the GATA-1 gene's open reading frame, e.g., at least about 5 kb, at least about 6 kb, at least about 7 kb, at least about 8 kb, at least about 9 kb, at least about 10 kb or further from the boundary of the GATA-1 gene's open reading frame. In some embodiments of any of the aspects, the posttranscriptional regulatory element sequence is located at least 5 kb from the boundary of the GATA-1 gene's open reading frame, e.g., at least 5 kb, at least 6 kb, at least 7 kb, at least 8 kb, at least 9 kb, at least 10 kb or further from the boundary of the GATA-1 gene's open reading frame. In some embodiments of any of the aspects, the posttranscriptional regulatory element sequence is located at about 5 kb from the boundary of the GATA-1 gene's open reading frame, e.g., at about 5 kb, at about 6 kb, at about 7 kb, at about 8 kb, at about 9 kb, or at about 10 kb from the boundary of the GATA-1 gene's open reading frame. In some embodiments of any of the aspects, the posttranscriptional regulatory element sequence can be in intergenic sequence or in the sequence of an intervening gene. In some embodiments of any of the aspects described herein, the posttranscriptional regulatory element sequence can be located within the sequence which is about 500 bp to about 10 kb from the end of the open reading frame, e.g., about 1 kb to about 9 kb, about 2 kb to about 8 kb, about 3 kb to about 7 kb, or about 4 kb to about 6 kb from the open reading frame. In some embodiments of any of the aspects described herein, the posttranscriptional regulatory element sequence can be located from about 500 bp to 10 kb from the end of the open reading frame, e.g., 1 kb to 9 kb, 2 kb to 8 kb, 3 kb to 7 kb, or 4 kb to 6 kb from the open reading frame.

In some embodiments of any of the aspects, a nucleic acid sequence described herein can further comprise an internal ribosome entry site. An internal ribosome entry site, abbreviated IRES, is an RNA element that allows for translation initiation in a cap-independent manner, as part of the greater process of protein synthesis. In eukaryotic translation, initiation typically occurs at the 5' end of mRNA molecules, since 5' cap recognition is required for the assembly of the initiation complex. The location for IRES elements is often in the 5'UTR, but can also occur elsewhere in mRNAs.

In some embodiments of any of the aspects, the internal ribosome entry site comprises, consists of, or consists essentially of the following nucleotide sequence (SEQ ID NO: 66)

```
CCCCTCTCCCTCCCCCCCCCCTAACGTTACTGGCCGAAGCCGCTTGGAAT
AAGGCCGGTGTGCGTTTGTCTATATGTTATTTTCCACCATATTGCCGTCT
TTTGGCAATGTGAGGGCCCGGAAACCTGGCCCTGTCTTCTTGACGAGCAT
TCCTAGGGGTCTTTCCCCTCTCGCCAAAGGAATGCAAGGTCTGTTGAATG
TCGTGAAGGAAGCAGTTCCTCTGGAAGCTTCTTGAAGACAAACAACGTCT
GTAGCGACCCTTTGCAGGCAGCGGAACCCCCCACCTGGCGACAGGTGCCT
CTGCGGCCAAAAGCCACGTGTATAAGATACACCTGCAAAGGCGGCACAAC
CCCAGTGCCACGTTGTGAGTTGGATAGTTGTGGAAAGAGTCAAATGGCTC
TCCTCAAGCGTATTCAACAAGGGGCTGAAGGATGCCCAGAAGGTACCCCA
TTGTATGGGATCTGATCTGGGGCCTCGGTACACATGCTTTACATGTGTTT
AGTCGAGGTTAAAAAAACGTCTAGGCCCCCCGAACCACGGGGACGTGGTT
TTCCTTTGAAAAACACGATGATAATATGGCCACAACC
```

In some embodiments of any of the aspects, described herein is a IRES comprising a sequence of at least 80% homology to a nucleotide sequence that is of: SEQ ID NO: 66. In some embodiments of any of the aspects, a IRES comprises a sequence of at least 60%, at least 80%, at least 85%, at least 90%, at least 95%, at least 98% or greater sequence identity to SEQ ID NO: 66. In some embodiments of any of the aspects, a IRES comprises a sequence with at least 60%, at least 80%, at least 85%, at least 90%, at least 95%, at least 98% or greater sequence identity to SEQ ID NO: 66, which retains the wild-type activity of SEQ ID NO: 66.

Nucleic acid sequences described herein can comprise multiple IRES', e.g., a nucleic acid sequence can comprise at least one, or at least 2, or at least 3, or at least 4, or at least 5, or at least 6, or at least 7, or at least 10, or at least 11, or at least 12, or at least 13, or at least 14, or at least 15, or at least 16, or at least 17, or at least 20, or at least 25, or at least 30 IRES sequences.

In some embodiments of any of the aspects, the IRES is located at least about 5 kb from the boundary of the GATA-1 gene's open reading frame, e.g., at least about 5 kb, at least about 6 kb, at least about 7 kb, at least about 8 kb, at least about 9 kb, at least about 10 kb or further from the boundary of the GATA-1 gene's open reading frame. In some embodiments of any of the aspects, the IRES sequence is located at least 5 kb from the boundary of the GATA-1 gene's open reading frame, e.g., at least 5 kb, at least 6 kb, at least 7 kb, at least 8 kb, at least 9 kb, at least 10 kb or further from the boundary of the GATA-1 gene's open reading frame. In some embodiments of any of the aspects, the IRES sequence is located at about 5 kb from the boundary of the GATA-1 gene's open reading frame, e.g., at about 5 kb, at about 6 kb, at about 7 kb, at about 8 kb, at about 9 kb, or at about 10 kb from the boundary of the GATA-1 gene's open reading frame. In some embodiments of any of the aspects, the IRES sequence can be in intergenic sequence or in the sequence of an intervening gene. In some embodiments of any of the aspects described herein, the IRES sequence can be located within the sequence which is about 500 bp to about 10 kb from the end of the open reading frame, e.g., about 1 kb to about 9 kb, about 2 kb to about 8 kb, about 3 kb to about 7 kb, or about 4 kb to about 6 kb from the open reading frame. In some embodiments of any of the aspects described herein, the IRES sequence can be located within the sequence which is 500 bp to 10 kb from the end of the open reading frame, e.g., 1 kb to 9 kb, 2 kb to 8 kb, 3 kb to 7 kb, or 4 kb to 6 kb from the open reading frame.

In some embodiments of any of the aspects, a nucleic acid sequence described herein can further comprise a self-cleaving 2 A polypeptide. A self-cleaving peptide, or 2A peptide, is a polypeptide which can induce the cleaving of a polypeptide of which it is a part, e.g., a recombinant GATA-1 described herein. Thus, a 2A peptide can be used to cleave a longer peptide into two shorter peptides, thereby two peptides can be generated with a single transcript. 2A peptides are derived from the 2A region in the genome of a virus. The 2A-peptide-mediated cleavage commences after the translation. The cleavage is trigged by breaking of peptide bond between the Proline (P) and Glycine (G) in C-terminal of 2A peptide. A 2A polypeptide can comprise at least 10, at least, 15, at least 20, at least 25, at least 30, or at least 40 amino acids.

In some embodiments of any of the aspects, 2A peptides can be combined with the IRES elements in a single nucleic acid sequence, thereby generating three separate polypeptides encoded within a single transcript.

Exemplary 2A peptides that can be used with the methods described herein include, but are not limited to P2A, E2A, F2A and T2A (see also Table 4, SEQ ID NOs: 57-60). F2A is derived from foot-and-mouth disease virus 18; E2A is derived from equine rhinitis A virus; P2A is derived from porcine teschovirus-1 2A; T2A is derived from those a asigna virus 2A.

TABLE 4

Names and sequences of 2A peptides that can be used in various embodiments described herein. An optional linker "GSG" (Gly-Ser-Gly) (bolded) can be added on the N-terminal of the 2A peptides listed.

| Name | Sequence |
|---|---|
| T2A | **GSG** EGRGSLLTCGDVEENPGP (SEQ ID NO: 57) |
| P2A | **GSG** ATNFSLLKQAGDVEENPGP (SEQ ID NO: 58) |
| E2A | **GSG** QCTNYALLKLAGDVESNPGP (SEQ ID NO: 59) |
| F2A | **GSG** VKQTLNFDLLKLAGDVESNPGP (SEQ ID NO: 60) |

In some embodiments of any of the aspects, the IRES and/or self-cleaving 2A polypeptide can be operably linked to a marker gene, e.g., a marker gene encoding an optically detectable protein or an enzyme. Optically detectable proteins/enzymes can comprise an optically detectable label and/or comprise the ability to generate a detectable signal (e.g. by catalyzing reaction converting a compound to a detectable product). Detectable labels can comprise, for example, a light-absorbing moiety or a fluorescent moiety. Detectable labels, marker genes, methods of detecting them, and methods of incorporating them into reagents (e.g. antibodies and nucleic acid probes) are well known in the art.

Optically detectable labels/signals can comprise those visible to the human eye or those detectable with optical equipment, e.g., by spectroscopic, photochemical, biochemical, immunochemical, electromagnetic, radiochemical, or chemical means, such as fluorescence, chemifluorescence, or chemiluminescence, or any other appropriate means. Detectable labels can include, but are not limited to radioisotopes, bioluminescent compounds, chromophores, antibodies, chemiluminescent compounds, fluorescent compounds, metal chelates, and enzymes.

Marker genes are well-known in the art, e.g., and can include but are not limited to naturally fluorescent proteins such as the Green Fluorescent Protein (GFP) of *Aequorea victoria* (Cubitt, A. B. et al. 1995. Understanding, improving, and using green fluorescent proteins. Trends Biochem. Sci. 20: 448-455; Chalfie, M., and Prasher, D. C. U.S. Pat. No. 5,491,084), a lacZ gene encoding a beta-galactosidase enzyme, horseradish peroxidase, alkaline phosphatase, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments of any of the aspects, the nucleic acid sequence described herein can comprise, consist of, or consists essentially of a sequence selected from SEQ ID NOs 8, 9, 61, and 62.

SEQ ID NO: 61 (also designated as R18 EF1a IRES GFP) comprises an EF1A promoter, an IRES sequence operably linked to a nucleotide sequence encoding GFP: GTCGACGGATCGGGAGATCTCCCGATCCCCTATGGTGCACTCTCAGTACAATCTGCTCTGATGCCGCATAGTTAAGCCA
GTATCTGCTCCCTGCTTGTGTGTTGGAGGTCGCTGAGTAGTGCGCGAGCAAAATTTAAGCTACAACAAGGCAAGGCTTGACCG
ACAATTGCATGAAGAATCTGCTTAGGGTTAGGCGTTTTGCGCTGCTTCGCGATGTACGGGCCAGATATACGCGTTGACATTGA
TTATTGACTAGTTATTAATAGTAATCAATTACGGGGTCATTAGTTCATAGCCCATATATGGAGTTCCGCGTTACATAACTTAC
GGTAAATGGCCCGCCTGGCTGACCGCCCAACGACCCCCGCCCATTGACGTCAATAATGACGTATGTTCCCATAGTAACGCCAA
TAGGGACTTTCCATTGACGTCAATGGGTGGAGTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGCAGTACATCAATGGGCGTGGATAGCGGT
TTGACTCACGGGGATTTCCAAGTCTCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCGTGTACGGTGGGAGGTCTATATAAGCAGCGCGTTTTG
CCTGTACTGGGTCTCTCTGGTTAGACCAGATCTGAGCCTGGGAGCTCTCTGGCTAACTAGGGAACCCACTGCTTAAGCCTCAA
TAAAGCTTGCCTTGAGTGCTTCAAGTAGTGTGTGCCCGTCTGTTGTGTGACTCTGGTAACTAGAGATCCCTCAGACCCTTTTA
GTCAGTGTGGAAAATCTCTAGCAGTGGCGCCCGAACAGGGACTTGAAAGCGAAAGGGAAACCAGAGGAGCTCTCTCGACGCAG
GACTCGGCTTGCTGAAGCGCGCACGGCAAGAGGCGAGGGGCGGCGACTGGTGAGTACGCCAAAAATTTTGACTAGCGGAGGCT
AGAAGGAGAGAGATGGGTGCGAGAGCGTCAGTATTAAGCGGGGGAGAATTAGATCGCGATGGGAAAAAATTCGGTTAAGGCCA
GGGGGAAAGAAAAAATATAAATTAAAACATATAGTATGGGCAAGCAGGGAGCTAGAACGATTCGCAGTTAATCCTGGCCTGTT
AGAAACATCAGAAGGCTGTAGACAAATACTGGGACAGCTACAACCATCCCTTCAGACAGGATCAGAAGAACTTAGATCATTAT
ATAATACAGTAGCAACCCTCTATTGTGTGCATCAAAGGATAGAGATAAAAGACACCAAGGAAGCTTTAGACAAGATAGAGGAA
GAGCAAAACAAAAGTAAGACCACCGCACAGCAAGCGGCCGGCCGCTGATCTTCAGACCTGGAGGAGGAGATATGAGGGACAAT
TGGAGAAGTGAATTATATAAATATAAAGTAGTAAAAATTGAACCATTAGGAGTAGCACCCACCAAGGCAAAGAGAAGAGTGGT
GCAGAGAGAAAAAAGAGCAGTGGGAATAGGAGCTTTGTTCCTTGGGTTCTTGGGAGCAGCAGGAAGCACTATGGGCGCAGCGT
CAATGACGCTGACGGTACAGGCCAGACAATTATTGTCTGGTATAGTGCAGCAGCAGAACAATTTGCTGAGGGCTATTGAGGCG
CAACAGCATCTGTTGCAACTCACAGTCTGGGGCATCAAGCAGCTCCAGGCAAGAATCCTGGCTGTGGAAAGATACCTAAAGGA
TCAACAGCTCCTGGGGATTTGGGGTTGCTCTGGAAAACTCATTTGCACCACTGCTGTGCCTTGGAATGCTAGTTGGAGTAATA
AATCTCTGGAACAGATTTGGAATCACACGACCTGGATGGAGTGGGACAGAGAAATTAACAATTACACAAGCTTAATACACTCC
TTAATTGAAGAATCGCAAAACCAGCAAGAAAAGAATGAACAAGAATTATTGGAATTAGATAAATGGGCAAGTTTGTGGAATTG
GTTTAACATAACAAATTGGCTGTGGTATATAAAATTATTCATAATGATAGTAGGAGGCTTGGTAGGTTTAAGAATAGTTTTTG
CTGTACTTTCTATAGTGAATAGAGTTAGGCAGGGATATTCACCATTATCGTTTCAGACCCACCTCCCAACCCCGAGGGGACCC
GACAGGCCCGAAGGAATAGAAGAAGAAGGTGGAGAGAGAGACAGAGACAGATCCATTCGATTAGTGAACGGATCGGCACTGCG
TGCGCCAATTCTGCAGACAAATGGCAGTATTCATCCACAATTTTAAAAGAAAAGGGGGGATTGGGGGGTACAGTGCAGGGGAA
AGAATAGTAGACATAATAGCAACAGACATACAAACTAAAGAATTACAAAAACAAATTACAAAAATTCAAAATTTTCGGGTTTA
TTACAGGGACAGCAGAGATCCAGTTTGGTTAGTACCGGGCCCGCTCTAGCGTGAGGCTCCGGTGCCCGTCAGTGGGCAGAGCG
CACATCGCCCACAGTCCCCGAGAAGTTGGGGGGAGGGGTCGGCAATTGAACCGGTGCCTAGAGAAGGTGGCGCGGGGTAAACT
GGGAAAGTGATGTCGTGTACTGGCTCCGCCTTTTTCCCGAGGGTGGGGGAGAACCGTATATAAGTGCAGTAGTCGCCGTGAAC
GTTCTTTTTCGCAACGGGTTTGCCGCCAGAACACAGGTAAGTGCCGTGTGTGGTTCCCGCGGGCCTGGCCTCTTTACGGGTTA
TGGCCCTTGCGTGCCTTGAATTACTTCCACCTGGCTGCAGTACGTGATTCTTGATCCCGAGCTTCGGGTTGGAAGTGGGTGGG
AGAGTTCGAGGCCTTGCGCTTAAGGAGCCCCTTCGCCTCGTGCTTGAGTTGAGGCCTGGCCTGGGCGCTGGGGCCGCCGCGTG
CGAATCTGGTGGCACCTTCGCGCCTGTCTCGCTGCTTTCGATAAGTCTCTAGCCATTTAAAATTTTTGATGACCTGCTGCGAC
GCTTTTTTTCTGGCAAGATAGTCTTGTAAATGCGGGCCAAGATCTGCACACTGGTATTTCGGTTTTTGGGGCCGCGGGCGGCG
ACGGGGCCCGTGCGTCCCAGCGCACATGTTCGGCGAGGCGGGGCCTGCGAGCGCGGCCACCGAGAATCGGACGGGGGTAGTCT
CAAGCTGGCCGGCCTGCTCTGGTGCCTGGCCTCGCGCCGCCGTGTATCGCCCCGCCCTGGGCGGCAAGGCTGGCCCGGTCGGC -continued ACCAGTTGCGTGAGCGGAAAGATGGCCGCTTCCCGGCCCTGCTGCAGGGAGCTCAAAATGGAGGACGCGGCGCTCGGGAGAGC GGGCGGGTGAGTCACCCACACAAAGGAAAAGGGCCTTTCCGTCCTCAGCCGTCGCTTCATGTGACTCCACGGAGTACCGGGCG CCGTCCAGGCACCTCGATTAGTTCTCGAGCTTTTGGAGTACGTCGTCTTTAGGTTGGGGGGAGGGGTTTTATGCGATGGAGTT TCCCCACACTGAGTGGGTGGAGACTGAAGTTAGGCCAGCTTGGCACTTGATGTAATTCTCCTTGGAATTTGCCCTTTTTGAGT TTGGATCTTGGTTCATTCTCAAGCCTCAGACAGTGGTTCAAAGTTTTTTTCTTCCATTTCAGGTGTCGTGAGCGGCCGCTGAG TTAACTATTCTAGACCCGGGCTAGGATCCGCCCCTCTCCCTCCCCCCCCCCTAACGTTACTGGCCGAAGCCGCTTGGAATAAG GCCGGTGTGCGTTTGTCTATATGTTATTTTCCACCATATTGCCGTCTTTTGGCAATGTGAGGGCCCGGAAACCTGGCCCTGTC TTCTTGACGAGCATTCCTAGGGGTCTTTCCCCTCTCGCCAAAGGAATGCAAGGTCTGTTGAATGTCGTGAAGGAAGCAGTTCC TCTGGAAGCTTCTTGAAGACAAACAACGTCTGTAGCGACCCTTTGCAGGCAGCGGAACCCCCCACCTGGCGACAGGTGCCTCT GCGGCCAAAAGCCACGTGTATAAGATACACCTGCAAAGGCGGCACAACCCCAGTGCCACGTTGTGAGTTGGATAGTTGTGGAA AGAGTCAAATGGCTCTCCTCAAGCGTATTCAACAAGGGGCTGAAGGATGCCCAGAAGGTACCCCATTGTATGGGATCTGATCT GGGGCCTCGGTACACATGCTTTACATGTGTTTAGTCGAGGTTAAAAAAACGTCTAGGCCCCCCGAACCACGGGGACGTGGTTT TCCTTTGAAAAACACGATGATAATATGGCCACAACCATGGTGAGCAAGGGCGAGGAGCTGTTCACCGGGGTGGTGCCCATCCT GGTCGAGCTGGACGGCGACGTAAACGGCCACAAGTTCAGCGTGTCCGGCGAGGGCGAGGGCGATGCCACCTACGGCAAGCTGA CCCTGAAGTTCATCTGCACCACCGGCAAGCTGCCCGTGCCCTGGCCCACCCTCGTGACCACCCTGACCTACGGCGTGCAGTGC TTCAGCCGCTACCCCGACCACATGAAGCAGCACGACTTCTTCAAGTCCGCCATGCCCGAAGGCTACGTCCAGGAGCGCACCAT CTTCTTCAAGGACGACGGCAACTACAAGACCCGCGCCGAGGTGAAGTTCGAGGGCGACACCCTGGTGAACCGCATCGAGCTGA AGGGCATCGACTTCAAGGAGGACGGCAACATCCTGGGGCACAAGCTGGAGTACAACTACAACAGCCACAACGTCTATATCATG GCCGACAAGCAGAAGAACGGCATCAAGGTGAACTTCAAGATCCGCCACAACATCGAGGACGGCAGCGTGCAGCTCGCCGACCA CTACCAGCAGAACACCCCCATCGGCGACGGCCCCGTGCTGCTGCCCGACAACCACTACCTGAGCACCCAGTCCGCCCTGAGCA AAGACCCCAACGAGAAGCGCGATCACATGGTCCTGCTGGAGTTCGTGACCGCCGCCGGGATCACTCTCGGCATGGACGAGCTG TACAAGTAAAGCGGCCGCATCGATACCGTCGACCTCGATCGAGACCTAGAAAAACATGGAGCAATCACAAGTAGCAATACAGC AGCTACCAATGCTGATTGTGCCTGGCTAGAAGCACAAGAGGAGGAGGAGGTGGGTTTTCCAGTCACACCTCAGGTACCTTTAA GACCAATGACTTACAAGGCAGCTGTAGATCTTAGCCACTTTTTAAAAGAAAAGGGGGGACTGGAAGGGCTAATTCACTCCCAA CGAAGACAAGATATCCTTGATCTGTGGATCTACCACACACAAGGCTACTTCCCTGATTGGCAGAACTACACACCAGGGCCAGG GATCAGATATCCACTGACCTTTGGATGGTGCTACAAGCTAGTACCAGTTGAGCAAGAGAAGGTAGAAGAAGCCAATGAAGGAG AGAACACCCGCTTGTTACACCCTGTGAGCCTGCATGGGATGGATGACCCGGAGAGAGAAGTATTAGAGTGGAGGTTTGACAGC CGCCTAGCATTTCATCACATGGCCCGAGAGCTGCATCCGGACTGTACTGGGTCTCTCTGGTTAGACCAGATCTGAGCCTGGGA GCTCTCTGGCTAACTAGGGAACCCACTGCTTAAGCCTCAATAAAGCTTGCCTTGAGTGCTTCAAGTAGTGTGTGCCCGTCTGT TGTGTGACTCTGGTAACTAGAGATCCCTCAGACCCTTTTAGTCAGTGTGGAAAATCTCTAGCAGCATGTGAGCAAAAGGCCAG CAAAAGGCCAGGAACCGTAAAAAGGCCGCGTTGCTGGCGTTTTTCCATAGGCTCCGCCCCCCTGACGAGCATCACAAAAATCG ACGCTCAAGTCAGAGGTGGCGAAACCCGACAGGACTATAAAGATACCAGGCGTTTCCCCCTGGAAGCTCCCTCGTGCGCTCTC CTGTTCCGACCCTGCCGCTTACCGGATACCTGTCCGCCTTTCTCCCTTCGGGAAGCGTGGCGCTTTCTCATAGCTCACGCTGT AGGTATCTCAGTTCGGTGTAGGTCGTTCGCTCCAAGCTGGGCTGTGTGCACGAACCCCCCGTTCAGCCCGACCGCTGCGCCTT ATCCGGTAACTATCGTCTTGAGTCCAACCCGGTAAGACACGACTTATCGCCACTGGCAGCAGCCACTGGTAACAGGATTAGCA GAGCGAGGTATGTAGGCGGTGCTACAGAGTTCTTGAAGTGGTGGCCTAACTACGGCTACACTAGAAGAACAGTATTTGGTATC TGCGCTCTGCTGAAGCCAGTTACCTTCGGAAAAAGAGTTGGTAGCTCTTGATCCGGCAAACAAACCACCGCTGGTAGCGGTGG TTTTTTTGTTTGCAAGCAGCAGATTACGCGCAGAAAAAAAGGATCTCAAGAAGATCCTTTGATCTTTTCTACGGGGTCTGACG CTCAGTGGAACGAAAACTCACGTTAAGGGATTTTGGTCATGAGATTATCAAAAAGGATCTTCACCTAGATCCTTTTAAATTAA AAATGAAGTTTTAAATCAATCTAAAGTATATATGAGTAAACTTGGTCTGACAGTTACCAATGCTTAATCAGTGAGGCACCTAT -continued

```
CTCAGCGATCTGTCTATTTCGTTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCAATAAACCAGCCAGCCGGAAGG

GCCGAGCGCAGAAGTGGTCCTGCAACTTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACGCTCGTCGTTTGGTATGGCTTCATTCA

GCTCCGGTTCCCAACGATCAAGGCGAGTTACATGATCCCCCATGTTGTGCAAAAAAGCGGTTAGCTCCTTCGGTCCTCCGATC

GTTGTCAGAAGTAAGTTGGCCGCAGTGTTATCACTCATGGTTATGGCAGCACTGCATAATTCTCTTACTGTCATGCCATCCGT

AAGATGCTTTTCTGTGACTGGTGAGTACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTGGAAAACGTTCTTCGGGGCGAAAACTC

TCAAGGATCTTACCGCTGTTGAGATCCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATAAGGGCGACACGGAAATGTTGAATACTCA

TACTCTTCCTTTTTCAATATTATTGAAGCATTTATCAGGGTTATTGTCTCATGAGCGGATACATATTTGAATGTATTTAGAAA

AATAAACAAATAGGGGTTCCGCGCACATTTCCCCGAAAAGTGCCACCTGAC
```

SEQ ID NO: 8 (also designated as R21 miR126) comprises an EF1A promoter, and an IRES sequence operably linked to a nucleotide sequence encoding GFP and four miRNAa binding site for the HSC restricted miRNA miR126:

```
GTCGACGGATCGGGAGATCTCCCGATCCCCTATGGTGCACTCTCAGTACAATCTGCTCTGATGCCGCATAGTTAA

GCCAGTATCTGCTCCCTGCTTGTGTGTTGGAGGTCGCTGAGTAGTGCGCGAGCAAAATTTAAGCTACAACAAGGC

AAGGCTTGACCGACAATTGCATGAAGAATCTGCTTAGGGTTAGGCGTTTTGCGCTGCTTCGCGATGTACGGGCCA

GATATACGCGTTGACATTGATTATTGACTAGTTATTAATAGTAATCAATTACGGGGTCATTAGTTCATAGCCCAT

ATATGGAGTTCCGCGTTACATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTCAATGGGTGGAGTATTTAC

GGTAAACTGCCCACTTGGCAGTACATCAAGTGTATCATATGCCAAGTACGCCCCCTATTGACGTCAATGACGGTA

AATGGCCCGCCTGGCATTATGCCCAGTACATGACCTTATGGGACTTTCCTACTTGGCAGTACATCTACGTATTAG

TCATCGCTATTACCATGGTGATGCGGTTTTGGCAGTACATCAATGGGCGTGGATAGCGGTTTGACTCACGGGGAT

TTCCAAGTCTCCACCCCATTGACGTCAATGGGAGTTTGTTTTGGCACCAAAATCAACGGGACTTTCCAAAATGTC

GTAACAACTCCGCCCCATTGACGCAAATGGGCGGTAGGCGTGTACGGTGGGAGGTCTATATAAGCAGCGCGTTTT

GCCTGTACTGGGTCTCTCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGACTCTGGTAACTAGAGA

TCCCTCAGACCCTTTTAGTCAGTGTGGAAAATCTCTAGCAGTGGCGCCCGAACAGGGACTTGAAAGCGAAAGGGA

AACCAGAGGAGCTCTCTCGACGCAGGACTCGGCTTGCTGAAGCGCGCACGGCAAGAGGCGAGGGGCGGCGACTGG

TGAGTACGCCAAAAATTTTGACTAGCGGAGGCTAGAAGGAGAGAGATGGGTGCGAGAGCGTCAGTATTAAGCGGG

GGAGAATTAGATCGCGATGGGAAAAAATTCGGTTAAGGCCAGGGGGAAAGAAAAAATATAAATTAAAACATATAG

TATGGGCAAGCAGGGAGCTAGAACGATTCGCAGTTAATCCTGGCCTGTTAGAAACATCAGAAGGCTGTAGACAAA

TACTGGGACAGCTACAACCATCCCTTCAGACAGGATCAGAAGAACTTAGATCATTATATAATACAGTAGCAACCC

TCTATTGTGTGCATCAAAGGATAGAGATAAAAGACACCAAGGAAGCTTTAGACAAGATAGAGGAAGAGCAAAACA

AAAGTAAGACCACCGCACAGCAAGCGGCCGGCCGCTGATCTTCAGACCTGGAGGAGGAGATATGAGGGACAATTG

GAGAAGTGAATTATATAAATATAAAGTAGTAAAAATTGAACCATTAGGAGTAGCACCCACCAAGGCAAAGAGAAG

AGTGGTGCAGAGAGAAAAAAGAGCAGTGGGAATAGGAGCTTTGTTCCTTGGGTTCTTGGGAGCAGCAGGAAGCAC

TATGGGCGCAGCGTCAATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCAAGCAGCTCCAGGCAAG

AATCCTGGCTGTGGAAAGATACCTAAAGGATCAACAGCTCCTGGGGATTTGGGGTTGCTCTGGAAAACTCATTTG
```

-continued

CACCACTGCTGTGCCTTGGAATGCTAGTTGGAGTAATAAATCTCTGGAACAGATTTGGAATCACACGACCTGGAT

GGAGTGGGACAGAGAAATTAACAATTACACAAGCTTAATACACTCCTTAATTGAAGAATCGCAAAACCAGCAAGA

AAAGAATGAACAAGAATTATTGGAATTAGATAAATGGGCAAGTTTGTGGAATTGGTTTAACATAACAAATTGGCT

GTGGTATATAAAATTATTCATAATGATAGTAGGAGGCTTGGTAGGTTTAAGAATAGTTTTTGCTGTACTTTCTAT

AGTGAATAGAGTTAGGCAGGGATATTCACCATTATCGTTTCAGACCCACCTCCCAACCCCGAGGGGACCCGACAG

GCCCGAAGGAATAGAAGAAGAAGGTGGAGAGAGAGACAGAGACAGATCCATTCGATTAGTGAACGGATCGGCACT

GCGTGCGCCAATTCTGCAGACAAATGGCAGTATTCATCCACAATTTTAAAAGAAAAGGGGGGATTGGGGGGTACA

GTGCAGGGGAAAGAATAGTAGACATAATAGCAACAGACATACAAACTAAAGAATTACAAAAACAAATTACAAAAA

TTCAAAATTTTCGGGTTTATTACAGGGACAGCAGAGATCCAGTTTGGTTAGTACCGGGCCCGCTCTAGCGTGAGG

CTCCGGTGCCCGTCAGTGGGCAGAGCGCACATCGCCCACAGTCCCCGAGAAGTTGGGGGGAGGGGTCGGCAATTG

AACCGGTGCCTAGAGAAGGTGGCGCGGGGTAAACTGGGAAAGTGATGTCGTGTACTGGCTCCGCCTTTTTCCCGA

GGGTGGGGGAGAACCGTATATAAGTGCAGTAGTCGCCGTGAACGTTCTTTTTCGCAACGGGTTTGCCGCCAGAAC

ACAGGTAAGTGCCGTGTGTGGTTCCCGCGGGCCTGGCCTCTTTACGGGTTATGGCCCTTGCGTGCCTTGAATTAC

TTCCACCTGGCTGCAGTACGTGATTCTTGATCCCGAGCTTCGGGTTGGAAGTGGGTGGGAGAGTTCGAGGCCTTG

CGCTTAAGGAGCCCCTTCGCCTCGTGCTTGAGTTGAGGCCTGGCCTGGGCGCTGGGGCCGCCGCGTGCGAATCTG

GTGGCACCTTCGCGCCTGTCTCGCTGCTTTCGATAAGTCTCTAGCCATTTAAAATTTTTGATGACCTGCTGCGAC

GCTTTTTTTCTGGCAAGATAGTCTTGTAAATGCGGGCCAAGATCTGCACACTGGTATTTCGGTTTTTGGGGCCGC

GGGCGGCGACGGGGCCCGTGCGTCCCAGCGCACATGTTCGGCGAGGCGGGGCCTGCGAGCGCGGCCACCGAGAAT

CGGACGGGGGTAGTCTCAAGCTGGCCGGCCTGCTCTGGTGCCTGGCCTCGCGCCGCCGTGTATCGCCCCGCCCTG

GGCGGCAAGGCTGGCCCGGTCGGCACCAGTTGCGTGAGCGGAAAGATGGCCGCTTCCCGGCCCTGCTGCAGGGAG

CTCAAAATGGAGGACGCGGCGCTCGGGAGAGCGGGCGGGTGAGTCACCCACACAAAGGAAAAGGGCCTTTCCGTC

CTCAGCCGTCGCTTCATGTGACTCCACGGAGTACCGGGCGCCGTCCAGGCACCTCGATTAGTTCTCGAGCTTTTG

GAGTACGTCGTCTTTAGGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTGGATCTTGGTTCATTCT

CAAGCCTCAGACAGTGGTTCAAAGTTTTTTTCTTCCATTTCAGGTGTCGTGAGCGGCCGCTGAGTTAACTATTCT

AGACCCGGGCTAGGATCCGCCCCTCTCCCTCCCCCCCCCCTAACGTTACTGGCCGAAGCCGCTTGGAATAAGGCC

GGTGTGCGTTTGTCTATATGTTATTTTCCACCATATTGCCGTCTTTTGGCAATGTGAGGGCCCGGAAACCTGGCC

CTGTCTTCTTGACGAGCATTCCTAGGGGTCTTTCCCCTCTCGCCAAAGGAATGCAAGGTCTGTTGAATGTCGTGA

AGGAAGCAGTTCCTCTGGAAGCTTCTTGAAGACAAACAACGTCTGTAGCGACCCTTTGCAGGCAGCGGAACCCCC

CACCTGGCGACAGGTGCCTCTGCGGCCAAAAGCCACGTGTATAAGATACACCTGCAAAGGCGGCACAACCCCAGT

GCCACGTTGTGAGTTGGATAGTTGTGGAAAGAGTCAAATGGCTCTCCTCAAGCGTATTCAACAAGGGGCTGAAGG

ATGCCCAGAAGGTACCCCATTGTATGGGATCTGATCTGGGGCCTCGGTACACATGCTTTACATGTGTTTAGTCGA

GGTTAAAAAAACGTCTAGGCCCCCCGAACCACGGGGACGTGGTTTTCCTTTGAAAAACACGATGATAATATGGCC

ACAACCATGGTGAGCAAGGGCGAGGAGCTGTTCACCGGGGTGGTGCCCATCCTGGTCGAGCTGGACGGCGACGTA

AACGGCCACAAGTTCAGCGTGTCCGGCGAGGGCGAGGGCGATGCCACCTACGGCAAGCTGACCCTGAAGTTCATC

TGCACCACCGGCAAGCTGCCCGTGCCCTGGCCCACCCTCGTGACCACCCTGACCTACGGCGTGCAGTGCTTCAGC

CGCTACCCCGACCACATGAAGCAGCACGACTTCTTCAAGTCCGCCATGCCCGAAGGCTACGTCCAGGAGCGCACC

ATCTTCTTCAAGGACGACGGCAACTACAAGACCCGCGCCGAGGTGAAGTTCGAGGGCGACACCCTGGTGAACCGC

ATCGAGCTGAAGGGCATCGACTTCAAGGAGGACGGCAACATCCTGGGGCACAAGCTGGAGTACAACTACAACAGC

CACAACGTCTATATCATGGCCGACAAGCAGAAGAACGGCATCAAGGTGAACTTCAAGATCCGCCACAACATCGAG

-continued

GACGGCAGCGTGCAGCTCGCCGACCACTACCAGCAGAACACCCCCATCGGCGACGGCCCCGTGCTGCTGCCCGAC

AACCACTACCTGAGCACCCAGTCCGCCCTGAGCAAAGACCCCAACGAGAAGCGCGATCACATGGTCCTGCTGGAG

TTCGTGACCGCCGCCGGGATCACTCTCGGCATGGACGAGCTGTACAAGTAAAGCGGCCGCATCGATAATCAACCT

CTGGATTACAAAATTTGTGAAAGATTGACTGGTATTCTTAACTATGTTGCTCCTTTTACGCTATGTGGATACGCT

GCTTTAATGCCTTTGTATCATGCTATTGCTTCCCGTATGGCTTTCATTTTCTCCTCCTTGTATAAATCCTGGTTG

CTGTCTCTTTATGAGGAGTTGTGGCCCGTTGTCAGGCAACGTGGCGTGGTGTGCACTGTGTTTGCTGACGCAACC

CCCACTGGTTGGGGCATTGCCACCACCTGTCAGCTCCTTTCCGGGACTTTCGCTTTCCCCCTCCCTATTGCCACG

GCGGAACTCATCGCCGCCTGCCTTGCCCGCTGCTGGACAGGGGCTCGGCTGTTGGGCACTGACAATTCCGTGGTG

TTGTCGGGGAAGCTGACGTCCTTTCCATGGCTGCTCGCCTGTGTTGCCACCTGGATTCTGCGCGGGACGTCCTTC

TGCTACGTCCCTTCGGCCCTCAATCCAGCGGACCTTCCTTCCCGCGGCCTGCTGCCGGCTCTGCGGCCTCTTCCG

CGTCTTCGCCTTCGCCCTCAGACGAGTCGGATCTCCCTTTGGGCCGCCTCCCCGCGAATTCGCATTATTACTCAC

GGTACGAGCATTATTACTCACGGTACGAGCATTATTACTCACGGTACGAGCATTATTACTCACGGTACGAGCGAT

CGCCCTCAGGTACCTTTAAGACCAATGACTTACAAGGCAGCTGTAGATCTTAGCCACTTTTTAAAAGAAAAGGGG

GGACTGGAAGGGCTAATTCACTCCCAACGAAGACAAGATATCCTTGATCTGTGGATCTACCACACACAAGGCTAC

TTCCCTGATTGGCAGAACTACACACCAGGGCCAGGGATCAGATATCCACTGACCTTTGGATGGTGCTACAAGCTA

GTACCAGTTGAGCAAGAGAAGGTAGAAGAAGCCAATGAAGGAGAGAACACCCGCTTGTTACACCCTGTGAGCCTG

CATGGGATGGATGACCCGGAGAGAGAAGTATTAGAGTGGAGGTTTGACAGCCGCCTAGCATTTCATCACATGGCC

CGAGAGCTGCATCCGGACTGTACTGGGTCTCTCTGGTTAGACCAGATCTGAGCCTGGGAGCTCTCTGGCTAACTA

GGGAACCCACTGCTTAAGCCTCAATAAAGCTTGCCTTGAGTGCTTCAAGTAGTGTGTGCCCGTCTGTTGTGTGAC

TCTGGTAACTAGAGATCCCTCAGACCCTTTTAGTCAGTGTGGAAAATCTCTAGCAGCATGTGAGCAAAAGGCCAG

CAAAAGGCCAGGAACCGTAAAAAGGCCGCGTTGCTGGCGTTTTTCCATAGGCTCCGCCCCCCTGACGAGCATCAC

AAAAATCGACGCTCAAGTCAGAGGTGGCGAAACCCGACAGGACTATAAAGATACCAGGCGTTTCCCCCTGGAAGC

TCCCTCGTGCGCTCTCCTGTTCCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCTCCAAGCTGGGCTGTGTGCAC

GAACCCCCCGTTCAGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGCTACAGAGTTCTTG

AAGTGGTGGCCTAACTACGGCTACACTAGAAGAACAGTATTTGGTATCTGCGCTCTGCTGAAGCCAGTTACCTTC

GGAAAAAGAGTTGGTAGCTCTTGATCCGGCAAACAAACCACCGCTGGTAGCGGTGGTTTTTTTGTTTGCAAGCAG

CAGATTACGCGCAGAAAAAAAGGATCTCAAGAAGATCCTTTGATCTTTTCTACGGGGTCTGACGCTCAGTGGAAC

GAAAACTCACGTTAAGGGATTTTGGTCATGAGATTATCAAAAAGGATCTTCACCTAGATCCTTTTAAATTAAAAA

TGAAGTTTTAAATCAATCTAAAGTATATATGAGTAAACTTGGTCTGACAGTTACCAATGCTTAATCAGTGAGGCA

CCTATCTCAGCGATCTGTCTATTTCGTTCATCCATAGTTGCCTGACTCCCCGTCGTGTAGATAACTACGATACGG

GAGGGCTTACCATCTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCATCCAGTCTATTAAT

TGTTGCCGGGAAGCTAGAGTAAGTAGTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCAACGATCAAGGCGAGTTACATGATCC

CCCATGTTGTGCAAAAAAGCGGTTAGCTCCTTCGGTCCTCCGATCGTTGTCAGAAGTAAGTTGGCCGCAGTGTTA

TCACTCATGGTTATGGCAGCACTGCATAATTCTCTTACTGTCATGCCATCCGTAAGATGCTTTTCTGTGACTGGT

GAGTACTCAACCAAGTCATTCTGAGAATAGTGTATGCGGCGACCGAGTTGCTCTTGCCCGGCGTCAATACGGGAT

AATACCGCGCCACATAGCAGAACTTTAAAAGTGCTCATCATTGGAAAACGTTCTTCGGGGCGAAAACTCTCAAGG

ATCTTACCGCTGTTGAGATCCAGTTCGATGTAACCCACTCGTGCACCCAACTGATCTTCAGCATCTTTTACTTTC

-continued

ACCAGCGTTTCTGGGTGAGCAAAAACAGGAAGGCAAAATGCCGCAAAAAAGGGAATAAGGGCGACACGGAAATGT

TGAATACTCATACTCTTCCTTTTTCAATATTATTGAAGCATTTATCAGGGTTATTGTCTCATGAGCGGATACATA

TTTGAATGTATTTAGAAAAATAAACAAATAGGGGTTCCGCGCACATTTCCCCGAAAAGTGCCACCTGAC

SEQ ID NO: 9 (also designated as R49 1 peak enhancer) comprises, an IRES sequence operably linked to a nucleotide sequence encoding GFP and one hematopoietic enhancer element:

GTCGACGGATCGGGAGATCTCCCGATCCCCTATGGTGCACTCTCAGTACAATCTGCTCTGATGCCGCATAGTTAAGCCAGTAT

CTGCTCCCTGCTTGTGTGTTGGAGGTCGCTGAGTAGTGCGCGAGCAAAATTTAAGCTACAACAAGGCAAGGCTTGACCGACAA

TTGCATGAAGAATCTGCTTAGGGTTAGGCGTTTTGCGCTGCTTCGCGATGTACGGGCCAGATATACGCGTTGACATTGATTAT

TGACTAGTTATTAATAGTAATCAATTACGGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGACGTATGTTCCCATAGTAACGCCAATAGG

GACTTTCCATTGACGTCAATGGGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACCTTATGGGACTTTCCTACTTGG

CAGTACATCTACGTATTAGTCATCGCTATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGCACCAAAATCAACGGGACTTTCCAAAAT

GTCGTAACAACTCCGCCCCATTGACGCAAATGGGCGGTAGGCGTGTACGGTGGGAGGTCTATATAAGCAGCGCGTTTTGCCTG

TACTGGGTCTCTCTGGTTAGACCAGATCTGAGCCTGGGAGCTCTCTGGCTAACTAGGGAACCCACTGCTTAAGCCTCAATAAA

GCTTGCCTTGAGTGCTTCAAGTAGTGTGTGCCCGTCTGTTGTGTGACTCTGGTAACTAGAGATCCCTCAGACCCTTTTAGTCA

GTGTGGAAAATCTCTAGCAGTGGCGCCCGAACAGGGACTTGAAAGCGAAAGGGAAACCAGAGGAGCTCTCTCGACGCAGGACT

CGGCTTGCTGAAGCGCGCACGGCAAGAGGCGAGGGGCGGCGACTGGTGAGTACGCCAAAAATTTTGACTAGCGGAGGCTAGAA

GGAGAGAGATGGGTGCGAGAGCGTCAGTATTAAGCGGGGGAGAATTAGATCGCGATGGGAAAAAATTCGGTTAAGGCCAGGGG

GAAAGAAAAAATATAAATTAAAACATATAGTATGGGCAAGCAGGGAGCTAGAACGATTCGCAGTTAATCCTGGCCTGTTAGAA

ACATCAGAAGGCTGTAGACAAATACTGGGACAGCTACAACCATCCCTTCAGACAGGATCAGAAGAACTTAGATCATTATATAA

TACAGTAGCAACCCTCTATTGTGTGCATCAAAGGATAGAGATAAAAGACACCAAGGAAGCTTTAGACAAGATAGAGGAAGAGC

AAAACAAAAGTAAGACCACCGCACAGCAAGCGGCCGGCCGCTGATCTTCAGACCTGGAGGAGGAGATATGAGGGACAATTGGA

GAAGTGAATTATATAAATATAAAGTAGTAAAAATTGAACCATTAGGAGTAGCACCCACCAAGGCAAAGAGAAGAGTGGTGCAG

AGAGAAAAAAGAGCAGTGGGAATAGGAGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGAATCCTGGCTGTGGAAAGATACCTAAAGGATCAA

CAGCTCCTGGGGATTTGGGGTTGCTCTGGAAAACTCATTTGCACCACTGCTGTGCCTTGGAATGCTAGTTGGAGTAATAAATC

TCTGGAACAGATTTGGAATCACACGACCTGGATGGAGTGGGACAGAGAAATTAACAATTACACAAGCTTAATACACTCCTTAA

TTGAAGAATCGCAAAACCAGCAAGAAAAGAATGAACAAGAATTATTGGAATTAGATAAATGGGCAAGTTTGTGGAATTGGTTT

AACATAACAAATTGGCTGTGGTATATAAAATTATTCATAATGATAGTAGGAGGCTTGGTAGGTTTAAGAATAGTTTTTGCTGT

ACTTTCTATAGTGAATAGAGTTAGGCAGGGATATTCACCATTATCGTTTCAGACCCACCTCCCAACCCCGAGGGGACCCGACA

GGCCCGAAGGAATAGAAGAAGAAGGTGGAGAGAGAGACAGAGACAGATCCATTCGATTAGTGAACGGATCGGCACTGCGTGCG

CCAATTCTGCAGACAAATGGCAGTATTCATCCACAATTTTAAAAGAAAAGGGGGGATTGGGGGGTACAGTGCAGGGGAAAGAA

TAGTAGACATAATAGCAACAGACATACAAACTAAAGAATTACAAAAACAAATTACAAAAATTCAAAATTTTCGGGTTTATTAC

AGGGACAGCAGAGATCCAGTTTGGTTAGTACCGGGCCCGCTCTAGCGTGAGGCTCCGGTGCCCGTCAGTGGGCAGAGCGCACA

TCGCCCACAGTCCCCGAGAAGTTGGGGGGAGGGGTCGGCAATTGAACCGGTGCTAGCATGGCGGGCAAGAAGTTGAGGCCACT

-continued

GTCCCTGGGTGTTCCTACCCCCACACCCTCACCCCAAGACAGCCTGTTACTGCGGCGCCAACAGCCACGGTCGCCTACATCTG

ATAAGACTTATCTGCTGCCCCAGGGCAGGCCGGAGCTGGCGTAAGCCCCAGTGGGGCGCTAAGTGAGTGTGCCCCTGCCTCCC

GCCAGCACTGGCCTGGCCTGCAGGCTTAGCCTGGGTCATCAAGGTATCCCACAGGCTCTAGTTCAAATCCAGCAGAACCTCTC

TGAGCCTCACTCTTCTCACCTGCAAAATGGGTACAGCCACATCCCTTCTCTCCCTGCAGCCAGGAAGACGCACATACACAGGA

GTCTAGCCCACACCGGCCCCGCACAAATTAAGGGCTTTACTCTCTGAAAAGCCCAGTGAAGTCATGAAACCATATCTGCTATT

TTCATTTATCTTGGTTTCAGCCTATTTTGCTTGTCTGGACACTACAGTCCACGGGAGCCTAGGTCGAGCGAGGTCCAAGAATC

CCCAGGGTGGGCAGGGAGGGTGGAAGAGGGCCTCCAGTGCCCAAGAGGTGCCCCACAAGCATGGGACCCGCCCCCTCCCCTGG

ACTGCCCCACCCACTGGGGCACCAGCCACTCCCTGGGGAGGAGGGAGGAGGGAGAAGGGAGGGAGGGAGGGAGGGAGGAAGGG

AGCCTCAAAGGCCAAGGCCAGCCAGGACACCCCCTGGGATCACACTGAGCTTGCCACATCCCCAAGGCGGCCGAACCCTCCGC

AACCACCAGCCCAGAGATCTAGAGTTAATCCCCAGAGGCTCCATGGTGAGCAAGGGCGAGGAGCTGTTCACCGGGGTGGTGCC

CATCCTGGTCGAGCTGGACGGCGACGTAAACGGCCACAAGTTCAGCGTGTCCGGCGAGGGCGAGGGCGATGCCACCTACGGCA

AGCTGACCCTGAAGTTCATCTGCACCACCGGCAAGCTGCCCGTGCCCTGGCCCACCCTCGTGACCACCCTGACCTACGGCGTG

CAGTGCTTCAGCCGCTACCCCGACCACATGAAGCAGCACGACTTCTTCAAGTCCGCCATGCCCGAAGGCTACGTCCAGGAGCG

CACCATCTTCTTCAAGGACGACGGCAACTACAAGACCCGCGCCGAGGTGAAGTTCGAGGGCGACACCCTGGTGAACCGCATCG

AGCTGAAGGGCATCGACTTCAAGGAGGACGGCAACATCCTGGGGCACAAGCTGGAGTACAACTACAACAGCCACAACGTCTAT

ATCATGGCCGACAAGCAGAAGAACGGCATCAAGGTGAACTTCAAGATCCGCCACAACATCGAGGACGGCAGCGTGCAGCTCGC

CGACCACTACCAGCAGAACACCCCCATCGGCGACGGCCCCGTGCTGCTGCCCGACAACCACTACCTGAGCACCCAGTCCGCCC

TGAGCAAAGACCCCAACGAGAAGCGCGATCACATGGTCCTGCTGGAGTTCGTGACCGCCGCCGGGATCACTCTCGGCATGGAC

GAGCTGTACAAGTAAAGCGGCCGCATCGATACCGTCGACCTCGATCGAGACCTAGAAAAACATGGAGCAATCACAAGTAGCAA

TACAGCAGCTACCAATGCTGATTGTGCCTGGCTAGAAGCACAAGAGGAGGAGGAGGTGGGTTTTCCAGTCACACCTCAGGTAC

CTTTAAGACCAATGACTTACAAGGCAGCTGTAGATCTTAGCCACTTTTTAAAAGAAAAGGGGGGACTGGAAGGGCTAATTCAC

TCCCAACGAAGACAAGATATCCTTGATCTGTGGATCTACCACACACAAGGCTACTTCCCTGATTGGCAGAACTACACACCAGG

GCCAGGGATCAGATATCCACTGACCTTTGGATGGTGCTACAAGCTAGTACCAGTTGAGCAAGAGAAGGTAGAAGAAGCCAATG

AAGGAGAGAACACCCGCTTGTTACACCCTGTGAGCCTGCATGGGATGGATGACCCGGAGAGAGAAGTATTAGAGTGGAGGTTT

GACAGCCGCCTAGCATTTCATCACATGGCCCGAGAGCTGCATCCGGACTGTACTGGGTCTCTCTGGTTAGACCAGATCTGAGC

CTGGGAGCTCTCTGGCTAACTAGGGAACCCACTGCTTAAGCCTCAATAAAGCTTGCCTTGAGTGCTTCAAGTAGTGTGTGCCC

GTCTGTTGTGTGACTCTGGTAACTAGAGATCCCTCAGACCCTTTTAGTCAGTGTGGAAAATCTCTAGCAGCATGTGAGCAAAA

GGCCAGCAAAAGGCCAGGAACCGTAAAAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGGCGTTTCCCCCTGGAAGCTCCCTCGTGC

GCTCTCCTGTTCCGACCCTGCCGCTTACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCACGAACCCCCCGTTCAGCCCGACCGCTG

CGCCTTATCCGGTAACTATCGTCTTGAGTCCAACCCGGTAAGACACGACTTATCGCCACTGGCAGCAGCCACTGGTAACAGGA

TTAGCAGAGCGAGGTATGTAGGCGGTGCTACAGAGTTCTTGAAGTGGTGGCCTAACTACGGCTACACTAGAAGAACAGTATTT

GGTATCTGCGCTCTGCTGAAGCCAGTTACCTTCGGAAAAAGAGTTGGTAGCTCTTGATCCGGCAAACAAACCACCGCTGGTAG

CGGTGGTTTTTTTGTTTGCAAGCAGCAGATTACGCGCAGAAAAAAAGGATCTCAAGAAGATCCTTTGATCTTTTCTACGGGGT

CTGACGCTCAGTGGAACGAAAACTCACGTTAAGGGATTTTGGTCATGAGATTATCAAAAAGGATCTTCACCTAGATCCTTTTA

AATTAAAAATGAAGTTTTAAATCAATCTAAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCGTGTAGATAACTACGATACGGGAGGGCT

TACCATCTGGCCCCAGTGCTGCAATGATACCGCGAGACCCACGCTCACCGGCTCCAGATTTATCAGCAATAAACCAGCCAGCC

GGAAGGGCCGAGCGCAGAAGTGGTCCTGCAACTTTATCCGCCTCCATCCAGTCTATTAATTGTTGCCGGGAAGCTAGAGTAAG

TAGTTCGCCAGTTAATAGTTTGCGCAACGTTGTTGCCATTGCTACAGGCATCGTGGTGTCACGCTCGTCGTTTGGTATGGCTT

-continued

CATTCAGCTCCGGTTCCCAACGATCAAGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCACTGCATAATTCTCTTACTGTCATGCC

ATCCGTAAGATGCTTTTCTGTGACTGGTGAGTACTCAACCAAGTCATTCTGAGAATAGTGTATGCGGCGACCGAGTTGCTCTT

GCCCGGCGTCAATACGGGATAATACCGCGCCACATAGCAGAACTTTAAAAGTGCTCATCATTGGAAAACGTTCTTCGGGGCGA

AAACTCTCAAGGATCTTACCGCTGTTGAGATCCAGTTCGATGTAACCCACTCGTGCACCCAACTGATCTTCAGCATCTTTTAC

TTTCACCAGCGTTTCTGGGTGAGCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCGGATACATATTTGAATGTATT

TAGAAAAATAAACAAATAGGGGTTCCGCGCACATTTCCCCGAAAAGTGCCACCTGAC

SEQ ID NO: 62 (also designated as R50 3 peak enhancer) comprises an IRES sequence operably linked to a nucleotide sequence encoding GFP and three hematopoietic enhancer elements:

GTCGACGGATCGGGAGATCTCCCGATCCCCTATGGTGCACTCTCAGTACAATCTGCTCTGATGCCGCATAGTTAAGCCAGTAT

CTGCTCCCTGCTTGTGTGTTGGAGGTCGCTGAGTAGTGCGCGAGCAAAATTTAAGCTACAACAAGGCAAGGCTTGACCGACAA

TTGCATGAAGAATCTGCTTAGGGTTAGGCGTTTTGCGCTGCTTCGCGATGTACGGGCCAGATATACGCGTTGACATTGATTAT

TGACTAGTTATTAATAGTAATCAATTACGGGGTCATTAGTTCATAGCCCATATATGGAGTTCCGCGTTACATAACTTACGGTA

AATGGCCCGCCTGGCTGACCGCCCAACGACCCCCGCCCATTGACGTCAATAATGACGTATGTTCCCATAGTAACGCCAATAGG

GACTTTCCATTGACGTCAATGGGTGGAGTATTTACGGTAAACTGCCCACTTGGCAGTACATCAAGTGTATCATATGCCAAGTA

CGCCCCCTATTGACGTCAATGACGGTAAATGGCCCGCCTGGCATTATGCCCAGTACATGACCTTATGGGACTTTCCTACTTGG

CAGTACATCTACGTATTAGTCATCGCTATTACCATGGTGATGCGGTTTTGGCAGTACATCAATGGGCGTGGATAGCGGTTTGA

CTCACGGGGATTTCCAAGTCTCCACCCCATTGACGTCAATGGGAGTTTGTTTTGGCACCAAAATCAACGGGACTTTCCAAAAT

GTCGTAACAACTCCGCCCCATTGACGCAAATGGGCGGTAGGCGTGTACGGTGGGAGGTCTATATAAGCAGCGCGTTTTGCCTG

TACTGGGTCTCTCTGGTTAGACCAGATCTGAGCCTGGGAGCTCTCTGGCTAACTAGGGAACCCACTGCTTAAGCCTCAATAAA

GCTTGCCTTGAGTGCTTCAAGTAGTGTGTGCCCGTCTGTTGTGTGACTCTGGTAACTAGAGATCCCTCAGACCCTTTTAGTCA

GTGTGGAAAATCTCTAGCAGTGGCGCCCGAACAGGGACTTGAAAGCGAAAGGGAAACCAGAGGAGCTCTCTCGACGCAGGACT

CGGCTTGCTGAAGCGCGCACGGCAAGAGGCGAGGGGCGGCGACTGGTGAGTACGCCAAAAATTTTGACTAGCGGAGGCTAGAA

GGAGAGAGATGGGTGCGAGAGCGTCAGTATTAAGCGGGGGAGAATTAGATCGCGATGGGAAAAAATTCGGTTAAGGCCAGGGG

GAAAGAAAAAATATAAATTAAAACATATAGTATGGGCAAGCAGGGAGCTAGAACGATTCGCAGTTAATCCTGGCCTGTTAGAA

ACATCAGAAGGCTGTAGACAAATACTGGGACAGCTACAACCATCCCTTCAGACAGGATCAGAAGAACTTAGATCATTATATAA

TACAGTAGCAACCCTCTATTGTGTGCATCAAAGGATAGAGATAAAAGACACCAAGGAAGCTTTAGACAAGATAGAGGAAGAGC

AAAACAAAAGTAAGACCACCGCACAGCAAGCGGCCGGCCGCTGATCTTCAGACCTGGAGGAGGAGATATGAGGGACAATTGGA

GAAGTGAATTATATAAATATAAAGTAGTAAAAATTGAACCATTAGGAGTAGCACCCACCAAGGCAAAGAGAAGAGTGGTGCAG

AGAGAAAAAAGAGCAGTGGGAATAGGAGCTTTGTTCCTTGGGTTCTTGGGAGCAGCAGGAAGCACTATGGGCGCAGCGTCAAT

GACGCTGACGGTACAGGCCAGACAATTATTGTCTGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGAATCCTGGCTGTGGAAAGATACCTAAAGGATCAA

CAGCTCCTGGGGATTTGGGGTTGCTCTGGAAAACTCATTTGCACCACTGCTGTGCCTTGGAATGCTAGTTGGAGTAATAAATC

TCTGGAACAGATTTGGAATCACACGACCTGGATGGAGTGGGACAGAGAAATTAACAATTACACAAGCTTAATACACTCCTTAA

TTGAAGAATCGCAAAACCAGCAAGAAAAGAATGAACAAGAATTATTGGAATTAGATAAATGGGCAAGTTTGTGGAATTGGTTT

AACATAACAAATTGGCTGTGGTATATAAAATTATTCATAATGATAGTAGGAGGCTTGGTAGGTTTAAGAATAGTTTTTGCTGT

ACTTTCTATAGTGAATAGAGTTAGGCAGGGATATTCACCATTATCGTTTCAGACCCACCTCCCAACCCCGAGGGGACCCGACA

-continued

GGCCCGAAGGAATAGAAGAAGAAGGTGGAGAGAGAGACAGAGACAGATCCATTCGATTAGTGAACGGATCGGCACTGCGTGCG

CCAATTCTGCAGACAAATGGCAGTATTCATCCACAATTTTAAAAGAAAAGGGGGGATTGGGGGGTACAGTGCAGGGGAAAGAA

TAGTAGACATAATAGCAACAGACATACAAACTAAAGAATTACAAAAACAAATTACAAAAATTCAAAATTTTCGGGTTTATTAC

AGGGACAGCAGAGATCCAGTTTGGTTAGTACCGGGCCCGCTCTAGCGTGAGGCTCCGGTGCCCGTCAGTGGGCAGAGCGCACA

TCGCCCACAGTCCCCGAGAAGTTGGGGGGAGGGGTCGGCAATTGAACCGGTACTGGCCTGGCCAACATAGTGAAACCCCATCT

CTCCTAATAATACAAAAATTAGCCAGGCATGGTGGCGGGTGCCTGTAATCCCAGCTACTCAGGAGACTGAGGCAGGATAATCA

CTTGAACCCAGCAGGTGGAGGCTGCAGTGAGCCAAGATCGTGCCACTGCACTCCAGCCTGGGTGACAGAGCAAGACTACATCT

CAAAAAAAAAAAAAAAAAAAAAAAGAAGATAGATGACCAACAAGTTTATGAAAATATGCTCAACATCAGTGGTCACAGGGAAA

TGCAAATCAAAACCATAACAAGATACCACTTCACACCCACACCCAGTAGGATGGCGCGATCGCAGAACCCCAGAAGATGCCAG

GAGGGAGTGAGCCAGTCAGGGAAGGCTTCCGAGAAGAGAGGACATTGAAGAAGAGTCTCAAACTTAGGCCTGACGGAGAAGAC

GCGCGGCCAGGACACCCCACCCCCGCCCTCGTCTCCCCCAAAGCCTGATCTGGCCCCACTGATTCCCTTATCTGCCCACTCCC

AGCTGCCTCCTTGCTGGCTGAACTGTCGCCGCAGACTTCTGAGCCTGCGCCCCCTCCACGGGGATGGGGGAGGGAATGGGGTG

AGGCCTGGCCTCACAGCCTCGGGGTTTCCAGCTCTTGCTGGAGGCAGGGCTCTGGGGCGCCCTACTCCTCACCCTTGGCTTCT

CTTCCTGAGCGCTCTGTGCTCTCCAGAGCTAGCATGGCGGGCAAGAAGTTGAGGCCACTGTCCCTGGGTGTTCCTACCCCCAC

ACCCTCACCCCAAGACAGCCTGTTACTGCGGCGCCAACAGCCACGGTCGCCTACATCTGATAAGACTTATCTGCTGCCCCAGG

GCAGGCCGGAGCTGGCGTAAGCCCCAGTGGGGCGCTAAGTGAGTGTGCCCCTGCCTCCCGCCAGCACTGGCCTGGCCTGCAGG

CTTAGCCTGGGTCATCAAGGTATCCCACAGGCTCTAGTTCAAATCCAGCAGAACCTCTCTGAGCCTCACTCTTCTCACCTGCA

AAATGGGTACAGCCACATCCCTTCTCTCCCTGCAGCCAGGAAGACGCACATACACAGGAGTCTAGCCCACACCGGCCCCGCAC

AAATTAAGGGCTTTACTCTCTGAAAAGCCCAGTGAAGTCATGAAACCATATCTGCTATTTTCATTTATCTTGGTTTCAGCCTA

TTTTGCTTGTCTGGACACTACAGTCCACGGGAGCCTAGGTCGAGCGAGGTCCAAGAATCCCCAGGGTGGGCAGGGAGGGTGGA

AGAGGGCCTCCAGTGCCCAAGAGGTGCCCCACAAGCATGGGACCCGCCCCCTCCCCTGGACTGCCCCACCCACTGGGGCACCA

GCCACTCCCTGGGGAGGAGGGAGGAGGGAGAAGGGAGGGAGGGAGGGAGGGAGGAAGGGAGCCTCAAAGGCCAAGGCCAGCCA

GGACACCCCCTGGGATCACACTGAGCTTGCCACATCCCCAAGGCGGCCGAACCCTCCGCAACCACCAGCCCAGAGATCTAGAG

TTAATCCCCAGAGGCTCCATGGTGAGCAAGGGCGAGGAGCTGTTCACCGGGGTGGTGCCCATCCTGGTCGAGCTGGACGGCGA

CGTAAACGGCCACAAGTTCAGCGTGTCCGGCGAGGGCGAGGGCGATGCCACCTACGGCAAGCTGACCCTGAAGTTCATCTGCA

CCACCGGCAAGCTGCCCGTGCCCTGGCCCACCCTCGTGACCACCCTGACCTACGGCGTGCAGTGCTTCAGCCGCTACCCCGAC

CACATGAAGCAGCACGACTTCTTCAAGTCCGCCATGCCCGAAGGCTACGTCCAGGAGCGCACCATCTTCTTCAAGGACGACGG

CAACTACAAGACCCGCGCCGAGGTGAAGTTCGAGGGCGACACCCTGGTGAACCGCATCGAGCTGAAGGGCATCGACTTCAAGG

AGGACGGCAACATCCTGGGGCACAAGCTGGAGTACAACTACAACAGCCACAACGTCTATATCATGGCCGACAAGCAGAAGAAC

GGCATCAAGGTGAACTTCAAGATCCGCCACAACATCGAGGACGGCAGCGTGCAGCTCGCCGACCACTACCAGCAGAACACCCC

CATCGGCGACGGCCCCGTGCTGCTGCCCGACAACCACTACCTGAGCACCCAGTCCGCCCTGAGCAAAGACCCCAACGAGAAGC

GCGATCACATGGTCCTGCTGGAGTTCGTGACCGCCGCCGGGATCACTCTCGGCATGGACGAGCTGTACAAGTAAAGCGGCCGC

ATCGATACCGTCGACCTCGATCGAGACCTAGAAAAACATGGAGCAATCACAAGTAGCAATACAGCAGCTACCAATGCTGATTG

TGCCTGGCTAGAAGCACAAGAGGAGGAGGAGGTGGGTTTTCCAGTCACACCTCAGGTACCTTTAAGACCAATGACTTACAAGG

CAGCTGTAGATCTTAGCCACTTTTTAAAAGAAAAGGGGGGACTGGAAGGGCTAATTCACTCCCAACGAAGACAAGATATCCTT

GATCTGTGGATCTACCACACACAAGGCTACTTCCCTGATTGGCAGAACTACACACCAGGGCCAGGGATCAGATATCCACTGAC

CTTTGGATGGTGCTACAAGCTAGTACCAGTTGAGCAAGAGAAGGTAGAAGAAGCCAATGAAGGAGAGAACACCCGCTTGTTAC

ACCCTGTGAGCCTGCATGGGATGGATGACCCGGAGAGAGAAGTATTAGAGTGGAGGTTTGACAGCCGCCTAGCATTTCATCAC

ATGGCCCGAGAGCTGCATCCGGACTGTACTGGGTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGCATGTGAGCAAAAGGCCAGCAAAAGGCCAGGAACCGT

-continued

AAAAAGGCCGCGTTGCTGGCGTTTTTCCATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGCCCGACCGCTGCGCCTTATCCGGTAACTATCGTCT

TGAGTCCAACCCGGTAAGACACGACTTATCGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGTATTTGGTATCTGCGCTCTGCTGAAGCCA

GTTACCTTCGGAAAAAGAGTTGGTAGCTCTTGATCCGGCAAACAAACCACCGCTGGTAGCGGTGGTTTTTTTGTTTGCAAGCA

GCAGATTACGCGCAGAAAAAAAGGATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTGAGGCACCTATCTCAGCGATCTGTCTATT

TCGTTCATCCATAGTTGCCTGACTCCCCGTCGTGTAGATAACTACGATACGGGAGGGCTTACCATCTGGCCCCAGTGCTGCAA

TGATACCGCGAGACCCACGCTCACCGGCTCCAGATTTATCAGCAATAAACCAGCCAGCCGGAAGGGCCGAGCGCAGAAGTGGT

CCTGCAACTTTATCCGCCTCCATCCAGTCTATTAATTGTTGCCGGGAAGCTAGAGTAAGTAGTTCGCCAGTTAATAGTTTGCG

CAACGTTGTTGCCATTGCTACAGGCATCGTGGTGTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCCTTCGGTCCTCCGATCGTTGTCAGAAGTAAGTTG

GCCGCAGTGTTATCACTCATGGTTATGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTCTTGCCCGGCGTCAATACGGGATAATA

CCGCGCCACATAGCAGAACTTTAAAAGTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATACTCATACTCTTCCTTTTTCAAT

ATTATTGAAGCATTTATCAGGGTTATTGTCTCATGAGCGGATACATATTTGAATGTATTTAGAAAAATAAACAAATAGGGGTT

CCGCGCACATTTCCCCGAAAAGTGCCACCTGAC

In some embodiments of any of the aspects, the nucleic acid sequence described herein is a vector or is comprised by or provided in a vector. The vector can be, e.g., a plasmid, viral vector, or an adenoviral, lentiviral or retroviral vector. As used herein, the term "retrovirus" refers a type of RNA virus that inserts a copy of its genome into the DNA of a host cell that it invades, thus changing the genome of that cell. Such viruses are either single stranded RNA or double stranded DNA viruses. In some embodiments of any of the aspects, the retrovirus is an alpha retrovirus. As used herein, the term "lentivirus" refers to a group (or genus) of complex retroviruses. lentiviruses are capable of infecting non-dividing and actively dividing cell types, whereas standard retroviruses can only infect mitotically active cell types. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). As used herein, the term "Adenoviruses" refers to nonenveloped viruses with an icosahedral nucleocapsid containing a double stranded DNA genome. As used herein, the term "viral vector" refers to a nucleic acid vector construct that includes at least one element of viral origin and has the capacity to be packaged into a viral vector particle. The viral vector can contain the nucleic acid described herein in place of non-essential viral genes. The vector and/or particle may be utilized for the purpose of transferring any nucleic acids into cells either in vitro or in vivo. Numerous forms of viral vectors are known in the art.

In some embodiments of any of the aspects, the nucleic acid sequence and/or vector described herein is comprised by, provided in, or located in, a viral particle (e.g., a lentiviral particle).

In one aspect of any of the embodiments, described herein is a composition comprising a nucleic acid sequence, vector, or particle as described herein and a pharmaceutically acceptable carrier.

In one aspect of any of the embodiments, described herein is to a pharmaceutical composition comprising a nucleic acid sequence as described herein (and/or a vector or virus particle comprising such a nucleic acid sequence), and optionally a pharmaceutically acceptable carrier. In some embodiments of any of the aspects, the active ingredients of the pharmaceutical composition comprise a nucleic acid as described herein (and/or a vector or virus particle comprising such a nucleic acid sequence). In some embodiments of any of the aspects, the active ingredients of the pharmaceutical composition consist of a nucleic acid as described herein (and/or a vector or virus particle comprising such a nucleic acid sequence). Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. of a nucleic acid comprising a sequence encoding a GATA-binding factor 1 (GATA1) polypeptide as described herein.

In some embodiments of any of the aspects, the pharmaceutical composition comprising a nucleic acid sequence comprising a sequence encoding a GATA-binding factor 1 (GATA1) polypeptide as described herein (and/or a vector or virus particle comprising such a nucleic acid sequence) can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of the pharmaceutical composition comprising a nucleic acid sequence comprising a sequence encoding a GATA-binding factor 1 (GATA1) polypeptide as described herein (and/or a vector or virus particle comprising such a nucleic acid sequence) are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of the pharmaceutical composition as disclosed herein can also be incorporated into the parenteral dosage forms of the disclosure, including conventional and controlled-release parenteral dosage forms.

Pharmaceutical compositions comprising a nucleic acid sequence comprising a sequence encoding a GATA-binding factor 1 (GATA1) polypeptide as disclosed herein (and/or a vector or virus particle comprising such a nucleic acid sequence) can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the comprising a nucleic acid sequence comprising a sequence encoding a GATA-binding factor 1 (GATA1) polypeptide as disclosed herein (and/or a vector or virus particle comprising such a nucleic acid sequence) can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some aspects of the embodiments, described herein is a method of treating Diamond-Blackfan Anemia in a subject in need thereof, the method comprising administering a therapeutically effective amount of a nucleic acid sequence, particle, or composition as described herein to the patient.

The compositions described herein can be administered to a subject having or diagnosed as having DBA. In some embodiments of any of the aspects, the methods described herein comprise administering an effective amount of a composition described herein, e.g. of a nucleic acid comprising a sequence encoding a GATA-binding factor 1 (GATA1) polypeptide as as described herein to a subject in order to alleviate a symptom of DBA. As used herein, "alleviating a symptom" is ameliorating any condition or symptom associated with DBA. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, or injection administration. Administration can be local or systemic.

The term "effective amount" as used herein refers to the amount of the active agent needed to alleviate at least one or more symptom of the disease or disorder, and relates to a sufficient amount of pharmacological composition to provide the desired effect. The term "therapeutically effective amount" therefore refers to an amount of the active agent that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assays for the levels of red blood cells and/or erythropoiesis, among others. The dosage can be determined by a physician and adjusted, as necessary, to suit observed effects of the treatment.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active agent. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition a nucleic acid sequence comprising a sequence encoding a GATA-binding factor 1 (GATA1) polypeptide as disclosed herein (and/or a vector or virus particle comprising such a nucleic acid sequence) can be administered over a period of time, such as over a 5 minute, 10 minute, 15 minute, 20 minute, or 25 minute period.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition by at least 10%, at least 15%, at least 20%, at least 25%, at least 30%, at least 40%, at least 50%, at least 60%, at least 70%, at least 80% or at least 90% or more.

The dosage ranges for the administration of a nucleic acid sequence comprising a sequence encoding a GATA-binding factor 1 (GATA1) polypeptide as disclosed herein (and/or a vector or virus particle comprising such a nucleic acid sequence), according to the methods described herein depend upon, for example, the form of the inhibitor, its potency, and the extent to which symptoms, markers, or indicators of a condition described herein are desired to be reduced, for example the percentage Generally, the dosage will vary with the age, condition, and sex of the patient and can be determined by one of skill in the art. The dosage can also be adjusted by the individual physician in the event of any complication.

The efficacy of a nucleic acid sequence comprising a sequence encoding a GATA-binding factor 1 (GATA1) polypeptide as disclosed herein (and/or a vector or virus particle comprising such a nucleic acid sequence) in, e.g. the treatment of DBA or any other condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms; or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of DBA.

In one aspect of any of the embodiments, described herein is a method of restoring early erythroid progenitor cell-specific GATA1 expression, the method comprising contacting a population of cells comprising early erythroid progenitor cells with a nucleic acid sequence, particle, or composition as described herein.

In some embodiments of any of the aspects, the early erythroid progenitor cells comprise a DBA-associated gene mutation including but not limited to the ones listed in Table 5. In some embodiments of any of the aspects, the erythroid progenitor cells comprise one or more DBA-associated gene mutations. DBA-associated gene mutations are well-known in the art and include but are not limited to mutations listed in Table 5 (e.g., see Int J Hematol. 2010 October; 92(3): 413-8).

TABLE 5

Exemplary DBA-associated gene mutations

| Gene Name | Exemplary DBA-associated cDNA mutations; predicted amino acid change |
|---|---|
| GALA1 | 220G>C; p.Leu74Val |
| RPL5 | c.535C>T; p.Arg179X |
| RPL11 | c.475_476ins11; p.Lys159ThrfsX39 |
| RPS19 | c.49G>C; p.Ala17Pro |

In some embodiments of any of the aspects, the level of GATA-1 can be measured, by way of non-limiting example, by Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy and/or immunoelectrophoresis assay.

RNA and/or DNA molecules can be isolated, derived, or amplified from a biological sample, such as a blood sample. Techniques for the detection of mRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments of any of the aspects, the level of an mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. “Next Generation Genome Sequencing” Ed. Michal Janitz, Wiley-VCH; “High-Throughput Next Generation Sequencing” Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In some embodiments of any of the aspects, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments of any of the aspects, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled reagent is exposed to light of the proper wavelength, its presence can then be detected due to fluorescence. In some embodiments of any of the aspects, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g. umbelliferone; benzamide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc.; BODIPY dyes and quinoline dyes. In some embodiments of any of the aspects, a detectable label can be a radiolabel including, but not limited to 3H, 125I, 35S, 14C, 32P, and 33P. In some embodiments of any of the aspects, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments of any of the aspects, a detectable label is a chemiluminescent label, including, but not limited to lucigenin, luminol, luciferin, isoluminol, theromatic acridinium ester, imidazole, acridinium salt and oxalate ester. In some embodiments of any of the aspects, a detectable label can be a spectral colorimetric label including, but not limited to colloidal gold or colored glass or plastic (e.g., polystyrene, polypropylene, and latex) beads.

In some embodiments of any of the aspects, detection reagents can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, CA A reagent can also be detectably labeled using fluorescence emitting metals such as 152Eu, or others of the lanthanide series. These metals can be attached to the reagent using such metal chelating groups as diethylenetriaminepentaacetic acid (DTPA) or ethylenediaminetetraacetic acid (EDTA).

A level which is less than a reference level can be a level which is less by at least about 5%, at least about 10%, at least about 15%, at least about 20%, at least about 50%, at least about 60%, at least about 80%, at least about 90%, or less relative to the reference level. In some embodiments of any of the aspects, a level which is less than a reference level can be a level which is statistically significantly less than the reference level.

A level which is more than a reference level can be a level which is greater by at least about 10%, at least about 20%, at least about 50%, at least about 60%, at least about 80%, at least about 90%, at least about 100%, at least about 200%, at least about 300%, at least about 500% or more than the reference level. In some embodiments of any of the aspects, a level which is more than a reference level can be a level which is statistically significantly greater than the reference level.

In some embodiments of any of the aspects, the reference can be a level of the target in a population of subjects who do not have or are not diagnosed as having, and/or do not exhibit signs or symptoms of lung infection and/or lung inflammation. In some embodiments of any of the aspects, the reference can also be a level of the target in a control sample, a pooled sample of control individuals or a numeric value or range of values based on the same. In some embodiments of any of the aspects, the reference can be the level of a target in a sample obtained from the same subject at an earlier point in time, e.g., the methods described herein can be used to determine if a subject's sensitivity or response to a given therapy is changing over time.

In some embodiments of the foregoing aspects, the expression level of a given gene can be normalized relative to the expression level of one or more reference genes or reference proteins.

In some embodiments of any of the aspects, the reference level can be the level in a sample of similar cell type, sample type, sample processing, and/or obtained from a subject of similar age, sex and other demographic parameters as the sample/subject for which the level of neutrophil accumulation and/or polyP is to be determined. In some embodiments of any of the aspects, the test sample and control reference sample are of the same type, that is, obtained from the same biological source, and comprising the same composition, e.g. the same number and type of cells.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, a tumor sample, biofluid sample; blood; serum; plasma; urine; sperm; mucus; tissue biopsy; organ biopsy; synovial fluid; bile fluid; cerebrospinal fluid; mucosal secretion; effusion; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be a lung sample, lung aspirate, sputum sample, airway sample, serum sample, or the like.

The test sample can be obtained by removing a sample from a subject, but can also be accomplished by using a previously isolated sample (e.g. isolated at a prior timepoint and isolated by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, filtration, thawing, purification, and any combinations thereof. In some embodiments of any of the aspects, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a condition. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

The terms "miRNA" and "microRNA" refer to 21-25 nt non-coding RNAs derived from endogenous genes. They are processed from longer (ca. 75 nt) hairpin-like precursors termed pre-miRNAs. MicroRNAs assemble in complexes termed miRNPs and recognize their targets by antisense complementarity. If the microRNAs match 100% their target, i.e., the complementarity is complete, the target mRNA is cleaved, and the miRNA acts like a siRNA. If the match is incomplete, i.e., the complementarity is partial, then the translation of the target mRNA is blocked.

The terms "miRNA target site" or "microRNA target site" refers to a specific target binding sequence of a microRNA in a mRNA target. Complementarity between the miRNA and its target site need not be perfect.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "Erythropoiesis" is the process which produces red blood cells, which is the development from erythropoietic stem cell to mature red blood cell. As used herein, the term "erythroid cells" refers to red blood cells.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect of any of the embodiments, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments of any of the aspects, the expression of a biomarker(s), target(s), or gene/polypeptide described herein is/are tissue-specific. In some embodiments of any of the aspects, the expression of a biomarker(s), target(s), or gene/polypeptide described herein is/are global. In some embodiments of any of the aspects, the expression of a biomarker(s), target(s), or gene/polypeptide described herein is systemic.

As used herein, "expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, "5'UTR" or "5' untranslated region" or "5' leader sequence" refers to regions of an mR A that are not translated. A 5'UTR typically begins at the transcription start site and ends just before the translation initiation site or start codon (usually AUG in an mRNA, ATG in a DNA sequence) of the coding region. The length of the 5'UTR may be modified by mutation for example substitution, deletion or insertion of the 5'UTR. The 5'UTR may be further modified by mutating a naturally occurring start codon or translation initiation site such that the codon no longer functions as start codon and translation may initiate at an alternate initiation site.

As used herein, an "expression enhancer", an "enhancer sequence" or an "enhancer element", refers to a nucleic acid sequence that can enhance expression of a downstream heterologous open reading frame (ORF) to which they are operably linked to.

As used herein, the term "post-transcriptional regulation", refers to the control of gene expression at the RNA level, between the transcription and the translation of the gene.

As used herein, the term "operably linked" refers to sequences that interact either directly or indirectly to carry out an intended function, e.g. the mediation or modulation of expression of a nucleic acid sequence. The interaction of operatively linked sequences may, for example, be mediated by proteins that interact with the operatively linked sequences. Typically, it refers to the functional relationship of a transcriptional regulatory sequence to a transcribed sequence. For example, a promoter sequence is operably linked to an open reading frame if it stimulates or modulates the transcription of the open reading frame in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the open reading frame s whose transcription they enhance.

“Marker” in the context of the present invention refers to an expression product, e.g., nucleic acid or polypeptide which is differentially present in a sample taken from subjects having increased neutrophil accumulation and/or polyP, as compared to a comparable sample taken from control subjects (e.g., a healthy subject). The term “biomarker” is used interchangeably with the term “marker.”

In some embodiments of any of the aspects, the methods described herein relate to measuring, detecting, or determining the level of at least one marker. As used herein, the term “detecting” or “measuring” refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, “engineered” refers to the aspect of having been manipulated by the hand of man. For example, a polypeptide is considered to be “engineered” when at least one aspect of the polypeptide, e.g., its sequence, has been manipulated by the hand of man to differ from the aspect as it exists in nature. As is common practice and is understood by those in the art, progeny of an engineered cell are typically still referred to as “engineered” even though the actual manipulation was performed on a prior entity.

As used herein, the term “distal” refers to a nucleic acid sequence upstream of the gene that may contain additional regulatory elements (e.g. distal promoter elements are regulatory DNA sequences that can be many kilobases distant from the gene that they regulate). Each strand of DNA or RNA has a 5' end and a 3' end, so named for the carbon position on the deoxyribose (or ribose) ring. As used herein, the term “upstream” refers to the relative positions of the genetic code in DNA and/or RNA. the 5' to 3' direction respectively in which RNA transcription takes place.

The term “exogenous” refers to a substance present in a cell other than its native source. The term “exogenous” when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, “exogenous” can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term “endogenous” refers to a substance that is native to the biological system or cell. As used herein, “ectopic” refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments of any of the aspects, a nucleic acid described herein, e.g., an inhibitory nucleic acid is or is provided or administered when it is comprised by a vector. In some of the aspects described herein, a nucleic acid sequence is operably linked to a vector. The term “vector”, as used herein, refers to a nucleic acid construct designed for delivery to a host cell or for transfer between different host cells. As used herein, a vector can be viral or non-viral.

The term “vector” encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. A vector can be a plasmid or lentiviral vector.

As used herein, the term “viral vector” refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By “recombinant vector” is meant a vector that includes a heterologous nucleic acid sequence, or “transgene” that is capable of expression in vivo. It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration. In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

As used herein, the term “heterologous” means a nucleic acid sequence or polypeptide that originates from a foreign species, or that is substantially modified from its original form if from the same species.

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

The term "regulatory sequence" is intended to include promoters, enhancers and other expression control elements (e.g., polyadenylation signals) that control the transcription or translation of a gene they are operably linked to. Such regulatory sequences are described, for example, in Goeddel; Gene Expression Technology. Methods in Enzymology 185, Academic Press, San Diego, Calif. (1990). Examples of regulatory sequences for mammalian host cell expression include viral elements that direct high levels of protein expression in mammalian cells, such as promoters and/or enhancers derived front cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter, Elongation factor 1-alpha 1 (eEF1a1) promoter or β-globin promoter. A eukaryotic promoter is a regulatory region of DNA located upstream of a gene that binds transcription factor II D (TFIID) and allows the subsequent coordination of components of the transcription initiation complex, facilitating recruitment of RNA polymerase II and initiation of transcription. Genes with complex promoters are likely to make use of regulatory elements, such as enhancers and silencers, selectively, allowing varying levels of expression as required.

As used herein, the terms "treat" "treatment," "treating," or "amelioration" refer to therapeutic treatments, wherein the object is to reverse, alleviate, ameliorate, inhibit, slow down or stop the progression or severity of a condition associated with a disease or disorder, e.g. a lung infection and/or lung inflammation. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments of any of the aspects, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments of any of the aspects, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Some embodiments of the technology described herein can be defined according to any of the following numbered paragraphs:

1. A nucleic acid sequence comprising
   a. at least one heterologous regulatory sequence selected from an hematopoietic enhancer element and miRNA binding site for a HSC restricted miRNA; and
   b. a sequence encoding a GATA-binding factor 1 (GATA1) polypeptide.
2. The nucleic acid sequence of paragraph 1, comprising at least one hematopoietic enhancer element.

3. The nucleic acid sequence of paragraph 2, wherein the enhancer element comprises a sequence of at least 80% homology to a nucleotide sequence that is selected from the group consisting of: SEQ ID NO: 10, SEQ ID NO: 11, SEQ ID NO: 12, SEQ ID NO: 38 and/or SEQ ID NO: 39.
4. The nucleic acid sequence of paragraph 2, wherein the enhancer element comprises an enhancer element of a gene selected from the group consisting of:
   Kell metalloendopeptidase (KEL); 5' aminolevulinate synthase 2 (ALAS2); and glycophorin A (GYPA).
5. The nucleic acid sequence of any of paragraphs 1-4, comprising at least one miRNA binding site for at least one HSC-restricted miRNA.
6. The nucleic acid sequence of any of paragraphs 1-5, wherein the at least one miRNA binding site for at least one HSC-restricted miRNA is selected from the group consisting of miR binding sites for miR10aT, miR125, miR155, miR130aT, miR142T, miR196bT, miR99, miR126miR126, miR181, miR193, miR223T, miR542, and let7e.
7. The nucleic acid sequence of any of paragraphs 1-6, comprising at least one hematopoietic enhancer element and at least one miRNA binding site for at least one HSC-restricted miRNA.
8. The nucleic acid sequence of any of paragraphs 1-7, further comprising:
   a. a heterologous 5' UTR comprising:
      i. a 5'UTR sequence of a hematopoietic transcription factor other than GATA1;
      ii. a sequence of at least 20 nucleotide acids; and/or
      iii. 1-25 upstream codons uAUGs; and/or
   b. a hematopoietic enhancer minigene.
9. A nucleic acid sequence comprising
   a. a 5' UTR comprising;
      i. a 5'UTR sequence of a hematopoietic transcription factor other than GATA1;
      ii. a sequence of at least 20 nucleotide acids; and/or
      iii. 1-25 upstream codons uAUGs.
   b. a sequence encoding a GATA-binding factor 1 (GATA1) polypeptide.
10. The nucleic acid sequence of any of paragraphs 1-9, wherein the 5'UTR comprises a 5'UTR of a gene selected from the group consisting of: Runt-related transcription factor 1 (RUNX1), LIM Domain Only 2 (LMO2), or ETS Variant 6 (ETV6).
11. The nucleic acid sequence of any of paragraphs 1-10, further comprising at least one hematopoietic enhancer element, miRNA binding site for a HSC restricted miRNA, and/or a hematopoietic enhancer minigene (G1HEM).
12. A nucleic acid sequence comprising
   a. an hematopoietic enhancer minigene (G1HEM);
   b. a sequence encoding a GATA-binding factor 1 (GATA1) polypeptide.
13. The nucleic acid sequence of paragraph 12, wherein the hematopoietic enhancer minigene (mG1HEM) comprises a sequence of at least 80% homology to a nucleotide sequence of: SEQ ID NO: 13.
14. The nucleic acid sequence of any of paragraphs 12-13, further comprising a 5' UTR comprising;
   i. a 5'UTR sequence of a hematopoietic transcription factor other than GATA1;
   ii. a sequence of at least 20 nucleotide acids; and/or
   iii. 1-25 upstream codons uAUGs; and/or
   at least one hematopoietic enhancer element; and/or at least one miRNA binding site for a HSC restricted miRNA.
15. The nucleic acid sequence of paragraph 14, wherein the 5' UTR sequence of a hematopoietic transcription factor other than GATA1 is a 5'UTR sequence of a; a gene selected from the group consisting of: Runt-related transcription factor 1 (RUNX1), at least one hematopoietic enhancer element; and/or at least one miRNA binding site for a HSC restricted miRNA.
16. The nucleic acid sequence of any of paragraphs 1-15, wherein the binding site for at least one HSC restricted miRNA comprises a sequence selected from SEQ ID NOs: 31-37 and 43-55.
17. The nucleic acid sequence of any of paragraphs 1-16, wherein the hematopoietic enhancer element comprises a sequence with at least 80% sequence identity to a sequence selected from SEQ ID NOs: 10, 11, 12, 38, and 39.
18. The nucleic acid sequence of any of paragraphs 1-17, wherein the 5' UTR sequence comprises a sequence with at least 80% sequence identity to a sequence selected from SEQ ID NOs: 14, 15, and 16.
19. The nucleic acid sequence of any of paragraphs 1-18, wherein the sequence comprises a promoter operably linked to the elements of a. and b.
20. The nucleic acid sequence of paragraph 19, wherein the promoter is not a GATA1 promoter.
21. The nucleic acid sequence of paragraph 20, wherein the promoter comprises a promoter sequence of Elongation factor 1-alpha 1 (eEF1a1).
22. The nucleic acid sequence of any of paragraphs 1-21, wherein the sequence encoding a GATA-binding factor 1 (GATA1) polypeptide comprises at least 60% sequence identity to a nucleotide sequence encoding a human GATA1 polypeptide.
23. The nucleic acid sequence of any of paragraphs 1-22, further comprising:
   a posttranscriptional regulatory element operably linked to the sequence encoding the GATA1 polypeptide.
24. The nucleic acid sequence of paragraph 23, wherein the posttranscriptional regulatory element comprises a Woodchuck Hepatitis Virus Posttranscriptional Regulatory Element (WPRE).
25. The nucleic acid sequence of any of paragraphs 1-24, further comprising an internal ribosome entry site.
26. The nucleic acid sequence of paragraph 25, wherein the internal ribosome entry site is operably linked to a marker gene and wherein the marker gene encodes an optically visible protein or an enzyme.
27. The nucleic acid sequence of any of paragraphs 1-26, wherein the sequence comprises a sequence selected from SEQ ID NOs 8, 9, 61, and 62.
28. The nucleic acid sequence of any of paragraphs 1-27, wherein the nucleic acid sequence is a vector.
29. The nucleic acid sequence of paragraph 28, wherein the vector is a plasmid, or an adenoviral, lentiviral or retroviral vector.
30. A lentiviral particle comprising the nucleic acid sequence of any of paragraphs 1-30.
31. A composition comprising a nucleic acid sequence or particle of any of paragraphs 1-31 and a pharmaceutically acceptable carrier.
32. A method of treating Diamond-Blackfan Anemia in a subject in need thereof, the method comprising administering a therapeutically effective amount of a nucleic acid sequence, particle, or composition of any of paragraphs 1-31 to the patient.

33. A method of restoring early erythroid progenitor cell-specific GATA1 expression, the method comprising contacting a population of cells comprising early erythroid progenitor cells with a nucleic acid sequence, particle, or composition of any of paragraphs 1-31.

34. The method of paragraph 33, wherein the early erythroid progenitor cells comprise a DBA-associated gene mutation.

Some embodiments of the technology described herein can be defined according to any of the following numbered paragraphs:

1. A nucleic acid sequence comprising
   a. at least one heterologous regulatory sequence selected from an hematopoietic enhancer element and miRNA binding site for a HSC restricted miRNA; and
   b. a sequence encoding a GATA-binding factor 1 (GATA1) polypeptide.
2. The nucleic acid sequence of paragraph 1, comprising at least one hematopoietic enhancer element.
3. The nucleic acid sequence of paragraph 2, wherein the enhancer element comprises a sequence of at least 80% homology to a nucleotide sequence that is selected from the group consisting of: SEQ ID NO: 10, SEQ ID NO: 11, SEQ ID NO: 12, SEQ ID NO: 38 and/or SEQ ID NO: 39.
4. The nucleic acid sequence of paragraph 2, wherein the enhancer element comprises an enhancer element of a gene selected from the group consisting of:
   Kell metalloendopeptidase (KEL); 5' aminolevulinate synthase 2 (ALAS2); and glycophorin A (GYPA).
5. The nucleic acid sequence of any of paragraphs 1-4, comprising at least one miRNA binding site for at least one HSC-restricted miRNA.
6. The nucleic acid sequence of any of paragraphs 1-5, wherein the at least one miRNA binding site for at least one HSC-restricted miRNA is selected from the group consisting of miR binding sites for miR10aT, miR125, miR155, miR130aT, miR142T, miR196bT, miR99, miR126miR126, miR181, miR193, miR223T, miR542, and let7e.
7. The nucleic acid sequence of any of paragraphs 1-6, comprising at least one hematopoietic enhancer element and at least one miRNA binding site for at least one HSC-restricted miRNA.
8. The nucleic acid sequence of any of paragraphs 1-7, further comprising:
   a. a heterologous 5' UTR comprising:
      i. a 5'UTR sequence of a hematopoietic transcription factor other than GATA1;
      ii. a sequence of at least 20 nucleotide acids; and/or
      iii. 1-25 upstream codons uAUGs; and/or
   b. a hematopoietic enhancer minigene.
9. A nucleic acid sequence comprising
   a. a 5' UTR comprising;
      i. a 5'UTR sequence of a hematopoietic transcription factor other than GATA1;
      ii. a sequence of at least 20 nucleotide acids; and/or
      iii. 1-25 upstream codons uAUGs.
   b. a sequence encoding a GATA-binding factor 1 (GATA1) polypeptide.
10. The nucleic acid sequence of any of paragraphs 1-9, wherein the 5'UTR comprises a 5'UTR of a gene selected from the group consisting of: Runt-related transcription factor 1 (RUNX1), LIM Domain Only 2 (LMO2), or ETS Variant 6 (ETV6).
11. The nucleic acid sequence of any of paragraphs 1-10, further comprising at least one hematopoietic enhancer element, miRNA binding site for a HSC restricted miRNA, and/or a hematopoietic enhancer minigene (G1HEM).
12. A nucleic acid sequence comprising
   a. an hematopoietic enhancer minigene (G1HEM);
   b. a sequence encoding a GATA-binding factor 1 (GATA1) polypeptide.
13. The nucleic acid sequence of paragraph 12, wherein the hematopoietic enhancer minigene (mG1HEM) comprises a sequence of at least 80% homology to a nucleotide sequence of: SEQ ID NO: 13.
14. The nucleic acid sequence of any of paragraphs 12-13, further comprising a 5' UTR comprising;
   i. a 5'UTR sequence of a hematopoietic transcription factor other than GATA1;
   ii. a sequence of at least 20 nucleotide acids; and/or
   iii. 1-25 upstream codons uAUGs; and/or
   at least one hematopoietic enhancer element; and/or at least one miRNA binding site for a HSC restricted miRNA.
15. The nucleic acid sequence of paragraph 14, wherein the 5' UTR sequence of a hematopoietic transcription factor other than GATA1 is a 5'UTR sequence of a; a gene selected from the group consisting of: Runt-related transcription factor 1 (RUNX1), at least one hematopoietic enhancer element; and/or at least one miRNA binding site for a HSC restricted miRNA.
16. The nucleic acid sequence of any of paragraphs 1-15, wherein the binding site for at least one HSC restricted miRNA comprises a sequence selected from SEQ ID NOs: 31-37 and 43-55.
17. The nucleic acid sequence of any of paragraphs 1-16, wherein the hematopoietic enhancer element comprises a sequence with at least 80% sequence identity to a sequence selected from SEQ ID NOs: 10, 11, 12, 38, and 39.
18. The nucleic acid sequence of any of paragraphs 1-17, wherein the 5' UTR sequence comprises a sequence with at least 80% sequence identity to a sequence selected from SEQ ID NOs: 14, 15, and 16.
19. The nucleic acid sequence of any of paragraphs 1-18, wherein the sequence comprises a promoter operably linked to the elements of a. and b.
20. The nucleic acid sequence of paragraph 19, wherein the promoter is not a GATA1 promoter.
21. The nucleic acid sequence of paragraph 20, wherein the promoter comprises a promoter sequence of Elongation factor 1-alpha 1 (eEF1a1).
22. The nucleic acid sequence of any of paragraphs 1-21, wherein the sequence encoding a GATA-binding factor 1 (GATA1) polypeptide comprises at least 60% sequence identity to a nucleotide sequence encoding a human GATA1 polypeptide.
23. The nucleic acid sequence of any of paragraphs 1-22, further comprising:
   a posttranscriptional regulatory element operably linked to the sequence encoding the GATA1 polypeptide.
24. The nucleic acid sequence of paragraph 23, wherein the posttranscriptional regulatory element comprises a Woodchuck Hepatitis Virus Posttranscriptional Regulatory Element (WPRE).

25. The nucleic acid sequence of any of paragraphs 1-24, further comprising an internal ribosome entry site.
26. The nucleic acid sequence of paragraph 25, wherein the internal ribosome entry site is operably linked to a marker gene and wherein the marker gene encodes an optically visible protein or an enzyme.
27. The nucleic acid sequence of any of paragraphs 1-26, wherein the sequence comprises a sequence selected from SEQ ID NOs 8, 9, 61, and 62.
28. The nucleic acid sequence of any of paragraphs 1-27, wherein the nucleic acid sequence is a vector.
29. The nucleic acid sequence of paragraph 28, wherein the vector is a plasmid, or an adenoviral, lentiviral or retroviral vector.
30. A lentiviral particle comprising the nucleic acid sequence of any of paragraphs 1-30.
31. A composition comprising a nucleic acid sequence or particle of any of paragraphs 1-31 and a pharmaceutically acceptable carrier.
32. A method of treating Diamond-Blackfan Anemia in a subject in need thereof, the method comprising administering a therapeutically effective amount of a nucleic acid sequence, particle, or composition of any of paragraphs 1-31 to the patient.
33. A method of restoring early erythroid progenitor cell-specific GATA1 expression, the method comprising contacting a population of cells comprising early erythroid progenitor cells with a nucleic acid sequence, particle, or composition of any of paragraphs 1-31.
34. The method of paragraph 33, wherein the early erythroid progenitor cells comprise a DBA-associated gene mutation.
35. A nucleic acid sequence, particle, or composition of any of paragraphs 1-31 for use in the treatment of Diamond-Blackfan Anemia in a subject in need thereof.

The technology described herein is further illustrated by the following examples which in no way should be construed as being further limiting.

EXAMPLES

Example 1: Methods for the Treatment of DBA Using Gata1 Gene Therapy

Diamond-Blackfan anemia (DBA), also known as congenital hypoplastic anemia, is a condition that was first described in 1938 and is characterized by a paucity of red blood cell progenitors and precursors in the bone marrow of patients, while all other aspects of hematopoiesis occur in an ostensibly normal manner (1, 2). DBA is estimated to occur in approximately 1 in 100,000 to 200,000 live births (3), although this may be an underestimate given a number of individuals who have been found to have variable expressivity or who may have been misdiagnosed. For many decades, the diagnosis of DBA was made primarily based upon clinical criteria and was assisted by the use of the biomarker erythrocyte adenosine deaminase, which is elevated in ~80% of patients with DBA (3).

After an extensive mapping effort that spanned much of the 1990s, the first gene mutated in DBA was discovered in 1999 through the identification of an individual with a translocation on chromosome 19 (4). Surprisingly, heterozygous loss of function mutations were identified in ~20-25% of DBA cases in this initial mutated gene, which was a ubiquitously expressed ribosomal protein (RP) gene, RPS19. This immediately raised a lot of speculation about underlying mechanisms and whether a ribosomal or non-ribosomal role for RPS19 may be involved. A number of subsequent studies demonstrated that impaired ribosome biogenesis appeared to be a major contributor to this phenotype as a result of RP haploinsufficiency, suggesting a role for ribosome activity/levels in this phenotype (5). However, the underlying basis for the erythroid-specificity of this disorder remained a mystery.

Subsequent studies in cohorts of patients with DBA that either employed targeting sequencing, assessment of copy number variation using single nucleotide polymorphism microarrays/comparative genomic hybridization, or whole exome sequencing have revealed a total of 19 distinct RPs harboring heterozygous loss of function mutations that result in RP haploinsufficiency (6, 7). Collectively, these mutations explain the cause in ~60-80% of DBA cases. These 19 RP gene mutations are heterogeneously distributed throughout the ribosome and involve both the large (60 S) and small (40 S) subunits of the ribosome. There is no clustering of mutations on a particular structural region of the ribosome (8). More recently, through whole exome sequencing on a cohort of over 450 patients with a diagnosis of DBA, the inventors have now identified an additional 7 RP gene mutations, bringing the total number of RP genes implicated in this disorder to 26 that collectively explain the underlying basis of ~80% of DBA cases (nearly ⅓ of RPs composing the ribosome) (9).

Despite the advances in understanding the majority of genetic causes of DBA, there have been two major limitations that have been present. Despite the robust findings of heterozygous RP loss of function mutations in the majority of DBA cases, how this can lead to the erythroid-specific hematopoietic defects in DBA has remained an enigma (10). Secondly, there are very limited therapies available to treat patients with DBA at the current time (3, 10). Some patients respond to corticosteroids, but there are often significant side effects limiting the long-term effectiveness of this therapy in the majority of patients. Many patients require chronic red blood cell transfusions, which can be associated with significant and difficult to control iron overload. Finally, some patients can be cured through the use of allogeneic bone marrow transplantation, but in general this is limited to those with matched sibling donors, given the poor outcomes noted with unrelated donor transplantation in this condition (11). Only limited candidate experimental therapeutics have been developed to date and many have unfortunately not shown robust efficacy in later stage preclinical or clinical studies (12). Therefore, there is a significant need for new and improved therapies for DBA that could be effective in the majority of patients with this condition, which is due to a large number of distinct mutations primarily affecting RP genes.

With these limitations in mind, the inventors reasoned that further study of DBA through the use of human genetics coupled with mechanistic follow up could give us further insight into this disorder and allow us to identify improved therapeutic strategies. The inventors subsequently identified the first non-RP gene mutation in this disorder. The inventors identified several patients with a diagnosis of DBA who had mutations that impaired the production of the long protein form of the hematopoietic master transcription factor GATA1 (13). Several other patients with similar types of mutations were subsequently reported, as well (14-16). While these findings demonstrated that GATA1 mutations could cause a phenotype resembling DBA, whether there was a molecular connection between the more commonly observed RP gene mutations and the GATA1 mutations remained unclear.

The inventors tested whether RP haploinsufficiency—the most common cause of DBA—could alter GATA1 translation. The inventors could demonstrate using both RP suppression in primary human hematopoietic stem and progenitor cells (HSPCs) and in DBA patient samples that GATA1 mRNA translation was impaired in the setting of RP haploinsufficiency, while a variety of other erythroid-important transcripts were not affected in terms of their translation in this setting (15). Moreover, the inventors demonstrated that increasing GATA1 protein levels through lentiviral expression was sufficient to rescue the erythroid differentiation defect present in mononuclear cells from DBA patients with various RP gene mutations (to the level that is seen in normal individuals). These results produced a model, as illustrated in FIG. 1, regarding the pathogenesis of DBA.

However, a number of questions have remained. (1) It was unclear exactly how the ribosome was being altered in the setting of RP haploinsufficiency. It was possible that the ribosome may be altered in composition in this case, although the finding of 28 distinct RP mutations in this condition made this seem less likely. An alternative, although not mutually exclusive, possibility was that ribosome levels were reduced in the setting of RP haploinsufficiency. (2) The range of transcripts beyond those that were specifically tested in initial studies and the features common to those transcripts remained unclear. (3) The stage of hematopoiesis at which these defects emerged was also unclear.

The inventors then employed a ribosome profiling approach to better understand at a genomic level what transcripts were affected by this reduction in ribosome levels due to DBA-associated molecular lesions (19, 20). The inventors were able to obtain high quality ribosome profiling data from RP haploinsufficient HSPCs undergoing erythroid lineage commitment—a stage at which the functional defects in erythroid differentiation arise. Importantly, through analysis of this data, the inventors could show that a limited set of ~500 transcripts display the most significant changes in translation efficiency in the setting of RP haploinsufficiency (similar for RPS19 or RPL5 suppression). Consistent with the inventors earlier targeted findings from polysome analysis, GATA1 mRNA was among the most downregulated transcripts in terms of translation efficiency. Interestingly, the majority of other transcripts showing translational downregulation were all components of the ribosome or ribosome-associated factors, including all RPs and a variety of translation initiation and elongation factors. Upon further analysis by using cap analysis of gene expression to define 5' untranslated regions (UTRs) for these transcripts, the inventors could show that those transcripts that were most highly translated at baseline and which had short and unstructured 5' UTRs tended to be the ones that were downregulated at the translational level in the setting of RP haploinsufficiency. Interestingly, among all hematopoietic master transcript factors, only GATA1 has a short 5' UTR and the inventors could show that replacing this 5' UTR with those of other master regulators (such as RUNX1, LMO2, or ETV6) altered the translation of this key hematopoietic transcription factor.

Figure 3:
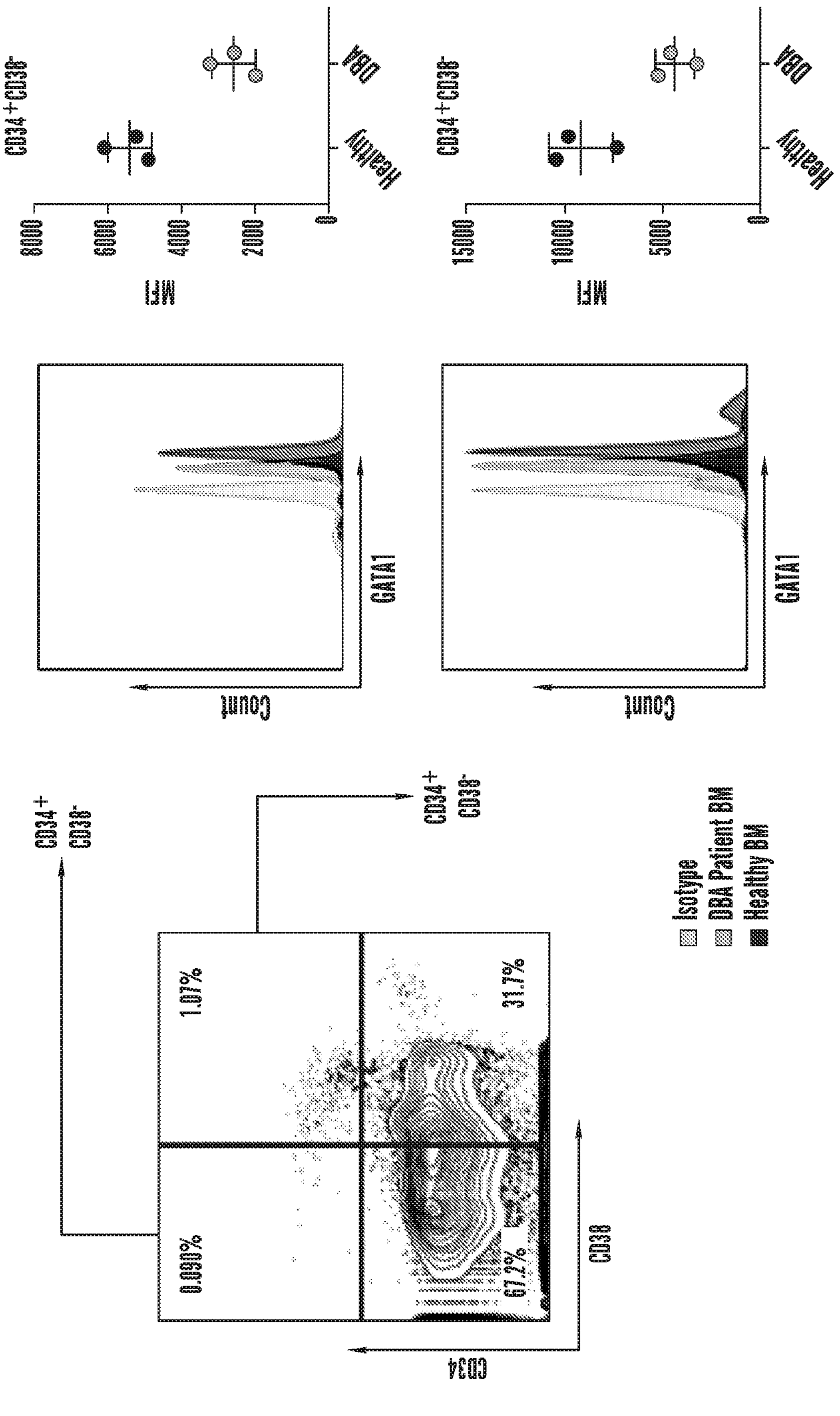
FIG. 3 demonstrates reduced GATA1 expression levels in hematopoietic stem cells (HSPCs) from DBA patients with RP gene mutations (RPS19, RPL5, and RPL35A mutations present in patients shown here).
Figure 4A:
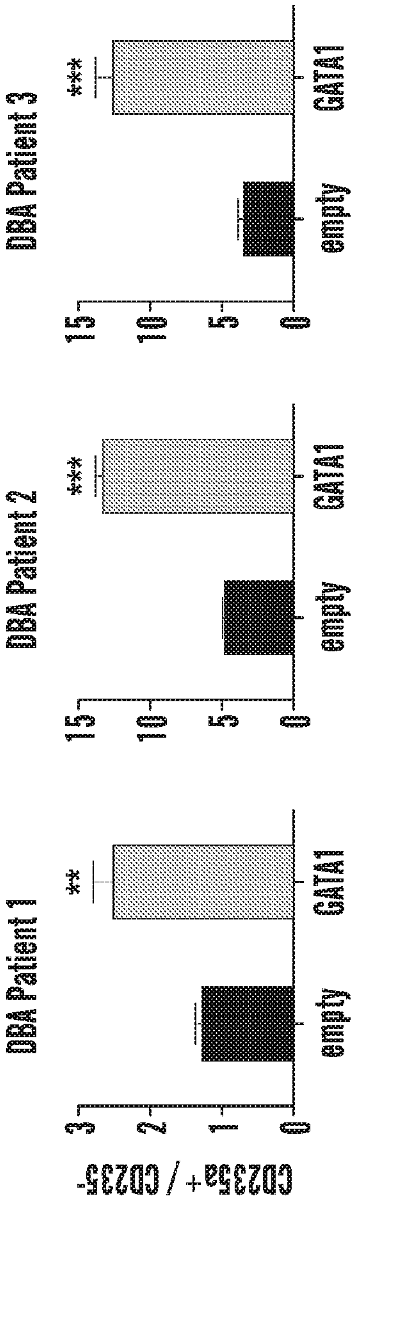
FIG. 4A, FIG. 4B, and FIG. 4C demonstrate the rescue of erythroid lineage commitment and differentiation (as assessed by morphology (FIG. 4B) and markers of terminal differentiation (FIG. 4C); bottom) in DBA patient HSPCs by GATA1 lentiviral transduction.
Figure 4C:
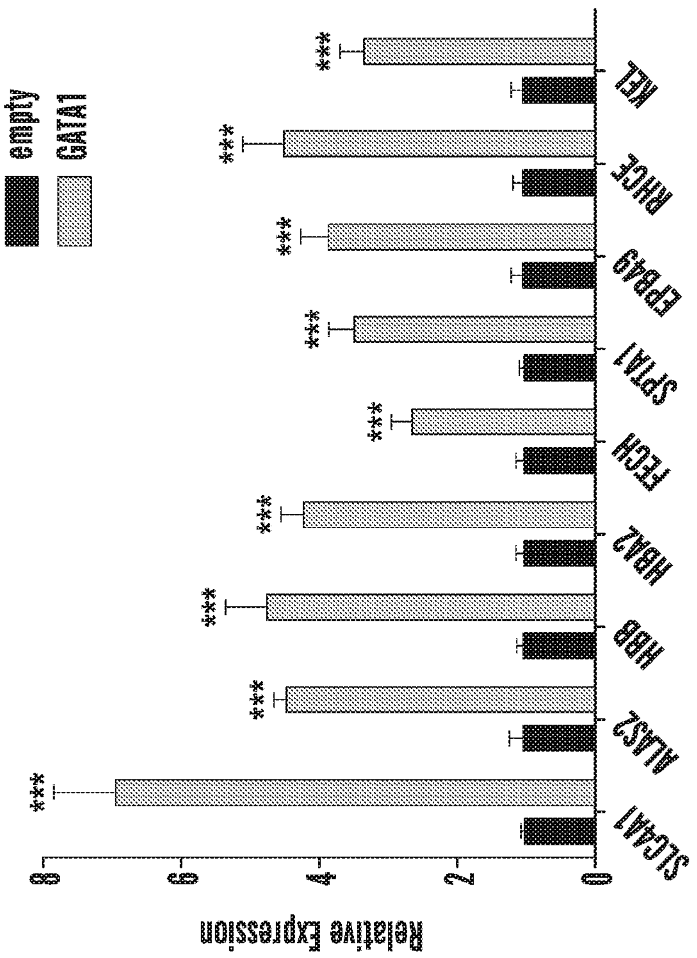
Figure 4B:
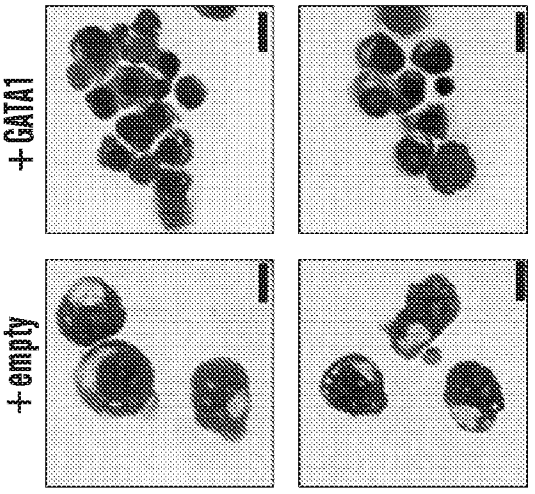

Finally, the inventors also demonstrated that this happens in vivo in DBA patients and the inventors assessed the stage of hematopoiesis at which these lesions emerge. The inventors showed by both immunohistochemistry for GATA1 in bone marrow biopsy specimens and using intracellular flow cytometry that GATA1 levels were reduced in hematopoietic progenitors from DBA patients. Importantly, the inventors demonstrated that GATA1 levels were reduced even upon its earliest expression in very primitive CD34+CD38− HSPCs from DBA patient bone marrow cells, as compared to control samples (FIG. 3). In addition, the inventors found that GATA1 levels continued to be lower in DBA patient cells, even as GATA1 levels increased in more mature CD34+CD38+ HSPCs. These results are consistent with the emerging model that hematopoietic lineage commitment occurs at the most primitive stages of stem and progenitor cells and demonstrates the relevance of these findings to human disease (21-23).

All of these mechanistic findings have important implications for improving the understanding of DBA pathogenesis. However, the challenge still remained as to how better therapies can be developed for DBA. As discussed above, the only currently available therapies are the chronic use of corticosteroids, regular blood transfusions, or allogeneic hematopoietic stem cell transplantation (10). An alternative and valuable approach would be to use autologous hematopoietic stem cell transplantation coupled to gene therapy (24). Indeed, there have been attempts to develop lentiviral vectors to allow for increased production of RPS19 (25). It is difficult to envision how this approach can be useful for the majority of patients, given the pleiotropic RP gene mutations present in DBA patients (28 mutations have been identified to date). Given the inventor's findings that impaired GATA1 protein production underlies all DBA cases and that increasing GATA1 protein is sufficient to rescue the erythroid differentiation defects present in these patients, the development of GATA1 gene therapy is a valuable approach for achieving curative treatment in DBA patients. The major limitation, as discussed in detail below, is that expression of GATA1 in the hematopoietic stem cell (HSC) compartment will cause the stem cells to differentiate precociously and the expression of GATA1 during terminal erythropoiesis needs to be regulated.

While GATA1 protein levels are suppressed in HSPCs from DBA patients and increasing GATA1 expression can ameliorate the erythroid lineage commitment defect characteristic of DBA, dysregulated expression of GATA1 can be problematic. HSCs can undergo precocious differentiation with exogenous GATA1 expression and effective terminal erythropoiesis requires regulation of GATA1 levels.

Based on the inventor's mechanistic studies, the development of GATA1 gene therapy for treatment of DBA is compelling and appears to be a promising approach. The inventors have been able to demonstrate that increasing GATA1 expression can rescue the erythroid differentiation defect in primary HSPCs from patients with DBA harboring a variety of molecular lesions in various RP genes. In addition, the inventors have also been able to show that they can regularly produce the same results across a variety of DBA-associated molecular lesions modeled in primary HSPCs through RNA interference-based approaches (15, 17). In these cases, the increased expression of GATA1 was achieved through the use of lentiviruses, where the GATA1 cDNA containing altered 5' and 3' UTR elements was under the transcriptional control of a lentiviral LTR that displays high-level and ubiquitous expression. For therapeutic purposes, such expression must be regulated and tuned at various stages of the differentiation process. GATA1 levels must be controlled to avoid any perturbations of hematopoiesis.

Prior studies have shown that exogenous unregulated expression of Gata1 in mouse HSCs can promote precocious differentiation toward the megakaryocytic and erythroid lineages, while preventing the maintenance of self-renewing HSCs capable of long-term engraftment (26, 27). Indeed, exogenous Gata1 expression can reprogram other hematopoietic lineages to take on an erythroid fate (26). However, regulated expression of a Gata1 transgene can allow long-term maintenance of HSCs (27). To bolster these findings in a human context, the inventors have utilized a serum-free culture system that allows for the maintenance of long-term engrafting human HSCs (capable of engrafting immunodeficient xenograft recipients) over the course of a few days in culture. In this setting, the introduction of exogenous GATA1 expression regulated by a lentiviral LTR element causes precocious differentiation of these cells, while the control cells maintained their phenotype and functional ability to give rise to long-term hematopoietic grafts. These findings extend the previously published results in mouse models (26). These results also collectively emphasize the need to prevent GATA1 expression in early HSCs to allow for effective engraftment, as would be required for a curative lentiviral gene therapy approach. In addition, GATA1 levels must not be excessively elevated during terminal erythroid differentiation, since this can impair effective erythropoiesis (28). To address these issues, the inventors undertook a series of studies to identify key regulatory elements that will permit regulated expression of GATA1 from lentiviral vectors.

To achieve regulated expression of GATA1 for effective gene therapy, the inventors have been employing two complementary and synergistic approaches to ensure that there will not be potentially detrimental ectopic expression, while also regulating levels of GATA1 during the course of erythroid differentiation. It is contemplated herein that either approach could be used alone, or that they can be combined.

The first regulatory element that is being used in the gene therapy vectors is a GATA1 hematopoietic enhancer minigene (G1HEM) that concatenates 4 distinct regulatory elements to achieve faithful expression of GATA1 during hematopoiesis (27, 29). These elements include a −3 kb hematopoietic enhancer, an upstream double GATA motif, an upstream CACCC box, and a segment of the first intron of GATA1. Indeed, the 979 nucleotides present in this minigene are sufficient to drive Gata1 cDNA expression appropriately to rescue a Gata1 knockout mouse and allow for ostensibly normal erythropoiesis.

For the development of the GATA1 expression vectors that are clinically usable and involve the first transcriptional regulatory element discussed above, the inventors utilize safe and well-designed vectors that have already been proven effective in human clinical studies. The pRRL.PPT.EFS vector that has demonstrated controlled and well-regulated exogenous cDNA expression in a variety of human hematopoietic cell types and which has been utilized in clinical settings (30) is one such vector. The G1HEM can be incorporated upstream of the GATA1 cDNA that is both driven by the endogenous promoter or by a modified (shortened) ubiquitous EF1α promoter (EFS), as an alternative and complementary approach. Importantly, as discussed above, the Gata1 regulatory elements contained in the G1HEM from mice are capable of driving regulated expression of marker genes solely in the cell types where Gata1 is normally expressed and are sufficient to allow appropriate rescue of knockout mice using Gata1 cDNA (27, 31).

Figure 6:
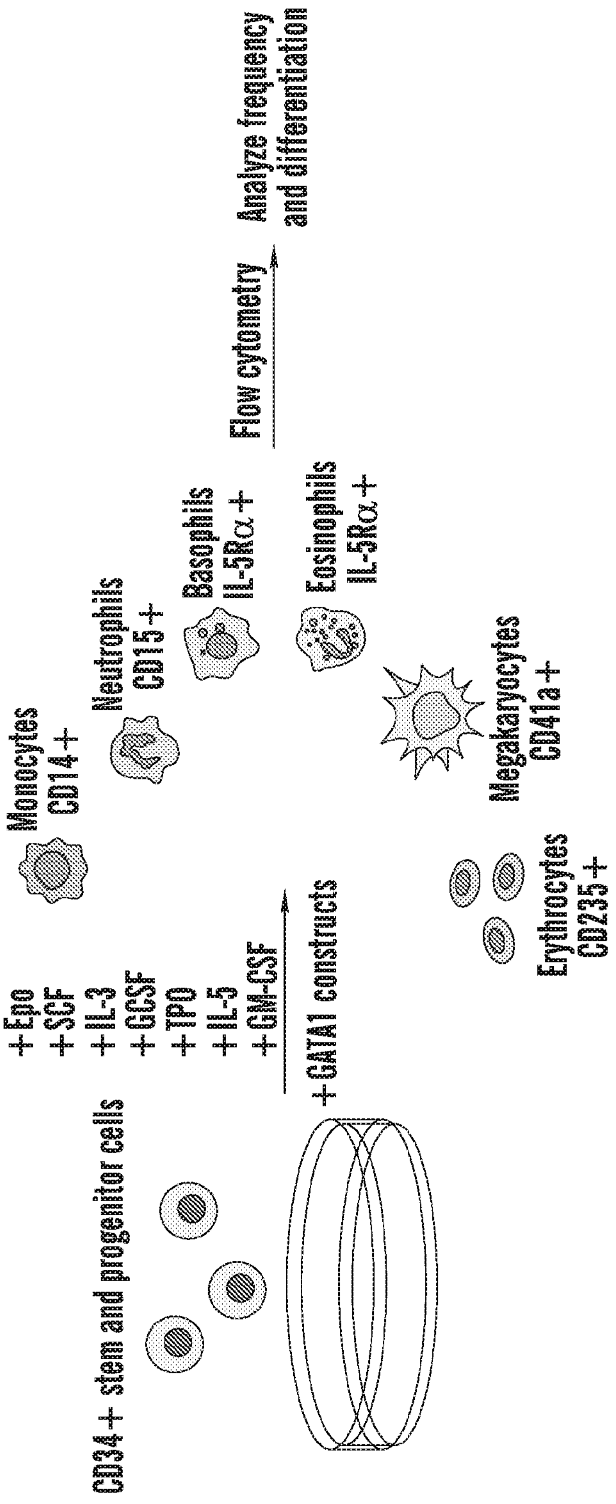
FIG. 6 depicts a schematic of the use of the claimed GATA1 vectors in primary human hematopoietic cells.

The inventors have produced a total of 4 different vectors (the 2 shown in FIG. 6, with both mouse and human regulatory elements used for all cases). The inventors incorporated a self-cleaving 2A peptide (P2A) element followed by the Venus fluorescent marker after the GATA1 cDNA to be able to readily track those cells expressing GATA1 in real time Flow cytometry assays were used to quantify the extent of Venus expression seen in the various hematopoietic cell types tested. The extent of increase in GATA1 expression in cell types that normally express this transcription factor can be assessed by performing cell sorting of particular populations. Finally, using this primary cell culture approach, the inventors can assess variation in phenotypes that occur with GATA1 expression (32-34). This powerful approach allows the inventors to simultaneously determine effectiveness, specificity, and effects upon hematopoietic differentiation using a streamlined approach that is directly relevant to the process of hematopoiesis in vivo. Every vector tested in 2-3 independent primary human hematopoietic cell samples to ascertain both specificity and effectiveness of expression.

While the transcriptional regulatory elements discussed above that compose the G1HEM permit regulated expression of GATA1 cDNA, studies have indicated that there can be leaky expression in the HSC compartment with the use of this regulatory element (27). As this could profoundly affect the ability to obtain long-term engraftment (26), expression in the HSC compartment must be prevented. To achieve this, the inventors incorporated a second gene regulatory element—binding elements for the HSC-restricted microRNA (miR), miR126, after the post transcriptional regulatory elements of the woodchuck hepatitis virus (PRE), e.g., in the modified pRRL.PPT.EES derivatives. Insertion of three repeated miR126 binding elements after the PRE prevents expression of transgenes in the HSC compartment. The inventors also modified the pRRL.PPT.EFS with the G1HEM and GATA1 cDNA to include these miR126 elements, as well. In vitro testing is performed in primary human hematopoietic cells to ensure effective and selective expression. HSCs that will be transplanted into the NOD.Cg-KitW-41J Tyr+ Prkdcscid Il2rgtm1Wj1 (NBSGW) mouse model that has previously used successfully and extensively to produce human hematopoietic xenograft models (36) can be transduced. HSC function can then be tested after 16 weeks of engraftment using phenotypic marker quantification, secondary transplantation into NBSGW recipients, and by assessing Venus expression in the phenotypic HSC compartment.

Described herein is the development of clinical-grade lentiviral vectors that permits the regulated expression of GATA1 cDNA for use in gene therapy. The studies in vitro and in vivo in primary human hematopoietic permit screening of multiple independent vectors incorporating both a critical set of transcriptional regulatory elements (the G1HEM or a derivative of it) and miR126 binding elements.

REFERENCES

1. Nathan D G, Clarke B J, Hillman D G, Alter B P, Housman D E. Erythroid precursors in congenital hypoplastic (Diamond-Blackfan) anemia. The Journal of clinical investigation. 1978; 61(2):489-98. doi: 10.1172/JCI108960. PubMed PMID: 621285; PMCID: PMC372560.
2. Iskander D, Psaila B, Gerrard G, Chaidos A, En Foong H, Harrington Y, Karnik L C, Roberts I, de la Fuente J, Karadimitris A. Elucidation of the EP defect in Diamond-Blackfan anemia by characterization and prospective isolation of human EPs. Blood. 2015; 125(16):2553-7. doi: 10.1182/blood-2014-10-608042. PubMed PMID: 25755292.
3. Vlachos A, Ball S, Dahl N, Alter B P, Sheth S, Ramenghi U, Meerpohl J, Karlsson S, Liu J M, Leblanc T, Paley C, Kang E M, Leder E J, Atsidaftos E, Shimamura A, Bessler M, Glader B, Lipton J M, Participants of Sixth Annual Daniella Maria Arturi International Consensus C. Diagnosing and treating Diamond Blackfan anaemia: results of an international clinical consensus conference. Br J Haematol. 2008; 142(6):859-76. doi: 10.1111/j.1365-2141.2008.07269.x. PubMed PMID: 18671700; PMCID: PMC2654478.

4. Draptchinskaia N, Gustavsson P, Andersson B, Pettersson M, Willig T N, Dianzani I, Ball S, Tchernia G, Klar J, Matsson H, Tentler D, Mohandas N, Carlsson B, Dahl N. The gene encoding ribosomal protein S19 is mutated in Diamond-Blackfan anaemia. Nat Genet. 1999; 21(2):169-75. doi: 10.1038/5951. PubMed PMID: 9988267.

5. Flygare J, Karlsson S. Diamond-Blackfan anemia: erythropoiesis lost in translation. Blood. 2007; 109(8):3152-4. doi: 10.1182/blood-2006-09-001222. PubMed PMID: 17164339.

6. Mirabello L, Khincha P P, Ellis S R, Giri N, Brodie S, Chandrasekharappa S C, Donovan F X, Zhou W, Hicks B D, Boland J F, Yeager M, Jones K, Zhu B, Wang M, Alter B P, Savage S A. Novel and known ribosomal causes of Diamond-Blackfan anaemia identified through comprehensive genomic characterisation. J Med Genet. 2017. doi: 10.1136/jmedgenet-2016-104346. PubMed PMID: 28280134.

7. Landowski M, O'Donohue M F, Buros C, Ghazvinian R, Montel-Lehry N, Vlachos A, Sieff C A, Newburger P E, Niewiadomska E, Matysiak M, Glader B, Atsidaftos E, Lipton J M, Beggs A H, Gleizes P E, Gazda H T. Novel deletion of RPL15 identified by array-comparative genomic hybridization in Diamond-Blackfan anemia. Hum Genet. 2013; 132(11):1265-74. doi: 10.1007/s00439-013-1326-z. PubMed PMID: 23812780; PMCID: PMC3797874.

8. Khatter H, Myasnikov A G, Natchiar S K, Klaholz B P. Structure of the human 80S ribosome. Nature. 2015; 520(7549):640-5. doi: 10.1038/nature14427. PubMed PMID: 25901680.

9. Ulirsch J C, Verboon J M, Kazerounian S, Guo M H, Yuan D, Ludwig L S, Handsaker R E, Abdulhay N J, Fiorini C, Genovese G, Lim E T, Cheng A, Cummings B B, Chao K R, Beggs A H, Genetti C A, Sieff C A, Newburger P E, Niewiadomska E, Matysiak M, Vlachos A, Lipton J M, Atsidaftos E, Glader B, Narla A, Gleizes P E, O'Donohue M F, Montel-Lehry N, Amor D J, McCarroll S A, O'Donnell-Luria A H, Gupta N, Gabriel S B, MacArthur D G, Lander E S, Lek M, Da Costa L, Nathan D G, Korostelev A A, Do R, Sankaran V G, Gazda H T. The Genetic Landscape of Diamond-Blackfan Anemia. Am J Hum Genet. 2018; 103(6):930-47. doi: 10.1016/j.ajhg.2018.10.027. PubMed PMID: 30503522.

10. Lipton J M, Ellis S R. Diamond-Blackfan anemia: diagnosis, treatment, and molecular pathogenesis. Hematology/oncology clinics of North America. 2009; 23(2): 261-82. doi: 10.1016/j.hoc.2009.01.004. PubMed PMID: 19327583; PMCID: PMC2886591.

11. Roy V, Perez W S, Eapen M, Marsh J C, Pasquini M, Pasquini R, Mustafa M M, Bredeson C N, Non-Malignant Marrow Disorders Working Committee of the International Bone Marrow Transplant R. Bone marrow transplantation for diamond-blackfan anemia. Biol Blood Marrow Transplant. 2005; 11(8):600-8. doi: 10.1016/j.bbmt.2005.05.005. PubMed PMID: 16041310.

12. Narla A, Vlachos A, Nathan D G. Diamond Blackfan anemia treatment: past, present, and future. Semin Hematol. 2011; 48(2):117-23. doi: 10.1053/j.seminhematol.2011.01.004. PubMed PMID: 21435508; PMCID: PMC3073777.

13. Sankaran V G, Ghazvinian R, Do R, Thiru P, Vergilio J A, Beggs A H, Sieff C A, Orkin S H, Nathan D G, Lander E S, Gazda H T. Exome sequencing identifies GATA1 mutations resulting in Diamond-Blackfan anemia. The Journal of clinical investigation. 2012; 122(7):2439-43. doi: 10.1172/JCI63597. PubMed PMID: 22706301; PMCID: PMC3386831.

14. Parrella S, Aspesi A, Quarello P, Garelli E, Pavesi E, Carando A, Nardi M, Ellis S R, Ramenghi U, Dianzani I. Loss of GATA-1 full length as a cause of Diamond-Blackfan anemia phenotype. Pediatr Blood Cancer. 2014; 61(7):1319-21. doi: 10.1002/pbc.24944. PubMed PMID: 24453067; PMCID: PMC4684094.

15. Ludwig L S, Gazda H T, Eng J C, Eichhorn S W, Thiru P, Ghazvinian R, George T I, Gotlib J R, Beggs A H, Sieff C A, Lodish H F, Lander E S, Sankaran V G. Altered translation of GATA1 in Diamond-Blackfan anemia. Nature medicine. 2014; 20(7):748-53. doi: 10.1038/nm.3557. PubMed PMID: 24952648; PMCID: PMC4087046.

16. Klar J, Khalfallah A, Arzoo P S, Gazda H T, Dahl N. Recurrent GATA1 mutations in Diamond-Blackfan anaemia. Br J Haematol. 2014; 166(6):949-51. doi: 10.1111/bjh.12919. PubMed PMID: 24766296.

17. Khajuria R K, Munschauer M, Ulirsch J C, Fiorini C, Ludwig L S, McFarland S K, Abdulhay N J, Specht H, Keshishian H, Mani D R, Jovanovic M, Ellis S R, Fulco C P, Engreitz J M, Schutz S, Lian J, Gripp K W, Weinberg O K, Pinkus G S, Gehrke L, Regev A, Lander E S, Gazda H T, Lee W Y, Panse V G, Carr S A, Sankaran V G. Ribosome Levels Selectively Regulate Translation and Lineage Commitment in Human Hematopoiesis. Cell. 2018; 173(1):90-103 e19. doi: 10.1016/j.cell.2018.02.036. PubMed PMID: 29551269; PMCID: PMC5866246.

18. Mills E W, Green R. Ribosomopathies: There's strength in numbers. Science. 2017; 358(6363). doi: 10.1126/science.aan2755. PubMed PMID: 29097519.

19. Ingolia N T, Ghaemmaghami S, Newman J R, Weissman J S. Genome-wide analysis in vivo of translation with nucleotide resolution using ribosome profiling. Science. 2009; 324(5924):218-23. doi: 10.1126/science.1168978. PubMed PMID: 19213877; PMCID: PMC2746483.

20. Ingolia N T. Ribosome Footprint Profiling of Translation throughout the Genome. Cell. 2016; 165(1):22-33. doi: 10.1016/j.cell.2016.02.066. PubMed PMID: 27015305; PMCID: PMC4917602.

21. Notta F, Zandi S, Takayama N, Dobson S, Gan O I, Wilson G, Kaufmann K B, McLeod J, Laurenti E, Dunant C F, McPherson J D, Stein L D, Dror Y, Dick J E. Distinct routes of lineage development reshape the human blood hierarchy across ontogeny. Science. 2016; 351(6269): aab2116. doi: 10.1126/science.aab2116. PubMed PMID: 26541609; PMCID: PMC4816201.

22. Velten L, Haas S F, Raffel S, Blaszkiewicz S, Islam S, Hennig B P, Hirche C, Lutz C, Buss E C, Nowak D, Boch T, Hofmann W K, Ho A D, Huber W, Trumpp A, Essers M A, Steinmetz L M. Human haematopoietic stem cell lineage commitment is a continuous process. Nature cell biology. 2017; 19(4):271-81. doi: 10.1038/ncb3493. PubMed PMID: 28319093; PMCID: PMC5496982.

23. Paul F, Arkin Y, Giladi A, Jaitin D A, Kenigsberg E, Keren-Shaul H, Winter D, Lara-Astiaso D, Gury M, Weiner A, David E, Cohen N, Lauridsen F K, Haas S, Schlitzer A, Mildner A, Ginhoux F, Jung S, Trumpp A, Porse B T, Tanay A, Amit I. Transcriptional Heterogeneity and Lineage Commitment in Myeloid Progenitors. Cell. 2015; 163(7):1663-77. doi: 10.1016/j.cell.2015.11.013. PubMed PMID: 26627738.

24. Sankaran V G, Weiss M I. Anemia: progress in molecular mechanisms and therapies. Nature medicine. 2015; 21(3): 221-30. doi: 10.1038/nm.3814. PubMed PMID: 25742458; PMCID: 4452951.

25. Debnath S, Jaako P, Siva K, Rothe M, Chen J, Dahl M, Gaspar H B, Flygare J, Schambach A, Karlsson S. Lentiviral Vectors with Cellular Promoters Correct Anemia and Lethal Bone Marrow Failure in a Mouse Model for Diamond-Blackfan Anemia. Molecular therapy: the journal of the American Society of Gene Therapy. 2017; 25(8):1805-14. doi: 10.1016/j.ymthe.2017.04.002. PubMed PMID: 28434866; PMCID: PMC5542636.

26. Iwasaki H, Mizuno S, Wells R A, Cantor A B, Watanabe S, Akashi K. GATA-1 converts lymphoid and myelomonocytic progenitors into the megakaryocyte/erythrocyte lineages. Immunity. 2003; 19(3):451-62. PubMed PMID: 14499119.

27. Takai J, Moriguchi T, Suzuki M, Yu L, Ohneda K, Yamamoto M. The Gata1 5' region harbors distinct cis-regulatory modules that direct gene activation in erythroid cells and gene inactivation in HSCs. Blood. 2013; 122 (20):3450-60. doi: 10.1182/blood-2013-01-476911. PubMed PMID: 24021675.

28. Whyatt D, Lindeboom F, Karis A, Ferreira R, Milot E, Hendriks R, de Bruijn M, Langeveld A, Gribnau J, Grosveld F, Philipsen S. An intrinsic but cell-nonautonomous defect in GATA-1-overexpressing mouse erythroid cells. Nature. 2000; 406(6795):519-24. doi: 10.1038/35020086. PubMed PMID: 10952313.

29. Ohneda K, Shimizu R, Nishimura S, Muraosa Y, Takahashi S, Engel J D, Yamamoto M. A minigene containing four discrete cis elements recapitulates GATA-1 gene expression in vivo. Genes Cells. 2002; 7(12):1243-54. PubMed PMID: 12485164.

30. Schambach A, Bohne J, Chandra S, Will E, Margison G P, Williams D A, Baum C. Equal potency of gammaretroviral and lentiviral SIN vectors for expression of 06-methylguanine-DNA methyltransferase in hematopoietic cells. Mol Ther. 2006; 13(2):391-400. Epub 2005/10/18. doi: 10.1016/j.ymthe.2005.08.012. PubMed PMID: 16226060.

31. Shimizu R, Hasegawa A, Ottolenghi S, Ronchi A, Yamamoto M. Verification of the in vivo activity of three distinct cis-acting elements within the Gata1 gene promoter-proximal enhancer in mice. Genes Cells. 2013; 18(11):1032-41. Epub 2013/10/15. doi: 10.1111/gtc.12096. PubMed PMID: 24118212.

32. Sankaran V G, Ludwig L S, Sicinska E, Xu J, Bauer D E, Eng J C, Patterson H C, Metcalf R A, Natkunam Y, Orkin S H, Sicinski P, Lander E S, Lodish H F. Cyclin D3 coordinates the cell cycle during differentiation to regulate erythrocyte size and number. Genes Dev. 2012; 26(18):2075-87. Epub 2012/08/30. doi: 10.1101/gad.197020.112. PubMed PMID: 22929040; PMCID: 3444733.

33. Sankaran V G, Menne T F, Scepanovic D, Vergilio J A, Ji P, Kim J, Thiru P, Orkin S H, Lander E S, Lodish H F. MicroRNA-15a and -16-1 act via MYB to elevate fetal hemoglobin expression in human trisomy 13. Proc Natl Acad Sci USA. 2011; 108(4):1519-24. Epub 2011/01/06. doi: 10.1073/pnas.1018384108. PubMed PMID: 21205891; PMCID: 3029749.

34. Sankaran V G, Xu J, Byron R, Greisman H A, Fisher C, Weatherall D J, Sabath D E, Groudine M, Orkin S H, Premawardhena A, Bender M A. A functional element necessary for fetal hemoglobin silencing. N Engl J Med. 2011; 365(9):807-14. Epub 2011/09/02. doi: 10.1056/NEJMoa1103070. PubMed PMID: 21879898; PMCID: 3174767.

35. Gentner B, Visigalli I, Hiramatsu H, Lechman E, Ungari S, Giustacchini A, Schira G, Amendola M, Quattrini A, Martino S, Orlacchio A, Dick J E, Biffi A, Naldini L. Identification of hematopoietic stem cell-specific miRNAs enables gene therapy of globoid cell leukodystrophy. Sci Transl Med. 2010; 2(58):58ra84. doi: 10.1126/scitranslmed.3001522. PubMed PMID: 21084719.

36. Fiorini C, Abdulhay N J, McFarland S K, Munschauer M, Ulirsch J C, Chiarle R, Sankaran V G. Developmentally-faithful and effective human erythropoiesis in immunodeficient and Kit mutant mice. Am J Hematol. 2017; 92(9):E513-E9. doi: 10.1002/ajh.24805. PubMed PMID: 28568895; PMCID: PMC5546987.

37. Ito E, Konno Y, Toki T, Terui K. Molecular pathogenesis in Diamond-Blackfan anemia. Int J Hematol. 2010 October; 92(3):413-8.

Figure 7:
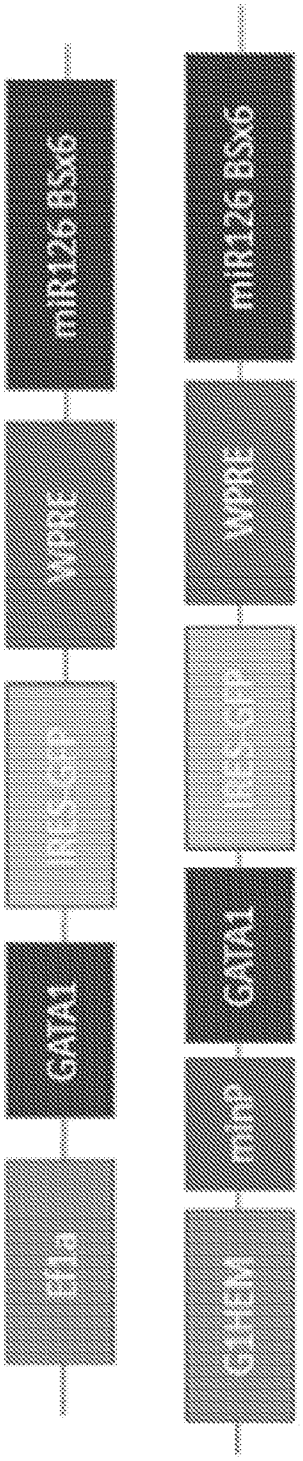
FIG. 7 depicts a schematic of the various combinations of vectors to achieve developmentally faithful expression of GATA1 in early erythroid progenitors but not in hematopoietic stem cells.
Figure 8A:
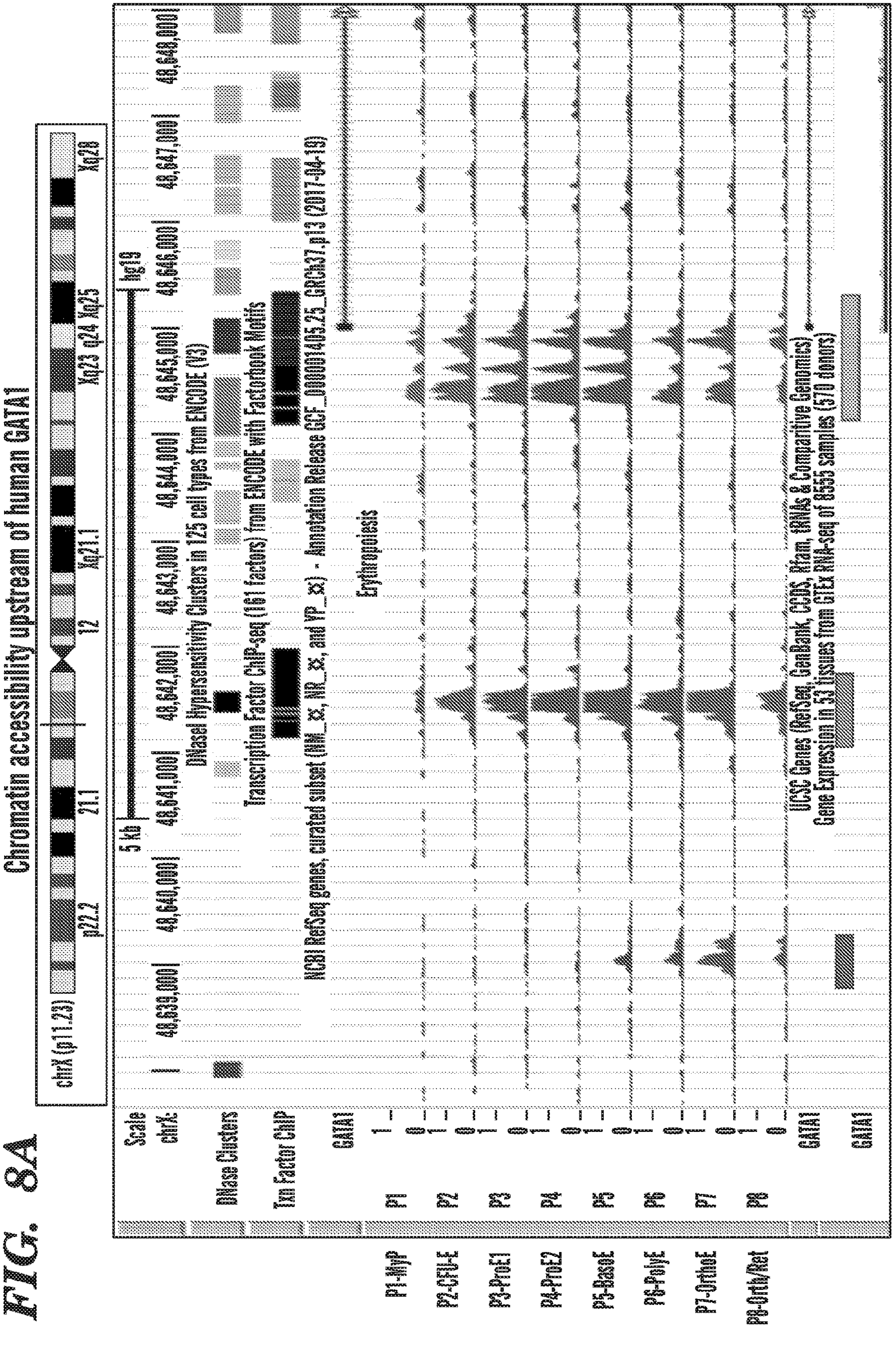
FIG. 8A, and FIG. 8B show genomic plots of human GATA1 and diagrams of two vectors.
Figure 8B:
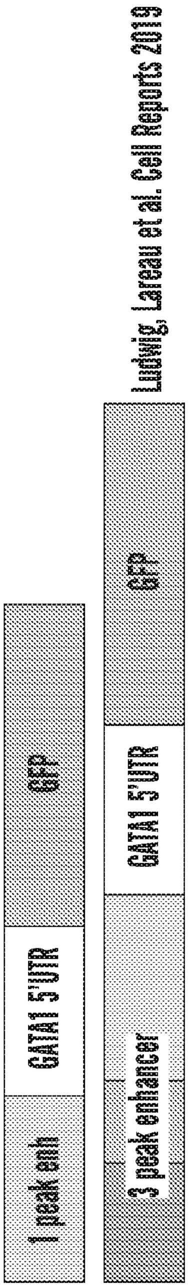
Figure 9A:
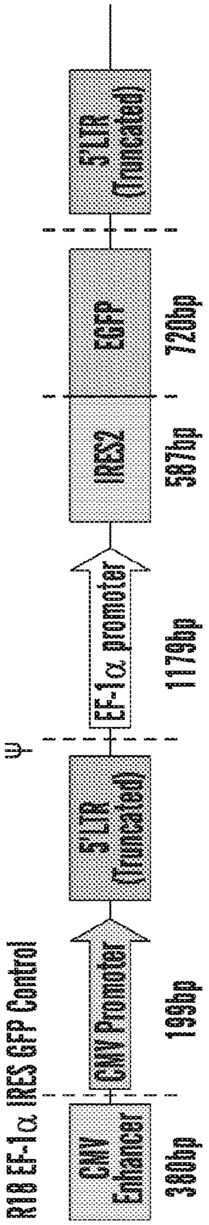
FIG. 9A, FIG. 9B, FIG. 9C, FIG. 9D, and FIG. 9E depict the five vectors including a control vector to achieve developmentally faithful expression of GATA1 in early erythroid progenitors but not in hematopoietic stem cells.
Figure 9B:
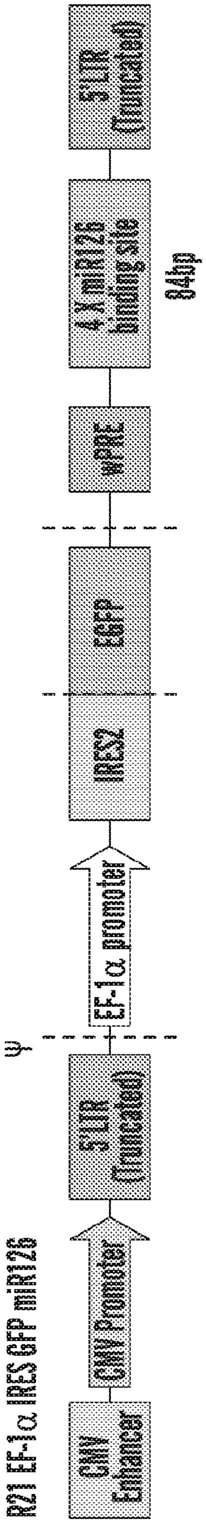
Figure 9C:
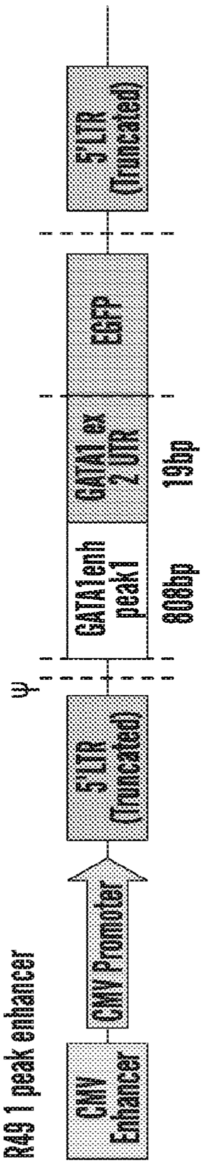
Figure 9D:
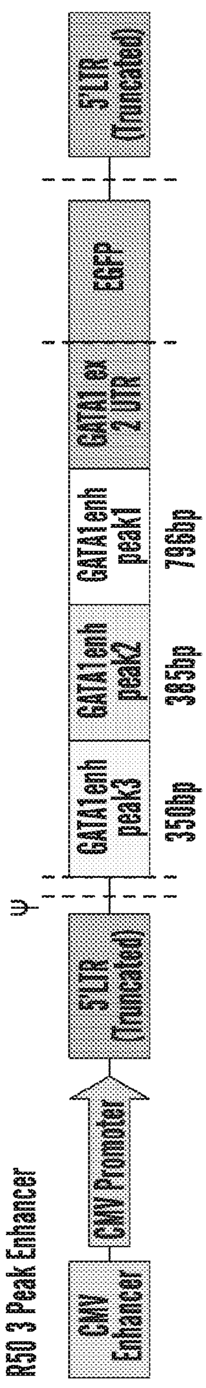
Figure 9E:
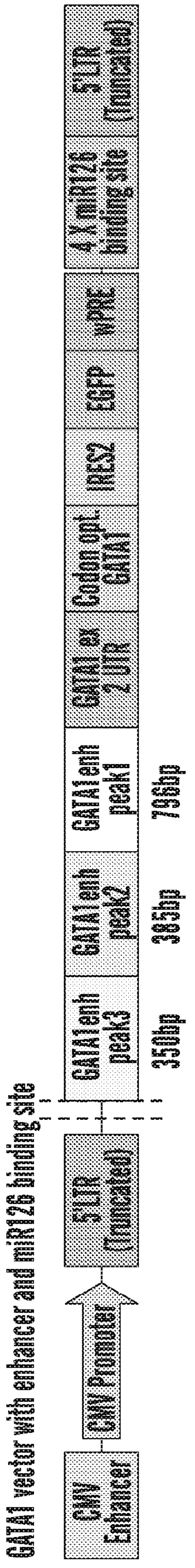
Figure 10:
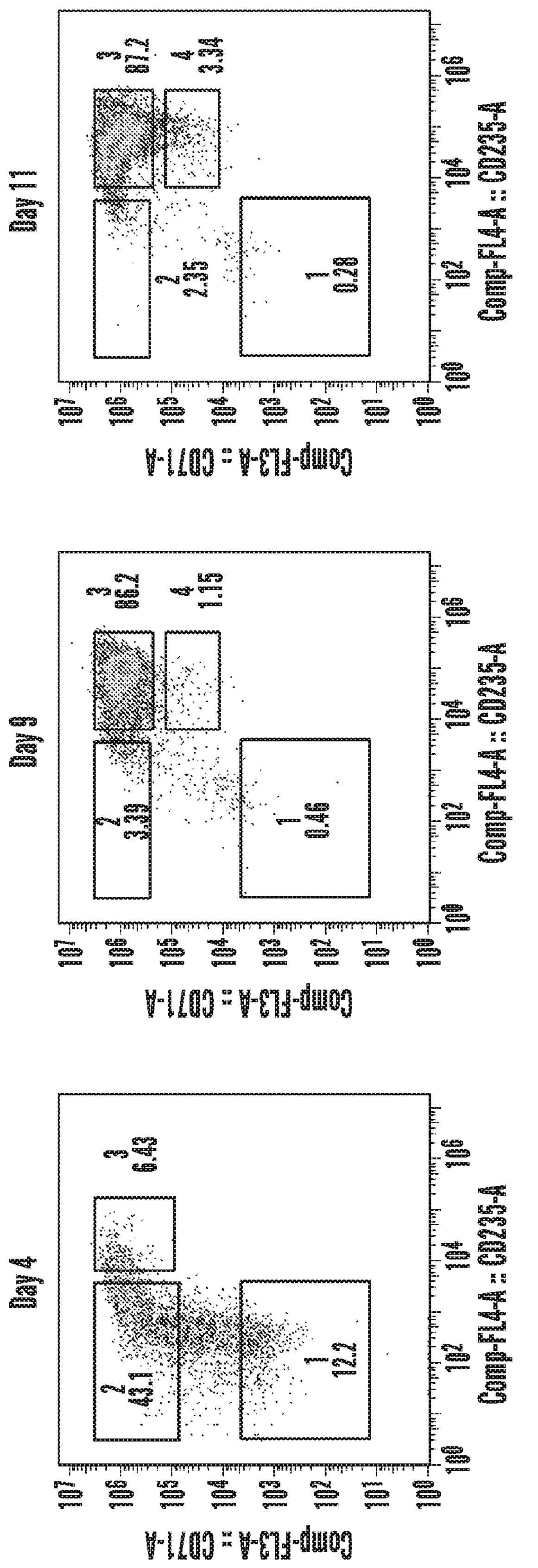
FIG. 10 shows a FACS analysis plot of cells transfected with the R18 EF-1α IRES GFP Control. day 4, day 9 and day 11 of CD71 and CD235a during in vitro differentiation. As cells move from quadrant 1 to 4, they are maturing down the erythroid lineage.
Figure 11:
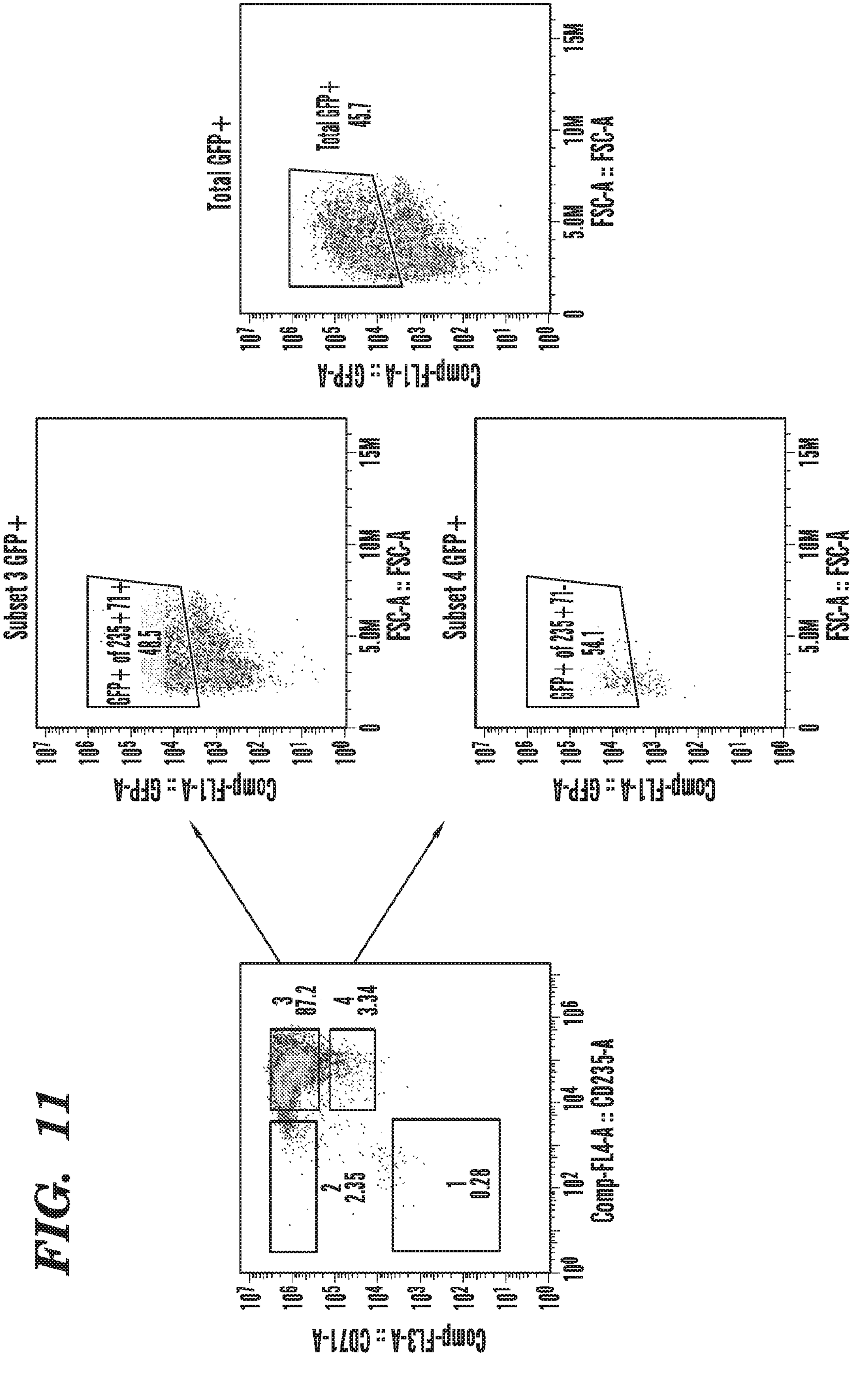
FIG. 11 shows a FACS analysis plot of cells transfected with the R21 EF-1α IRES GFP.
Figure 12:
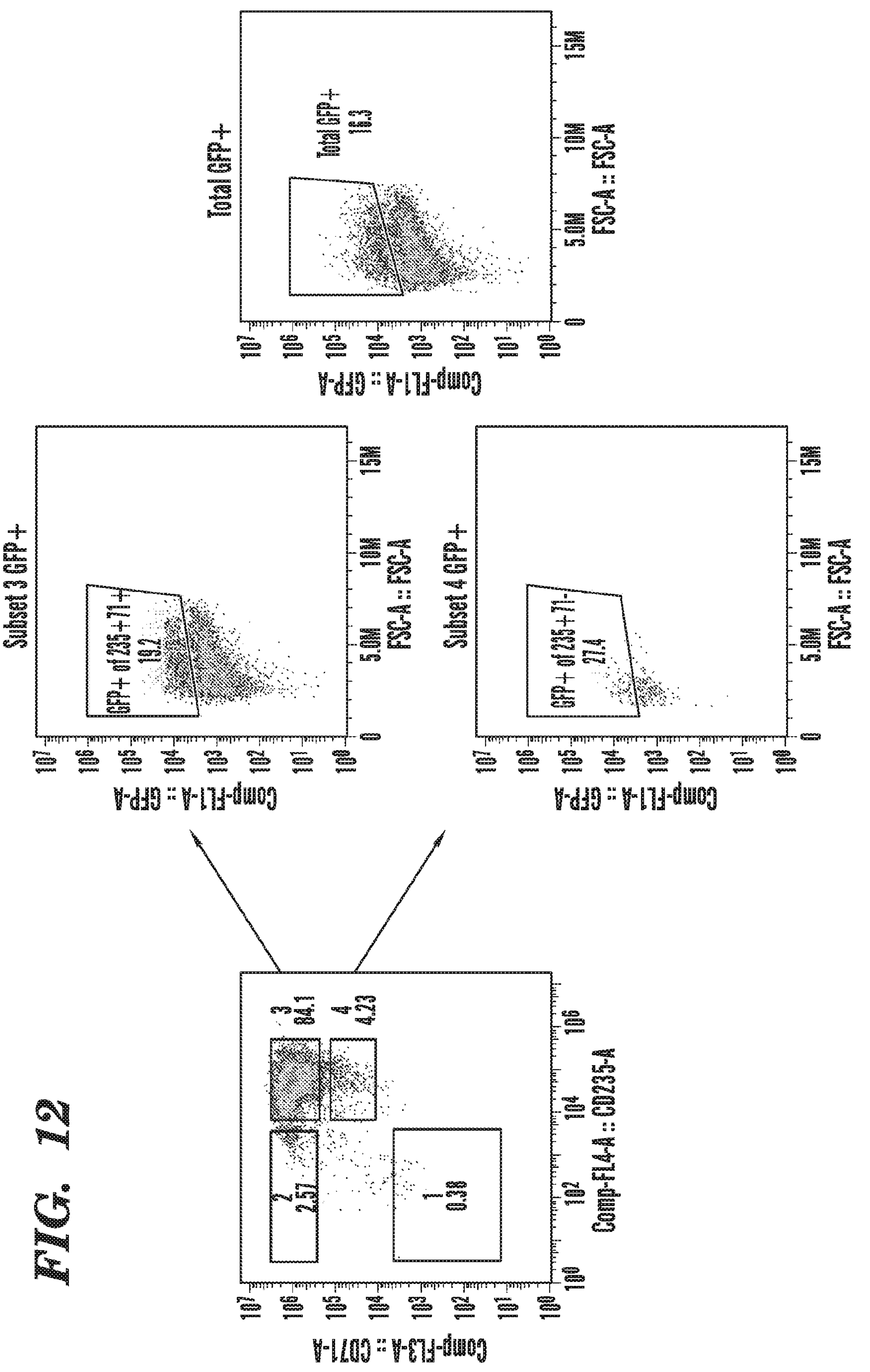
FIG. 12 shows a FACS analysis plot of cells transfected with the R21 EF-1α IRES GFP miR126.
Figure 13:
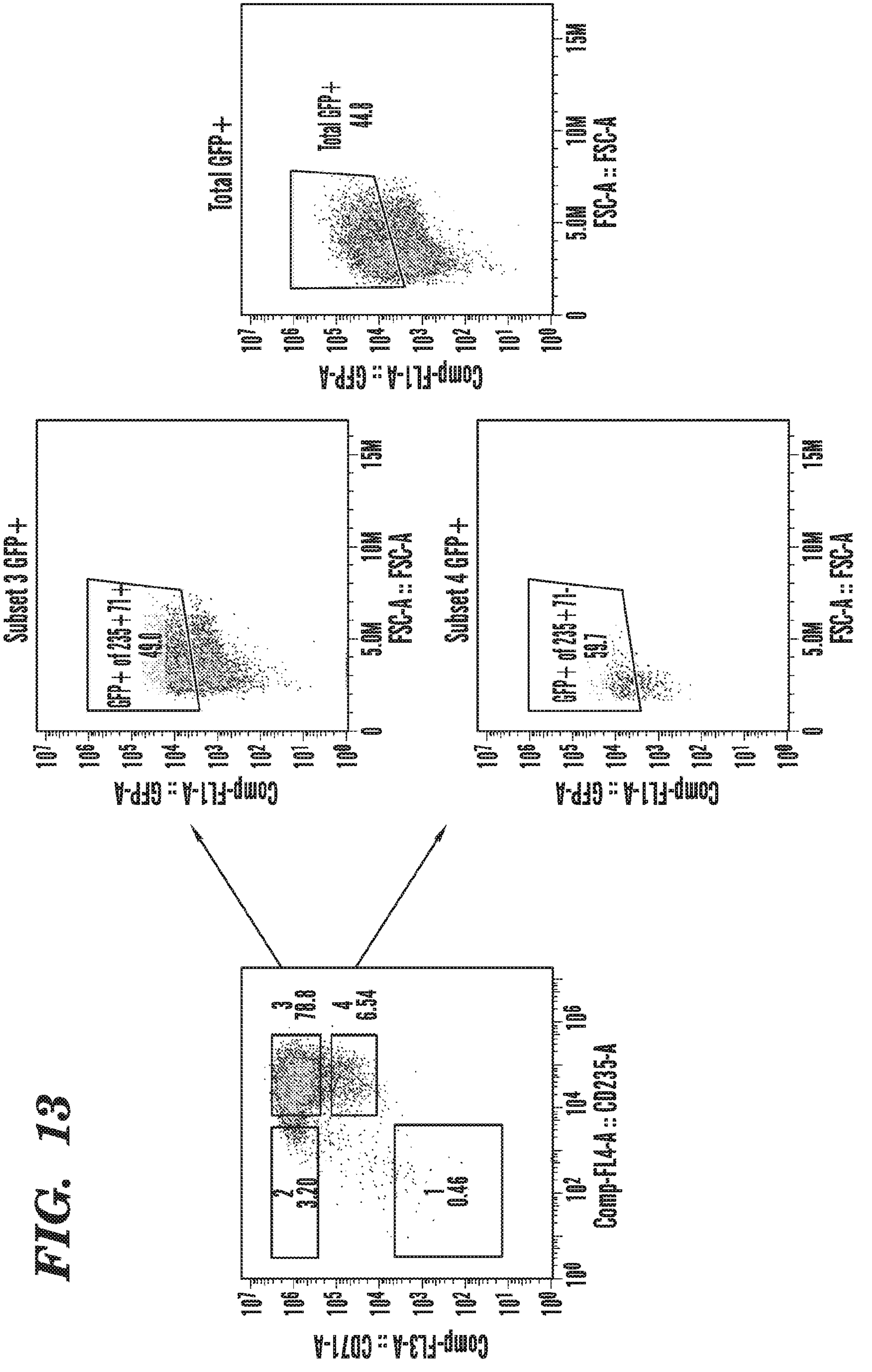
FIG. 13 shows a FACS analysis plot of cells transfected with the R49 EF-1α 1 peak enhancer GFP.
Figure 14:
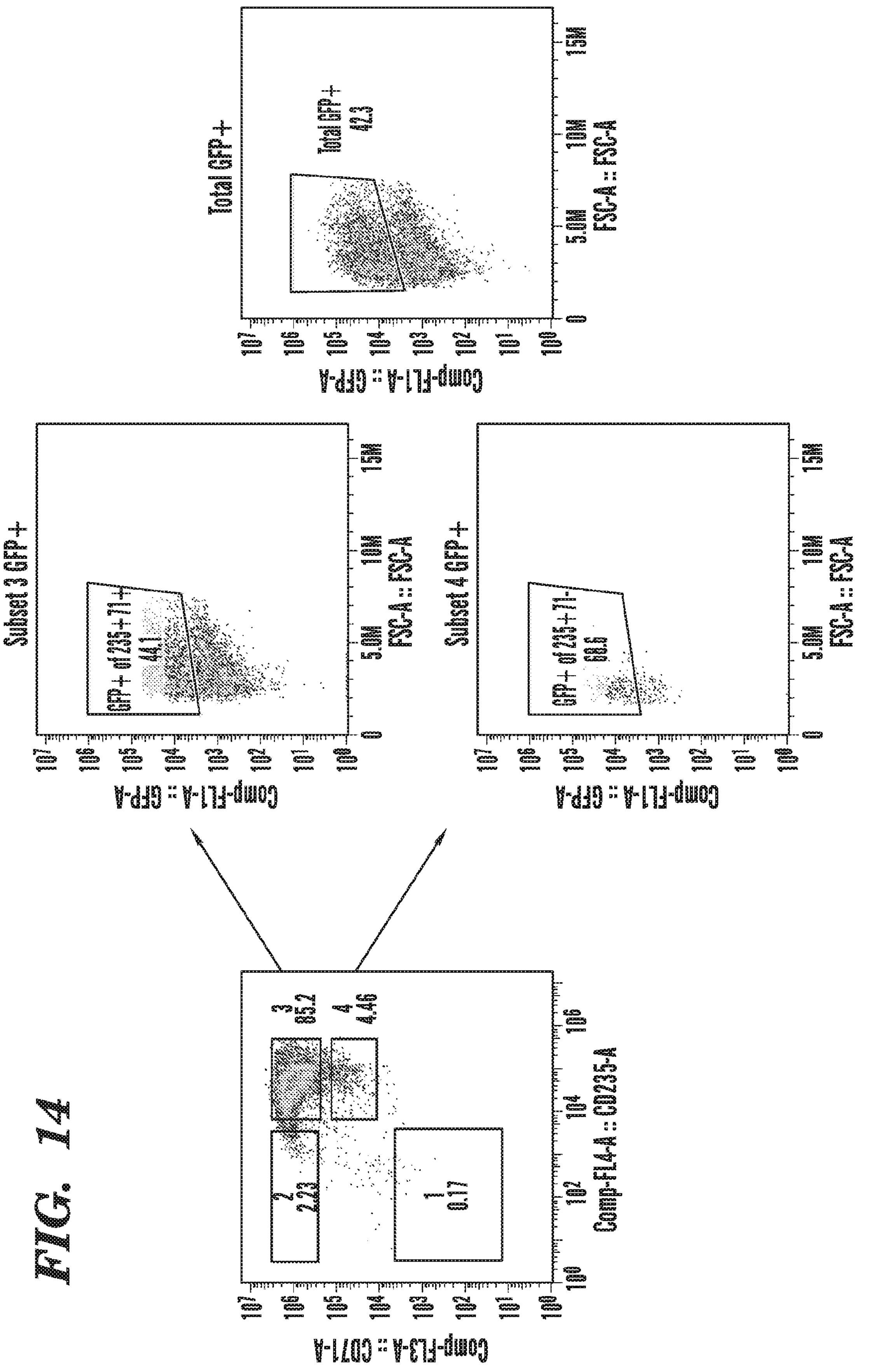
FIG. 14 shows a FACS analysis plot of cells transfected with the R49 EF-1α 3 peak enhancer GFP.
Figure 15:
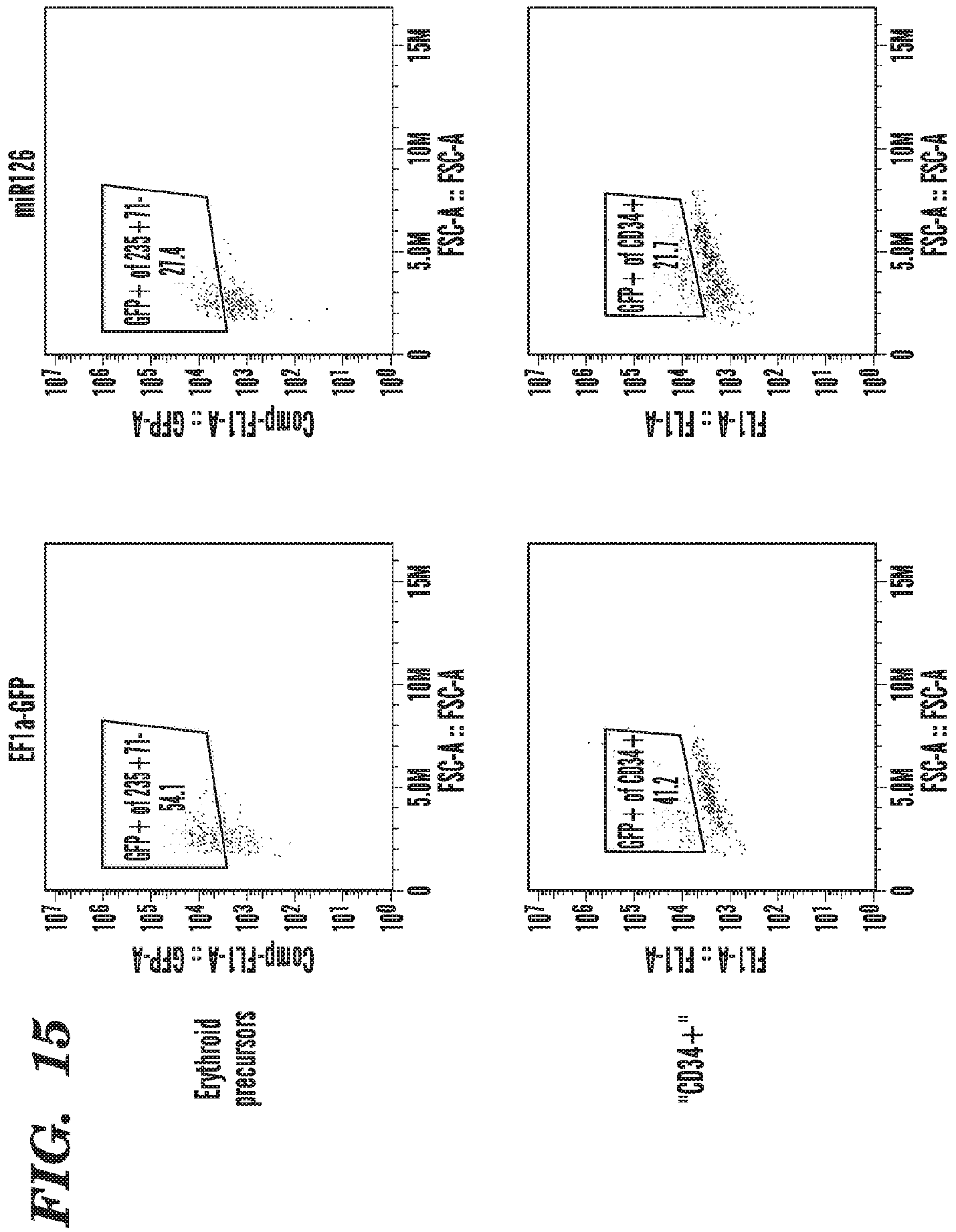
FIG. 15 shows a FACS analysis plots of cells transfected with R18 EF-1α IRES GFP Control, R21 EF-1α IRES GFP miR126, R49 EF-1α 1 peak enhancer GFP, R50 3 Peak Enhancer GFP.
Figure 15:
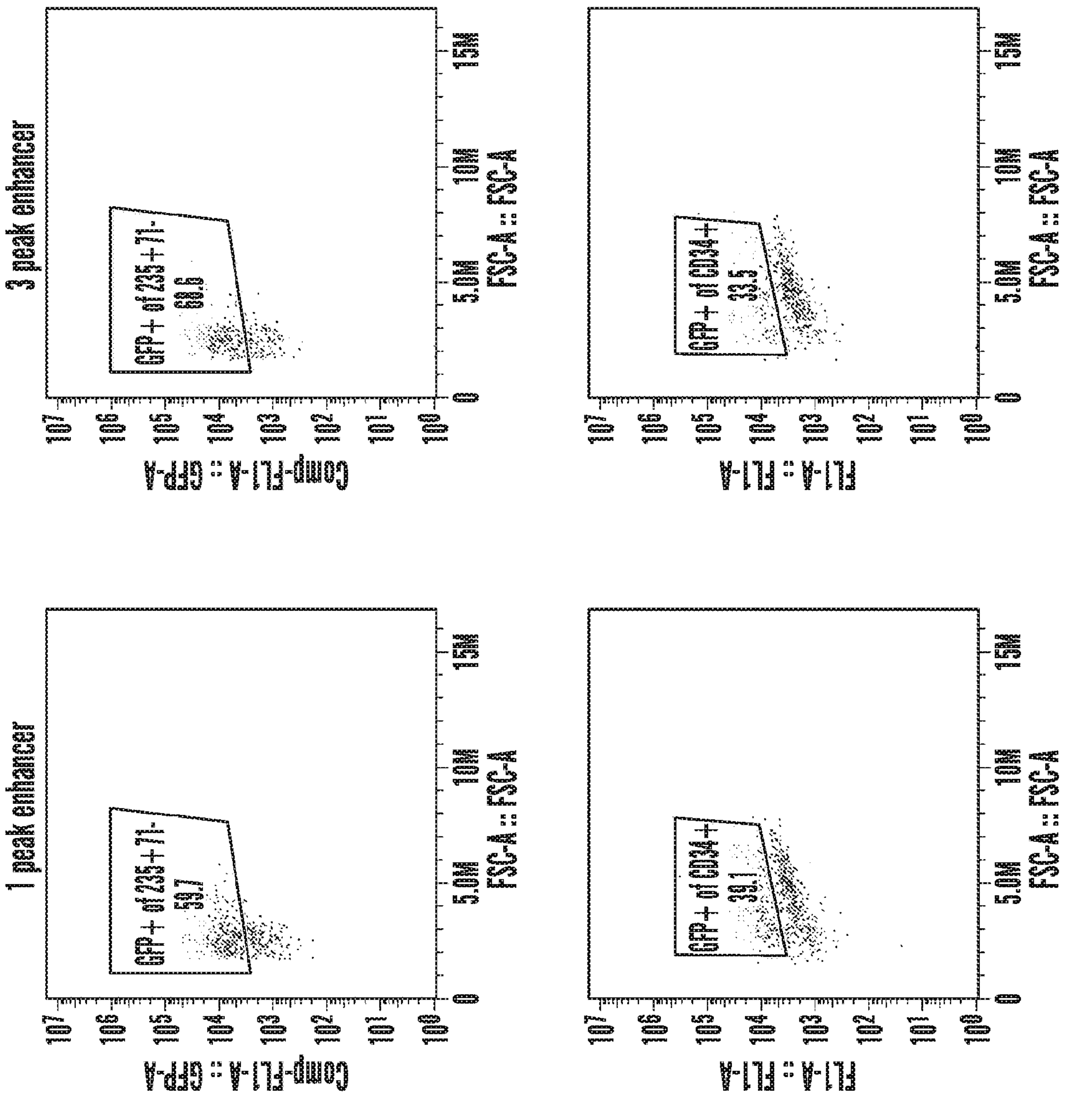
Figure 16:
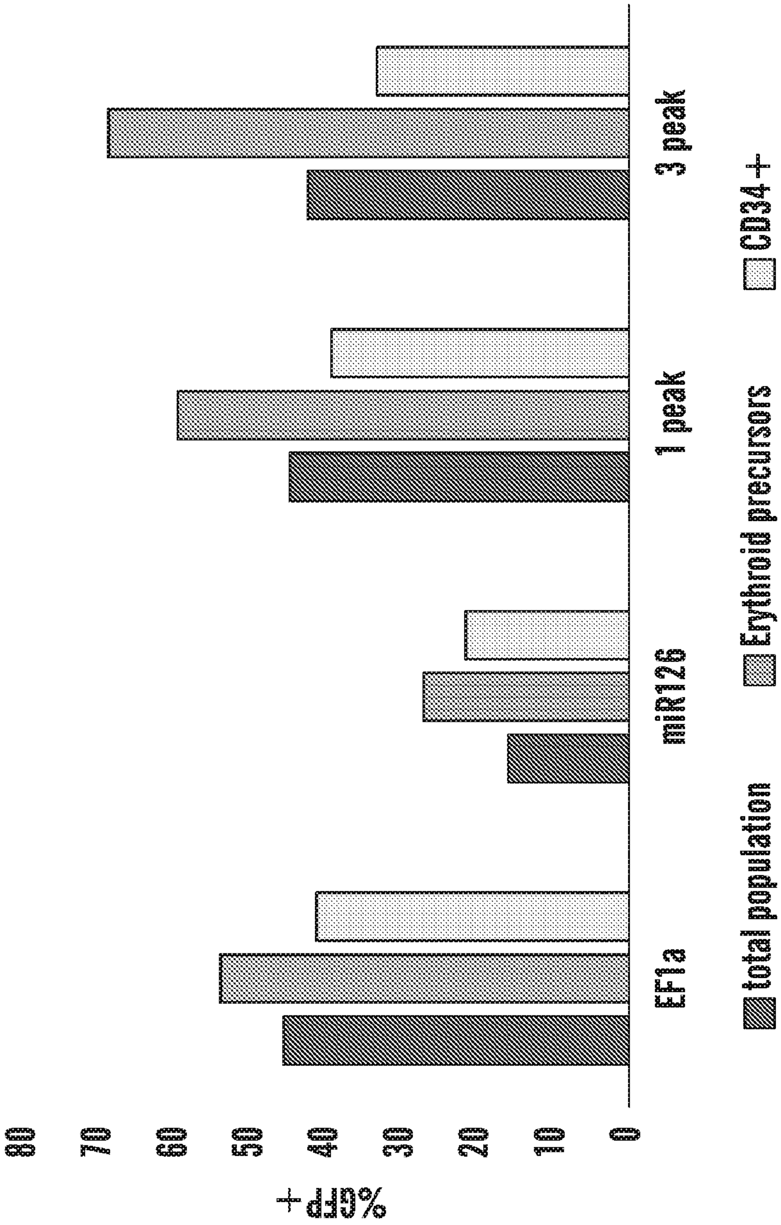
FIG. 16 demonstrates that R50 3 Peak Enhancer GFP of Human GATA enhancer preferentially drives erythroid transgene expression but not CD34+ cells.
Figure 17:
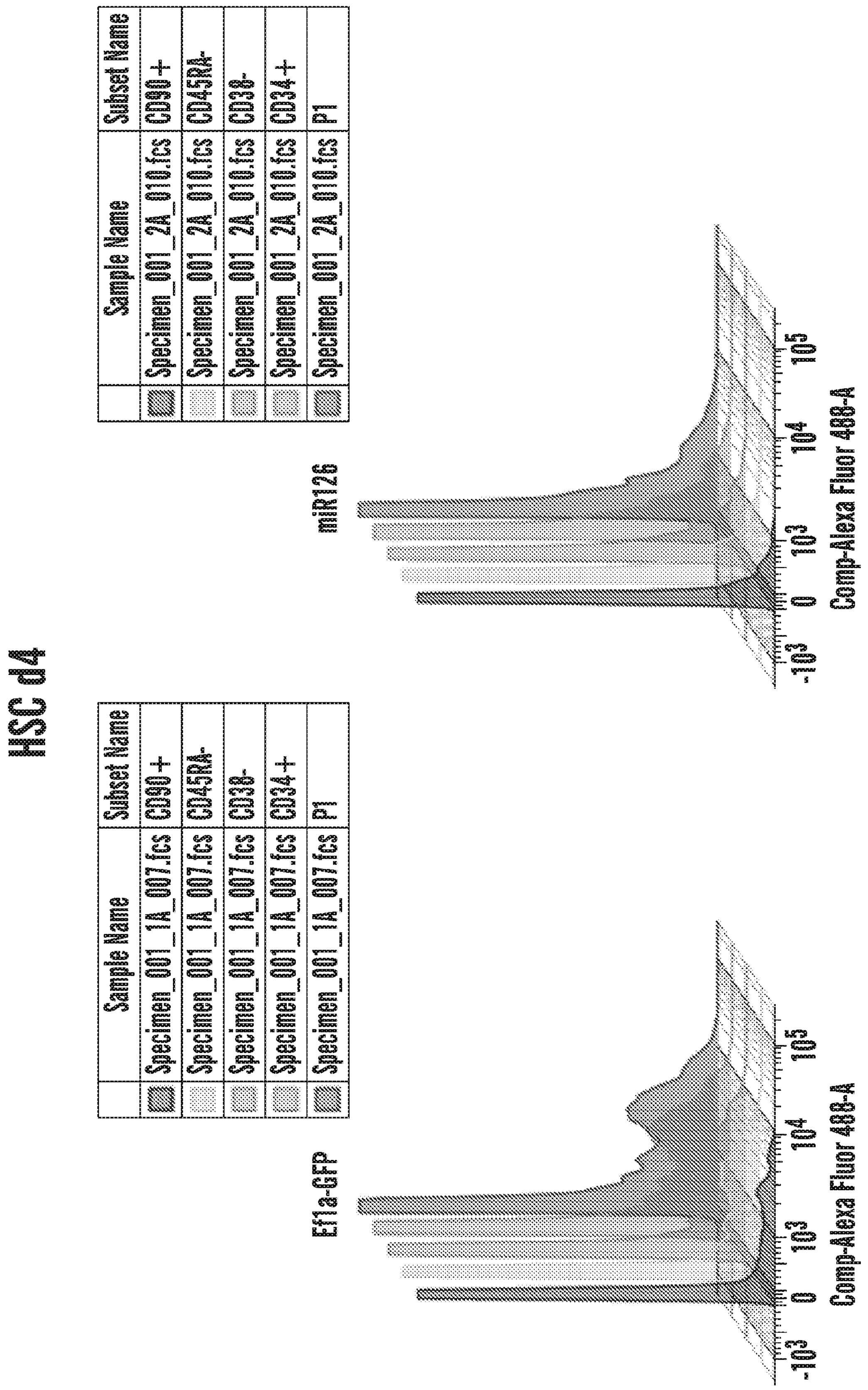
FIG. 17 depicts the FACS analysis plots using HSC d4 of Ef1a-GFP, miR126, miR223T, 1peak, 3peak, 1peak-miR126, 1peak-miR223T, 3peak-miR126, and 3peak-miR223T. Experimental outline: D0: Thaw CD34+ cells into SSII+cc100+TPO, culture at 5% O2. D2: Lentiviral infection, recover overnight in SSII+cc100+TPO. HSC D3: split culture—half in HSC conditions, half in RBC differentiation conditions. HSC D4 and D7: Analysis by flow cytometry. RBC D4: Analysis by flow cytometry (to continue every 3-4 days).
Figure 17:
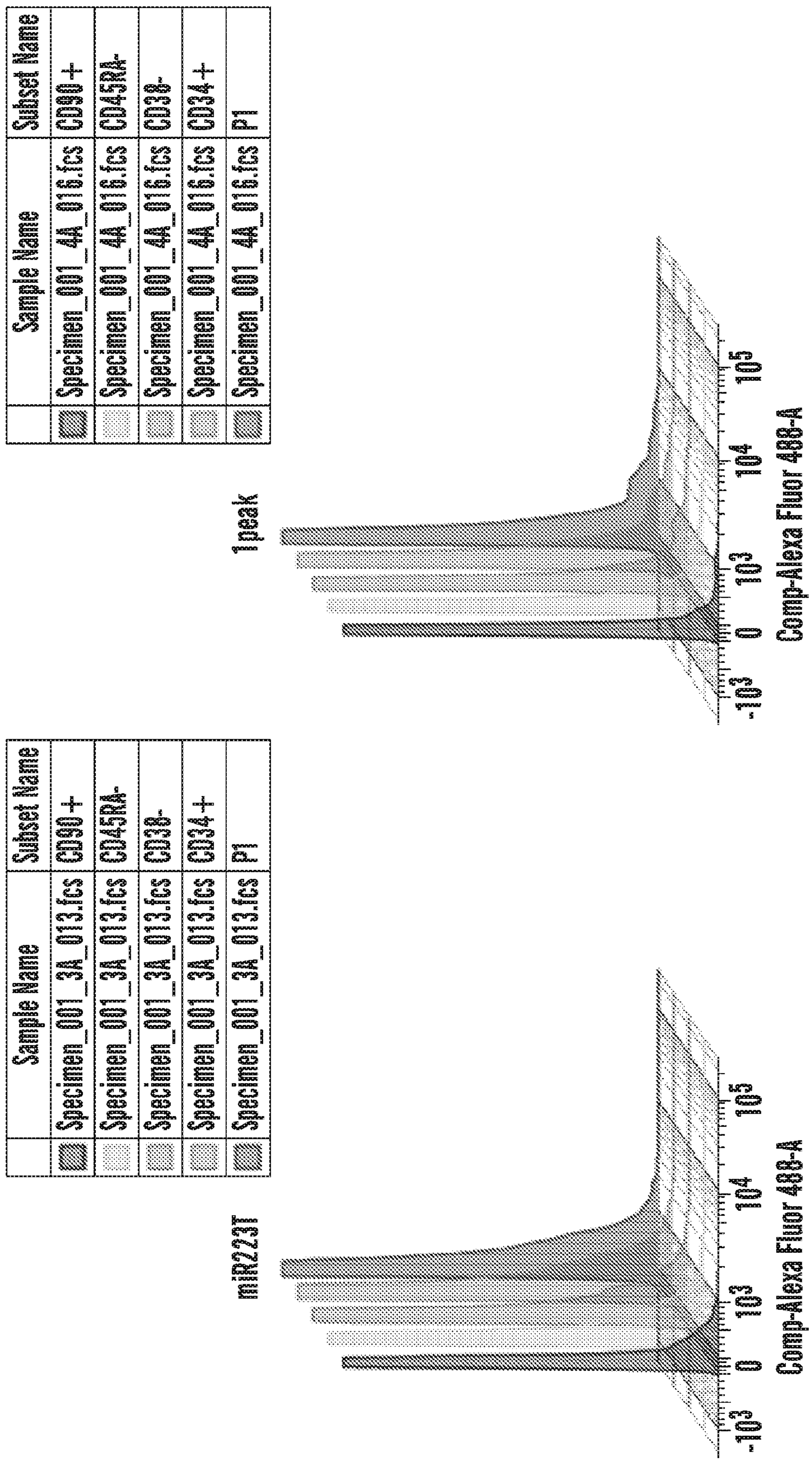
Figure 17:
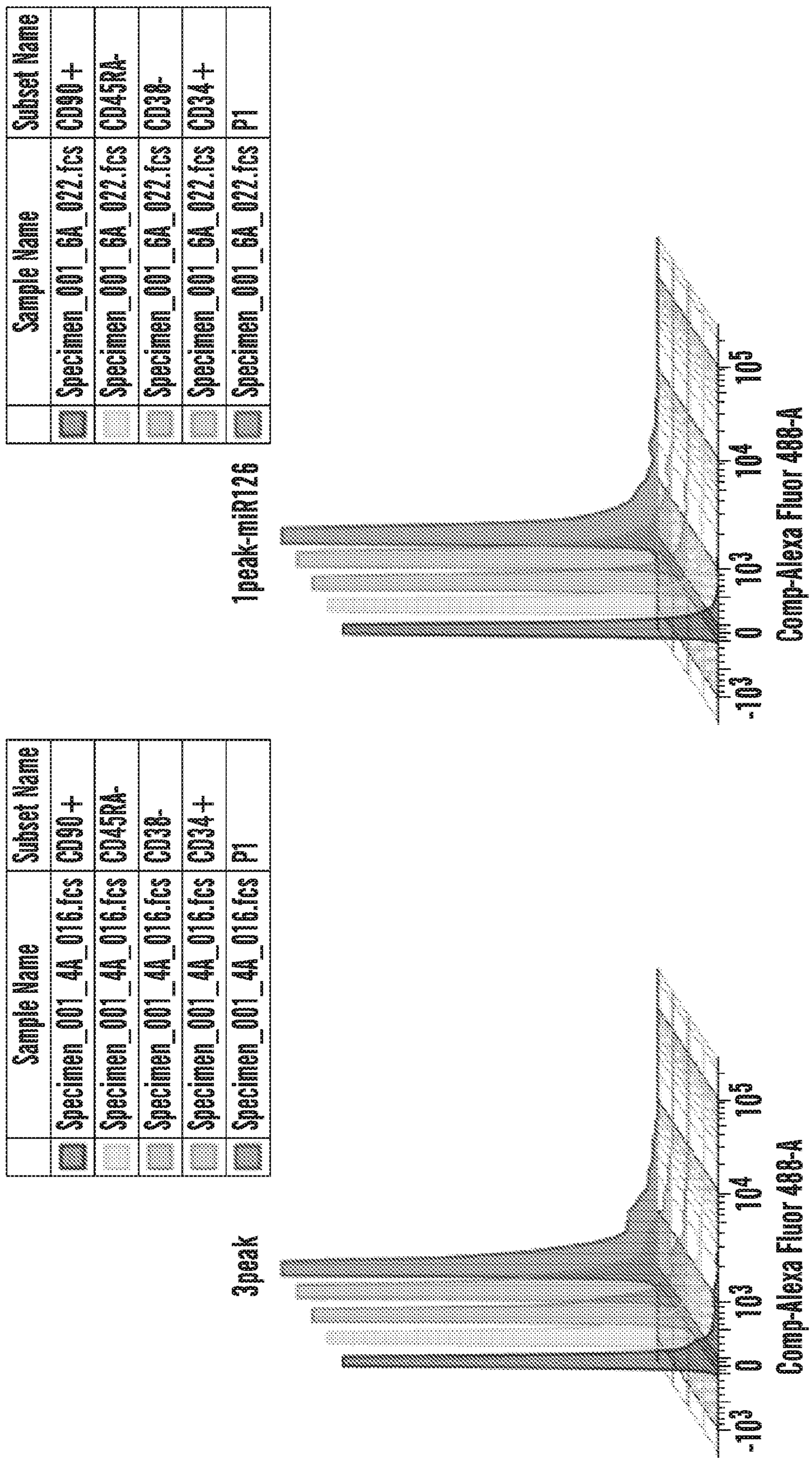
Figure 17:
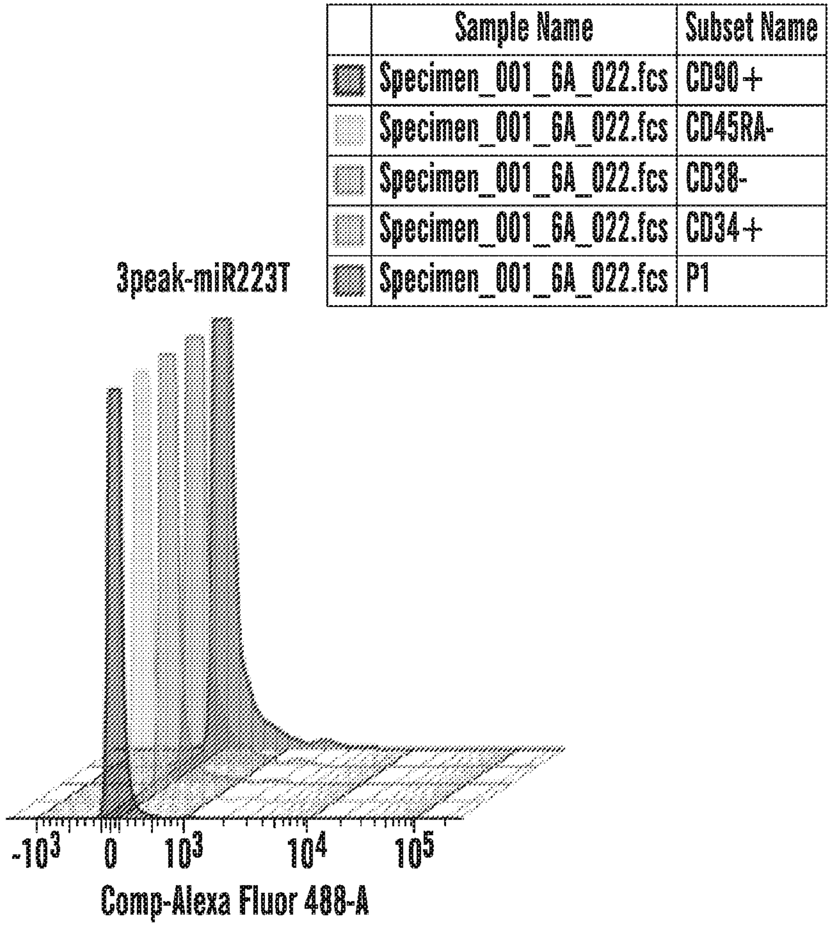
Figure 18A:
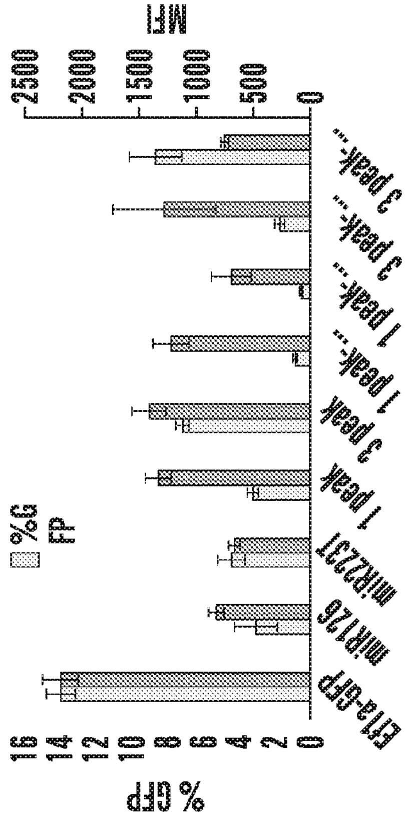
FIG. 18A and FIG. 18B show bar graphs depicting GFP expression in a CD34+CD38-CD45RA-CD90+ subset at day 4 (FIG. 18A) and at day 7 (FIG. 18B).
Figure 18B:
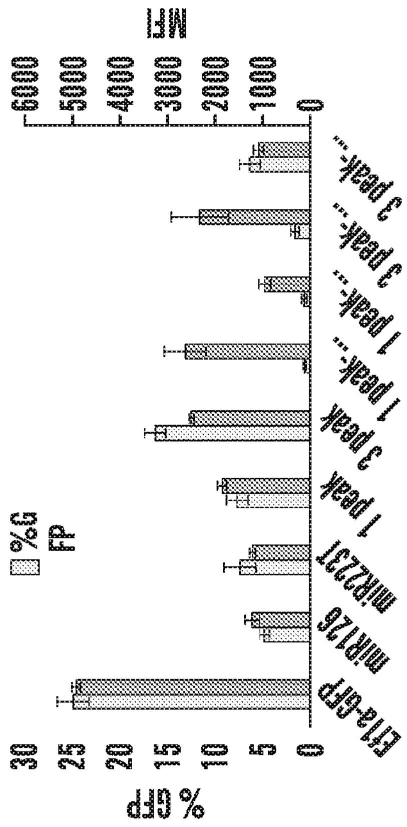
Figure 19:
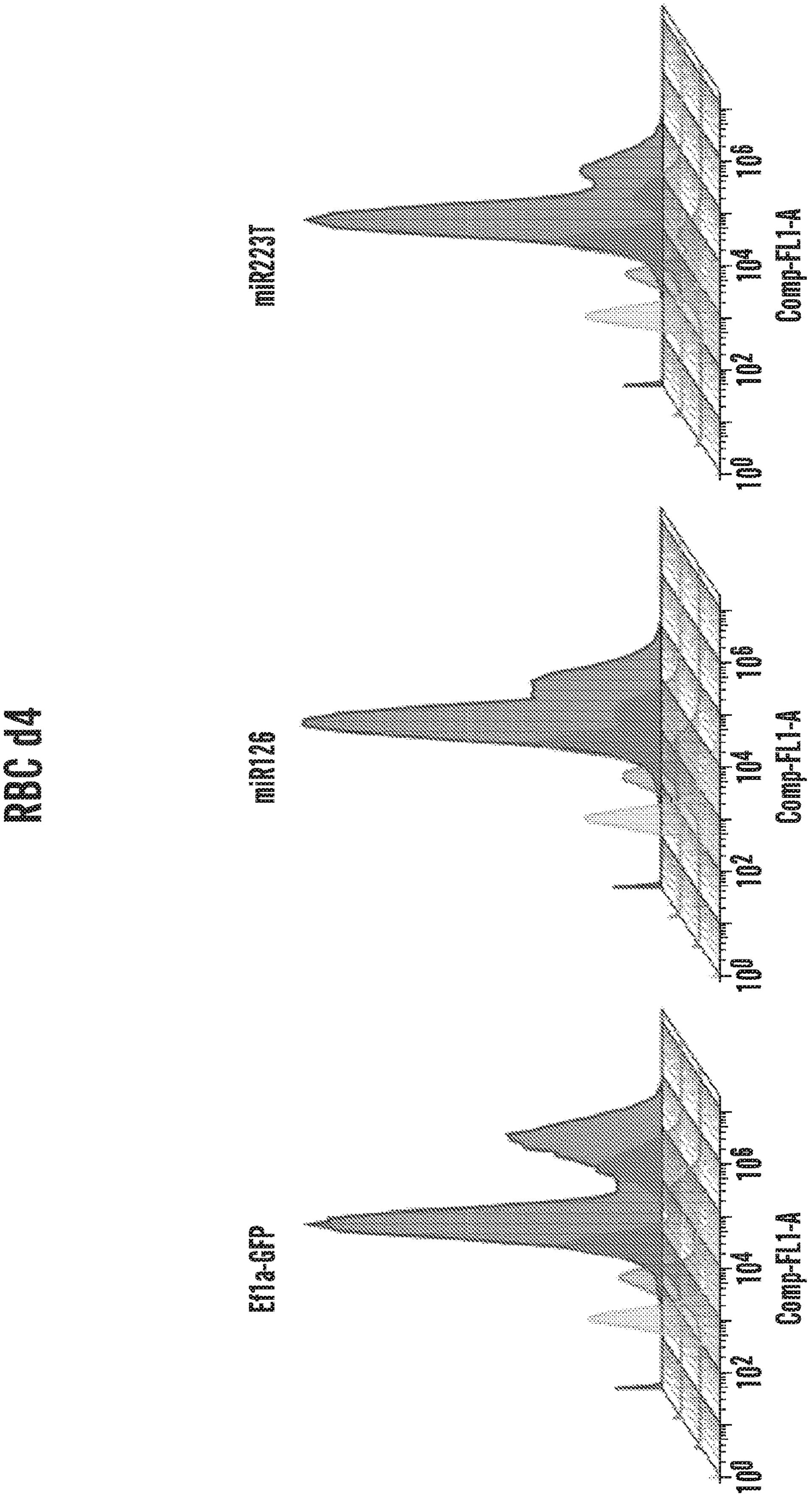
FIG. 19 depicts FACS analysis plots using RBC D4 of Ef1a-GFP, miR126, miR223T, 1peak, 3peak, 1peak-miR126, 1peak-miR223T, 3peak-miR126, and 3peak-miR223T.
Figure 19:
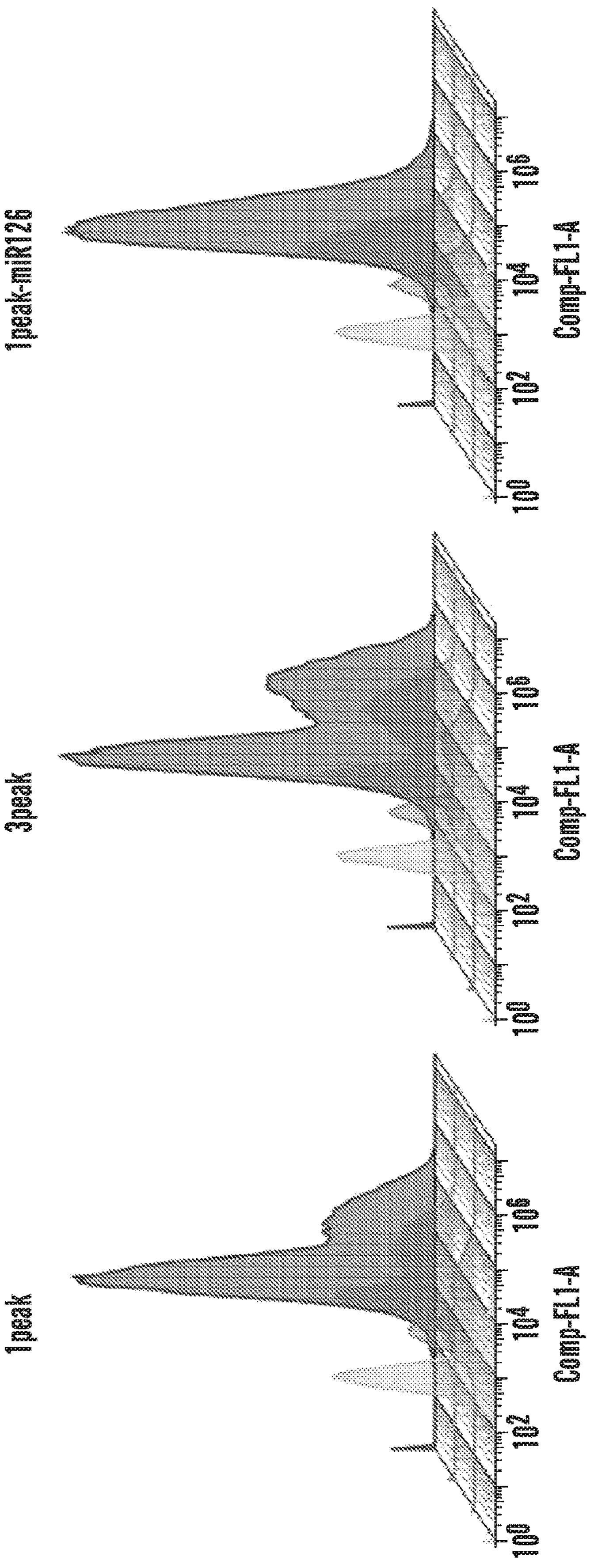
Figure 19:
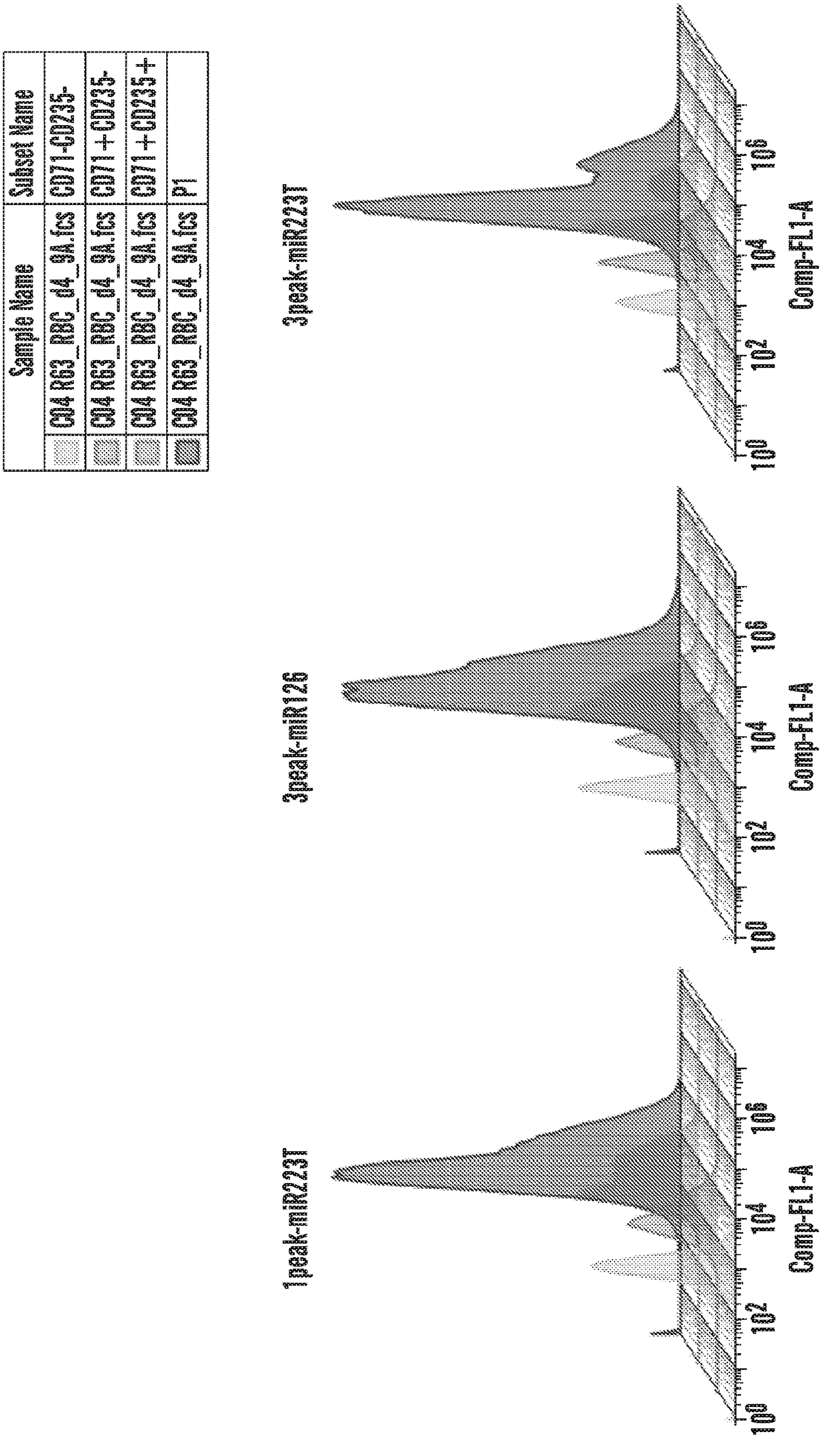
Figure 20:
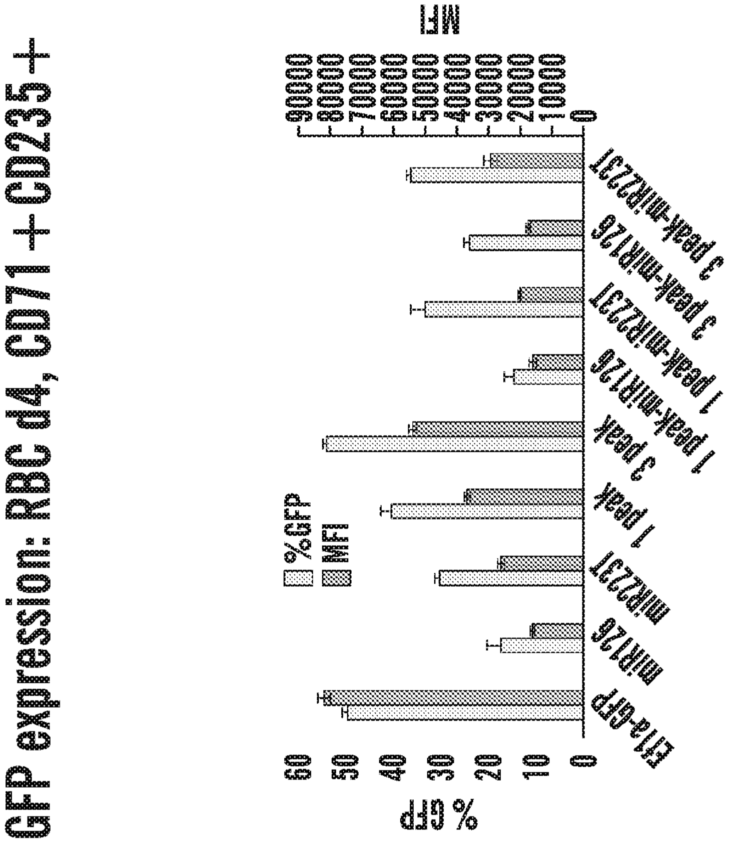
FIG. 20 shows a bar graph depicting GFP expression of RBC d4, CD71+CD235+.
Figure 21:
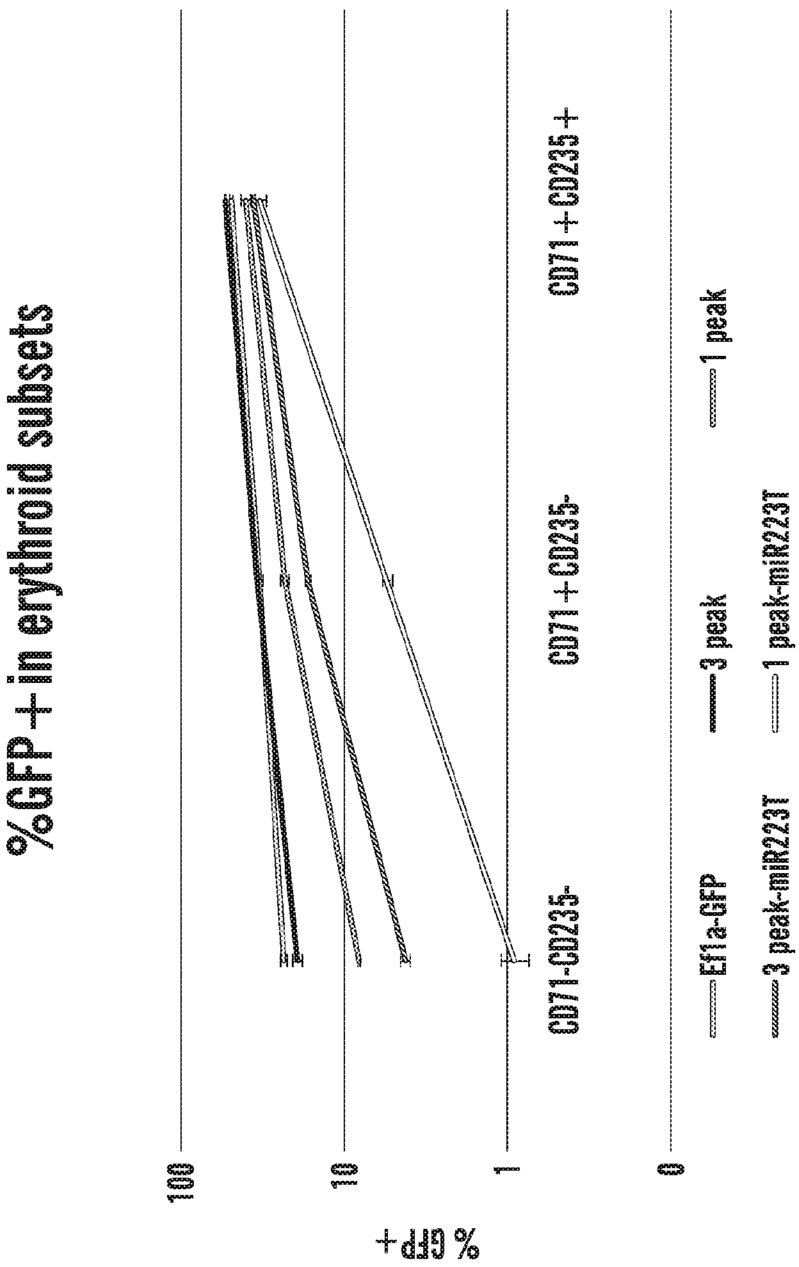
FIG. 21 depicts the % of GFP in erythroid subsets. CD71−CD235−, CD71+CD235−, and CD71+CD235+.
Figure 22:
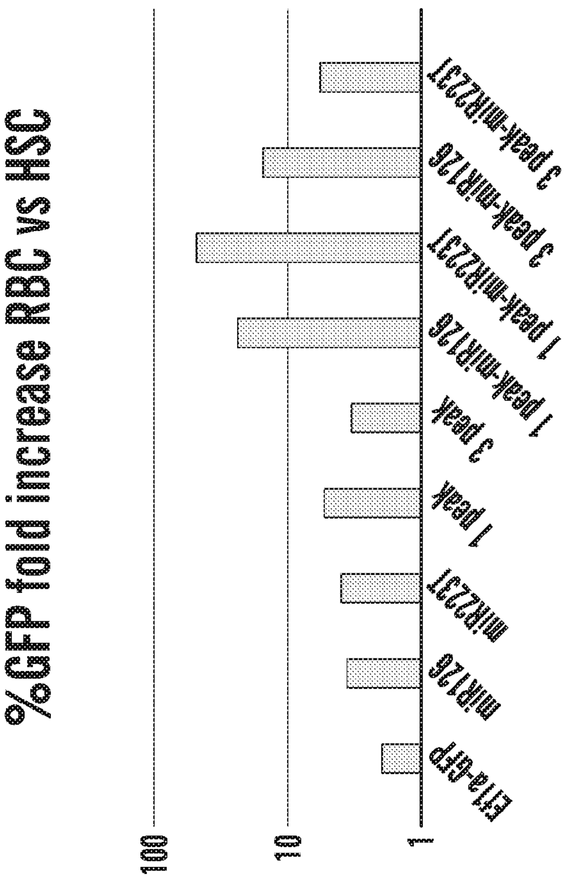
FIG. 22 show a bar graph depicting the % GFP fold increase RBC vs HSC. Results are showing for of Ef1a-GFP, miR126, miR223T, 1peak, 3peak, 1peak-miR126, 1peak-miR223T, 3peak-miR126, and 3peak-miR223T.
Figure 23:
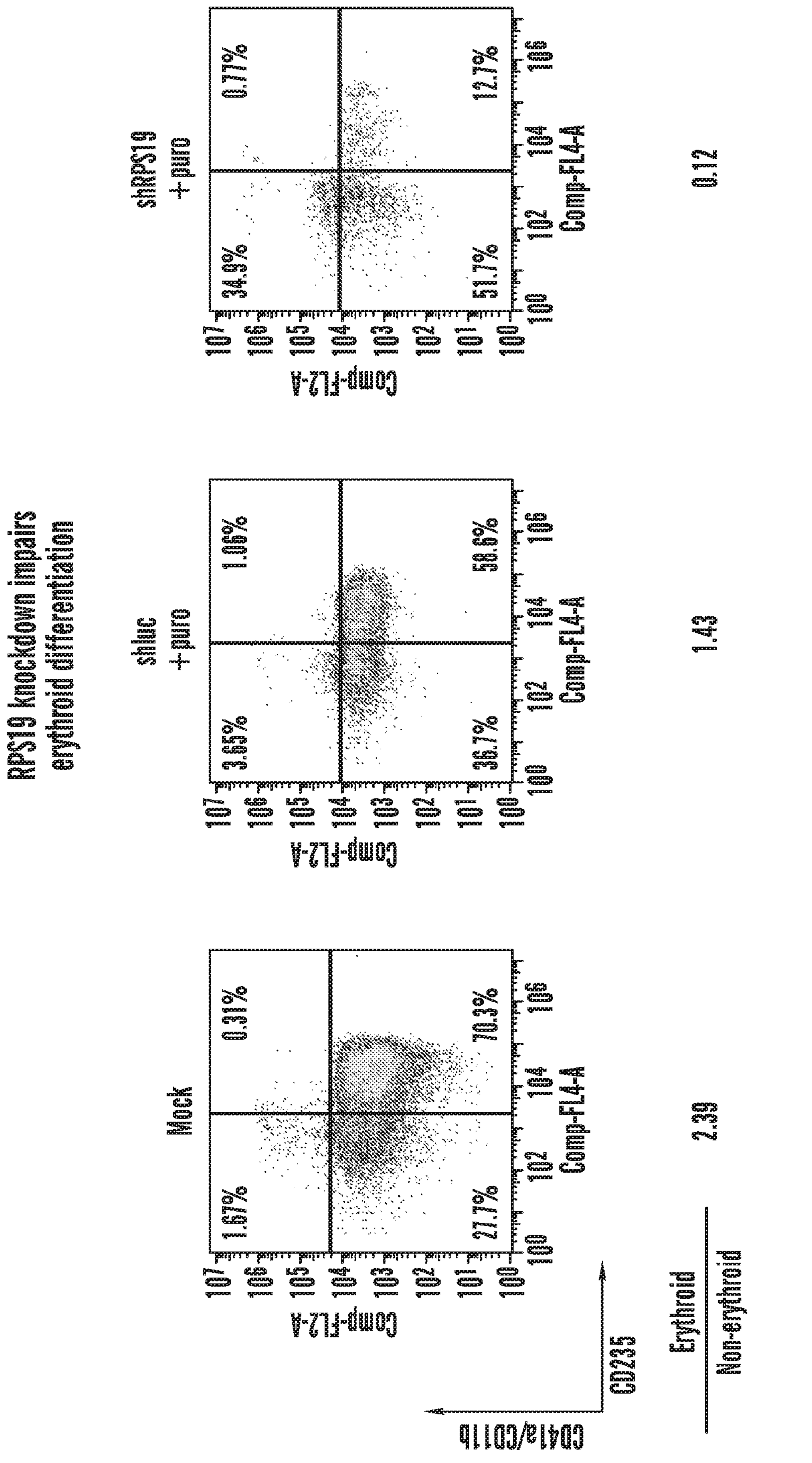
FIG. 23 shows FACs analysis plots of RPS19 knockdown impairs erythroid differentiation. Experimental outline: D0: thaw cells into Phase I media. D2: spinfect with shRNA lenti+/−GATA1 expression constructs. D4: begin puro selection. D6: remove puro. D7 flow analysis.
Figure 24:
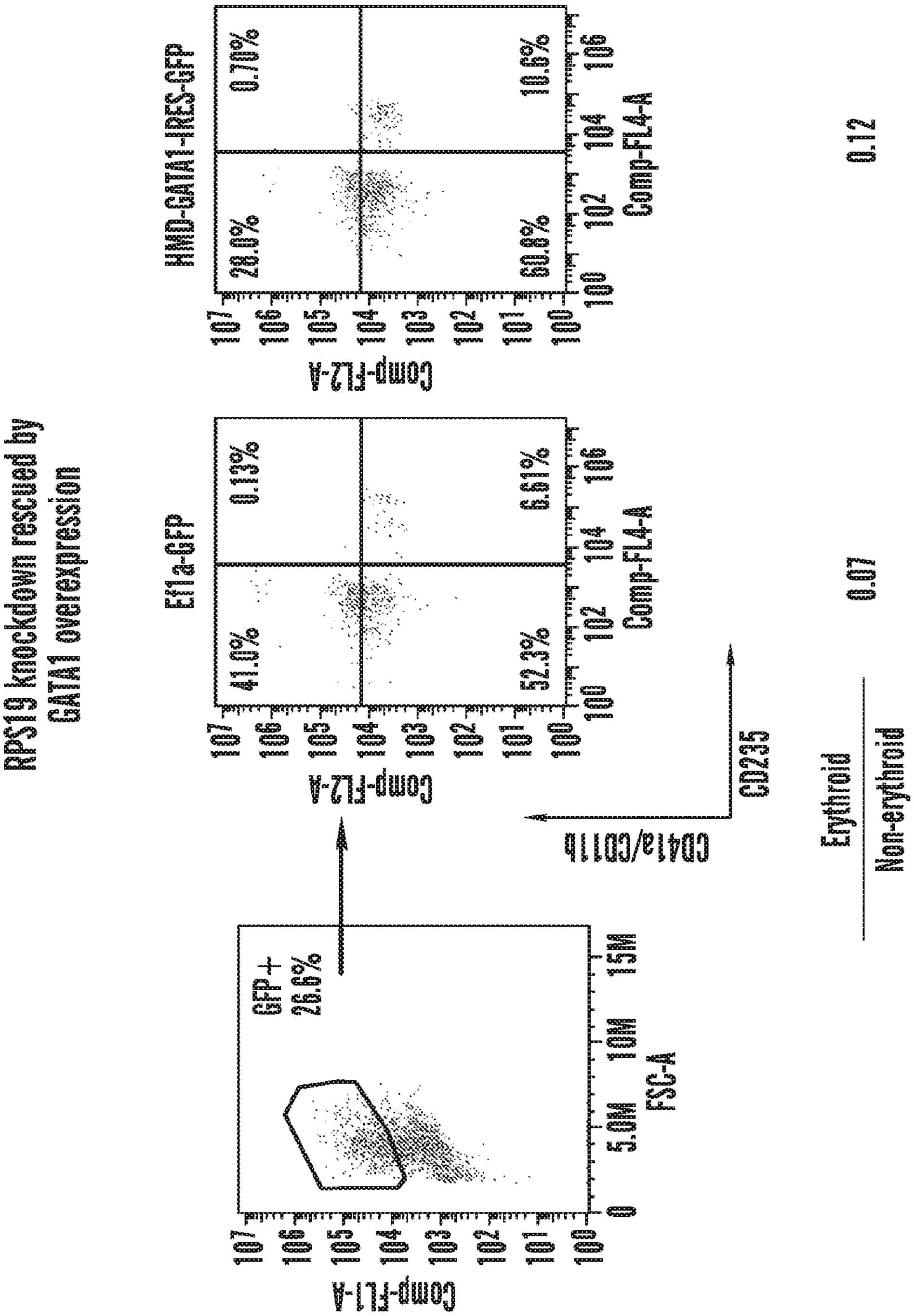
FIG. 24 shows FACs analysis plots of RPS19 knockdown rescued by GATA1 overexpression.
Figure 25:
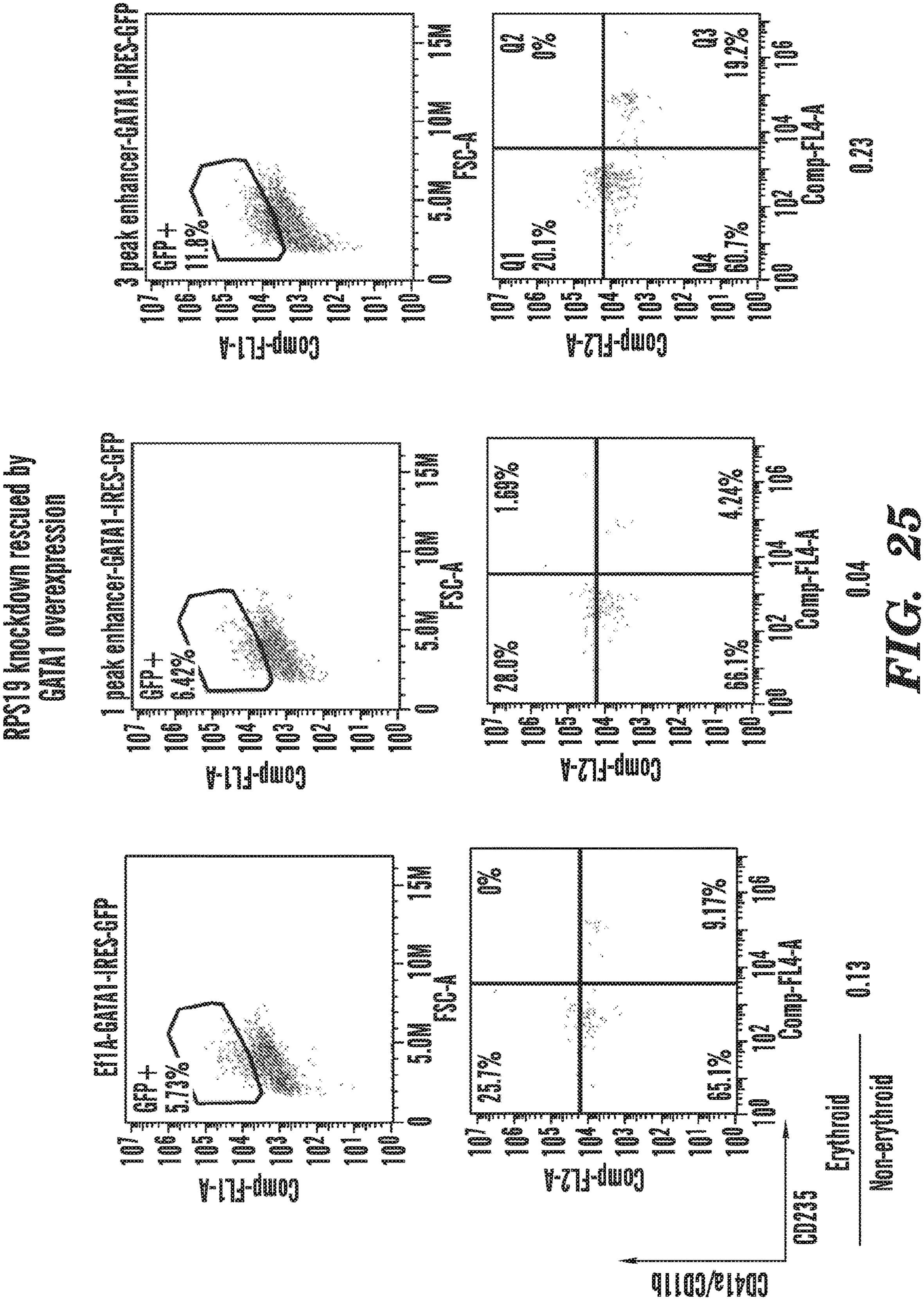
FIG. 25 shows FACs analysis plots of RPS19 knockdown rescued by GATA1 overexpression.
Figure 26:
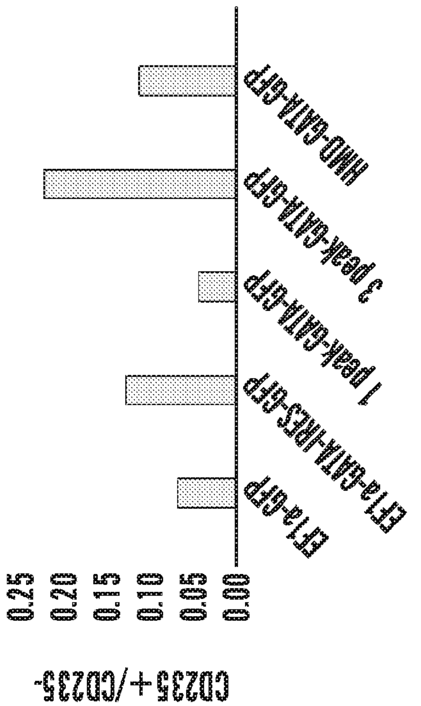
FIG. 26 shows a bar graph depicting CD235+/CD235− level of EF1a-GFP, EF1a-GATA-IRES-GFP, 1 peak-GATA-GFP, 3 peak-GATA-GFP, and HMD-GATA-GFP.

Example 2: Vector Design for Lineage-Specific Expression of Gata1 as a Therapy for Diamond-Blackfan Anemia In some embodiments of any of the aspects, described herein are various combinations of the following lentiviral vectors (FIG. 7):

1) Lentiviral backbone: 3rd generation self-inactivating lentiviral backbone based on pHIV-GFP (Welm et al Cell Stem Cell. 2008 Jan. 10. 2(1):90-102), driven by an EF1a promoter and containing an IRES-GFP sequence for initial characterization and testing but which will be removed from the final vector sequence.
2) Mouse GATA1 hematopoietic enhancer minigene (mG1HEM): concatenation of 3 sequences upstream of the mouse GATA1 transcription start site and a fourth sequence from the first intron of mouse GATA1 that have been shown to faithfully allow expression of GATA1 in erythroid cells but not hematopoietic stem cells (Takai et al. Blood. 2013 Nov. 14 122(20):3450-3460).
3) Minimal promoter (minP): either from 5'UTR of mouse GATA1 or from firefly luciferase reporter vector pGL4.25, Genbank accession number DQ904457.1
4) Human GATA1 cDNA (GATA1) with codon optimization for optimal expression in human cells with or without FLAG tag
5) Woodchuck Hepatitis Virus Posttranscriptional Regulatory Element (WPRE) for enhanced stability of transgene mRNA.
6) miR126 binding site (miR126 BS): repeated sequence which is bound by miR126, a microRNA expressed in hematopoietic stem cells, and causes decreased transgene expression in the stem cell compartment (Gentner et al. Sci Trans Med. 2010 Nov. 17 2(58):58-84).

REFERENCES

Welm et al Cell Stem Cell. 2008 Jan. 10. 2(1):90-102.Gentner et al. Sci Trans Med. 2010 Nov. 17 2(58): 58-84.

Example 3: Gata1 Gene Therapy as a Therapy for Diamond-Blackfan Anemia

Pre-clinical studies by the inventors have shown that GATA-1 augmentation in erythroid cells shows therapeutic effects in Diamond-Blackfan anemia (DBA). Herein, the inventors show the results of further experiments that demonstrate that the regulated increase in GATA1 expression in erythroid precursors, but not in hematopoietic stem cells, provides therapeutic effects in DBA.

A clinically relevant GATA1 gene therapy vector for DBA must achieve four crucial functions (FIG. 27). First, despite the requirement that a gene therapy vector gets incorporated into the genome of long-term, undifferentiated hematopoietic stem cells (LT-HSCs), there must be very little expression of the GATA1 transgene in the stem cell compartment, since GATA1 expression in HSCs leads to a loss of self-renewing stem cells. Second, to overcome the erythroid differentiation defect that is the hallmark of DBA, the gene therapy vector must drive robust expression in early progenitors once they have become committed to erythroid differentiation. Third, to mimic the pattern of endogenous GATA1 expression and achieve normal terminal erythroid differentiation, the expression from the gene therapy vector should decline at late stages of erythroid development. Fourth, developmentally regulated increased GATA1 expression must be sufficient to overcome the erythroid maturation block caused by ribosomal protein haploinsufficiency in experimental model systems and in primary patient samples.

Figure 28A:
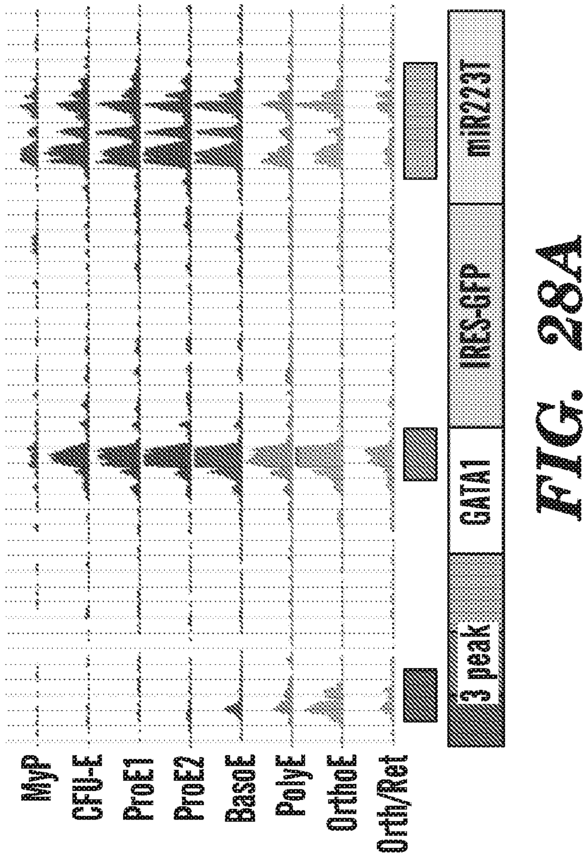
FIG. 28A, FIG. 29B, FIG. 28C, and FIG. 28D show that developmentally regulated expression of GATA1 rescues DBA phenotype in vitro.

To design a vector that incorporates the four key features above, the inventors first analyzed accessible chromatin peaks upstream of GATA1, and identified chromatin that is open in differentiating erythroid cellsut not in HSCs or other early progenitors. The inventors provide evidence that these regions of DNA contain regulatory elements that are responsible for erythroid-specific expression of GATA1. The inventors constructed a human GATA1 enhancer (hG1E) element (FIG. 28A) by concatenating the 3 regions of DNA with open chromatin upstream of GATA1. The inventors developed a vector that uses the hG1E element to drive both GATA1 and GFP expression by including an internal ribosomal entry site (IRES) sequence between the two genes. As an additional mechanism to achieve developmentally regulated transgene expression, the inventors combined the hG1E element with a miR223T binding site that has been previously used to restrict transgene expression in the HSC compartment.

Figure 28C:
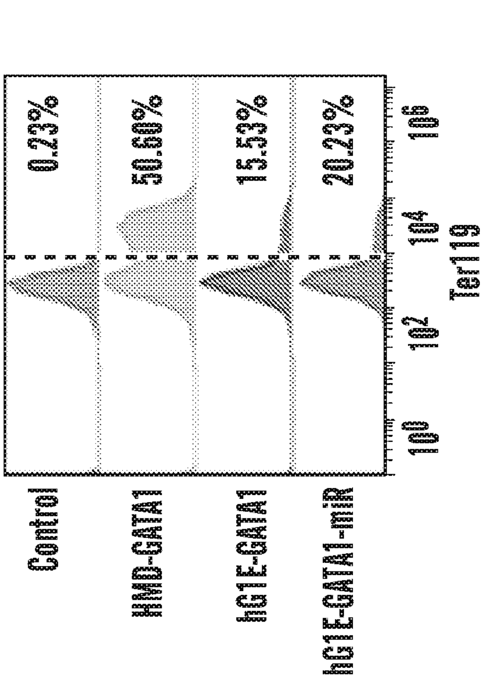
Figure 28B:
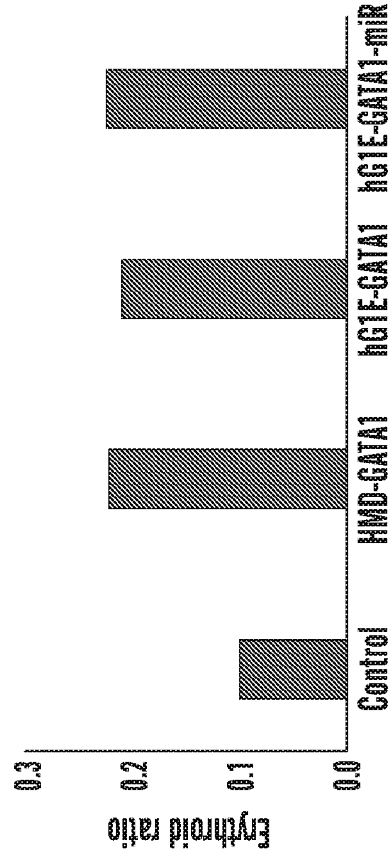
FIG. 28B. shRNA knockdown of RPS19 in primary human HSPCs impairs erythroid development and is rescued by GATA1 expression.

To assess whether hG1E-GATA1 or hG1E-GATA1-miR constructs can drive sufficient increases in GATA1 expression, the inventors used an in vitro model of DBA. Primary human CD34+ HSPCs were infected with an shRNA vector targeting the DBA gene RPS19 which the inventors have previously shown can mimic the erythroid differentiation defects in vitro that are characteristic of DBA. The inventors defined the erythroid ratio as the proportion of cells that express erythroid markers when cultured under erythropoietic conditions. When co-infected with the hG1E-GATA1 or hG1E-GATA1-miR vector, CD34+ HSPCs had a restored erythroid ratio after RPS19 knockdown at levels comparable to constitutive GATA1 overexpression with the HMD-GATA1 vector, showing rescue of the DBA phenotype (FIG. 28B). As further evidence that hG1E-GATA1 and hG1E-GATA1-miR vectors can drive enough GATA1 expression to be physiologically relevant, the inventors used the G1E murine hematopoietic cell line that lacks endogenous GATA1 expression. Infection of G1E cells with the hG1E-GATA1 and hG1E-GATA1-miR vectors induced terminal erythroid differentiation, as measured by Ter119 expression (FIG. 28C).

Figure 28D:
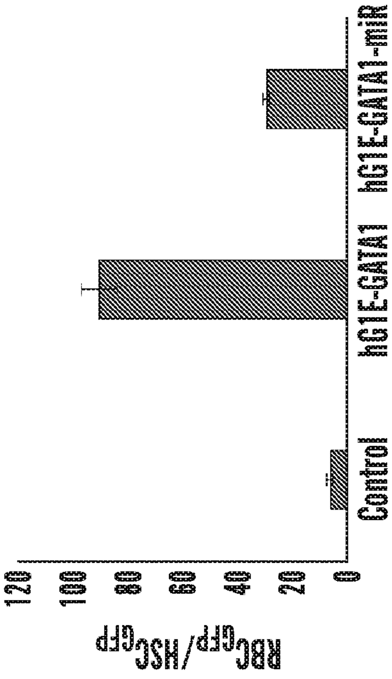

Having achieved functionally sufficient increased GATA1 expression in erythroid progenitors, the inventors sought to determine whether the inventors novel regulatory elements can restrict GATA1 expression in the LT-HSC compartment, since GATA1 expression in these cells would impair the maintenance of stem cells in the bone marrow. The inventors infected CD34+ HSPCs with the hG1E-GATA1 or hG1E-GATA1-miR vector and cultured them in conditions that enable short-term HSC maintenance in vitro. Two days after infection, GFP expression and surface expression of LT-HSC markers were assessed by flow cytometry to quantify transgene expression in LT-HSCs. These cells were then transferred to media that promotes erythroid development and GFP expression was measured in differentiated erythroid precursors. There was a significant increase in the ratio of GFP expression in erythroid cells to GFP in HSCs (RBCGFP/HSCGFP ratio) in the cells infected with hG1E-GATA1 and hG1E-GATA1-miR viruses compared to HMD-GATA1 virus that has constitutive expression of GATA1 (FIG. 28D). The increased RBCGFP/HSCGFP ratio is due to restricted expression of the experimental vectors in HSCs. These data reveal that regulated, increased GATA1 expression in erythroid precursors is sufficient to overcome the differentiation block in two distinct in vitro DBA models and has restricted expression in the LT-HSC compartment. This developmentally faithful increase in GATA1 expression provides shows that a gene therapy approach based on regulated GATA1 overexpression can be a viable cure for Diamond-Blackfan anemia.

Figure 5:
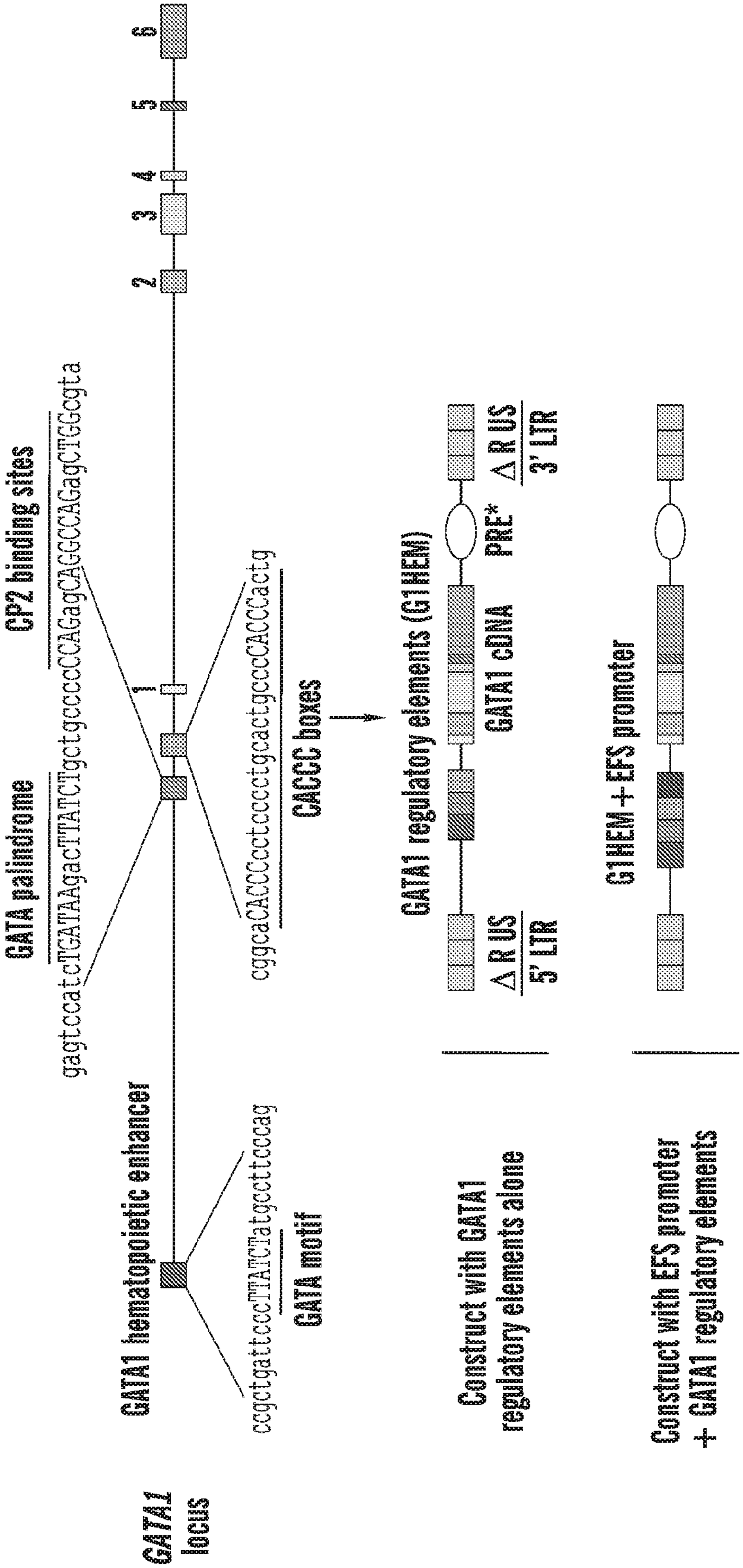
FIG. 5 depicts a schematic of the claimed vectors allowing regulated GATA1 expression. The endogenous GATA1 locus is shown above and below the pRRL.PPT.EFS vectors (including self-inactivating long-terminal repeat elements [LTR] with safety modifications and post transcriptional regulatory elements of the woodchuck hepatitis virus) are shown. The vectors either include the endogenous GATA1 promoter or the short EF1α (EFS) promoter. The GATA1 cDNA is codon optimized for improved expression.
Figure 29A:
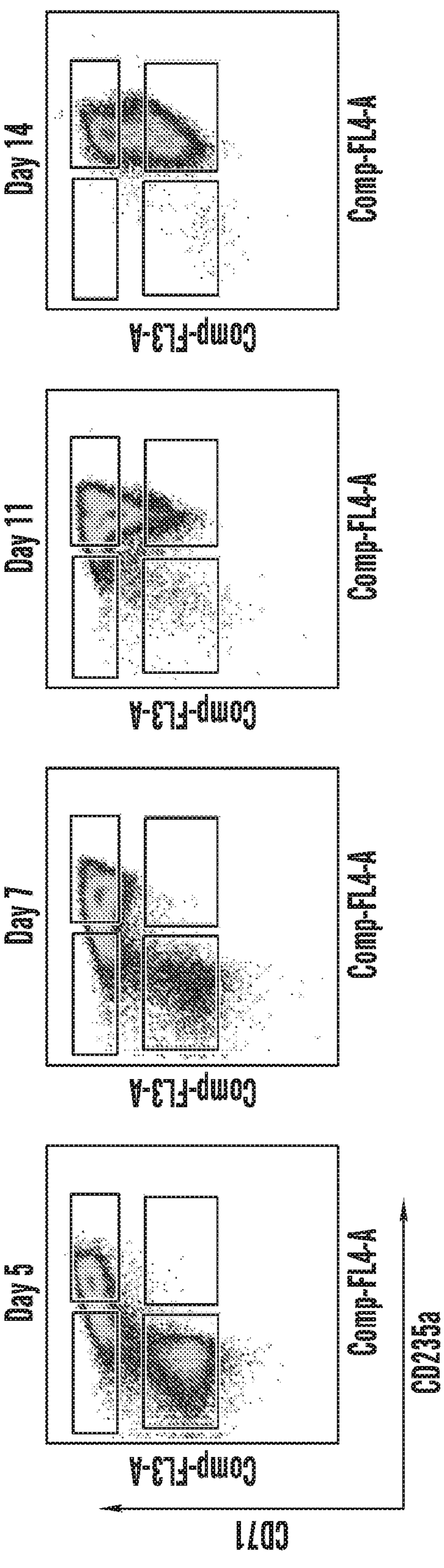
Figure 29B:
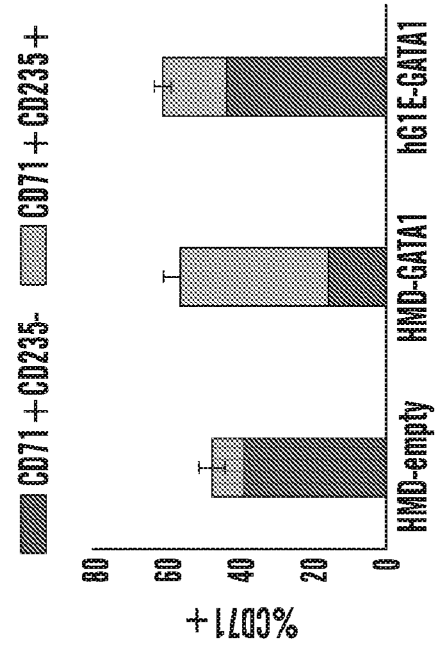
Figure 29C:
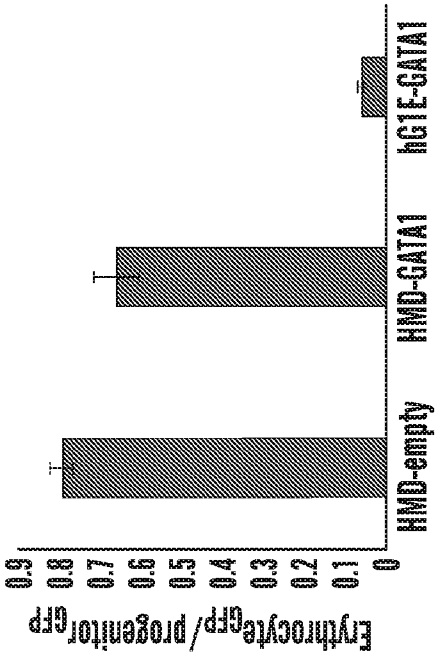

To further investigate the expression of GATA1 from the hG1E-GATA1 vector in developing erythroid cells, the inventors used a three-phase culture system to induce human HSPCs to differentiate into fully hemoglobinized, enucleated red blood cells in vitro. During in vitro differentiation, developing erythroid progenitors and precursors first express high levels of the transferrin receptor CD71. Several days later, glycophorin A (CD235a) is highly expressed, followed by loss of CD71 expression in terminally differentiated RBCs (FIG. 5*a*). Following transduction with HMD-GATA1 or hG1E-GATA1, cells that are already primed for erythroid development undergo more rapid early differentiation measured by percentage of cells expressing CD71 compared to negative controls (FIG. 29B). Next, the inventors compared the GFP expression in the terminally differentiated CD71−CD235a+ subset with GFP expression in the more primitive CD71+CD235a+ subset (ErythrocyteGFP/progenitorGFP). There is significantly decreased GFP expression from the hG1E-GATA1 vector in terminally differentiated erythrocytes, faithfully recapitulating the pattern of decreased GATA1 expression during terminal differentiation. Notably, but not unexpectedly, this decreased GFP expression was not seen in the HMD-GATA1 samples, indicating impaired terminal differentiation with unregulated GATA1 expression (FIG. 29C).

Figure 30A:
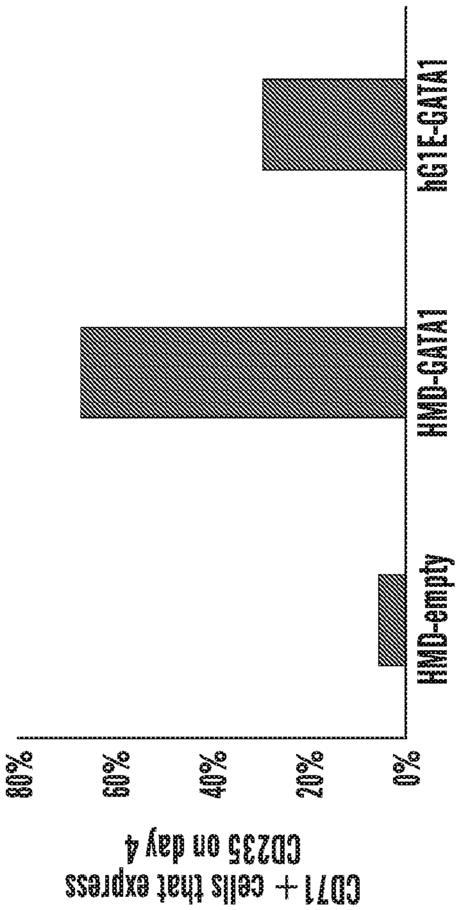
FIG. 30A and FIG. 30B. Regulated GATA1 rescues erythroid block after RPS19 editing.
Figure 30B:
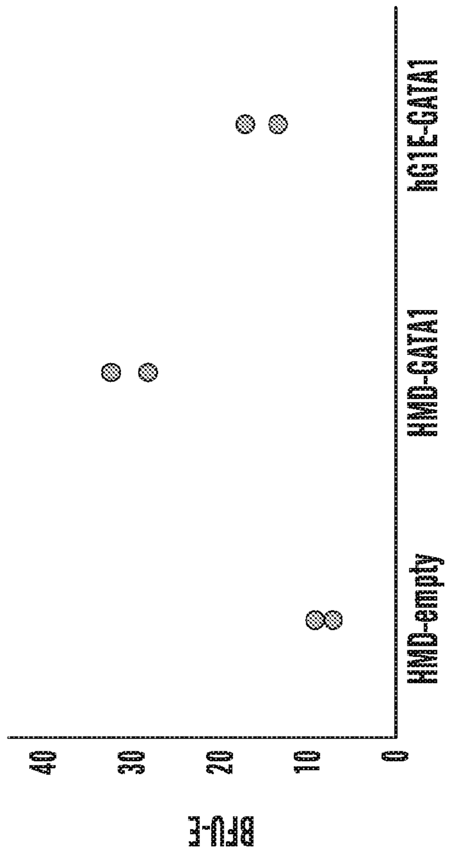

Next the inventors sought to recapitulate RPS19 haploinsufficiency in primary HSPCs isolated from healthy adult donors by using CRISPR/Cas9 mediated gene-disruption of RPS19. The inventors showed that efficient editing of RPS19 led to an erythroid maturation block with significantly fewer cells expressing CD71 during early erythroid culture. The inventors then transduced RPS19-edited HSPCs with HMD-empty, HMD-GATA1, or hG1E-GATA1 virus. Of the cells that were committed to erythroid differentiation on day 4 in culture (as measured by CD71 expression), the population infected with HMD-GATA1 or hG1E-GATA1 virus had more CD235 expression (FIG. 30A), confirming the ability of regulated increase of GATA1 expression to rescue the block in erythroid differentiation induced by loss of a ribosomal protein as is seen in DBA. Finally, there was a significant reduction in erythroid colonies detected in a methylcellulose colony forming assay after RPS19 editing that was partially rescued by hG1E-GATA1 (FIG. 30B). Altogether, the inventors data reveal that the hG1E-GATA1 vector satisfies all four criteria that are required to be a gene therapy cure for DBA (FIG. 27).

What is claimed herein is:

1. A nucleic acid molecule comprising:

a) a sequence encoding a GATA-binding factor 1 (GATA1) polypeptide; and b) a sequence comprising a concatenation of:

a first human sequence that is nucleotides 2708-3043 of SEQ ID NO: 62, a second human sequence that is nucleotides 3052-3430 of SEQ ID NO: 62, and a third human sequence that is nucleotides 3437-4251 of SEQ ID NO: 62.

2. The nucleic acid molecule of claim 1, wherein the molecule comprises a promoter operably linked to the elements of a) and b).

3. The nucleic acid molecule of claim 2, wherein the promoter is not a GATA1 promoter.

4. The nucleic acid molecule of claim 2, wherein the promoter comprises a promoter sequence of Elongation factor 1-alpha 1 (eEF1a1).

5. The nucleic acid molecule of claim 1, wherein the sequence encoding a GATA-binding factor 1 (GATA1) polypeptide comprises a sequence with at least 95% sequence identity to the nucleotide sequence of one of SEQ ID NOs: 1-5.

6. The nucleic acid molecule of claim 1, wherein the sequence encoding a GATA-binding factor 1 (GATA1) polypeptide is selected from any of SEQ ID NOs: 1-5.

7. The nucleic acid molecule of claim 1, further comprising a posttranscriptional regulatory element operably linked to the sequence encoding the GATA1 polypeptide.

8. The nucleic acid molecule of claim 7, wherein the posttranscriptional regulatory element comprises a Woodchuck Hepatitis Virus Posttranscriptional Regulatory Element (WPRE).

9. The nucleic acid molecule of claim 1, further comprising an internal ribosome entry site.

10. The nucleic acid molecule of claim 9, wherein the internal ribosome entry site is operably linked to a marker gene.

11. The nucleic acid molecule of claim 10, wherein the marker gene encodes an optically visible protein or an enzyme.

12. A vector comprising the nucleic acid molecule of claim 1.

13. The vector of claim 12, wherein the vector is a plasmid, an adenoviral vector, a lentiviral vector, or a retroviral vector.

14. A lentiviral particle comprising the nucleic acid molecule of claim 1.

15. A composition comprising a nucleic acid molecule of claim 1 and a pharmaceutically acceptable carrier.

* * * * *